US007824679B2

(12) United States Patent
Hanson et al.

(10) Patent No.: US 7,824,679 B2
(45) Date of Patent: *Nov. 2, 2010

(54) HUMAN MONOCLONAL ANTIBODIES TO CTLA-4

(75) Inventors: Douglas Charles Hanson, Niantic, CT (US); Mark Joseph Neveu, Hartford, CT (US); Eileen Elliott Mueller, Old Lyme, CT (US); Jeffrey Herbert Hanke, Reading, MA (US); Steven Christopher Gilman, Cambridge, MA (US); C. Geoffrey Davis, Burlingame, CA (US); Jose Ramon Corvalan, Foster City, CA (US)

(73) Assignees: Amgen Fremont Inc., Fremont, CA (US); Pfizer Inc., New York, NY (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/981,810

(22) Filed: Oct. 31, 2007

(65) Prior Publication Data

US 2008/0233122 A1    Sep. 25, 2008

Related U.S. Application Data

(63) Continuation of application No. 11/128,900, filed on May 12, 2005, now Pat. No. 7,411,057, which is a continuation of application No. 10/776,649, filed on Feb. 10, 2004, now Pat. No. 7,132,281, which is a continuation of application No. 10/612,497, filed on Jul. 1, 2003, now Pat. No. 7,109,003, which is a continuation of application No. 09/472,087, filed on Dec. 23, 1999, now Pat. No. 6,682,736.

(60) Provisional application No. 60/113,647, filed on Dec. 23, 1998.

(51) Int. Cl.
*A61K 39/395* (2006.01)
(52) U.S. Cl. .................................................. 424/142.1
(58) Field of Classification Search ........................ None
See application file for complete search history.

(56) References Cited

U.S. PATENT DOCUMENTS

| | | | |
|---|---|---|---|
| 4,399,216 A | 8/1983 | Axel et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,740,461 A | 4/1988 | Kaufman |
| 4,816,397 A | 3/1989 | Boss et al. |
| 4,912,040 A | 3/1990 | Kaufman et al. |
| 4,959,455 A | 9/1990 | Clark et al. |
| 5,101,827 A | 4/1992 | Goldenberg |
| 5,102,990 A | 4/1992 | Rhodes |
| 5,151,510 A | 9/1992 | Stec et al. |
| 5,194,594 A | 3/1993 | Khawli et al. |
| 5,434,131 A | 7/1995 | Linsley et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torii et al. |
| 5,697,902 A | 12/1997 | Godenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnson et al. |

(Continued)

FOREIGN PATENT DOCUMENTS

CA    2205680    11/1998

(Continued)

OTHER PUBLICATIONS

United States Patent and Trademark Office, "Notice of Allowance and Fee(s) Due," U.S. Appl. No. 11/128,900, filed Mar. 25, 2008.

(Continued)

*Primary Examiner*—Ilia Ouspenski
(74) *Attorney, Agent, or Firm*—Ropes & Gray LLP; Jane T. Gunnison; Z. Ying Li

(57) ABSTRACT

In accordance with the present invention, there are provided fully human monoclonal antibodies against human cytotoxic T-lymphocyte antigen 4 (CTLA-4). Nucelotide sequences encoding and amino acid sequences comprising heavy and light chain immunoglobulin molecules, particularly contiguous heavy and light chain sequences spanning the complementarity determining regions (CDRs), specifically from within FR1 and/or CDR1 through CDR3 and/or within FR4, are provided. Further provided are antibodies having similar binding properties and antibodies (or other antagonists) having similar functionality as antibodies disclosed herein.

19 Claims, 48 Drawing Sheets

U.S. PATENT DOCUMENTS

| | | | |
|---|---|---|---|
| 5,741,957 | A | 4/1998 | Deboer et al. |
| 5,750,172 | A | 5/1998 | Meade et al. |
| 5,756,687 | A | 5/1998 | Denman et al. |
| 5,770,197 | A | 6/1998 | Linsley et al. |
| 5,770,429 | A | 6/1998 | Lonberg et al. |
| 5,773,253 | A | 6/1998 | Linsley et al. |
| 5,777,085 | A | 7/1998 | Co et al. |
| 5,789,215 | A | 8/1998 | Berns et al. |
| 5,789,650 | A | 8/1998 | Lonberg et al. |
| 5,811,097 | A | 9/1998 | Allison et al. |
| 5,814,318 | A | 9/1998 | Lonberg et al. |
| 5,827,690 | A | 10/1998 | Meade et al. |
| 5,855,887 | A | 1/1999 | Allison et al. |
| 5,916,771 | A | 6/1999 | Hori et al. |
| 5,939,598 | A | 8/1999 | Kucherlapati et al. |
| 5,968,510 | A | 10/1999 | Linsley et al. |
| 5,977,318 | A | 11/1999 | Linsley et al. |
| 6,051,227 | A | 4/2000 | Allison et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,207,156 | B1 | 3/2001 | Kuchroo et al. |
| 6,255,458 | B1 | 7/2001 | Lonberg et al. |
| 6,682,736 | B1 | 1/2004 | Hanson et al. |
| 7,109,003 | B2 | 9/2006 | Hanson et al. |
| 7,132,281 | B2 | 11/2006 | Hanson et al. |
| 2002/0086014 | A1 | 7/2002 | Korman et al. |
| 2003/0086930 | A1 | 5/2003 | Mueller et al. |
| 2008/0233116 | A1* | 9/2008 | Hanson et al. ........... 424/133.1 |

FOREIGN PATENT DOCUMENTS

| | | |
|---|---|---|
| CL | 1021-2002 | 5/2002 |
| EP | 0 216 846 | 4/1987 |
| EP | 0 323 997 | 7/1989 |
| EP | 0 338 841 | 10/1989 |
| EP | 0 463 151 | 1/1992 |
| EP | 0 546 073 | 6/1993 |
| EP | 0 239 400 | 8/1994 |
| EP | 0 256 055 | 2/1998 |
| WO | WO 91/10741 | 7/1991 |
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/00431 | 1/1993 |
| WO | WO 93/12227 | 6/1993 |
| WO | WO 94/00569 | 1/1994 |
| WO | WO 94/02602 | 2/1994 |
| WO | WO 94/25585 | 11/1994 |
| WO | WO 94/29444 | 12/1994 |
| WO | WO 95/01994 | 1/1995 |
| WO | WO 95/03408 | 2/1995 |
| WO | WO 95/24217 | 9/1995 |
| WO | WO 95/33770 | 12/1995 |
| WO | WO 96/14436 | 5/1996 |
| WO | WO 96/22380 | 7/1996 |
| WO | WO 96/33735 | 10/1996 |
| WO | WO 96/34096 | 10/1996 |
| WO | WO 97/13852 | 4/1997 |
| WO | WO 97/20574 | 6/1997 |
| WO | WO 97/38137 | 10/1997 |
| WO | WO 98/04281 | 2/1998 |
| WO | WO 98/24884 | 6/1998 |
| WO | WO 98/24893 | 6/1998 |
| WO | WO 98/42752 | 10/1998 |
| WO | WO 98/46996 | 10/1998 |
| WO | WO 98/50433 | 11/1998 |
| WO | WO 00/32231 | 6/2000 |
| WO | WO 01/14424 | 3/2001 |

OTHER PUBLICATIONS

United States Patent and Trademark Office, "Notice of Allowability," U.S. Appl. No. 11/128,900, filed Mar. 25, 2008.
U.S. Appl. No. 11/128,900, filed Dec. 29, 2005, Hanson et al.
U.S. Appl. No. 11/981,771, Not Yet Published, Hanson et al.
U.S. Appl. No. 11/981,824, Not Yet Published, Hanson et al.
Alegre et al., Regulation of surface and intracellular expression of CTLA4 on mouse T cells,: *J. Immunol.*, 157:4762-4770 (1996).
Allison & Krummel, "The Yin and Yang of T cell costimulation," *Science*, 270:932-933 (1995).
Balzano et al., "CTLA-4 and CD28: Similar proteins, neighbouring genes," *Int. J. Cancer: Supplement*, 7:28-32 (1992).
Barker and Dayhoff, "Detecting distant relationships: computer methods and results," *Atlas of Protein Sequence and Structure*, pp. 101-110 (vol. 5, National Biomedical Research Foundation (1972).
Blair et al., "Cutting edge: CTLA-4 ligation delivers a unique signal to resting human CD4 T cells that inhibits interleukin-2 secretion but allows Bcl-$X_L$ induction," *J Immunol*, 160:12-15 (1998).
Blake and Litzi-Davis, "Evaluation of peptide libraries: An iterative strategy to analyze the reactivity of peptide mixtures with antibodies," *Bioconjugate Chem.*, 3:510-513 (1992).
Boussiotis et al., "Activated human B lymphocytes express three CTLA-4 counterreceptors that costimulate T-cell activation," *Proc Natl Acad Sci USA*, 90:11059-11063 (1993).
Bowie et al., "A method to identify protein sequences that fold into a known three-dimensional structure," *Science*, 253:164-170 (1991).
Bruggemann et al., "A repertoire of monoclonal antibodies with human heavy chains from transgenic mice," *PNAS USA*, 86:6709-6713 (1989).
Bruggemann and Neuberger, "Generation of antibody repertoires in transgenic mice," *Methods: A companion to Methods in Enzymology*, 2:159-165 (1991).
Bruggemann et al., "Human antibody production in transgenic mice: expression from 100 kb of the human IgH locus," *Eur. J. Immunol.*, 21:1323-1326 (1991).
Bruggemann and Neuberger, "Strategies for expressing human antibody repertoires in transgenic mice," *Immunology Today*, 17:391-397 (1996).
Brunet et al., "A new member of the immunoglobulin superfamily—CTLA-4," *Nature*, 328:267-270 (1987).
Bumpers et al., "Consistent hepatic metastasis of human colorectal cancer in severe combined immunodeficient mice," *J. Surgical Res.*, 61:282-288 (1996).
Castan et al., "Accumulation of CTLA-4 expressing T lymphocytes in the germinal centres of human lymphoid tissues," *Immunology*, 90:265-271 (1997).
Chen et al., "Costimulation of antitumor immunity by the B7 counter-receptor for the T lymphocyte molecules Cd28 and CTLA-4," *Cell*, 71:1093-1102 (1992).
Chen et al. "Immunoglobulin gene rearrangement in B-cell deficient mice generated by targeted deletion of the $J_H$ locus," *International Immunology*, 5:647-656 (1993).
Chen et al., "Intracellular antibodies as a new class of therapeutic molecules for gene therapy," *Human Gene Therapy*, 5:595-601 (1994).
Chiswell and McCafferty, "Phage antibodies: will new 'coliclonal' antibodies replace monoclonal antibodies?" *TIBTECH*, 10:80-84 (1992).
Choi et al., "Transgenic mice containing a human heavy chain immunoglobulin gene fragment cloned in a yeast artificial chromosome," *Nature Genetics*, 4:117-123 (1993).
Chothia & Lesk, "Canonical structures for the hypervariable regions of immunoglobulins," *J. Mol. Biol.*, 196:901-917 (1987).
Chothia et al., "Conformations of immunoglobulin hypervariable regions," *Nature*, 342:877-883 (1989).
Chuang et al., "Interaction of CTLA-4 with the clathrin-associated protein AP50 results in ligand-independent endocytosis that limits cell surface expression," *J. Immunol.*, 159:144-151 (1997).
Coligan et al., "Unit 2.1, Enzyme-linked immunosorbent assays," *Current Protocols in Immunology*, 2.1.1-2.1.22 (1994).

Cwirla et al., "Peptides on phage: a vast library of peptides for identifying ligands," *PNAS USA*, 87:6378-6382 (1990).
Dariavach et al., "Human Ig superfamily CTLA-4 gene: chromosomal localization and identity of protein sequence between murine and human CTLA-4 cytoplasmic domains," *Eur. J. Immunol.*, 18:1901-1905 (1988).
Dayhoff, "Survey of new data and computer methods of analysis," *Atlas of Protein Sequence and Structure*, pp. 1-10 (vol. 5, Supplement 2, National Biomedical Research Foundation (1976)).
de Boer et al., "Ligation of B7 with CD28/CTLA-4 on T cells results in CD40 ligand expression, interleukin-4 secretion and efficient help for antibody production by B cells," *Eur J Immunol*, 23:3120-3125 (1993).
Evans et al., "Design of nonpeptidal ligands for a peptide receptor: cholecystokinin antagonists," *J. Med. Chem.*, 30:1229-1239 (1987.
Fallarino et al., "B7-1 Engagement of cytotoxic T lymphocyte antigen 4 inhibits T cell activation in the absence of CD28," *J Exp Med*, 188:205-210 (1998.
Fanger et al., "Production and use of anti-FcR bispecific antibodies," *ImmunoMethods*, 4:72-81 (1994).
Fauchere, "Elements for the rational design of peptide drugs," *Adv. Drug Res.*, 15:29-69 (1986).
Fishwild et al., "High-avidity human IgGκ monoclonal antibodies from a novel strain of minilocus transgenic mice," *Nature Biotech.*, 14:845-851 (1996).
Foster et al., "Molecular Mechanisms and Selective Influences That Shape the Kappa Gene Repertoire of IgM+ B Cells," *J. Clin. Invest.*: 99, No. 7:1614-1627 (1997).
Freeman et al., "Murine B7-2, an alternative CTLA4 counter-receptor that costimulates T cell proliferation and interleukin 2 production," *J Exp Med.*, 178:2185-2192 (1993).
Freeman et al., "Uncovering of functional alternative CTLA-4 counter-receptor in B7-deficient mice," *Science*, 262:907-909 (1993).
Freeman et al.,"The BB1 monoclonal antibody recognizes both cell surface CD74 (MHC class II-associated invariant chain) as well as B7-1 (CD80), resolving the question regarding a third CD28/CTLA-4 counterreceptor," *J Immunol*, 161:2708-2715 (1998).
Fry et al., "Specific, irreversible inactivation of the epidermal growth factor receptor and erbB2, by a new class of tyrosine kinase inhibitor," *Proc Nat'l Acad Sci USA*, 95:12022-12027 (1998).
Furet et al., "Modelling study of protein kinase inhibitors: binding mode of staurosporine and origin of the selectivity of CGP 52411," *Journal of Computer-Aided Molecular Design*, 9:465-472 (1995).
Galfre and Milstein, "Preparation of monoclonal antibodies: strategies and procedures." *Methods Enzymol.*, 73:3-46 (1981).
Ginalski et al., "Modelling of active forms of protein kinases: p38—a case study," *Acta Biochimica Polonica*, 44:557-564 (1997).
Gorman et al., "The Rous sarcoma virus long terminal repeat is a strong promoter when introduced into a variety of eukaryotic cells by DNA-mediated transfection," *Proc Nat'l Acad Sci USA*, 79:6777-6781 (1982).
Green and Jakobovits, "Regulation of B cell development by variable gene complexity in mice reconstituted with human immunoglobulin yeast artificial chromosomes," *J. Exp. Med.*, 188:483-495 (1998).
Green et al., "Antigen-specific human monoclonal antibodies from mice engineered with human Ig heavy and light chain YACs," *Nature Genetics*, 7:13-21 (1994).
Gribben et al., "CTLA4 mediates antigen-specific apoptosis of human T cells," *Proc. Natl. Acad. Sci.*, 92:811-815 (1995.
Grosschedl and Baltimore, "Cell-type specificity of immunoglobulin gene expression is regulated by at least three DNA sequence elements," *Cell*, 41:885-897(1985).
Hanes and Plückthun, "In vitro selection and evolution of functional proteins by using ribosome display," *Proc Nat'l Acad Sci USA*, 94:4937-4942 (1997).
Harding et al., "CD28-mediated signalling co-stimulates murine T cells and prevents induction of anergy in T-cell clones," *Nature*, 356:607-609 (1992).
Harper et al., "CTLA-4 and CD28 activated lymphocyte molecules are closely related in both mouse and human as to sequence, message expression, gene structure, and chromosomal location," *J Immunol*, 147:1037-1044 (1991).

Hathcock et al., "Identification of an alternative CTLA-4 ligand costimulatory for T cell activation," *Science*, 262:905-907 (1993).
Hofmann et al., "A model of Cdc25 phosphatase catalytic Domain and Cdk-interaction surface based on the presence of a rhodanese homology domain," *J Mol Biol*, 282:195-208 (1998).
Holliger et al., "'Diabodies': Small bivalent and bispecific antibody fragments," *PNAS USA* 90:6444-6448 (1993).
Hoogenboom et al., "Building antibodies from their genes," *Immunol. Reviews*, 130:43-68 (1992).
Horspool et al., "Nucleic acid vaccine-induced immune responses require CD28 costimulation and are regulated by CTLA4," *J Immunol*, 160:2706-2714 (1998).
Houghten et al., "The use of synthetic peptide combinatorial libraries for the identification of bioactive peptides," *BioTechniques*, 13:412-421 (1992).
Houghten, "General method for the rapid solid-phase synthesis of large numbers of peptides: Specificity of antigen-antibody interaction at the level of individual amino acids," *Proc Nat'l Acad Sci USA*, 82:5131-5135 (1985).
Hurwitz et al., "Specific blockade of CTLA-4/B7 interactions results in exacerbated clinical and histologic disease in an actively-induced model of experimental allergic encephalomyelitis," *J Neuroimmunol*, 73:57-62 (1997).
Hurwitz et al., "CTLA-4 blockade synergizes with tumor-derived granulocyte-macrophage colony-stimulating factor for treatment of an experimental mammary carcinoma," *Proc Natl Acad Sci USA*, 95:10067-10071 (1998.
Ill et al., "Design and construction of a hybrid immunoglobulin domain with properties of both heavy and light chain variable regions," *Protein Engineering*, 10:949-957 (1997).
Jakobovits et al., "Germ-line transmission and expression of a human-derived yeast artificial-chromosome." *Nature*, 362:255-258 (1993).
Jakobovits et al., "Analysis of homozygous mutant chimeric mice: Deletion of the immunoglobulin heavy-chain joining region blocks B-cell development and antibody production." *Proc. Natl. Acad. Sci. USA*, 90:2551-2555 (1993).
Jakobovits, "Humanizing the mouse genome." *Current Biology*, 4:761-763 (1994).
Jakobovits, "Production of fully human antibodies by transgenic mice." *Current Opinion in Biotechnology*, 6:561-566 (1995).
Jakobovits, "The long-awaited magic bullets: therapeutic human monoclonal antibodies from transgenic mice," *Expert Opinion on Investigational Drugs*, 7:607-614 (1998.
Jones et al., "Replacing the complementarity-determining regions in a human antibody with those from a mouse," *Nature*, 321:522-525 (1986).
Joukov et al., "Identification of Csk tyrosine phosphorylation sites and a tyrosine residue important for kinase domain structure," *Biochem J*, 322:927-935 (1997).
Junghans et al. in *Cancer Chemotherapy and Biotherapy*, 655-686 (2d edition, Chafner and Longo, eds., Lippincott Raven (1996)).
Karandikar et al., "CTLA-4: A Negative Regulator of Autoimmune Disease," *J. Exp. Med.*, 184:783-788 (1996).
Kostelny et al., "Formation of a bispecific antibody by the use of leucine zippers," *J. Immunol.*, 148:1547-1553 (1992).
Krummel and Allison, "CD28 and CTLA-4 have opposing effects on the response of T cells to stimulation," *J Exp Med*, 182:459-465 (1995).
Krummel et al., "Superantigen responses and co-stimulation: CD28 and CTLA-4 have opposing efffects on T cell expansion in vitro and in vivo," *Int Immunol*, 8:519-523 (1996).
Kuchroo et al., "B7-1 and B7-2 costimulatory molecules activate differentially the Th1/Th2 developmental pathways: application to autoimmune disease therapy," *Cell*, 80:707-718 (1995).
Kwon et al., "Manipulation of T cell costimulatory and inhibitory signals for immunotherapy of prostate cancer," *Pro Nat'l Acad Sci USA*, 94:8099-80103 (1997).
Laplanche et al., "Phosphorothioate-modified oligodeoxyribonucleotides. III NMR and UV spectroscopic studies of the $R_p$-$R_p$, $S_p$-$S_p$ duplexes. [d(GG$_s$ AATTCC)]$_2$, derived from diastereomeric O-ethyl phosphorothioates," *Nucl. Acids Res.*, 14:9081-9093 (1986).

Lenschow et al., "Expression and functional significance of an additional ligand for CTLA-4," *Proc Nat'l Acad Sci USA*, 90:11054-11058 (1993).

Lenschow et al., "Long-term survival of xenogeneic pancreatic islet grafts induced by CTLA4Ig," *Science*, 257:789-792 (1992).

"Leucocyte Typing VI: White Cell Differentiation Antigens," *Garland Publishing*, New York, NY, pp. 30-31, 95-98 and 1213-1214, (1998).

Lin et al., "Cytotoxic T lymphocyte antigen 4 (CTLA4) blockade accelerates the acute rejection of cardiac allografts in CD28-deficient mice: CTLA4 can function independently of CD28," *J Exp Med*, 188:199-204 (1998).

Linsley et al., "CTLA-4 is a second receptor for the B cell activation antigen B7," *J. Exp. Med.*, 174:561-569 (1991).

Linsley et al., "Coexpression and functional cooperation of CTLA-4 and CD-28 on activated T lymphocytes," *J Exp Med*, 176:1595-1604 (1992).

Linsley et al., "Immunosuppression in vivo by a soluble form of the CTLA-4 T cell activation molecule," *Science*, 257:792-795 (1992).

Liu et al., Production of a mouse-human chimeric monoclonal antibody to CD20 with potent Fc-dependent biologic activity, *J.Immunol.*, 139:3521-3526 (1987).

Liu et al., "Chimeric mouse-human IgG1 antibody that can mediate lysis of cancer cells," *Proc Nat'l Acad Sci USA*, 84:3439-3443 (1987).

Lonberg et al., "Antigen-specific human antibodies from mice comprising four distinct genetic modifications," *Nature*, 368:856-859 (1994).

Luhder et al., "Cytotoxic T lymphocyte-associated antigen 4 (CTLA-4) regulates the unfolding of autoimmune diabetes," *J Exp Med*, 187:427-432 (1998).

Mandal et al., "ABGEN: A knowledge-based automated approach for antibody structure modeling," *Nature Biotechnology*, 14:323-328 (1996).

Marasco, "Intrabodies: turning the humoral immune system outside in for intracellular immunization," *Gene Therapy*, 4:11-15 (1997).

Markees et al., "Long-term survival of skin allografts induced by donor splenocytes and anti-CD154 antibody in thymectomized mice requires CD4(+) T cells, interferon-gamma, and CTLA4," *J Clin Invest*, 101:2446-2455 (1998.

Marks et al., "Oligonucleotide primers for polymerase chain reaction amplification of human immunoglobulin variable genes and design of family-specific oligonucleotide probes." *Eur. J. Immunol.*, 21:985-991 (1991).

Marrack et al., "The Staphylococcal Enterotoxins and Their Relatives," *Science*, 705-711 (1990).

Martin et al., "The affinity-selection of a minibody polypeptide inhibitor of human interleukin-6," *The EMBO Journal*, 13:5303-5309 (1994).

McCoy et al., "Protective immunity to nematode infection is induced by CTLA-4 blockade," *J Exp Med*, 186:183-187 (1997).

Mendez et al., "Functional transplant of megabase human immunoglobulin loci recapitulates human antibody response in mice," *Nature Genetics*, 15:146-156 (1997).

Monfardini et al. "Rational design, analysis, and potential utility of GM-CSF antagonists," *Proc Assoc Am Physicians*, 108:420-431 (1996).

Morrison, "Transfectomas provide novel chimeric antibodies," *Science*, 229:1202-1207 (1985).

Murphy et al., "Blockade of CTLA-4 enhances host resistance to the intercellular pathogen, *Leishmania donovani*," *J. Immunol.*, 161:4153-4160 (1998).

Needleman and Wunsch, "A general method applicable to the search for similarities in the amino acid sequence to two proteins," *Mol. Biol.*, 48:443-453 (1970).

Neuberger et al., "A hapten-specific chimaeric IgE antibody with human physiological effector function," *Nature*, 314:268-270 (1985).

Oi et al., "Chimeric antibodies," *Biotechniques*, 4(3):214-221 (1986).

Okayama et al., "A cDNA cloning vector that permits expression of cDNA inserts in mammalian cells," *Mol. Cell. Bio.*, 3:280-289 (1983).

O'Kennedy et al., "Antibody engineering: an overview," *Essays in Biochemistry*, 46:59-75 (1991).

Parmley and Smith, "Antibody-selectable filamentous fd phage vectors: affinity purification of target genes," *Gene*, 73:305-318 (1988.

Parren, "Preparation of genetically engineered monoclonal antibodies for human immunotherapy," *Human Antibodies and Hybridomas*, 3:137-145 (1992).

Pearson and Lipman, "Improved tools for biological sequence comparison," *Proc. Natl. Acad. Sci. U.S.A.*, 85:2444-2448 (1988).

Perez et al., "Induction of peripheral T cell tolerance in vivo requires CTLA-4 engagement," *Immunity*, 6:411-417 (1997).

Perrin et al., "B7-mediated costimulation can either provoke or prevent clinical manifestations of experimental allergic encephalomyelitis," *Immunol Res*, 14:189-199 (1995).

Perrin et al. CTLA-4 blockade enhances clinical disease and cytokine production during experimental allergic encephalomyelitis *J Immunol*,157:1333-1336 (1996).

Pinilla et al., "Rapid identification of high affinity peptide ligands using positional scanning synthetic peptide combinatorial libraries," *Biotechniques*, 13:901-905 (1992).

Powell et al., "Compendium of excipients for parenteral formulations," *PDA J Pharm Sci Technol*. 52:238-311 (1998).

Razi-Wolf et al., "Evidence for an additional ligand, distinct from B7, for the CTLA-4 receptor," *Proc Natl Acad Sci USA*, 90:11182-11186 (1993).

Riechmann et al., "Reshaping human antibodies for therapy," *Nature*, 332:323-327 (1988).

Rizo and Gierasch,"Constrained peptides: models of bioactive peptides and protein substructures," *Annu. Rev. Biochem.*, 61:387-418 (1992).

Rudikoff et al., "Single Amino Acid Substitution Altering Antigen-Binding Specificity," *Proc. Natl. Acad. Sci. USA*, 79:1979-1983 (1982).

Russel et al., "Retroviral vectors displaying functional antibody fragments," *Nucl. Acids Research*, 21:1081-1085 (1993).

Schwartz, "Costimulation of T lymphocytes: The role of CD28, CTLA-4, and B7/BB1 in interleukin-2 production and immunotherapy," *Cell*, 71:1065-1068 (1992).

Scott, "Discovering peptide ligands using epitope libraries," *Trends in Biochemical Sciences*, 17:241-245 (1992).

Singh et al., "Structure-based design of a potent, selective, and irreversible inhibitor of the catalytic domain of the erbB receptor subfamily of protein tyrosine kinases," *J Med Chem*, 40:1130-1135 (1997).

Smith and Waterman, "Comparison of Biosequences," *Adv. Appl. Math.*, 2:482-489 (1981).

Songsivilai and Lachmann, "Bispecific antibody: a tool for diagnosis and treatment of disease," *Clin. Exp. Immunol.*, 79: 315-321 (1990).

Stec et al., "Automated solid-phase synthesis, separation, and stereochemistry of phosphorothioate analogues of oligodeoxyribonucleotides," *J. Am. Chem. Soc.*, 106:6077-6079 (1984).

Stein et al., "Physicochemical properties of phosphorothioate oligodeoxynucleotides," *Nucl. Acids Res.*, 16:3209-3221 (1988).

Taylor et al., "A transgenic mouse that expresses a diversity of human sequence heavy and light chain immunoglobulins," *Nucleic Acids Research*, 20:6287-6295 (1992).

Taylor et al., "Human immunoglobulin transgenes undergo rearrangement, somatic mutation and class switching in mice that lack endogenous IgM," *International Immunology*, 6:579-591 (1994).

Thornton et al., "Prediction of progress at last" *Nature*, 354:105-106 (1991).

Tivol et al., "Loss of CTLA-4 leads to massive lymphoproliferation and fatal multiorgan tissue destruction, revealing a critical negative regulatory role of CTLA-4," *Immunity*, 3:541-547 (1995).

Townsend and Allison, "Tumor rejection after direct costimulation of CD8+ T cells by B7-transfected melanoma cells," *Science*, 259:368-370 (1993).

Traunecker et al., "Bispecific single chain molecules (Janusins) target cytotoxic lymphocytes on HIV infected cells," *EMBO J*, 10:3655-3659 (1991).

Traunecker et al., "Janusin: new molecular design for bispecific reagents," *Int. J. Cancer (Suppl.)*, 7:51-52 (1992).

Tuaillon et al., "Analysis of direct and inverted $DJ_H$ rearrangements in a human Ig heavy chain transgenic minilocus," *J. Immunol.*, 154:6453-6465 (1995.

Tuaillon et al., "Human immunoglobulin heavy-chain minilocus recombination in transgenic mice: gene-segment use in μ and γ transcripts," *Proc. Natl. Acad. Sci. USA*, 90:3720-3724 (1993).

Uhlmann and Peyman, "Antisense RNA: A natural gene expression control system," *Chemical Reviews*, 90:543-584 (1990).

Van Parijs et al., "Role of interleukin 12 and costimulators in T cell anergy in vivo," *The Journal of Experimental Medicine*, 186, 1119-1128 (1997).

Vaswani et al., "Humanized antibodies as potential therapeutic drugs," *Annals of Allergy, Asthma & Immunology*, 81:105-119 (1998).

Veber and Freidinger, "The design of metabolically-stable peptide analogs," *Trends in Neuro Sciences*, pp. 392-396 (1985).

Verhoeyen et al., "Reshaping human antibodies: grafting an antilysozyme activity," *Science*, 239:1534-1536 (1988).

Vitetta et al., "Immunotoxins: magic bullets or misguided missiles," *Immunol Today*, 14:252-259 (1993).

Walunas et al., "CTLA-4 can function as a negative regulator of T cell activation," *Immunity*, 1:405-413 (1994).

Walunas et al., "CTLA-4 ligation blocks CD28-dependent T cell activation," *J Exp Med*, 183:2541-2550 (1996).

Waterhouse et al., "Lymphoproliferative disorders with early lethality in mice deficient in CTLA-4," *Science*, 270:985-988 (1995).

Winter and Harris, "Humanized Antibodies," *Immunol Today*, 14:243-246 (1993).

Wright et al., "Genetically engineered antibodies: Progress and prospects," *Crit. Reviews in Immunol.*, 12:125-168 (1992).

Wu, "From esoteric theory to therapeutic antibodies," *Applied Biochemistry and Biotechnology*, 47(2/3):107-118 (1994).

Yang et al., "Enhanced induction of antitumor T-cell responses by cytotoxic T lymphocyte-associated molecule-4 blockade: The effect is manifested only at the restricted tumor-bearing stages," *Cancer Res*, 57:4036-4041 (1997).

Yi-Qun et al., "Differential requirements for co-stimulatory signals from B7 family members by resting versus recently activated memory T cells towards soluble recall antigens," *Int Immunol*, 8:37-44 (1996).

Zon et al., "Phosphorothioate oligonucleotides: chemistry, purification, analysis, scale-up and future directions," *Anti-Cancer Drug Design*, 6:539-568 (1991).

Zon et al., "Phosphorothioate oligonucleotides," Oligonucleotides and Analogues: A Practical Approach, pp. 87-108 (F. Eckstein, Ed., Oxford University Press, Oxford England (1991)).

Camacho, "Novel therapies targeting the immune system: CTLA4 blockade with tremelimumab (CP-675,206), a fully human monoclonal antibody," *Expert Opinion on Investigational Drugs*, 17(3):371-385 (2008).

O'Day et al., "Targeting cytotoxic T-lymphocyte antigen-4 (CTLA-4): a novel strategy for the treatment of melanoma and other malignancies," *Cancer*, 110(12):2614-2627 (2007).

Cranmer et al., "The role of the CTLA4 blockade in the treatment of malignant melanoma," *Cancer Investigation*, 25:613-631 (2007).

United States Patent and Trademark Office, "Notice of Allowance and Fee(s) Due," U.S. Appl. No. 11/981,771, Jan. 12, 2010.

United States Patent and Trademark Office, "Notice of Allowability," U.S. Appl. No. 11/981,771, Jan. 12, 2010.

\* cited by examiner

Figure 1A 4.1.1 Heavy Chain DNA

```
ATGGAGTTTG GGCTGAGCTG GGTTTTCCTC GTTGCTCTTT TAAGAGGTGT 50
CCAGTGTCAG GTGCAGCTGG TGGAGTCTGG GGGAGGCGTG GTCCAGCCTG 100
GGAGGTCCCT GAGACTCTCC TGTGTAGCGT CTGGATTCAC CTTCAGTAGC 150
CATGGCATGC ACTGGGTCCG CCAGGCTCCA GGCAAGGGGC TGGAGTGGGT 200
GGCAGTTATA TGGTATGATG GAAGAAATAA ATACTATGCA GACTCCGTGA 250
AGGGCCGATT CACCATCTCC AGAGACAATT CCAAGAACAC GCTGTTTCTG 300
CAAATGAACA GCCTGAGAGC CGAGGACACG GCTGTGTATT ACTGTGCGAG 350
AGGAGGTCAC TTCGGTCCTT TTGACTACTG GGGCCAGGGA ACCCTGGTCA 400
CCGTCTCCTC AGCCTCCACC AAGGGCCCAT CGGTCTTCCC CCTGGCGCCC 450
TGCTCCAGGA GCACCTCCGA GAGCACAGCG GCCCTGGGCT GCCTGGTCAA 500
GGACTACTTC CCCGAACCGG TGACGGTGTC GTGGAACTCA GGCGCTCTGA 550
CCAGCGGCGT GCACACCTTC CCAGCTGTCC TACAGTCCTC AGGACTCTAC 600
TCCCTCAGCA GCGTGGTGAC CGTGCCCTCC AGCAACTTCG GCACCCAGAC 650
CTACACCTGC AACGTAGATC ACAAGCCCAG CAACACCAAG GTGGACAAGA 700
CAGTTGAGCG CAAATGTTGT GTCGAGTGCC CACCGTGCCC AGCACCACCT 750
GTGGCAGGAC CGTCAGTCTT CCTCTTCCCC CCAAAACCCA AGGACACCCT 800
CATGATCTCC CGGACCCCTG AGGTCACGTG CGTGGTGGTG GACGTGAGCC 850
ACGAAGACCC CGAGGTCCAG TTCAACTGGT ACGTGGACGG CGTGGAGGTG 900
CATAATGCCA AGACAAAGCC ACGGGAGGAG CAGTTCAACA GCACGTTCCG 950
TGTGGTCAGC GTCCTCACCG TTGTGCACCA GGACTGGCTG AACGGCAAGG 1000
AGTACAAGTG CAAGGTCTCC AACAAAGGCC TCCCAGCCCC CATCGAGAAA 1050
ACCATCTCCA AAACCAAAGG GCAGCCCCGA GAACCACAGG TGTACACCCT 1100
GCCCCCATCC CGGGAGGAGA TGACCAAGAA CCAGGTCAGC CTGACCTGCC 1150
TGGTCAAAGG CTTCTACCCC AGCGACATCG CCGTGGAGTG GGAGAGCAAT 1200
GGGCAGCCGG AGAACAACTA CAAGACCACA CCTCCCATGC TGGACTCCGA 1250
CGGCTCCTTC TTCCTCTACA GCAAGCTCAC CGTGGACAAG AGCAGGTGGC 1300
AGCAGGGGAA CGTCTTCTCA TGCTCCGTGA TGCATGAGGC TCTGCACAAC 1350
CACTACACGC AGAAGAGCCT CTCCCTGTCT CCGGGTAAAT GA        1392
```

(SEQ ID NO:27)

4.1.1 Heavy Chain Protein

```
MEFGLSWVFL VALLRGVQCQ VQLVESGGGV VQPGRSLRLS CVASGFTFSS 50
HGMHWVRQAP GKGLEWVAVI WYDGRNKYYA DSVKGRFTIS RDNSKNTLFL 100
QMNSLRAEDT AVYYCARGGH FGPFDYWGQG TLVTVSSAST KGPSVFPLAP 150
CSRSTSESTA ALGCLVKDYF PEPVTVSWNS GALTSGVHTF PAVLQSSGLY 200
SLSSVVTVPS SNFGTQTYTC NVDHKPSNTK VDKTVERKCC VECPPCPAPP 250
VAGPSVFLFP PKPKDTLMIS RTPEVTCVVV DVSHEDPEVQ FNWYVDGVEV 300
HNAKTKPREE QFNSTFRVVS VLTVVHQDWL NGKEYKCKVS NKGLPAPIEK 350
TISKTKGQPR EPQVYTLPPS REEMTKNQVS LTCLVKGFYP SDIAVEWESN 400
GQPENNYKTT PPMLDSDGSF FLYSKLTVDK SRWQQGNVFS CSVMHEALHN 450
HYTQKSLSLS PGK                                       463
```

(SEQ ID NO:1)

Figure 1A (continued)

4.1.1 Kappa Chain DNA

```
ATGGAAACCC CAGCGCAGCT TCTCTTCCTC CTGCTACTCT GGCTCCCAGA   50
TACCACCGGA GAAATTGTGT TGACGCAGTC TCCAGGCACC CTGTCTTTGT  100
CTCCAGGGGA AAGAGCCACC CTCTCCTGCA GGGCCAGTCA GAGTATTAGC  150
AGCAGCTTCT TAGCCTGGTA CCAGCAGAGA CCTGGCCAGG CTCCCAGGCT  200
CCTCATCTAT GGTGCATCCA GCAGGGCCAC TGGCATCCCA GACAGGTTCA  250
GTGGCAGTGG GTCTGGGACA GACTTCACTC TCACCATCAG CAGACTGGAG  300
CCTGAAGATT TTGCAGTGTA TTACTGTCAG CAGTATGGTA CCTCACCCTG  350
GACGTTCGGC CAAGGGACCA AGGTGGAAAT CAAACGAACT GTGGCTGCAC  400
CATCTGTCTT CATCTTCCCG CCATCTGATG AGCAGTTGAA ATCTGGAACT  450
GCCTCTGTTG TGTGCCTGCT GAATAACTTC TATCCCAGAG AGGCCAAAGT  500
ACAGTGGAAG GTGGATAACG CCCTCCAATC GGGTAACTCC CAGGAGAGTG  550
TCACAGAGCA GGACAGCAAG GACAGCACCT ACAGCCTCAG CAGCACCCTG  600
ACGCTGAGCA AAGCAGACTA CGAGAAACAC AAAGTCTACG CCTGCGAAGT  650
CACCCATCAG GGCCTGAGCT CGCCCGTCAC AAAGAGCTTC AACAGGGGAG  700
AGTGTTAG                                                708
```

(SEQ ID NO:40)

4.1.1 Kappa Chain Protein

```
METPAQLLFL LLLWLPDTTG EIVLTQSPGT LSLSPGERAT LSCRASQSIS   50
SSFLAWYQQR PGQAPRLLIY GASSRATGIP DRFSGSGSGT DFTLTISRLE  100
PEDFAVYYCQ QYGTSPWTFG QGTKVEIKRT VAAPSVFIFP PSDEQLKSGT  150
ASVVCLLNNF YPREAKVQWK VDNALQSGNS QESVTEQDSK DSTYSLSSTL  200
TLSKADYEKH KVYACEVTHQ GLSSPVTKSF NRGEC                  235
```

(SEQ ID NO:14)

Figure 1B

4.8.1 Heavy Chain DNA

| | | | | | |
|---|---|---|---|---|---|
| ATGGAGTTTG | GGCTGAGCTG | GGTTTTCCTC | GTTGCTCTTT | TAAGAGGTGT | 50 |
| CCAGTGTCAG | GTGCAGCTGG | TGGAGTCTGG | GGGAGGCGTG | GTCCAGCCTG | 100 |
| GGAGGTCCCT | GAGACTCTCC | TGTACAGCGT | CTGGATTCAC | CTTCAGTAAC | 150 |
| TATGGCATGC | ACTGGGTCCG | CCAGGCTCCA | GGCAAGGGGC | TGGAGTGGGT | 200 |
| GGCAGTTATA | TGGTATGATG | GAAGTAATAA | ACACTATGGA | GACTCCGTGA | 250 |
| AGGGCCGATT | CACCATCTCC | AGTGACAATT | CCAAGAACAC | GCTGTATCTG | 300 |
| CAAATGAACA | GCCTGAGAGC | CGAGGACACG | GCTGTGTATT | ACTGTGCGAG | 350 |
| AGGAGAGAGA | CTGGGGTCCT | ACTTTGACTA | CTGGGGCCAG | GGAACCCTGG | 400 |
| TCACCGTCTC | CTCAGCCTCC | ACCAAGGGCC | CATCGGTCTT | CCCCCTGGCG | 450 |
| CCCTGCTCCA | GGAGCACCTC | CGAGAGCACA | GCGGCCCTGG | GCTGCCTGGT | 500 |
| CAAGGACTAC | TTCCCCGAAC | CGGTGACGGT | GTCGTGGAAC | TCAGGCGCTC | 550 |
| TGACCAGCGG | CGTGCACACC | TTCCCAGCTG | TCCTACAGTC | CTCAGGACTC | 600 |
| TACTCCCTCA | GCAGCGTGGT | GACCGTGCCC | TCCAGCAACT | TCGGCACCCA | 650 |
| GACCTACACC | TGCAACGTAG | ATCACAAGCC | CAGCAACACC | AAGGTGGACA | 700 |
| AGACAGTTGA | GCGCAAATGT | TGTGTCGAGT | GCCCACCGTG | CCCAGCACCA | 750 |
| CCTGTGGCAG | GACCGTCAGT | CTTCCTCTTC | CCCCCAAAAC | CCAAGGACAC | 800 |
| CCTCATGATC | TCCCGGACCC | CTGAGGTCAC | GTGCGTGGTG | GTGGACGTGA | 850 |
| GCCACGAAGA | CCCCGAGGTC | CAGTTCAACT | GGTACGTGGA | CGGCGTGGAG | 900 |
| GTGCATAATG | CCAAGACAAA | GCCACGGGAG | GAGCAGTTCA | ACAGCACGTT | 950 |
| CCGTGTGGTC | AGCGTCCTCA | CCGTTGTGCA | CCAGGACTGG | CTGAACGGCA | 1000 |
| AGGAGTACAA | GTGCAAGGTC | TCCAACAAAG | CCCTCCCAGC | CCCCATCGAG | 1050 |
| AAAACCATCT | CCAAAACCAA | AGGGCAGCCC | CGAGAACCAC | AGGTGTACAC | 1100 |
| CCTGCCCCCA | TCCCGGGAGG | AGATGACCAA | GAACCAGGTC | AGCCTGACCT | 1150 |
| GCCTGGTCAA | AGGCTTCTAC | CCCAGCGACA | TCGCCGTGGA | GTGGGAGAGC | 1200 |
| AATGGGCAGC | CGGAGAACAA | CTACAAGACC | ACACCTCCCA | TGCTGGACTC | 1250 |
| CGACGGCTCC | TTCTTCCTCT | ACAGCAAGCT | CACCGTGGAC | AAGAGCAGGT | 1300 |
| GGCAGCAGGG | GAACGTCTTC | TCATGCTCCG | TGATGCATGA | GGCTCTGCAC | 1350 |
| AACCACTACA | CGCAGAAGAG | CCTCTCCCTG | TCTCCGGGTA | AATGA | 1395 |

(SEQ ID NO:28)

4.8.1 Heavy Chain Protein

| | | | | | |
|---|---|---|---|---|---|
| MEFGLSWVFL | VALLRGVQCQ | VQLVESGGGV | VQPGRSLRLS | CTASGFTFSN | 50 |
| YGMHWVRQAP | GKGLEWVAVI | WYDGSNKHYG | DSVKGRFTIS | SDNSKNTLYL | 100 |
| QMNSLRAEDT | AVYYCARGER | LGSYFDYWGQ | GTLVTVSSAS | TKGPSVFPLA | 150 |
| PCSRSTSEST | AALGCLVKDY | FPEPVTVSWN | SGALTSGVHT | FPAVLQSSGL | 200 |
| YSLSSVVTVP | SSNFGTQTYT | CNVDHKPSNT | KVDKTVERKC | CVECPPCPAP | 250 |
| PVAGPSVFLF | PPKPKDTLMI | SRTPEVTCVV | VDVSHEDPEV | QFNWYVDGVE | 300 |
| VHNAKTKPRE | EQFNSTFRVV | SVLTVVHQDW | LNGKEYKCKV | SNKGLPAPIE | 350 |
| KTISKTKGQP | REPQVYTLPP | SREEMTKNQV | SLTCLVKGFY | PSDIAVEWES | 400 |
| NGQPENNYKT | TPPMLDSDGS | FFLYSKLTVD | KSRWQQGNVF | SCSVMHEALH | 450 |
| NHYTQKSLSL | SPGK | | | | 464 |

(SEQ ID NO:2)

Figure 1B (continued)

4.8.1 Kappa Chain DNA

```
ATGGAAACCC CAGCGCAGCT TCTCTTCCTC CTGCTACTCT GGCTCCCAGA  50
TACCACCGGA GAAATTGTGT TGACGCAGTC TCCAGGCACC CTGTCTTTGT 100
CTCCAGGGGA AAGAGCCACC CTCTCCTGCA GGACCAGTGT TAGCAGCAGT 150
TACTTAGCCT GGTACCAGCA GAAACCTGGC CAGGCTCCCA GGCTCCTCAT 200
CTATGGTGCA TCCAGCAGGG CCACTGGCAT CCCAGACAGG TTCAGTGGCA 250
GTGGGTCTGG GACAGACTTC ACTCTCACCA TCAGCAGACT GGAGCCTGAA 300
GATTTTGCAG TCTATTACTG TCAGCAGTAT GGCATCTCAC CCTTCACTTT 350
CGGCGGAGGG ACCAAGGTGG AGATCAAGCG AACTGTGGCT GCACCATCTG 400
TCTTCATCTT CCCGCCATCT GATGAGCAGT TGAAATCTGG AACTGCCTCT 450
GTTGTGTGCC TGCTGAATAA CTTCTATCCC AGAGAGGCCA AAGTACAGTG 500
GAAGGTGGAT AACGCCCTCC AATCGGGTAA CTCCCAGGAG AGTGTCACAG 550
AGCAGGACAG CAAGGACAGC ACCTACAGCC TCAGCAGCAC CCTGACGCTG 600
AGCAAAGCAG ACTACGAGAA ACACAAAGTC TACGCCTGCG AAGTCACCCA 650
TCAGGGCCTG AGCTCGCCCG TCACAAAGAG CTTCAACAGG GGAGAGTGTT 700
AG                                                    702
```

(SEQ ID NO:41)

4.8.1 Kappa Chain Protein

```
METPAQLLFL LLLWLPDTTG EIVLTQSPGT LSLSPGERAT LSCRTSVSSS  50
YLAWYQQKPG QAPRLLIYGA SSRATGIPDR FSGSGSGTDF TLTISRLEPE 100
DFAVYYCQQY GISPFTFGGG TKVEIKRTVA APSVFIFPPS DEQLKSGTAS 150
VVCLLNNFYP REAKVQWKVD NALQSGNSQE SVTEQDSKDS TYSLSSTLTL 200
SKADYEKHKV YACEVTHQGL SSPVTKSFNR GEC                  233
```

(SEQ ID NO:15)

Figure 1C

4.14.3 Heavy Chain DNA

```
CCTGGGAGGT CCCTGAGACT CTCCTGTGCA GCGTCTGGAT TCACCTTCAG  50
TAGTCATGGC ATCCACTGGG TCCGCCAGGC TCCAGGCAAG GGGCTGGAGT 100
GGGTGGCAGT TATATGGTAT GATGGAAGAA ATAAAGACTA TGCAGACTCC 150
GTGAAGGGCC GATTCACCAT CTCCAGAGAC AATTCCAAGA AGACGCTGTA 200
TTTGCAAATG AACAGCCTGA GAGCCGAGGA CACGGCTGTG TATTACTGTG 250
CGAGAGTGGC CCCACTGGGG CCACTTGACT ACTGGGCCA GGGAACCCTG 300
GTCACCGTCT CCTCAGCCTC CACCAAGGGC CCATCGGTCT TCCCCCTGGC 350
GCCCTGCTCC AGGAGCACCT CCGAGAGCAC AGCGGCCCTG GGCTGCCTGG 400
TCAAGGACTA CTTCCCCGAA CCGGTGACGG TGTCGTGGAA CTCAGGCGCT 450
CTGACCAGCG GCGTGCACAC CTTCCCAGCT GTCCTACAG            489
```

(SEQ ID NO:29)

4.14.3 Heavy Chain Protein

```
PGRSLRLSCA ASGFTFSSHG IHWVRQAPGK GLEWVAVIWY DGRNKDYADS  50
VKGRFTISRD NSKKTLYLQM NSLRAEDTAV YYCARVAPLG PLDYWGQGTL 100
VTVSSASTKG PSVFPLAPCS RSTSESTAAL GCLVKDYFPE PVTVSWNSGA 150
LTSGVHTFPA VLQ                                        163
```

(SEQ ID NO:3)

4.14.3 Kappa Chain DNA

```
GGCACCCTGT CTTTGTCTCC AGGGGAAAGA GCCACCCTCT CCTGCAGGGC  50
CAGTCAGAGT GTCAGCAGCT ACTTAGCCTG GTACCAGCAG AAACCTGGCC 100
AGGCTCCCAG ACTCCTCATC TATGGTGCAT CCAGCAGGGC CACTGGCATC 150
CCAGACAGGT TCAGTGGCAG TGGGTCTGGG ACAGACTTCA CTCTCACCAT 200
CAGCAGACTG GAGCCTGAGG ATTTTGCAGT GTATTACTGT CAGCAGTATG 250
GTAGGTCACC ATTCACTTTC GGCCCTGGGA CCAAAGTGGA TATCAAGCGA 300
ACTGTGGCTG CACCATCTGT CTTCATCTTC CCGCCATCTG ATGAGCAGTT 350
GAAATCTGGA ACTGCCTCTG TTGTGTGCCT GCTGAATAAC TTCTATCCCA 400
GAGAGGCCAA AGTACAG                                    417
```

(SEQ ID NO:42)

4.14.3 Kappa Chain Protein

```
GTLSLSPGER ATLSCRASQS VSSYLAWYQQ KPGQAPRLLI YGASSRATGI  50
PDRFSGSGSG TDFTLTISRL EPEDFAVYYC QQYGRSPFTF GPGTKVDIKR 100
TVAAPSVFIF PPSDEQLKSG TASVVCLLNN FYPREAKVQ            139
```

(SEQ ID NO:16)

Figure 1D

6.1.1 Heavy Chain DNA

```
ATGGAGTTTG GGCTGAGCTG GGTTTTCCTC GTTGCTCTTT TAAGAGGTGT   50
CCAGTGTCAG GTGCAGCTGG TGGAGTCTGG GGGAGGCGTG GTCGAGCCTG  100
GGAGGTCCCT GAGACTCTCC TGTACAGCGT CTGGATTCAC CTTCAGTAGT  150
TATGGCATGC ACTGGGTCCG CCAGGCTCCA GGCAAGGGGC TGGAGTGGGT  200
GGCAGTTATA TGGTATGATG GAAGCAATAA ACACTATGCA GACTCCGCGA  250
AGGGCCGATT CACCATCTCC AGAGACAATT CCAAGAACAC GCTGTATCTG  300
CAAATGAACA GCCTGAGAGC CGAGGACACG GCTGTGTATT ACTGTGCGAG  350
AGCCGGACTG CTGGGTTACT TTGACTACTG GGGCCAGGGA ACCCTGGTCA  400
CCGTCTCCTC AGCCTCCACC AAGGGCCCAT CGGTCTTCCC CCTGGCGCCC  450
TGCTCCAGGA GCACCTCCGA GAGCACAGCG GCCCTGGGCT GCCTGGTCAA  500
GGACTACTTC CCCGAACCGG TGACGGTGTC GTGGAACTCA GGCGCTCTGA  550
CCAGCGGCGT GCACACCTTC CCAGCTGTCC TACAGTCCTC AGGACTCTAC  600
TCCCTCAGCA GCGTGGTGAC CGTGCCCTCC AGCAACTTCG GCACCCAGAC  650
CTACACCTGC AACGTAGATC ACAAGCCCAG CAACACCAAG GTGGACAAGA  700
CAGTTGAGCG CAAATGTTGT GTCGAGTGCC CACCGTGCCC AGCACCACCT  750
GTGGCAGGAC CGTCAGTCTT CCTCTTCCCC CCAAAACCCA AGGACACCCT  800
CATGATCTCC CGGACCCCTG AGGTCACGTG CGTGGTGGTG GACGTGAGCC  850
ACGAAGACCC CGAGGTCCAG TTCAACTGGT ACGTGGACGG CGTGGAGGTG  900
CATAATGCCA AGACAAAGCC ACGGGAGGAG CAGTTCAACA GCACGTTCCG  950
TGTGGTCAGC GTCCTCACCG TTGTGCACCA GGACTGGCTG AACGGCAAGG 1000
AGTACAAGTG CAAGGTCTCC AACAAAGGCC TCCCAGCCCC CATCGAGAAA 1050
ACCATCTCCA AAACCAAAGG GCAGCCCCGA GAACCACAGG TGTACACCCT 1100
GCCCCCATCC CGGGAGGAGA TGACCAAGAA CCAGGTCAGC CTGACCTGCC 1150
TGGTCAAAGG CTTCTACCCC AGCGACATCG CCGTGGAGTG GGAGAGCAAT 1200
GGGCAGCCGG AGAACAACTA CAAGACCACA CCTCCCATGC TGGACTCCGA 1250
CGGCTCCTTC TTCCTCTACA GCAAGCTCAC CGTGGACAAG AGCAGGTGGC 1300
AGCAGGGGAA CGTCTTCTCA TGCTCCGTGA TGCATGAGGC TCTGCACAAC 1350
CACTACACGC AGAAGAGCCT CTCCCTGTCT CCGGGTAAAT GA          1392
```

(SEQ ID NO:30)

6.1.1 Heavy Chain Protein

```
MEFGLSWVFL VALLRGVQCQ VQLVESGGGV VEPGRSLRLS CTASGFTFSS  50
YGMHWVRQAP GKGLEWVAVI WYDGSNKHYA DSAKGRFTIS RDNSKNTLYL 100
QMNSLRAEDT AVYYCARAGL LGYFDYWGQG TLVTVSSAST KGPSVFPLAP 150
CSRSTSESTA ALGCLVKDYF PEPVTVSWNS GALTSGVHTF PAVLQSSGLY 200
SLSSVVTVPS SNFGTQTYTC NVDHKPSNTK VDKTVERKCC VECPPCPAPP 250
VAGPSVFLFP PKPKDTLMIS RTPEVTCVVV DVSHEDPEVQ FNWYVDGVEV 300
HNAKTKPREE QFNSTFRVVS VLTVVHQDWL NGKEYKCKVS NKGLPAPIEK 350
TISKTKGQPR EPQVYTLPPS REEMTKNQVS LTCLVKGFYP SDIAVEWESN 400
GQPENNYKTT PPMLDSDGSF FLYSKLTVDK SRWQQGNVFS CSVMHEALHN 450
HYTQKSLSLS PGK                                         463
```

(SEQ ID NO:4)

Figure 1D (continued)

6.1.1 Kappa Chain DNA

```
ATGGAAACCC CAGCGCAGCT TCTCTTCCTC CTGCTACTCT GGCTCCCAGA  50
TACCACCGGA GAAATTGTGT TGACGCAGTC TCCAGGCACC CTGTCTTTGT 100
CTCCAGGGGA AAGAGCCACC CTCTCCTGTA GGGCCAGTCA AAGTGTTAGC 150
AGCTACTTAG CCTGGTACCA ACAGAAACCT GGCCAGGCTC CCAGGCCCCT 200
CATCTATGGT GTATCCAGCA GGGCCACTGG CATCCCAGAC AGGTTCAGTG 250
GCAGTGGGTC TGGGACAGAC TTCACTCTCA CCATCAGCAG ACTGGAGCCT 300
GAAGATTTTG CAGTGTATTA CTGTCAGCAG TATGGTATCT CACCATTCAC 350
TTTCGGCCCT GGGACCAAAG TGGATATCAA ACGAACTGTG GCTGCACCAT 400
CTGTCTTCAT CTTCCCGCCA TCTGATGAGC AGTTGAAATC TGGAACTGCC 450
TCTGTTGTGT GCCTGCTGAA TAACTTCTAT CCCAGAGAGG CCAAAGTACA 500
GTGGAAGGTG GATAACGCCC TCCAATCGGG TAACTCCCAG GAGAGTGTCA 550
CAGAGCAGGA CAGCAAGGAC AGCACCTACA GCCTCAGCAG CACCCTGACG 600
CTGAGCAAAG CAGACTACGA GAAACACAAA GTCTACGCCT GCGAAGTCAC 650
CCATCAGGGC CTGAGCTCGC CCGTCACAAA GAGCTTCAAC AGGGGAGAGT 700
GTTAG                                                  705
```

(SEQ ID NO:43)

6.1.1 Kappa Chain Protein

```
METPAQLLFL LLLWLPDTTG EIVLTQSPGT LSLSPGERAT LSCRASQSVS  50
SYLAWYQQKP GQAPRPLIYG VSSRATGIPD RFSGSGSGTD FTLTISRLEP 100
EDFAVYYCQQ YGISPFTFGP GTKVDIKRTV AAPSVFIFPP SDEQLKSGTA 150
SVVCLLNNFY PREAKVQWKV DNALQSGNSQ ESVTEQDSKD STYSLSSTLT 200
LSKADYEKHK VYACEVTHQG LSSPVTKSFN RGEC                 234
```

(SEQ ID NO:17)

Figure 1E

3.1.1 Heavy Chain DNA

```
GGCGTGGTCC AGCCTGGGAG GTCCCTGAGA CTCTCCTGTG CAGCGTCTGG  50
ATTCACCTTC AGTAGCTATG GCATGCACTG GGTCCGCCAG GCTCCAGGCA 100
AGGGGCTGGA GTGGGTGGCA GTTATATGGT ATGATGGAAG TAATAAATAC 150
TATGCAGACT CCGTGAAGGG CCGATTCACC ATCTCCAGAG ACAATTCCAA 200
GAACACGCTG TATCTGCAAA TGAACAGCCT GAGAGCCGAG GACACGGCTG 250
TGTATTACTG TGCGAGAGGG GCCCGTATAA TAACCCCTTG TATGGACGTC 300
TGGGGCCAAG GGACCACGGT CACCGTCTCC TCAGCCTCCA CCAAGGGCCC 350
ATCGGTCTTC CCCCTGGCGC CCTGCTCCAG GAGCACCTCC GAGAGCACAG 400
CGGCCCTGGG CTGCCTGGTC AAGGACTACT TCCCCGAACC GGTGACGGTG 450
TCGTGGAACT CAGGCGCTCT GACCAGCGGC GTGCACACCT TCCCAGCTGT 500
CCTACAG                                                507
```

(SEQ ID NO:31)

3.1.1 Heavy Chain Protein

```
GVVQPGRSLR LSCAASGFTF SSYGMHWVRQ APGKGLEWVA VIWYDGSNKY  50
YADSVKGRFT ISRDNSKNTL YLQMNSLRAE DTAVYYCARG ARIITPCMDV 100
WGQGTTVTVS SASTKGPSVF PLAPCSRSTS ESTAALGCLV KDYFPEPVTV 150
SWNSGALTSG VHTFPAVLQ                                   169
```

(SEQ ID NO:5)

3.1.1 Kappa Chain DNA

```
CAGTCTCCAT CCTCCCTGTC TGCATCTGTA GGAGACAGAG TCACCATCAC  50
TTGCCGGGCA AGTCAGAGCA TTAACACCTA TTTAATTTGG TATCAGCAGA 100
AACCAGGGAA AGCCCCTAAC TTCCTGATCT CTGCTACATC CATTTTGCAA 150
AGTGGGGTCC CATCAAGGTT CCGTGGCAGT GGCTCTGGGA CAAATTTCAC 200
TCTCACCATC AACAGTCTTC ATCCTGAAGA TTTTGCAACT TACTACTGTC 250
AACAGAGTTA CAGTACCCCA TTCACTTTCG GCCCTGGGAC CAAAGTGGAT 300
ATCAAACGAA CTGTGGCTGC ACCATCTGTC TTCATCTTCC CGCCATCTGA 350
TGAGCAGTTG AAATCTGGAA CTGCCTCTGT TGTGTGCCTG CTGAATAACT 400
TCTATCCCAG AGAGGCCAAA GTACAGTGGA AGGTGGATAA CGCCCTCCAA 450
TCGGGTAA                                               458
```

(SEQ ID NO:44)

3.1.1 Kappa Chain Protein

```
QSPSSLSASV GDRVTITCRA SQSINTYLIW YQQKPGKAPN FLISATSILQ  50
SGVPSRFRGS GSGTNFTLTI NSLHPEDFAT YYCQQSYSTP FTFGPGTKVD 100
IKRTVAAPSV FIFPPSDEQL KSGTASVVCL LNNFYPREAK VQWKVDNALQ 150
SG                                                     152
```

(SEQ ID NO:18)

Figure 1F

4.10.2 Heavy Chain DNA

```
GGCGTGGTCC AGCCTGGGAG GTCCCTGAGA CTCTCCTGTG TAGCGTCTGG  50
ATTCATCTTC AGTAGTCATG GCATCCACTG GGTCCGCCAG GCTCCAGGCA 100
AGGGGCTGGA GTGGGTGGCA GTTATATGGT ATGATGGAAG AAATAAAGAC 150
TATGCAGACT CCGTGAAGGG CCGATTCACC ATCTCCAGAG ACAATTCCAA 200
GAACACGCTG TATTTGCAAA TGAACAGCCT GAGAGCCGAG GACACGGCTG 250
TGTATTACTG TGCGAGAGTG GCCCCACTGG GGCCACTTGA CTACTGGGGC 300
CAGGGAACCC TGGTCACCGT CTCCTCAGCC TCCACCAAGG GCCCATCGGT 350
CTTCCCCCTG GCGCCCTGCT CCAGGAGCAC CTCCGAGAGC ACAGCGGCCC 400
TGGGCTGCCT GGTCAAGGAC TACTTCCCCG AACCGGTGAC GGTGTCGTGG 450
AACTCAGGCG CTCTGACCAG CGGCGTGCAC ACCTTCCCAG CTGTCCTACA 500
G                                                     501
```

(SEQ ID NO:32)

4.10.2 Heavy Chain Protein

```
GVVQPGRSLR LSCVASGFIF SSHGIHWVRQ APGKGLEWVA VIWYDGRNKD  50
YADSVKGRFT ISRDNSKNTL YLQMNSLRAE DTAVYYCARV APLGPLDYWG 100
QGTLVTVSSA STKGPSVFPL APCSRSTSES TAALGCLVKD YFPEPVTVSW 150
NSGALTSGVH TFPAVLQ                                    167
```

(SEQ ID NO:6)

4.10.2 Kappa Chain DNA

```
TCTCCAGGCA CCCTGTCTTT GTCTCCAGGG GAAAGAGCCA CCCTCTCCTG  50
CAGGGCCAGT CAGAGTATTA GCAGCAATTT CTTAGCCTGG TACCAGCAGA 100
AACCTGGCCA GGCTCCCAGG CTCCTCATCT ATCGTCCATC CAGCAGGGCC 150
ACTGGCATCC CAGACAGTTT CAGTGGCAGT GGGTCTGGGA CAGACTTCAC 200
TCTCACCATC AGCAGACTGG AGCCTGAGGA TTTTGCATTA TATTACTGTC 250
AGCAGTATGG TACGTCACCA TTCACTTTCG GCCCTGGGAC CAAAGTGGAT 300
ATCAAGCGAA CTGTGGCTGC ACCATCTGTC TTCATCTTCC CGCCATCTGA 350
TGAGCAGTTG AAATCTGGAA CTGCCTCTGT TGTGTGCCTG CTGAATAACT 400
TCTATCCCAG AGAGGCCAAA GTACAG                          426
```

(SEQ ID NO:45)

4.10.2 Kappa Chain Protein

```
SPGTLSLSPG ERATLSCRAS QSISSNFLAW YQQKPGQAPR LLIYRPSSRA  50
TGIPDSFSGS GSTDFTLTI SRLEPEDFAL YYCQQYGTSP FTFGPGTKVD 100
IKRTVAAPSV FIFPPSDEQL KSGTASVVCL LNNFYPREAK VQ        142
```

(SEQ ID NO:19)

Figure 1G

2.1.3 Heavy Chain DNA

```
TCGGGCCCAG GACTGGTGAA GCCTTCACAG ATCCTGTCCC TCACCTGCAC  50
TGTCTCTGGT GGCTCCATCA GCAGTGGTGG TCACTACTGG AGCTGGATCC 100
GCCAGCACCC AGGGAAGGGC CTGGAGTGGA TTGGGTACAT CTATTACATT 150
GGGAACACCT ACTACAACCC GTCCCTCAAG AGTCGAGTTA CCATATCAGT 200
AGACACGTCT AAGAACCAGT TCTCCCTGAA GCTGAGCTCT GTGACTGCCG 250
CGGACACGGC CGTGTATTAT TGTGCGAGAG ATAGTGGGGA CTACTACGGT 300
ATAGACGTCT GGGGCCAAGG GACCACGGTC ACCGTCTCCT CAGCTTCCAC 350
CAAGGGCCCA TCCGTCTTCC CCCTGGCGCC CTGCTCCAGG AGCACCTCCG 400
AGAGCACAGC CGCCCTGGGC TGCCTGGTCA AGGACTACTT CCCCGAACCG 450
GTGACGGTGT CGTGGAACTC AGGCGCCCTG ACCAGCGGCG TGCACACCTT 500
CCCGGCTGTC CTACAA                                      516
```

(SEQ ID NO:33)

2.1.3 Heavy Chain Protein

```
SGPGLVKPSQ ILSLTCTVSG GSISSGGHYW SWIRQHPGKG LEWIGYIYYI  50
GNTYYNPSLK SRVTISVDTS KNQFSLKLSS VTAADTAVYY CARDSGDYYG 100
IDVWGQGTTV TVSSASTKGP SVFPLAPCSR STSESTAALG CLVKDYFPEP 150
VTVSWNSGAL TSGVHTFPAV LQ                               172
```

(SEQ ID NO:7)

2.1.3 Kappa Chain DNA

```
TCTCCAGACT TCAGTCTGT GACTCCAAAG GAGAAAGTCA CCATCACCTG  50
CCGGGCCAGT CAGAGCATTG GTAGTAGCTT ACATTGGTAT CAGCAGAAAC 100
CAGATCAGTC TCCAAAGCTC CTCATCAAGT ATGCTTCCCA GTCCTTCTCT 150
GGGGTCCCCT CGAGGTTCAG TGGCAGTGGA TCTGGGACAG ATTTCACCCT 200
CACCATCAAT AGCCTGGAAG CTGAAGATGC TGCAACGTAT TACTGTCATC 250
AGAGTAGTAG TTTACCGCTC ACTTTCGGCG GAGGGACCAA GGTGGAGATC 300
AAACGAACTG TGGCTGCACC ATCTGTCTTC ATCTTCCCGC CATCTGATGA 350
GCAGTTGAAA TCTGGAACTG CCTCTGTTGT GTGCCTGCTG AATAACTTCT 400
ATCCCAGAGA GGCCAAAGTA CAGTGGAAGG TGGATAACGC CCTCCAATCG 450
GGTAACTCCC AGGAG                                       465
```

(SEQ ID NO:46)

2.1.3 Kappa Chain Protein

```
SPDFQSVTPK EKVTITCRAS QSIGSSLHWY QQKPDQSPKL LIKYASQSFS  50
GVPSRFSGSG SGTDFTLTIN SLEAEDAATY YCHQSSSLPL TFGGGTKVEI 100
KRTVAAPSVF IFPPSDEQLK SGTASVVCLL NNFYPREAKV QWKVDNALQS 150
GNSQE                                                  155
```

(SEQ ID NO:20)

Figure 1H

4.13.1 Heavy Chain DNA

```
CCTGGGAGGT CCCTGAGACT CTCCTGTGCA GCGTCTGGAT TCACCTTCAG  50
TAGTCATGGC ATCCACTGGG TCCGCCAGGC TCCAGGCAAG GGGCTGGAGT 100
GGGTGGCAGT TATATGGTAT GATGGAAGAA ATAAAGACTA TGCAGACTCC 150
GTGAAGGGCC GATTCACCAT CTCCAGAGAC AATTCCAAGA ACACGCTGTA 200
TTTGCAAATG AACAGCCTGA GAGCCGAGGA CACGGCTGTG TATTACTGTG 250
CGAGAGTGGC CCCACTGGGG CCACTTGACT ACTGGGGCCA GGGAACCCTG 300
GTCACCGTCT CCTCAGCCTC CACCAAGGGC CCATCGGTCT TCCCCCTGGC 350
GCCCTGCTCC AGGAGCACCT CCGAGAGCAC AGCGGCCCTG GGCTGCCTGG 400
TCAAGGACTA CTTCCCCGAA CCGGTGACGG TGTCGTGGAA CTCAGGCGCT 450
CTGACCAGC                                              459
```

(SEQ ID NO:34)

4.13.1 Heavy Chain Protein

```
PGRSLRLSCA ASGFTFSSHG IHWVRQAPGK GLEWVAVIWY DGRNKDYADS  50
VKGRFTISRD NSKNTLYLQM NSLRAEDTAV YYCARVAPLG PLDYWGQGTL 100
VTVSSASTKG PSVFPLAPCS RSTSESTAAL GCLVKDYFPE PVTVSWNSGA 150
LTS                                                    153
```

(SEQ ID NO:8)

4.13.1 Kappa Chain DNA

```
CAGTCTCCAG GCACCCTGTC TTTGTCTCCA GGGGAAAGAG CCACCCTCTC  50
CTGCAGGGCC AGTCAGAGTG TCAGCAGCTA CTTAGCCTGG TACCAGCAGA 100
AACCTGGCCA GGCTCCCAGG CTCCTCATCT ATGGTGCATC CAGCAGGGCC 150
ACTGGCATCC CAGACAGGTT CAGTGGCAGT GGGTCTGGGA CAGACTTCAC 200
TCTCACCATC AGCAGACTGG AGCCTGAGGA TTTTGCAGTG TATTACTGTC 250
AACAGTATGG TAGGTCACCA TTCACTTTCG GCCCTGGGAC CAAAGTAGAT 300
ATCAAGCGAA CTGTGGCTGC ACCATCTGTC TTCATCTTCC CGCCATCTGA 350
TGAGCAGTTG AAATCTGGAA CTGCCTCTGT TGTGTGCCTG CTGAATAACT 400
TCTATCCCAG AGAGGCCAAA GTACAGTGGA AGGTGGATA            440
```

(SEQ ID NO:47)

4.13.1 Kappa Chain Protein

```
QSPGTLSLSP GERATLSCRA SQSVSSYLAW YQQKPGQAPR LLIYGASSRA  50
TGIPDRFSGS GSGTDFTLTI SRLEPEDFAV YYCQQYGRSP FTFGPGTKVD 100
IKRTVAAPSV FIFPPSDEQL KSGTASVVCL LNNFYPREAK VQWKGG     146
```

(SEQ ID NO:21)

Figure 1I

11.2.1 Heavy Chain DNA

| | | | | | |
|---|---|---|---|---|---|
| GGCGTGGTCC | AGCCTGGGAG | GTCCCTGAGA | CTCTCCTGTG | CAGCGTCTGG | 50 |
| ATTCACCTTC | AGTAGCTATG | GCATGCACTG | GGTCCGCCAG | GCTCCAGGCA | 100 |
| AGGGGCTGGA | GTGGGTGGCA | GTTATATGGT | ATGATGGAAG | TAATAAATAC | 150 |
| TATGCAGACT | CCGTGAAGGG | CCGATTCACC | ATCTCCAGAG | ACAATTCCAA | 200 |
| GAACACGCTG | TATCTGCAAA | TGAACAGCCT | GAGAGCCGAG | GACACGGCTG | 250 |
| TGTATTACTG | TGCGAGAGAT | CCGAGGGGAG | CTACCCTTTA | CTACTACTAC | 300 |
| TACCGGTKGG | ACGTCTGGGG | CCAAGGGACC | ACGGTCACCG | TCTCCTCAGC | 350 |
| CTCCACCAAG | GGCCCATCGG | TCTTCCCCCT | GGCGCCCTGC | TCCAGGAGCA | 400 |
| CCTCCGAGAG | CACAGCGGCC | CTGGGCTGCC | TGGTCAAGGA | CTACTTCCCC | 450 |
| GAACCGGTGA | CGGTGTCGTG | GAACTCAGGC | GCTCTGACCA | GCGGCGTGCA | 500 |
| CAC | | | | | 503 |

(SEQ ID NO:35)

11.2.1 Heavy Chain Protein

| | | | | |
|---|---|---|---|---|
| GVVQPGRSLR | LSCAASGFTF | SSYGMHWVRQ | APGKGLEWVA | VIWYDGSNKY | 50 |
| YADSVKGRFT | ISRDNSKNTL | YLQMNSLRAE | DTAVYYCARD | PRGATLYYYY | 100 |
| YRXDVWGQGT | TVTVSSASTK | GPSVFPLAPC | SRSTSESTAA | LGCLVKDYFP | 150 |
| EPVTVSWNSG | ALTSGVH | | | | 167 |

(SEQ ID NO:9)

11.2.1 Kappa Chain DNA

| | | | | | |
|---|---|---|---|---|---|
| CCATCCTCCC | TGTCTGCATC | TGTAGGAGAC | AGAGTCACCA | TCACTTGCCG | 50 |
| GGCAAGTCAG | AGCATTAACA | GCTATTTAGA | TTGGTATCAG | CAGAAACCAG | 100 |
| GGAAAGCCCC | TAAACTCCTG | ATCTATGCTG | CATCCAGTTT | GCAAAGTGGG | 150 |
| GTCCCATCAA | GGTTCAGTGG | CAGTGGATCT | GGGACAGATT | TCACTCTCAC | 200 |
| CATCAGCAGT | CTGCAACCTG | AAGATTTTGC | AACTTACTAC | TGTCAACAGT | 250 |
| ATTACAGTAC | TCCATTCACT | TTCGGCCCTG | GGACCAAAGT | GGAAATCAAA | 300 |
| CGAACTGTGG | CTGCACCATC | TGTCTTCATC | TTCCCGCCAT | CTGATGAGCA | 350 |
| GTTGAAATCT | GGAACTGCCT | CTGTTGTGTG | CCTGCTGAAT | AACTTCTATC | 400 |
| CCAGAGAGGC | CAAAGTA | | | | 417 |

(SEQ ID NO:48)

11.2.1 Kappa Chain Protein

| | | | | |
|---|---|---|---|---|
| PSSLSASVGD | RVTITCRASQ | SINSYLDWYQ | QKPGKAPKLL | IYAASSLQSG | 50 |
| VPSRFSGSGS | GTDFTLTISS | LQPEDFATYY | CQQYYSTPFT | FGPGTKVEIK | 100 |
| RTVAAPSVFI | FPPSDEQLKS | GTASVVCLLN | NFYPREAKV | | 139 |

(SEQ ID NO:22)

Figure 1J

11.6.1 Heavy Chain DNA

```
GGCGTGGTCC AGCCTGGGAG GTCCCTGAGA CTCTCCTGTG CAGCGTCTGG  50
ATTCACCTTC AGTAGCTATG GCATGCACTG GGTCCGCCAG GCTCCAGGCA 100
AGGGGCTGGA GTGGGTGGCA GTTATATGGT ATGATGGAAG TCATAAATAC 150
TATGCAGACT CCGTGAAGGG CCGATTCACC ATCTCCAGAG ACAATTCCAA 200
GAACACGCTG TATCTGCAAA TGAACAGCCT GAGAGCCGAG GACACGGCTG 250
TGTATTACTG TGCGAGAGGC GCTGTAGTAG TACCAGCTGC TATGGACGTC 300
TGGGGCCAAG GGACCACGGT CACCGTCTCC TCAGCCTCCA CCAAGGGCCC 350
ATCGGTCTTC CCCCTGGCGC CCTGCTCCAG GAGCACCTCC GAGAGCACAG 400
CGGCCCTGGG CTGCCTGGTC AAGGACTACT TCCCCGAACC GGTGACGGTG 450
T                                                    451
```

(SEQ ID NO:36)

11.6.1 Heavy Chain Protein

```
GVVQPGRSLR LSCAASGFTF SSYGMHWVRQ APGKGLEWVA VIWYDGSHKY  50
YADSVKGRFT ISRDNSKNTL YLQMNSLRAE DTAVYYCARG AVVVPAAMDV 100
WGQGTTVTVS SASTKGPSVF PLAPCSRSTS ESTAALGCLV KDYFPEPVTV 150
S                                                    151
```

(SEQ ID NO:10)

11.6.1 Kappa Chain DNA

```
ACCCAGTCTC CATCCTCCCT GTCTGCATCT GTAGGAGACA GAGTCACCAT  50
CACTTGCCGG GCAAGTCAGA ACATTAGCAG GTATTTAAAT TGGTATCAAC 100
AGAAACCAGG GAAAGCCCCT AAGTTCCTGA TCTATGTTGC ATCTATTTTG 150
CAAAGTGGGG TCCCATCAGG GTTCAGTGCC AGTGGATCTG GGCCAGATTT 200
CACTCTNACC ATCAGCAGTC TGCAACCTGA AGATTTTGCA ACTTACTACT 250
GTCAACAGAG TTACAGTACC CCATTCACTT TCGGCCCTGG GACCAAAGTG 300
GATATCAAAC GAACTGTGGC TGCACCATCT GTCTTCATCT TCCCGCCATC 350
TGATGAGCAG TTGAAATCTG GAACTGCCTC TGTTGTGTGC CTGCTGAATA 400
AC                                                   402
```

(SEQ ID NO:49)

11.6.1 Kappa Chain Protein

```
TQSPSSLSAS VGDRVTITCR ASQNISRYLN WYQQKPGKAP KFLIYVASIL  50
QSGVPSGFSA SGSGPDFTLT ISSLQPEDFA TYYCQQSYST PFTFGPGTKV 100
DIKRTVAAPS VFIFPPSDEQ LKSGTASVVC LLNN                134
```

(SEQ ID NO:23)

Figure 1K 11.7.1 Heavy Chain DNA

```
GTGGTCCAGC CTGGGAGGTC CCTGAGACTC TCCTGTGCAG CGTCTGGATT  50
CACCTTCAGT AGCNGTGGCA TGCACTGGGT CCGCCAGGCT CCAGGCAAGG 100
GGCTGGAGTG GGTGGCAGTT ATATGGTCTG ATGAAGTCA TAAATACTAT 150
GCAGACTCCG TGAAGGGCCG ATTCACCATC TCCAGAGACA ATTCCAAGAA 200
CACGCTGTAT CTGCAAATGA ACAGCCTGAG AGCCGAGGAC ACGGCTGTGT 250
ATTACTGTGC GAGAGGAACT ATGATAGTAG TGGGTACCCT TGACTACTGG 300
GGCCAGGGAA CCCTGGTCAC CGTCTCCTCA GCCTCCACCA AGGGCCCATC 350
GGTCTTCCCC CTGGCGCCCT GCTCCAGGAG CACCTCCGAG AGCACAGCGG 400
CCCTGGGCTG CCTGGTCAAG GACTACTTCC CCGAACCG            438
```

(SEQ ID NO:37)

11.7.1 Heavy Chain Protein

```
VVQPGRSLRL SCAASGFTFS SXGMHWVRQA PGKGLEWVAV IWSDGSHKYY  50
ADSVKGRFTI SRDNSKNTLY LQMNSLRAED TAVYYCARGT MIVVGTLDYW 100
GQGTLVTVSS ASTKGPSVFP LAPCSRSTSE STAALGCLVK DYFPEP     146
```

(SEQ ID NO:11)

11.7.1 Kappa Chain DNA

```
ACCCAGTCTC CATCCTCCCT GTCTGCATCT GTAGGAGACA GAGTCACCAT  50
CACTTGCCGG GCAAGTCAGA GCATTTGCAA CTATTTAAAT TGGTATCAGC 100
AGAAACCAGG AAAAGCCCCT AGGGTCCTGA TCTATGCTGC ATCCAGTTTG 150
CAAGGTGGGG TCCCGTCAAG GTTCAGTGGC AGTGGATCTG GGACAGATTG 200
CACTCTCACC ATCAGCAGTC TGCAACCTGA AGATTTTGCA ACTTACTACT 250
GTCAACAGAG TTACACTACC CCATTCACTT TCGGCCCTGG GACCAGAGTG 300
GATATCGAAC GAACTGTGGC TGCACCATCT GTCTTCATCT TCCCGCCATC 350
TGATGAGCAG TTGAAATCTG GAACTGCCTC TGTTGTGTGC CTGCTGAATA 400
ACTTCTATCC CAGAGAGGCC AAAGTACAGT GGAAGGTGGA TAACGCCTAT 450
T                                                    451
```

(SEQ ID NO:50)

11.7.1 Kappa Chain Protein

```
TQSPSSLSAS VGDRVTITCR ASQSICNYLN WYQQKPGKAP RVLIYAASSL  50
QGGVPSRFSG SGSGIDCTLT ISSLQPEDFA TYYCQQSYIT PFTFGPGTRV 100
DIERTVAAPS VFIFPPSDEQ LKSGTASVVC LLNNFYPREA KVQWKVDNAY 150
```

(SEQ ID NO:24)

Figure 1L

12.3.1.1 Heavy Chain DNA

| | | | | | |
|---|---|---|---|---|---|
| TCCTGTGCAG | CGTCTGGATT | CACCTTCAGT | TACTATGGCG | TCTGGGGGAG | 50 |
| GCGTGGTCCA | GCCTGGGAGG | TCCCTGAGAC | TCTCCTGTGC | AGCGTCTGGA | 100 |
| TTCACCTTCA | GTAGCTATGG | CGTGCACTGG | GTCCGCCAGG | CTCCAGGCAA | 150 |
| GGGGCTGGAG | TGGGTGGCAG | TTATATGGTA | TGATGGAAGT | AATAAATACT | 200 |
| ATGCAGACTC | CGTGAAGGGC | CGATTCACCA | TCTCCAGAGA | CAATTCCAAG | 250 |
| AGCACGCTGT | ATCTGCAAAT | GAACAGCCTG | AGAGCCGAGG | ACACGGCTGT | 300 |
| GTATTATTGT | GCGAGAGACT | CGTATTACGA | TTTTTGGAGT | GGTCGGGGCG | 350 |
| GTATGGACGT | CTGGGGCCAA | GGGACCACGG | TCACCGTCTC | CTCAGCCTCC | 400 |
| ACCAAGGGCC | CATCGGTCTT | CCCCCTGGCG | CCCTGCTCCA | GGAGCACCTC | 450 |
| CGAGAGCACA | GCGGCCCTGG | GCTGCCTGGT | CAAGGACTAC | TTCCCCGAAC | 500 |
| CGGTGACGGT | GTCGTGGAAC | TCAGGCGCTC | TGACCAGCGG | CGTGCACACC | 550 |
| TTCCCAGCTG | TC | | | | 562 |

(SEQ ID NO:38)

12.3.1.1 Heavy Chain Protein

| | | | | | |
|---|---|---|---|---|---|
| SGGGVVQPGR | SLRLSCAASG | FTFSSYGVHW | VRQAPGKGLE | WVAVIWYDGS | 50 |
| NKYYADSVKG | RFTISRDNSK | STLYLQMNSL | RAEDTAVYYC | ARDSYYDFWS | 100 |
| GRGGMDVWGQ | GTTVTVSSAS | TKGPSVFPLA | PCSRSTSEST | AALGCLVKDY | 150 |
| FPEPVTVSWN | SGALTSGVHT | FPAV | | | 174 |

(SEQ ID NO:12)

12.3.1.1 Kappa Chain DNA

| | | | | | |
|---|---|---|---|---|---|
| CCACTCTCCC | TGCCCGTCAC | CCTTGGACAG | CCGGCCTCCA | TCTCCTGCAG | 50 |
| GTCTAGTCAA | AGCCTCGTAT | ACAGTGATGG | AAACACCTAC | TTGAATTGGT | 100 |
| TTCAGCAGAG | GCCAGGCCAA | TCTCCAAGGC | GCCTAATTTA | TAAGGTTTCT | 150 |
| AACTGGGACT | CTGGGGTCCC | AGACAGATTC | AGCGGCAGTG | GGTCAGGCAC | 200 |
| TGATTTCACA | CTGAAAATCA | GCAGGGTGGA | GGCTGAGGAT | GTTGGGGTTT | 250 |
| ATTACTGCAT | GCAAGGTTCA | CACTGGCCTC | CGACGTTCGG | CCAAGGGACC | 300 |
| AAGGTGGAAA | TCAAACGAAC | TGTGGCTGCA | CCATCTGTCT | TCATCTTCCC | 350 |
| GCCATCTGAT | GAGCAGTTGA | AATCTGGAAC | TGCCTCTGTT | GTGTGCCTGC | 400 |
| TGAATAACTT | CTATCCCAC | | | | 419 |

(SEQ ID NO:51)

12.3.1.1 Kappa Chain Protein

| | | | | | |
|---|---|---|---|---|---|
| PLSLPVTLGQ | PASISCRSSQ | SLVYSDGNTY | LNWFQQRPGQ | SPRRLIYKVS | 50 |
| NWDSGVPDRF | SGSGSGTDFT | LKISRVEAED | VGVYYCMQGS | HWPPTFGQGT | 100 |
| KVEIKRTVAA | PSVFIFPPSD | EQLKSGTASV | VCLLNNFYP | | 139 |

(SEQ ID NO:25)

Figure 1M 12.9.1.1 Heavy Chain DNA

```
GTCCAGCCTG GGAGGTCCCT GAGACTCTCC TGTGCAGCGT CTGGATTCAC  50
CTTCAGTAAC TATGCCATGC ACTGGGTCCG CCAGGCTCCA GGCAAGGGGC 100
TGGAGTGGGT GGTAGTTATT TGGCATGATG GAAATAATAA ATACTATGCA 150
GAGTCCGTGA AGGGCCGATT CACCATCTCC AGAGACAATT CCAAGAACAC 200
GCTGTATCTG CAAATGAACA GCCTGAGAGC CGAGGACACG GCTGTATATT 250
ACTGTGCGAG AGATCAGGGC ACTGGCTGGT ACGGAGGCTT TGACTTCTGG 300
GGCCAGGGAA CCCTGGTCAC CGTCTCCTCA GCCTCCACCA AGGGCCCATC 350
GGTCTTCCCC CTGGCGCCCT GCTCCAGGAG CACCTCCGAG AGCACAGCGG 400
CCCTGGGCTG CCTGGTCAAG GACTACTTCC CCGAACCGGT GACGGTGTCG 450
TGGAACTCAG GCGCTCTGAC CAGCGGCGTG CACACCTTCC           490
```

(SEQ ID NO:39)

12.9.1.1 Heavy Chain Protein

```
VQPGRSLRLS CAASGFTFSN YAMHWVRQAP GKGLEWVVVI WHDGNNKYYA  50
ESVKGRFTIS RDNSKNTLYL QMNSLRAEDT AVYYCARDQG TGWYGGFDFW 100
GQGTLVTVSS ASTKGPSVFP LAPCSRSTSE STAALGCLVK DYFPEPVTVS 150
WNSGALTSGV HTF                                        163
```

(SEQ ID NO:13)

12.9.1.1 Kappa Chain DNA

```
CCTGGAGAGC CGGCTTCCAT CTCTTGCAGG TCTAGTCAGA GCCTCCTGCA  50
TAGTAATGGA TACAACTATT TGGATTGGTA CCTGCAGAAG CCAGGACAGT 100
CTCCACAGCT CCTGATCTAT TTGGGTTCTA ATCGGGCCTC CGGGGTCCCT 150
GACAGGTTCA GTGGCAGTGG ATCAGGCACA GATTTTACAC TGAAACTCAG 200
CAGAGTGGAG GCTGAGGATG TTGGGGTTTA TTACTGCATG CAAGCTCTAC 250
AAACTCCTCT CACTTTCGGC GGAGGGACCA AGGTGGAGAT CAAACGAACT 300
GTGGCTGCAC CATCTGTCTT CATCTTCCCG CCATCTGATG AGCAGTTGAA 350
ATCTGGAACT GCCTCTGTTG TGTGCCTGCT GAATAACTTC TATCCCAGAR 400
AGGCCAAAGT ACATTCCAT                                  419
```

(SEQ ID NO:52)

12.9.1.1 Kappa Chain Protein

```
PGEPASISCR SSQSLLHSNG YNYLDWYLQK PGQSPQLLIY LGSNRASGVP  50
DRFSGSGSGT DFTLKLSRVE AEDVGVYYCM QALQTPLTFG GGTKVEIKRT 100
VAAPSVFIFP PSDEQLKSGT ASVVCLLNNF YPR                  133
```

(SEQ ID NO:26)

*Figure 2A*

| CDR | DP50 | 3.1.1 | 4.1.1 | 4.8.1 | 4.10.2 | 4.13.1 | 4.14.3 | 6.1.1 | 11.2.1 | 11.6.1 | 11.7.1 | 12.3.1.1 | 12.9.1.1 |
|---|---|---|---|---|---|---|---|---|---|---|---|---|---|
|  |  |  |  |  |  |  |  | G |  |  |  |  |  |
|  | G | G | G | G | G |  |  | G | G | G |  | G |  |
|  | V | V | V | V | V |  |  | V | V | V | V | V |  |
|  | V | V | V | V | V |  |  | V | V | V | V | V | V |
|  | Q | Q | Q | Q | Q |  |  | E | Q | Q | Q | Q | Q |
|  | P | P | P | P | P | P | P | P | P | P | P | P | P |
|  | G | G | G | G | G | G | G | G | G | G | G | G | G |
|  | R | R | R | R | R | R | R | R | R | R | R | R | R |
|  | S | S | S | S | S | S | S | S | S | S | S | S | S |
|  | L | L | L | L | L | L | L | L | L | L | L | L | L |
|  | R | R | R | R | R | R | R | R | R | R | R | R | R |
|  | L | L | L | L | L | L | L | L | L | L | L | L | L |
|  | S | S | S | S | S | S | S | S | S | S | S | S | S |
|  | C | C | C | C | C | C | C | C | C | C | C | C | C |
|  | A | A | V | T | V | A | A | T | A | A | A | A | A |
|  | A | A | A | A | A | A | A | A | A | A | A | A | A |
|  | S | S | S | S | S | S | S | S | S | S | S | S | S |
|  | G | G | G | G | G | G | G | G | G | G | G | G | G |
|  | F | F | F | F | F | F | F | F | F | F | F | F | F |
|  | T | T | T | T | I | T | T | T | T | T | T | T | T |
|  | F | F | F | F | F | F | F | F | F | F | F | F | F |
| CDR1 | S | S | S | S | S | S | S | S | S | S | S | S | S |
|  | S | S | S | N | S | S | S | S | S | S | S | S | N |
|  | Y | Y | H | Y | H | H | H | Y | Y | Y | C | Y | Y |
|  | G | G | G | G | G | G | G | G | G | G | G | G | A |
|  | M | M | M | M | I | I | I | M | M | M | M | V | M |
|  | H | H | H | H | H | H | H | H | H | H | H | H | H |
|  | W | W | W | W | W | W | W | W | W | W | W | W | W |
|  | V | V | V | V | V | V | V | V | V | V | V | V | V |
|  | R | R | R | R | R | R | R | R | R | R | R | R | R |
|  | Q | Q | Q | Q | Q | Q | Q | Q | Q | Q | Q | Q | Q |
|  | A | A | A | A | A | A | A | A | A | A | A | A | A |
|  | P | P | P | P | P | P | P | P | P | P | P | P | P |
|  | G | G | G | G | G | G | G | G | G | G | G | G | G |
|  | K | K | K | K | K | K | K | K | K | K | K | K | K |
|  | G | G | G | G | G | G | G | G | G | G | G | G | G |
|  | L | L | L | L | L | L | L | L | L | L | L | L | L |
|  | E | E | E | E | E | E | E | E | E | E | E | E | E |
|  | W | W | W | W | W | W | W | W | W | W | W | W | W |
|  | V | V | V | V | V | V | V | V | V | V | V | V | V |
|  | A | A | A | A | A | A | A | A | A | A | A | A | V |
|  | V | V | V | V | V | V | V | V | V | V | V | V | V |
|  | I | I | I | I | I | I | I | I | I | I | I | I | I |
|  | W | W | W | W | W | W | W | W | W | W | W | W | W |
|  | Y | Y | Y | Y | Y | Y | Y | Y | Y | Y | S | Y | H |
|  | D | D | D | D | D | D | D | D | D | D | D | D | D |
|  | G | G | G | G | G | G | G | G | G | G | G | G | G |
| CDR2 | S | S | R | S | R | R | R | S | S | S | S | S | N |

*Figure 2B*

| CDR | DP50 | 3.1.1 | 4.1.1 | 4.8.1 | 4.10.2 | 4.13.1 | 4.14.3 | 6.1.1 | 11.2.1 | 11.6.1 | 11.7.1 | 12.3.1.1 | 12.9.1.1 |
|---|---|---|---|---|---|---|---|---|---|---|---|---|---|
| | N | N | N | N | N | N | N | N | N | H | H | N | N |
| | K | K | K | K | K | K | K | K | K | K | K | K | K |
| | Y | Y | Y | H | D | D | D | H | Y | Y | Y | Y | Y |
| | Y | Y | Y | Y | Y | Y | Y | Y | Y | Y | Y | Y | Y |
| | A | A | A | G | A | A | A | A | A | A | A | A | A |
| | D | D | D | D | D | D | D | D | D | D | D | D | E |
| | S | S | S | S | S | S | S | S | S | S | S | S | S |
| | V | V | V | V | V | V | V | A | V | V | V | V | V |
| | | K | K | K | K | K | K | K | K | K | K | K | K |
| | | G | G | G | G | G | G | G | G | G | G | G | G |
| | | R | R | R | R | R | R | R | R | R | R | R | R |
| | | F | F | F | F | F | F | F | F | F | F | F | F |
| | | T | T | T | T | T | T | T | T | T | T | T | T |
| | | I | I | I | I | I | I | I | I | I | I | I | I |
| | | S | S | S | S | S | S | S | S | S | S | S | S |
| | | R | R | S | R | R | R | R | R | R | R | R | R |
| | | D | D | D | D | D | D | D | D | D | D | D | D |
| | | N | N | N | N | N | N | N | N | N | N | N | N |
| | | S | S | S | S | S | S | S | S | S | S | S | S |
| | | K | K | K | K | K | K | K | K | K | K | K | K |
| | | N | N | N | N | N | N | K | N | N | N | N | S | N |
| | | T | T | T | T | T | T | T | T | T | T | T | T |
| | | L | L | L | L | L | L | L | L | L | L | L | L |
| | | Y | Y | F | Y | Y | Y | Y | Y | Y | Y | Y | Y |
| | | L | L | L | L | L | L | L | L | L | L | L | L |
| | | Q | Q | Q | Q | Q | Q | Q | Q | Q | Q | Q | Q |
| | | M | M | M | M | M | M | M | M | M | M | M | M |
| | | N | N | N | N | N | N | N | N | N | N | N | N |
| | | S | S | S | S | S | S | S | S | S | S | S | S |
| | | L | L | L | L | L | L | L | L | L | L | L | L |
| | | R | R | R | R | R | R | R | R | R | R | R | R |
| | | A | A | A | A | A | A | A | A | A | A | A | A |
| | | E | E | E | E | E | E | E | E | E | E | E | E |
| | | D | D | D | D | D | D | D | D | D | D | D | D |
| | | T | T | T | T | T | T | T | T | T | T | T | T |
| | | A | A | A | A | A | A | A | A | A | A | A | A |
| | | V | V | V | V | V | V | V | V | V | V | V | V |
| | | Y | Y | Y | Y | Y | Y | Y | Y | Y | Y | Y | Y |
| | | Y | Y | Y | Y | Y | Y | Y | Y | Y | Y | Y | Y |
| | | C | C | C | C | C | C | C | C | C | C | C | C |
| | | A | A | A | A | A | A | A | A | A | A | A | A |
| | | R | R | R | R | R | R | R | R | R | R | R | R |
| | | G | G | G | V | V | V | A | D | G | G | D | D |
| | | A | G | G | E | A | A | A | G | P | A | T | S | Q |
| | | R | H | R | P | P | P | L | R | V | M | Y | G |
| | | I | F | L | L | L | L | L | G | V | I | Y | T |
| CDR3 | | I | G | G | G | G | G | A | V | V | V | D | G |

*Figure 2C*

| CDR | DP50 | 3.1.1 | 4.1.1 | 4.8.1 | 4.10.2 | 4.13.1 | 4.14.3 | 6.1.1 | 11.2.1 | 11.6.1 | 11.7.1 | 12.3.1.1 | 12.9.1.1 |
|---|---|---|---|---|---|---|---|---|---|---|---|---|---|
| | | T | P | S | P | P | P | Y | T | P | V | F | W |
| | | P | E | Y | L | L | L | F | L | A | G | W | Y |
| | | C | D | F | D | D | D | D | Y | A | T | S | G |
| | | M | Y | D | Y | Y | Y | Y | Y | M | L | G | G |
| | | D | W | Y | W | W | W | W | Y | D | D | R | F |
| | | V | G | W | G | G | G | G | Y | V | Y | G | D |
| | | W | Q | G | Q | Q | Q | Q | Y | W | W | G | F |
| | | G | G | Q | G | G | G | G | G | G | G | M | W |
| | | Q | T | G | T | T | T | T | M | Q | Q | D | G |
| | | G | L | T | L | L | L | L | D | G | G | V | Q |
| | | T | V | L | V | V | V | V | V | T | T | W | G |
| | | T | T | V | T | T | T | T | W | T | L | G | T |
| | | V | V | T | V | V | V | V | G | V | V | Q | L |
| | | T | S | V | S | S | S | S | Q | T | T | G | V |
| | | V | S | S | S | S | S | S | G | V | V | T | T |
| | | S | A | S | A | A | A | A | T | S | S | T | V |
| | | S | S | A | S | S | S | S | T | S | S | V | S |
| | | A | T | S | T | T | T | T | V | A | A | T | S |
| | | S | K | T | K | K | K | K | T | S | S | V | A |
| | | T | G | K | G | G | G | G | V | T | T | S | S |
| | | K | P | G | P | P | P | P | S | K | K | S | T |
| | | G | S | P | S | S | S | S | S | G | G | A | K |
| | | P | V | S | V | V | V | V | A | P | P | S | G |
| | | S | F | V | F | F | F | F | S | S | S | T | P |
| | | V | P | F | P | P | P | P | T | V | V | K | S |
| | | F | L | P | L | L | L | L | K | F | F | G | V |
| | | P | A | L | A | A | A | A | G | P | P | P | F |
| | | L | P | A | P | P | P | P | P | L | L | S | P |
| | | A | C | P | C | C | C | C | S | A | A | V | L |
| | | P | S | C | S | S | S | S | V | P | P | F | A |
| | | C | R | S | R | R | R | R | F | C | C | P | P |
| | | S | S | R | S | S | S | S | P | S | S | L | C |
| | | R | T | S | T | T | T | T | L | R | R | A | S |
| | | S | S | T | S | S | S | S | A | S | S | P | R |
| | | T | E | S | E | E | E | E | P | T | T | C | S |
| | | S | S | E | S | S | S | S | C | S | S | S | T |
| | | E | T | S | T | T | T | T | S | E | E | R | S |
| | | S | A | T | A | A | A | A | R | S | S | S | E |
| | | T | A | A | A | A | A | A | S | T | T | T | S |
| | | A | L | A | L | L | L | L | T | A | A | S | T |
| | | A | G | L | G | G | G | G | S | A | A | E | A |
| | | L | C | G | C | C | C | C | E | L | L | S | A |
| | | G | L | C | L | L | L | L | S | G | G | T | L |
| | | C | V | L | V | V | V | | T | C | C | A | G |
| | | L | K | V | K | K | K | | A | L | L | A | C |
| | | V | D | K | D | D | D | | A | V | V | L | L |
| | | K | Y | D | Y | Y | Y | | L | K | K | G | V |
| | | D | F | Y | F | F | F | | G | D | D | C | K |
| | | Y | P | F | P | P | P | | C | Y | Y | L | D |

Figure 2D

| CDR | DP50 | 3.1.1 | 4.1.1 | 4.8.1 | 4.10.2 | 4.13.1 | 4.14.3 | 6.1.1 | 11.2.1 | 11.6.1 | 11.7.1 | 12.3.1.1 | 12.9.1.1 |
|---|---|---|---|---|---|---|---|---|---|---|---|---|---|
| | | F | E | P | E | E | E | | L | F | F | V | Y |
| | | P | P | E | P | P | P | | V | P | P | K | F |
| | | E | V | P | V | V | V | | K | E | E | D | P |
| | | P | T | V | T | T | T | | D | P | P | Y | E |
| | | V | V | T | V | V | V | | Y | V | | F | P |
| | | T | S | V | S | S | S | | F | T | | P | V |
| | | V | W | S | W | W | W | | P | V | | E | T |
| | | S | N | W | N | N | N | | E | | | P | V |
| | | W | S | N | S | S | S | | P | | | V | S |
| | | N | G | S | G | G | G | | V | | | T | W |
| | | S | A | G | A | A | A | | T | | | V | N |
| | | G | L | A | L | L | L | | V | | | S | S |
| | | A | T | L | T | T | T | | S | | | W | G |
| | | L | S | T | S | S | S | | W | | | N | A |
| | | T | G | S | G | | G | | N | | | S | L |
| | | S | V | G | V | | V | | S | | | G | T |
| | | G | H | V | H | | H | | G | | | A | S |
| | | V | T | H | T | | T | | A | | | L | G |
| | | H | F | T | F | | F | | L | | | T | V |
| | | T | P | F | P | | P | | T | | | S | H |
| | | F | A | P | A | | A | | S | | | G | T |
| | | P | V | A | V | | V | | G | | | V | F |
| | | A | L | V | L | | L | | V | | | H | |
| | | V | Q | | Q | | Q | | H | | | T | |
| | | L | | | | | | | | | | F | |
| | | Q | | | | | | | | | | P | |
| | | | | | | | | | | | | A | |
| | | | | | | | | | | | | V | |

Figure 3

DP-65 or 4-31 gene product

VSGGSISSGGYYWSWIRQHPGKGLEWIGYIYYSGSTYYNPSLKSRVTISVDTSKNQFSLKLSSVTAADTAVYYCAR
　　　　CDR1　　　　　　　　　　　　CDR2

2.1.3 Heavy Chain Protein

SGPGLVKPSQILSLTCTVSGGSISSGGHYWSWIRQHPGKGLEWIGYIYYIGNTYYNPSLKSRVTISVDTSKNQFSLKLSSVTAADTAVYYCAR
　　　　　　　　　　　　　　CDR1　　　　　　　　　　　　CDR2

DSGDYYGIDVWGQGTTVTVSSASTKGPSVFPLAPCSRSTSESTAALGCLVKDYFPEPVTVSWNSGALTSGVHTFPAVLQ
CDR3

Figure 4

A27 Gene Product
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP
　　　　　　　　　　　　　　CDR1　　　　　　　　　　　　　　　CDR2　　　　　　　　　　　　　　　　　　　　CDR3

4.1.1 Kappa Chain Protein
QSPGTLSLSPGERATLSCRASQSISSSFLAWYQQRPGQAPRLLIYGASSRATGIPDRFSGSGSGTDFTLTISRLEPEDFAVYYCQQYGISPWT
　　　　　　　　　CDR1　　　　　　　　　　　　　CDR2　　　　　　　　　　　　　　　　　　　CDR3
FGQGTKVEIKRTVAAPSVFIFPPSDEQLKSGTASVVCLLNNFYPREAK

4.8.1 Kappa Chain Protein
QSPGTLSLSPGERATLSCRTSQQVSSSYLAWYQQKPGQAPRLLIYGASSRATGIPDRFSGSGSGTDFTLTISRLEPEDFAVYYCQQYGISPET
　　　　　　　　　CDR1　　　　　　　　　　　　　CDR2　　　　　　　　　　　　　　　　　　　CDR3
FGGGTKVEIKRTVAAPSVFIFPPSDEQLKSGTASVVCLLNNFYPREAKVQ

4.14.3 Kappa Chain Protein
GTLSLSPGERATLSCRASQSV0SSYLAWYQQKPGQAPRLLIYGASSRATGIPDRFSGSGSGTDFTLTISRLEPEDFAVYYCQQYGRSPET
　　　　　　　CDR1　　　　　　　　　　　　　CDR2　　　　　　　　　　　　　　　　　　　　CDR3
FGPGTKVDIKRTVAAPSVFIFPPSDEQLKSGTASVVCLLNNFYPREAKVQ

6.1.1 Kappa Chain Protein
QSPGTLSLSPGERATLSCRASQSV0SSYLAWYQQKPGQAPRLLIYGVSSRATGIPDRFSGSGSGTDFTLTISRLEPEDFAVYYCQQYGISPET
　　　　　　　　　CDR1　　　　　　　　　　　　　CDR2　　　　　　　　　　　　　　　　　　　CDR3
FGPGTKVDIKRTVAAPSVFIFPPSDEQLKSGTASVVCLLNNFYPREAKVQ

4.10.2 Kappa Chain Protein
SPGTLSLSPGERATLSCRASQSISSNFLAWYQQKPGQAPRLLIYRPSSRATGIPDSFSGSGSGTDFTLTISRLEPEDFALYYCQQYGISPET
　　　　　　CDR1　　　　　　　　　　　　　CDR2　　　　　　　　　　　　　　　　　　　　CDR3
FGPGTKVDIKRTVAAPSVFIFPPSDEQLKSGTASVVCLLNNFYPREAKVQ

4.13.1 Kappa Chain Protein
QSPGTLSLSPGERATLSCRASQSVSSSYLAWYQQKPGQAPRLLIYGASSRATGIPDRFSGSGSGTDFTLTISRLEPEDFAVYYCQQYGRSPET
　　　　　　　　　CDR1　　　　　　　　　　　　　CDR2　　　　　　　　　　　　　　　　　　　CDR3
FGPGTKVDIKRTVAAPSVFIFPPSDEQLKSGTASVVCLLNNFYPREAKVQWKGG

*Figure 5*

O12 Gene Product

DIQMTQSPSSLSASVGDRVTITCRASQSISSYLNWYQQKPGKAPKLLIYAASSLQSGVPSRFSGSGSGTDFTLTISSLQPEDFATYYCQQSYSTP
　　　　　　　　　　　　　　 CDR1　　　　　　　　　　　　　 CDR2　　　　　　　　　　　　　　　　　　　　　 CDR3

3.1.1 Kappa Chain Protein

QSPSSLSASVGDRVTITCRASQSINTYLIWYQQKPGKAPNFLISATSILQSGVPSRFRGSGSGTNFTLTINSLHPEDFATYYCQQSYSTPFT
　　　　　　　　　　　 CDR1　　　　　　　　　　　　　　 CDR2　　　　　　　　　　　　　　　　　　　　　　 CDR3
FGPGTKVDIKRTVAAPSVFIFPPSDEQLKSGTASVVCLLNNFYPREAKVQWKVDNALQSG

11.2.1 Kappa Chain Protein

PSSLSASVGDRVTITCRASQSINSYLDWYQQKPGKAPKLLIYAASSLQSGVPSRFSGSGSGTDFTLTISSLQPEDFATYYCQQSYSTPFT
　　　　　　　　　 CDR1　　　　　　　　　　　　　 CDR2　　　　　　　　　　　　　　　　　　　　　 CDR3
FGPGTKVEIKRTVAAPSVFIFPPSDEQLKSGTASVVCLLNNFYPREAKV

11.6.1 Kappa Chain Protein

TQSPSSLSASVGDRVTITCRASQNISRYLNWYQQKPGKAPKFLIYASILQSGVPSGFSASGSGPDFTLTISSLQPEDFATYYCQQSYSTPFT
　　　　　　　　　　　 CDR1　　　　　　　　　　　　　 CDR2　　　　　　　　　　　　　　　　　　　　　 CDR3
FGPGTKVDIKRTVAAPSVFIFPPSDEQLKSGTASVVCLLNN

11.7.1 Kappa Chain Protein

TQSPSSLSASVGDRVTITCRASQSICNYLNWYQQKPGKAPRVLIYAASSLQGGVPSRFSGSGSGIDCTLTISSLQPEDFATYYCQQSYITPFT
　　　　　　　　　　　 CDR1　　　　　　　　　　　　　 CDR2　　　　　　　　　　　　　　　　　　　　　 CDR3
FGPGTRVDIERTVAAPSVFIFPPSDEQLKSGTASVVCLLNNFYPREAKVQWKVDNAY

Figure 6

A10/A26 Gene Product

EIVLTQSPDFQSVTPKEKVTITCRASQSIGSSLHWYQQKPDQSPKLLIKYASQSESGVPSRFSGSGSGTDFTLTINSLEAEDAATYYCHQSSSLPQ
                                CDR1                                     CDR2                                                CDR3

2L3 Kappa Chain Protein

SPDFQSVTPKEKVTITCRASQSIGSSLHWYQQKPDQSPKLLIKYASQSESGVPSRFSGSGSGTDFTLTINSLEAEDAATYYCHQSSSLPLT
                    CDR1                                         CDR2                                               CDR3

FGGGTKVEIKRTVAAPSVFIFPPSDEQLKSGTASVVCLLNNFYPREAKVQWKVDNALQSGNSQE

Figure 7

A17 Gene Product

DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWP
                                    CDR1                                            CDR2                                          CDR3

12.3.1 Kappa Chain Protein

PLSLPVTLGQPASISCRSSQSLVYSDGNTYLNWFQQRPGQSPRRLIYKVSNWDSGVPDRFSGSGSGTDFTLKISRVEAEDVGVYYCMQGSHWPPT
                      CDR1                                                CDR2                                        CDR3

FGQGTKVEIKRTVAAPSVFIFPPSDEQLKSGTASVVCLLNNFYP

*Figure 8*

A3/A19 Gene Product

DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTP
　　　　　　　　　　　　　　　　　　CDR1　　　　　　　　　　　　　　　　　CDR2　　　　　　　　　　　　　　　　　　CDR3

12.9.1 Kappa Chain Protein

PGEPASISCRSSQSLLHSNGYNYLDWYLQKPGQSPQLLIYLGSNRASGVPDRFSGSGSGTDFTLKLSRVEAEDVGVYYCMQALQTPLT
　　　　　　CDR1　　　　　　　　　　　　　　　　　CDR2　　　　　　　　　　　　　　　　　　CDR3
FGGGTKVEIKRTVAAPSVFIFPPSDEQLKSGTASVVCLLNNFYPR

Figure 9  Amino-terminal amino acid sequence analysis

| Hybridoma | Light chain | MW |
|---|---|---|
| CT2.1.3 | ND | ND |
| CT3.1.1 | NH2-DIQMTQSPSSLSASVGDRVT | 26,119 |
| CT4.1.1 | NH2-EIVLTQSPGTLSLSPGERAT | 23,917 |
| CT4.8.1 | NH2-EIVLTQSPGTLSLSPGERAT | 23,617 |
| CT4.9.1 | NH2-DIQMTQSPSSVSASVGDRVT | 23,702 |
| CT4.10.2 | NH2-TGEFVLTQSPGTLSLSPGER (60%)<br>NH2-EFVLTQSPGTLSLSPGERAT (40%) | 24,101 |
| CT4.14.3 | NH2-EIVLTQSPGTLSLSPGERAT | 23,770 |
| CT4.13.1 | NH$_2$-EIVLTQSPGTLSLSPGERAT | 23,802 |
| CT6.1.1 | NH2-EIVLTQSPGTLSLSPGERAT | 23,747 |

| Hybridoma | Heavy chain | MW |
|---|---|---|
| CT2.1.3 | ND | ND |
| CT3.1.1 | NH$_2$-Blocked. Following treatment with Pyroglutmate Aminopeptidase:<br>NH$_2$-pQ-VQLVESGGGVVQPGRSLRLS (major sequence~80%)<br>NH$_2$-PEVQF...(minor sequence~20%) | 51,813 |
| CT4.1.1 | NH$_2$-Blocked. Following treatment with Pyroglutmate Aminopeptidase:<br>NH$_2$-pQ-VQLVESGGGVVQPGRSLRLS (major sequence~65%)<br>NH$_2$-PEVQFNWYVD...(minor sequence~35%) | 51,502 |
| CT4.8.1 | NH$_2$-Blocked. Following treatment with Pyroglutmate Aminopeptidase:<br>NH$_2$-pQ-VQLVESGGGVVQPG(R)SL... (major sequence~60%)<br>NH$_2$-PEVQFNWY...(minor sequence~40%) | 51,597 |
| CT4.9.1 | NH$_2$-EVQLLESGGGLVQPGGSLRL (free amino terminus) | 51,437 |
| CT4.10.2 | NH$_2$-Blocked. Following treatment with Pyroglutmate Aminopeptidase:<br>NH$_2$-pQ-VQLVESGGGVVQPGRSLRLS (major sequence~60%)<br>NH$_2$-PEVQFNWYVD...(minor sequence~40%) | 51,502 |
| CT4.14.3 | NH$_2$-Blocked. Following treatment with Pyroglutmate Aminopeptidase:<br>NH$_2$-pQ-VQLVESGGGVVQPGRSL(R)(L)(S) (major sequence~65%)<br>NH$_2$-PEVQFNWYV...(minor sequence~35%) | 51,293 |
| CT4.13.1 | NH$_2$-Blocked. Following treatment with Pyroglutmate Aminopeptidase:<br>NH$_2$-pQ-VQLVESGGGVVQPGRSLRLS (major sequence~75%)<br>NH$_2$-PEVQFN...(minor sequence~25%) | 51,305 |
| CT6.1.1 | NH$_2$-Blocked. Following treatment with Pyroglutmate Aminopeptidase:<br>NH$_2$-pQ-VQLVESGGGVVEPGRSLRLS* (major sequence~65%)<br>NH$_2$-PEVQFNWYVD... (minor sequence~35%) | 51,476 |

* This heavy chain sequence is similar to the other blocked heavy chain sequences except for a unique Gln->Glu change at position 13.

*Figure 10A*

| antibody | Conc. (mg/ml) (Ec1.58) reported | Conc. (mg/ml) (Ec1.58) observed | IEF observed | SDS-PAGE (+) b-me | SDS-PAGE (-) b-me | SEC observed | reported MALDI Hc | reported MALDI Lc | n-term. seq. (lc)* reported | n-term. seq. (lc)* observed |
|---|---|---|---|---|---|---|---|---|---|---|
| CT 3.1.1 | 1.1 | 1.57 | smear | 50 & 28 kDa | 6 bands | 139,400 | 51,813 | 26,119 | DIQMTQSP (SEQ ID NO: 141) | DIQMTQSP (SEQ ID NO: 141) |
| CT 4.1.1 | 1.54 | 1.65 | smear | 50 & 24 kDa | 6 bands | 79,900 | 51,502 | 23,917 | EIVLTQSP (SEQ ID NO: 142) | EIVLTQSP (SEQ ID NO: 142) |
| CT 4.8.1 | 1.52 | 1.54 | 4 bands | 50 & 24 kDa | 6 bands | 110,300 | 51,597 | 23,617 | EIVLTQSP (SEQ ID NO: 143) | EIVLTQSP (SEQ ID NO: 143) |
| CT 4.10.2 | 1.29 | 1.77 | 4 bands | 50 & 25 kDa | 6 bands | 107,200 | 51,502 | 24,101 | ** | *** |
| CT 4.14.3 | 1.75 | 1.65 | smear | 50 & 24 kDa | 6 bands | 82,800 | 51,293 | 23,770 | EIVLTQSP (SEQ ID NO: 146) | EIVLTQSP (SEQ ID NO: 146) |
| CT 6.1.1 | 1.36 | 1.3 | 4 bands | 50 & 24 kDa | 6 bands | 101,100 | 51,476 | 23,747 | EIVLTQSP (SEQ ID NO: 147) | EIVLTQSP (SEQ ID NO: 147) |

* all heavy chains n-terminally blocked (not sequenced in-house)

** mixed sequence reported: TGEFVLTQSP (60) (SEQ ID NO: 144) & EFVLTQSP (40) (SEQ ID NO: 145)

*** mixed sequence observed TGEFVLTQSP (60) (SEQ ID NO: 144) & EFVLTQSP (40) (SEQ ID NO: 145)

$IOD_{280nm} = 0.633$ mg/ml
Ec-1.58

Expression of B7.1 and B7.2 on Raji Cells

Enhancement of Human T Cell IL-2 Production Induced by Anti-CTLA4 MAbs in the 72 Hour T Blast / Raji Assay

- Signal peptides shown in bold and large text
- Open reading frame for genomic clone underlined
- Mutations introduced to make deglycosylated Ab (N294Q) double underlined and large text

Figure 22A  4.1.1 IgG2 Heavy Chain cDNA

**ATGGAGTTTGGGCTGAGCTGGGTTTTCCTCGTTGCTCTTTTAAGAG
GTGTCCAGTGT**CAGGTGCAGCTGGTGGAGTCTGGGGGAGGCGTGGTCCAGC
CTGGGAGGTCCCTGAGACTCTCCTGTGTAGCGTCTGGATTCACCTTCAGTAGC
CATGGCATGCACTGGGTCCGCCAGGCTCCAGGCAAGGGGCTGGAGTGGGTGGC
AGTTATATGGTATGATGGAAGAAATAAATACTATGCAGACTCCGTGAAGGGCC
GATTCACCATCTCCAGAGACAATTCCAAGAACACGCTGTTTCTGCAAATGAAC
AGCCTGAGAGCCGAGGACACGGCTGTGTATTACTGTGCGAGAGGAGGTCACTT
CGGTCCTTTTGACTACTGGGGCCAGGGAACCCTGGTCACCGTCTCCTCAGCCT
CCACCAAGGGCCCATCGGTCTTCCCCCTGGCGCCCTGCTCCAGGAGCACCTCC
GAGAGCACAGCGGCCCTGGGCTGCCTGGTCAAGGACTACTTCCCCGAACCGGT
GACGGTGTCGTGGAACTCAGGCGCTCTGACCAGCGGCGTGCACACCTTCCCAG
CTGTCCTACAGTCCTCAGGACTCTACTCCCTCAGCAGCGTGGTGACCGTGCCC
TCCAGCAACTTCGGCACCCAGACCTACACCTGCAACGTAGATCACAAGCCCAG
CAACACCAAGGTGGACAAGACAGTTGAGCGCAAATGTTGTGTCGAGTGCCCAC
CGTGCCCAGCACCACCTGTGGCAGGACCGTCAGTCTTCCTCTTCCCCCCAAAA
CCCAAGGACACCCTCATGATCTCCCGGACCCCTGAGGTCACGTGCGTGGTGGT
GGACGTGAGCCACGAAGACCCCGAGGTCCAGTTCAACTGGTACGTGGACGGCG
TGGAGGTGCATAATGCCAAGACAAAGCCACGGGAGGAGCAGTTCAACAGCACG
TTCCGTGTGGTCAGCGTCCTCACCGTTGTGCACCAGGACTGGCTGAACGGCAA
GGAGTACAAGTGCAAGGTCTCCAACAAAGGCCTCCCAGCCCCCATCGAGAAAA
CCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAA
AGGCTTCTACCCCAGCGACATCGCCGTGGAGTGGGAGAGCAATGGGCAGCCGG
AGAACAACTACAAGACCACACCTCCCATGCTGGACTCCGACGGCTCCTTCTTC
CTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCC
TCTCCCTGTCTCCGGGTAAATGA (SEQ ID NO:53)

Figure 22B  4.1.1 IgG2 Heavy Chain Genomic DNA

ATGGAGTTTGGGCTGAGCTGGGTTTTCCTCGTTGCTCTTTTAAGAG
GTGTCCAGTGTCAGGTGCAGCTGGTGGAGTCTGGGGGAGGCGTGGTCCAGC
CTGGGAGGTCCCTGAGACTCTCCTGTGTAGCGTCTGGATTCACCTTCAGTAGC
CATGGCATGCACTGGGTCCGCCAGGCTCCAGGCAAGGGGCTGGAGTGGGTGGC
AGTTATATGGTATGATGGAAGAAATAAATACTATGCAGACTCCGTGAAGGGCC
GATTCACCATCTCCAGAGACAATTCCAAGAACACGCTGTTTCTGCAAATGAAC
AGCCTGAGAGCCGAGGACACGGCTGTGTATTACTGTGCGAGAGGAGGTCACTT
CGGTCCTTTTGACTACTGGGGCCAGGGAACCCTGGTCACCGTCTCCTCAGCTA
GCACCAAGGGCCCATCGGTCTTCCCCCTGGCGCCCTGCTCCAGGAGCACCTCC
GAGAGCACAGCGGCCCTGGGCTGCCTGGTCAAGGACTACTTCCCCGAACCGGT
GACGGTGTCGTGGAACTCAGGCGCTCTGACCAGCGGCGTGCACACCTTCCCAG
CTGTCCTACAGTCCTCAGGACTCTACTCCCTCAGCAGCGTGGTGACCGTGCCC
TCCAGCAACTTCGGCACCCAGACCTACACCTGCAACGTAGATCACAAGCCCAG
CAACACCAAGGTGGACAAGACAGTTGGTGAGAGGCCAGCTCAGGGAGGGAGGG
TGTCTGCTGGAAGCCAGGCTCAGCCCTCCTGCCTGGACGCACCCCGGCTGTGC
AGCCCCAGCCCAGGGCAGCAAGGCAGGCCCCATCTGTCTCCTCACCCGGAGGC
CTCTGCCCGCCCCACTCATGCTCAGGGAGAGGGTCTTCTGGCTTTTTCCACCA
GGCTCCAGGCAGGCACAGGCTGGGTGCCCCTACCCCAGGCCCTTCACACACAG
GGGCAGGTGCTTGGCTCAGACCTGCCAAAAGCCATATCCGGGAGGACCCTGCC
CCTGACCTAAGCCGACCCCAAAGGCCAAACTGTCCACTCCCTCAGCTCGGACA
CCTTCTCTCCTCCCAGATCCGAGTAACTCCCAATCTTCTCTCTGCAGAGCGCA
AATGTTGTGTCGAGTGCCCACCGTGCCCAGGTAAGCCAGCCCAGGCCTCGCCC
TCCAGCTCAAGGCGGGACAGGTGCCCTAGAGTAGCCTGCATCCAGGGACAGGC
CCCAGCTGGGTGCTGACACGTCCACCTCCATCTCTTCCTCAGCACCACCTGTG
GCAGGACCGTCAGTCTTCCTCTTCCCCCCAAAACCCAAGGACACCCTCATGAT
CTCCCGGACCCCTGAGGTCACGTGCGTGGTGGTGGACGTGAGCCACGAAGACC
CCGAGGTCCAGTTCAACTGGTACGTGGACGGCGTGGAGGTGCATAATGCCAAG
ACAAAGCCACGGGAGGAGCAGTTCAACAGCACGTTCCGTGTGGTCAGCGTCCT
CACCGTTGTGCACCAGGACTGGCTGAACGGCAAGGAGTACAAGTGCAAGGTCT
CCAACAAAGGCCTCCCAGCCCCCATCGAGAAAACCATCTCCAAAACCAAAGGT
GGGACCCGCGGGGTATGAGGGCCACATGGACAGAGGCCGGCTCGGCCCACCCT
CTGCCCTGGGAGTGACCGCTGTGCCAACCTCTGTCCCTACAGGGCAGCCCCGA
GAACCACAGGTGTACACCCTGCCCCCATCCCGGGAGGAGATGACCAAGAACCA
GGTCAGCCTGACCTGCCTGGTCAAAGGCTTCTACCCCAGCGACATCGCCGTGG
AGTGGGAGAGCAATGGGCAGCCGGAGAACAACTACAAGACCACACCTCCCATG
CTGGACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTCTGC
ACAACCACTACACGCAGAAGAGCCTCTCCCTGTCTCCGGGTAAATGA (SEQ
ID NO:54)

Figure 22C  4.1.1 IgG2 Heavy Chain Protein

MEFGLSWVFLVALLRGVQCQVQLVESGGGVVQPGRSLRLSCVASGFTFSS
HGMHWVRQAPGKGLEWVAVIWYDGRNKYYADSVKGRFTISRDNSKNTLFLQMN
SLRAEDTAVYYCARGGHFGPFDYWGQGTLVTVSSASTKGPSVFPLAPCSRSTS
ESTAALGCLVKDYFPEPVTVSWNSGALTSGVHTFPAVLQSSGLYSLSSVVTVP
SSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFNST
FRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK (SEQ ID NO:63)

Figure 22D  4.1.1 IgG2 Heavy Chain cDNA N294Q

ATGGAGTTTGGGCTGAGCTGGGTTTTCCTCGTTGCTCTTTTAAGAG
GTGTCCAGTGTCAGGTGCAGCTGGTGGAGTCTGGGGGAGGCGTGGTCCAGC
CTGGGAGGTCCCTGAGACTCTCCTGTGTAGCGTCTGGATTCACCTTCAGTAGC
CATGGCATGCACTGGGTCCGCCAGGCTCCAGGCAAGGGGCTGGAGTGGGTGGC
AGTTATATGGTATGATGGAAGAAATAAATACTATGCAGACTCCGTGAAGGGCC
GATTCACCATCTCCAGAGACAATTCCAAGAACACGCTGTTTCTGCAAATGAAC
AGCCTGAGAGCCGAGGACACGGCTGTGTATTACTGTGCGAGAGGAGGTCACTT
CGGTCCTTTTGACTACTGGGGCCAGGGAACCCTGGTCACCGTCTCCTCAGCCT
CCACCAAGGGCCCATCGGTCTTCCCCCTGGCGCCCTGCTCCAGGAGCACCTCC
GAGAGCACAGCGGCCCTGGGCTGCCTGGTCAAGGACTACTTCCCCGAACCGGT
GACGGTGTCGTGGAACTCAGGCGCTCTGACCAGCGGCGTGCACACCTTCCCAG
CTGTCCTACAGTCCTCAGGACTCTACTCCCTCAGCAGCGTGGTGACCGTGCCC
TCCAGCAACTTCGGCACCCAGACCTACACCTGCAACGTAGATCACAAGCCCAG
CAACACCAAGGTGGACAAGACAGTTGAGCGCAAATGTTGTGTCGAGTGCCCAC
CGTGCCCAGCACCACCTGTGGCAGGACCGTCAGTCTTCCTCTTCCCCCCAAAA
CCCAAGGACACCCTCATGATCTCCCGGACCCCTGAGGTCACGTGCGTGGTGGT
GGACGTGAGCCACGAAGACCCCGAGGTCCAGTTCAACTGGTACGTGGACGGCG
TGGAGGTGCATAATGCCAAGACAAAGCCACGGGAGGAGCAGTTCCAAAGCACG
TTCCGTGTGGTCAGCGTCCTCACCGTTGTGCACCAGGACTGGCTGAACGGCAA
GGAGTACAAGTGCAAGGTCTCCAACAAAGGCCTCCCAGCCCCCATCGAGAAAA
CCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAA
AGGCTTCTACCCCAGCGACATCGCCGTGGAGTGGGAGAGCAATGGGCAGCCGG
AGAACAACTACAAGACCACACCTCCCATGCTGGACTCCGACGGCTCCTTCTTC
CTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCC
TCTCCCTGTCTCCGGGTAAATGA (SEQ ID NO:55)

Figure 22E  4.1.1 IgG2 Heavy Chain Protein N294Q

MEFGLSWVFLVALLRGVQCQVQLVESGGGVVQPGRSLRLSCVASGFTFSS
HGMHWVRQAPGKGLEWVAVIWYDGRNKYYADSVKGRFTISRDNSKNTLFLQMN
SLRAEDTAVYYCARGGHFGPFDYWGQGTLVTVSSASTKGPSVFPLAPCSRSTS
ESTAALGCLVKDYFPEPVTVSWNSGALTSGVHTFPAVLQSSGLYSLSSVVTVP
SSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFQST
FRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFF
LYSKLTVDKSRWQQGNVFSCSVMHEALHNHYTQKSLSLSPGK (SEQ ID NO:64)

Figure 22F  4.1.1 Kappa Chain DNA

ATGGAAACCCCAGCGCAGCTTCTCTTCCTCCTGCTACTCTGGCTCC
CAGATACCACCGGAGAAATTGTGTTGACGCAGTCTCCAGGCACCCTGTCTT
TGTCTCCAGGGGAAAGAGCCACCCTCTCCTGCAGGGCCAGTCAGAGTATTAGC
AGCAGCTTCTTAGCCTGGTACCAGCAGAGACCTGGCCAGGCTCCCAGGCTCCT
CATCTATGGTGCATCCAGCAGGGCCACTGGCATCCCAGACAGGTTCAGTGGCA
GTGGGTCTGGGACAGACTTCACTCTCACCATCAGCAGACTGGAGCCTGAAGAT
TTTGCAGTGTATTACTGTCAGCAGTATGGTACCTCACCCTGGACGTTCGGCCA
AGGGACCAAGGTGGAAATCAAACGAACTGTGGCTGCACCATCTGTCTTCATCT
TCCCGCCATCTGATGAGCAGTTGAAATCTGGAACTGCCTCTGTTGTGTGCCTG
CTGAATAACTTCTATCCCAGAGAGGCCAAAGTACAGTGGAAGGTGGATAACGC
CCTCCAATCGGGTAACTCCCAGGAGAGTGTCACAGAGCAGGACAGCAAGGACA
GCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCAC
AAAGAGCTTCAACAGGGGAGAGTGTTAG (SEQ ID NO:56)

Figure 22G  4.1.1 Kappa Chain Protein

METPAQLLFLLLLWLPDTTGEIVLTQSPGTLSLSPGERATLSCRASQSIS
SSFLAWYQQRPGQAPRLLIYGASSRATGIPDRFSGSGSGTDFTLTISRLEPED
FAVYYCQQYGTSPWTFGQGTKVEIKRTVAAPSVFIFPPSDEQLKSGTASVVCL
LNNFYPREAKVQWKVDNALQSGNSQESVTEQDSKDSTYSLSSTLTLSKADYEK
HKVYACEVTHQGLSSPVTKSFNRGEC (SEQ ID NO:65)

Figure 22H  4.8.1 Heavy Chain DNA

ATGGAGTTTGGGCTGAGCTGGGTTTTCCTCGTTGCTCTTTTAAGAG
GTGTCCAGTGTCAGGTGCAGCTGGTGGAGTCTGGGGGAGGCGTGGTCCAGC
CTGGGAGGTCCCTGAGACTCTCCTGTACAGCGTCTGGATTCACCTTCAGTAAC
TATGGCATGCACTGGGTCCGCCAGGCTCCAGGCAAGGGGCTGGAGTGGGTGGC
AGTTATATGGTATGATGGAAGTAATAAACACTATGGAGACTCCGTGAAGGGCC
GATTCACCATCTCCAGTGACAATTCCAAGAACACGCTGTATCTGCAAATGAAC
AGCCTGAGAGCCGAGGACACGGCTGTGTATTACTGTGCGAGAGGAGAGAGACT
GGGGTCCTACTTTGACTACTGGGGCCAGGGAACCCTGGTCACCGTCTCCTCAG
CCTCCACCAAGGGCCCATCGGTCTTCCCCCTGGCGCCCTGCTCCAGGAGCACC
TCCGAGAGCACAGCGGCCCTGGGCTGCCTGGTCAAGGACTACTTCCCCGAACC
GGTGACGGTGTCGTGGAACTCAGGCGCTCTGACCAGCGGCGTGCACACCTTCC
CAGCTGTCCTACAGTCCTCAGGACTCTACTCCCTCAGCAGCGTGGTGACCGTG
CCCTCCAGCAACTTCGGCACCCAGACCTACACCTGCAACGTAGATCACAAGCC
CAGCAACACCAAGGTGGACAAGACAGTTGAGCGCAAATGTTGTGTCGAGTGCC
CACCGTGCCCAGCACCACCTGTGGCAGGACCGTCAGTCTTCCTCTTCCCCCCA
AAACCCAAGGACACCCTCATGATCTCCCGGACCCCTGAGGTCACGTGCGTGGT
GGTGGACGTGAGCCACGAAGACCCCGAGGTCCAGTTCAACTGGTACGTGGACG
GCGTGGAGGTGCATAATGCCAAGACAAAGCCACGGGAGGAGCAGTTCAACAGC
ACGTTCCGTGTGGTCAGCGTCCTCACCGTTGTGCACCAGGACTGGCTGAACGG
CAAGGAGTACAAGTGCAAGGTCTCCAACAAAGGCCTCCCAGCCCCCATCGAGA
AAACCATCTCCAAAACCAAAGGGCAGCCCCGAGAACCACAGGTGTACACCCTG
CCCCCATCCCGGGAGGAGATGACCAAGAACCAGGTCAGCCTGACCTGCCTGGT
CAAAGGCTTCTACCCCAGCGACATCGCCGTGGAGTGGGAGAGCAATGGGCAGC
CGGAGAACAACTACAAGACCACACCTCCCATGCTGGACTCCGACGGCTCCTTC
TTCCTCTACAGCAAGCTCACCGTGGACAAGAGCAGGTGGCAGCAGGGGAACGT

CTTCTCATGCTCCGTGATGCATGAGGCTCTGCACAACCACTACACGCAGAAGA
GCCTCTCCCTGTCTCCGGGTAAATGA (SEQ ID NO:57)

Figure 22I  4.8.1 Heavy Chain Protein

MEFGLSWVFLVALLRGVQCQVQLVESGGGVVQPGRSLRLSCTASGFTFSN
YGMHWVRQAPGKGLEWVAVIWYDGSNKHYGDSVKGRFTISSDNSKNTLYLQMN
SLRAEDTAVYYCARGERLGSYFDYWGQGTLVTVSSASTKGPSVFPLAPCSRST
SESTAALGCLVKDYFPEPVTVSWNSGALTSGVHTFPAVLQSSGLYSLSSVVTV
PSSNFGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTL
PPSREEMTKNQVSLTCLVKGFYPSDIAVEWESNGQPENNYKTTPPMLDSDGSF
FLYSKLTVDKSRWQQGNVFSCSVMHEALHNHYTQKSLSLSPGK (SEQ ID
NO:66)

Figure 22J  4.8.1 Kappa Chain DNA

ATGGAAACCCCAGCGCAGCTTCTCTTCCTCCTGCTACTCTGGCTCC
CAGATACCACCGGAGAAATTGTGTTGACGCAGTCTCCAGGCACCCTGTCTT
TGTCTCCAGGGGAAAGAGCCACCCTCTCCTGCAGGACCAGTGTTAGCAGCAGT
TACTTAGCCTGGTACCAGCAGAAACCTGGCCAGGCTCCCAGGCTCCTCATCTA
TGGTGCATCCAGCAGGGCCACTGGCATCCCAGACAGGTTCAGTGGCAGTGGGT
CTGGGACAGACTTCACTCTCACCATCAGCAGACTGGAGCCTGAAGATTTTGCA
GTCTATTACTGTCAGCAGTATGGCATCTCACCCTTCACTTTCGGCGGAGGGAC
CAAGGTGGAGATCAAGCGAACTGTGGCTGCACCATCTGTCTTCATCTTCCCGC
CATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCACCT
ACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAG
CTTCAACAGGGGAGAGTGTTAG (SEQ ID NO:58)

Figure 22K  4.8.1 Kappa Chain Protein

METPAQLLFLLLLWLPDTTGEIVLTQSPGTLSLSPGERATLSCRTSVSSS
YLAWYQQKPGQAPRLLIYGASSRATGIPDRFSGSGSGTDFTLTISRLEPEDFA
VYYCQQYGISPFTFGGGTKVEIKRTVAAPSVFIFPPSDEQLKSGTASVVCLLN
NFYPREAKVQWKVDNALQSGNSQESVTEQDSKDSTYSLSSTLTLSKADYEKHK
VYACEVTHQGLSSPVTKSFNRGEC (SEQ ID NO:67)

Figure 22L  6.1.1 Heavy Chain DNA

ATGGAGTTTGGGCTGAGCTGGGTTTTCCTCGTTGCTCTTTTAAGAG
GTGTCCAGTGTCAGGTGCAGCTGGTGGAGTCTGGGGGAGGCGTGGTCGAGC
CTGGGAGGTCCCTGAGACTCTCCTGTACAGCGTCTGGATTCACCTTCAGTAGT
TATGGCATGCACTGGGTCCGCCAGGCTCCAGGCAAGGGGCTGGAGTGGGTGGC
AGTTATATGGTATGATGGAAGCAATAAACACTATGCAGACTCCGCGAAGGGCC
GATTCACCATCTCCAGAGACAATTCCAAGAACACGCTGTATCTGCAAATGAAC
AGCCTGAGAGCCGAGGACACGGCTGTGTATTACTGTGCGAGAGCCGGACTGCT
GGGTTACTTTGACTACTGGGGCCAGGGAACCCTGGTCACCGTCTCCTCAGCCT
CCACCAAGGGCCCATCGGTCTTCCCCCTGGCGCCCTGCTCCAGGAGCACCTCC
GAGAGCACAGCGGCCCTGGGCTGCCTGGTCAAGGACTACTTCCCCGAACCGGT
GACGGTGTCGTGGAACTCAGGCGCTCTGACCAGCGGCGTGCACACCTTCCCAG
CTGTCCTACAGTCCTCAGGACTCTACTCCCTCAGCAGCGTGGTGACCGTGCCC
TCCAGCAACTTCGGCACCCAGACCTACACCTGCAACGTAGATCACAAGCCCAG
CAACACCAAGGTGGACAAGACAGTTGAGCGCAAATGTTGTGTCGAGTGCCCAC
CGTGCCCAGCACCACCTGTGGCAGGACCGTCAGTCTTCCTCTTCCCCCCAAAA
CCCAAGGACACCCTCATGATCTCCCGGACCCCTGAGGTCACGTGCGTGGTGGT
GGACGTGAGCCACGAAGACCCCGAGGTCCAGTTCAACTGGTACGTGGACGGCG
TGGAGGTGCATAATGCCAAGACAAAGCCACGGGAGGAGCAGTTCAACAGCACG
TTCCGTGTGGTCAGCGTCCTCACCGTTGTGCACCAGGACTGGCTGAACGGCAA
GGAGTACAAGTGCAAGGTCTCCAACAAAGGCCTCCCAGCCCCCATCGAGAAAA
CCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAA
AGGCTTCTACCCCAGCGACATCGCCGTGGAGTGGGAGAGCAATGGGCAGCCGG
AGAACAACTACAAGACCACACCTCCCATGCTGGACTCCGACGGCTCCTTCTTC
CTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCC
TCTCCCTGTCTCCGGGTAAATGA (SEQ ID NO:59)

Figure 22M  6.1.1 Heavy Chain Protein

MEFGLSWVFLVALLRGVQCQVQLVESGGGVVEPGRSLRLSCTASGFTFSS
YGMHWVRQAPGKGLEWVAVIWYDGSNKHYADSAKGRFTISRDNSKNTLYLQMN
SLRAEDTAVYYCARAGLLGYFDYWGQGTLVTVSSASTKGPSVFPLAPCSRSTS
ESTAALGCLVKDYFPEPVTVSWNSGALTSGVHTFPAVLQSSGLYSLSSVVTVP
SSNFGTQTYTCNVDHKPSNTKVDKTVERKCCVECPPCPAPPVAGPSVFLFPPK
PKDTLMISRTPEVTCVVVDVSHEDPEVQFNWYVDGVEVHNAKTKPREEQFNST
FRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFF
LYSKLTVDKSRWQQGNVFSCSVMHEALHNHYTQKSLSLSPGK (SEQ ID
NO:68)

Figure 22N  6.1.1 Kappa Chain DNA

ATGGAAACCCCAGCGCAGCTTCTCTTCCTCCTGCTACTCTGGCTCC
CAGATACCACCGGAGAAATTGTGTTGACGCAGTCTCCAGGCACCCTGTCTT
TGTCTCCAGGGGAAAGAGCCACCCTCTCCTGTAGGGCCAGTCAAAGTGTTAGC
AGCTACTTAGCCTGGTACCAACAGAAACCTGGCCAGGCTCCCAGGCCCCTCAT
CTATGGTGTATCCAGCAGGGCCACTGGCATCCAGACAGGTTCAGTGGCAGTG
GGTCTGGGACAGACTTCACTCTCACCATCAGCAGACTGGAGCCTGAAGATTTT
GCAGTGTATTACTGTCAGCAGTATGGTATCTCACCATTCACTTTCGGCCCTGG
GACCAAAGTGGATATCAAACGAACTGTGGCTGCACCATCTGTCTTCATCTTCC
CGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCT
CCAATCGGGTAACTCCCAGGAGAGTGTCACAGAGCAGGACAGCAAGGACAGCA
CCTACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCACAAA
GAGCTTCAACAGGGGAGAGTGTTAG (SEQ ID NO:60)

Figure 22O  6.1.1 Kappa Chain Protein

METPAQLLFLLLLWLPDTTGEIVLTQSPGTLSLSPGERATLSCRASQSVS
SYLAWYQQKPGQAPRPLIYGVSSRATGIPDRFSGSGSGTDFTLTISRLEPEDF
AVYYCQQYGISPFTFGPGTKVDIKRTVAAPSVFIFPPSDEQLKSGTASVVCLL
NNFYPREAKVQWKVDNALQSGNSQESVTEQDSKDSTYSLSSTLTLSKADYEKH
KVYACEVTHQGLSSPVTKSFNRGEC (SEQ ID NO:69)

Figure 22P  11.2.1 IgG2 Heavy Chain DNA:

ATGGAGTTTGGGCTGAGCTGGGTTTTCCTCGTTGCTCTTTTAAGAG
GTGTCCAGTGTCAGGTGCAGCTGGTGGAGTCTGGGGGAGGCGTGGTCCAGC
CTGGGAGGTCCCTGAGACTCTCCTGTGCAGCGTCTGGATTCACCTTCAGTAGC
TATGGCATGCACTGGGTCCGCCAGGCTCCAGGCAAGGGGCTGGAGTGGGTGGC
AGTTATATGGTATGATGGAAGTAATAAATACTATGCAGACTCCGTGAAGGGCC
GATTCACCATCTCCAGAGACAATTCCAAGAACACGCTGTATCTGCAAATGAAC
AGCCTGAGAGCCGAGGACACGGCTGTGTATTACTGTGCGAGAGATCCGAGGGG
AGCTACCCTTTACTACTACTACGGTATGGACGTCTGGGGCCAAGGGACCA
CGGTCACCGTCTCCTCAGCCTCCACCAAGGGCCCATCGGTCTTCCCCCTGGCG
CCCTGCTCCAGGAGCACCTCCGAGAGCACAGCGGCCCTGGGCTGCCTGGTCAA
GGACTACTTCCCCGAACCGGTGACGGTGTCGTGGAACTCAGGCGCTCTGACCA
GCGGCGTGCACACCTTCCCAGCTGTCCTACAGTCCTCAGGACTCTACTCCCTC
AGCAGCGTGGTGACCGTGCCCTCCAGCAACTTCGGCACCCAGACCTACACCTG
CAACGTAGATCACAAGCCCAGCAACACCAAGGTGGACAAGACAGTTGAGCGCA
AATGTTGTGTCGAGTGCCCACCGTGCCCAGCACCACCTGTGGCAGGACCGTCA
GTCTTCCTCTTCCCCCCAAAACCCAAGGACACCCTCATGATCTCCCGGACCCC
TGAGGTCACGTGCGTGGTGGTGGACGTGAGCCACGAAGACCCCGAGGTCCAGT
TCAACTGGTACGTGGACGGCGTGGAGGTGCATAATGCCAAGACAAAGCCACGG
GAGGAGCAGTTCAACAGCACGTTCCGTGTGGTCAGCGTCCTCACCGTTGTGCA
CCAGGACTGGCTGAACGGCAAGGAGTACAAGTGCAAGGTCTCCAACAAAGGCC
TCCCAGCCCCCATCGAGAAAACCATCTCCAAAACCAAAGGGCAGCCCCGAGAA
CCACAGGTGTACACCCTGCCCCCATCCCGGGAGGAGATGACCAAGAACCAGGT
CAGCCTGACCTGCCTGGTCAAAGGCTTCTACCCCAGCGACATCGCCGTGGAGT
GGGAGAGCAATGGGCAGCCGGAGAACAACTACAAGACCACACCTCCCATGCTG
GACTCCGACGGCTCCTTCTTCCTCTACAGCAAGCTCACCGTGGACAAGAGCAG
GTGGCAGCAGGGGAACGTCTTCTCATGCTCCGTGATGCATGAGGCTCTGCACA
ACCACTACACGCAGAAGAGCCTCTCCCTGTCTCCGGGTAAATGA (SEQ ID NO:61)

Figure 22Q  11.2.1 IgG2 Heavy Chain Protein:

QVQLVESGGGVVQPGRSLRLSCAASGFTFSSYGMHWVRQAPGKGLEWVAVIWY
DGSNKYYADSVKGRFTISRDNSKNTLYLQMNSLRAEDTAVYYCARDPRGATLY
YYYYGMDVWGQGTTVTVSSASTKGPSVFPLAPCSRSTSESTAALGCLVKDYFP
EPVTVSWNSGALTSGVHTFPAVLQSSGLYSLSSVVTVPSSNFGTQTYTCNVDH
KPSNTKVDKTVERKCCVECPPCPAPPVAGPSVFLFPPKPKDTLMISRTPEVTC
VVVDVSHEDPEVQFNWYVDGVEVHNAKTKPREEQFNSTFRVVSVLTVVHQDWL
NGKEYKCKVSNKGLPAPIEKTISKTKGQPREPQVYTLPPSREEMTKNQVSLTC
LVKGFYPSDIAVEWESNGQPENNYKTTPPMLDSDGSFFLYSKLTVDKSRWQQG
NVFSCSVMHEALHNHYTQKSLSLSPGK (SEQ ID NO:70)

Figure 22R  11.2.1 IgG2 Kappa Chain DNA:

ATGGACATGAGGGTCCCCGCTCAGCTCCTGGGGCTCCTGCTACTCT
GGCTCCGAGGTGCCAGATGTGACATCCAGATGACCCAGTCTCCATCCTCC
CTGTCTGCATCTGTAGGAGACAGAGTCACCATCACTTGCCGGGCAAGTCAGAG
CATTAACAGCTATTTAGATTGGTATCAGCAGAAACCAGGGAAAGCCCCTAAAC
TCCTGATCTATGCTGCATCCAGTTTGCAAAGTGGGGTCCCATCAAGGTTCAGT
GGCAGTGGATCTGGGACAGATTTCACTCTCACCATCAGCAGTCTGCAACCTGA
AGATTTTGCAACTTACTACTGTCAACAGTATTACAGTACTCCATTCACTTTCG
GCCCTGGGACCAAAGTGGAAATCAAACGAACTGTGGCTGCACCATCTGTCTTC
ATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGATA
ACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCG
TCACAAAGAGCTTCAACAGGGGAGAGTGTTAGTGA (SEQ ID NO:62)

Figure 22S  11.2.1 IgG2 Kappa Chain Protein:

DIQMTQSPSSLSASVGDRVTITCRASQSINSYLDWYQQKPGKAPKLLIYAASS
LQSGVPSRFSGSGSGTDFTLTISSLQPEDFATYYCQQYYSTPFTFGPGTKVEI
KRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRG
EC (SEQ ID NO:71)

HUMAN MONOCLONAL ANTIBODIES TO CTLA-4

CROSS-REFERENCE TO RELATED APPLICATIONS

The present application is a continuation application of U.S. patent application Ser. No. 11/128,900, filed May 12, 2005, now U.S. Pat. No. 7,411,057 which is a continuation application of U.S. patent application Ser. No. 10/776,649, filed Feb. 10, 2004, issued as U.S. Pat. No. 7,132,281 on Nov. 7, 2006, which is a continuation application of U.S. patent application Ser. No. 10/612,497, filed Jul. 1, 2003, issued as U.S. Pat. No. 7,109,003 on Sep. 19, 2006, which is a continuation application of U.S. patent application Ser. No. 09/472,087, filed Dec. 23, 1999, issued as U.S. Pat. No. 6,682,736 on Jan. 27, 2004, which claims priority to U.S. Provisional Patent Application No. 60/113,647, filed Dec. 23, 1998. The disclosures of all the aforementioned priority applications are incorporated by reference in their entirety herein.

BACKGROUND OF THE INVENTION

1. Summary of the Invention

In accordance with the present invention, there are provided fully human monoclonal antibodies against human cytotoxic T-lymphocyte antigen 4 (CTLA-4). Nucleotide sequences encoding and amino acid sequences comprising heavy and light chain immunoglobulin molecules, particularly contiguous heavy and light chain sequences spanning the complementarity determining regions (CDRs), specifically from within FR1 and/or CDR1 through CDR3 and/or within FR4, are provided. Further provided are antibodies having similar binding properties and antibodies (or other antagonists) having similar functionality as antibodies disclosed herein.

2. Background of the Technology

Regulation of immune response in patients would provide a desirable treatment of many human diseases that could lead to a specificity of action that is rarely found through the use of conventional drugs. Both up-regulation and down-regulation of responses of the immune system would be possible. The roles of T cells and B cells have been extensively studied and characterized in connection with the regulation of immune response. From these studies, the role of T cells appear, in many cases, to be particularly important in disease prevention and treatment.

T cells possess very complex systems for controlling their interactions. Interactions between T cells utilize numerous receptors and soluble factors for the process. Thus, what effect any particular signal may have on the immune response generally varies and depends on the particular factors, receptors and counter-receptors that are involved in the pathway. The pathways for down-regulating responses are as important as those required for activation. Thymic education leading to T-cell tolerance is one mechanism for preventing an immune response to a particular antigen. Other mechanisms, such as secretion of suppressive cytokines, are also known.

Activation of T cells requires not only stimulation through the antigen receptor (T cell receptor (TCR)), but additional signaling through co-stimulatory surface molecules such as CD28. The ligands for CD28 are the B7-1 (CD80) and B7-2 (CD86) proteins, which are expressed on antigen-presenting cells such as dendritic cells, activated B-cells or monocytes that interact with T-cell CD28 or CTLA-4 to deliver a costimulatory signal. The role of costimulatory signaling was studied in experimental allergic encephalomyelitis (EAE) by Perrin et al. *Immunol Res* 14:189-99 (1995). EAE is an autoimmune disorder, induced by Th1 cells directed against myelin antigens that provides an in vivo model for studying the role of B7-mediated costimulation in the induction of a pathological immune response. Using a soluble fusion protein ligand for the B7 receptors, as well as monoclonal antibodies specific for either CD80 or CD86, Perrin et al. demonstrated that B7 costimulation plays a prominent role in determining clinical disease outcome in EAE.

The interaction between B7 and CD28 is one of several co-stimulatory signaling pathways that appear to be sufficient to trigger the maturation and proliferation of antigen specific T-cells. Lack of co-stimulation, and the concomitant inadequacy of IL-2 production, prevent subsequent proliferation of the T cell and induce a state of non-reactivity termed "anergy". A variety of viruses and tumors may block T cell activation and proliferation, leading to insufficient activity or non-reactivity of the host's immune system to the infected or transformed cells. Among a number of possible T-cell disturbances, anergy may be at least partly responsible for the failure of the host to clear the pathogenic or tumorgenic cells.

The use of the B7 protein to mediate anti-tumor immunity has been described in Chen et al. *Cell* 71:1093-1102 (1992) and Townsend and Allison *Science* 259:368 (1993). Schwartz *Cell* 71:1065 (1992) reviews the role of CD28, CTLA-4, and B7 in IL-2 production and immunotherapy. Harding et al. *Nature* 356:607-609 (1994) demonstrates that CD28 mediated signaling co-stimulates murine T cells and prevents the induction of anergy in T cell clones. See also U.S. Pat. Nos. 5,434,131, 5,770,197, and 5,773,253, and International Patent Application Nos. WO 93/00431, WO 95/01994, WO 95/03408, WO 95/24217, and WO 95/33770.

From the foregoing, it was clear that T-cells required two types of signals from the antigen presenting cell (APC) for activation and subsequent differentiation to effector function. First, there is an antigen specific signal generated by interactions between the TCR on the T-cell and MHC molecules presenting peptides on the APC. Second, there is an antigen-independent signal that is mediated by the interaction of CD28 with members of the B7 family (B7-1 (CD80) or B7-2 (CD86)). Exactly where CTLA-4 fit into the milieu of immune responsiveness was initially evasive. Murine CTLA-4 was first identified and cloned by Brunet et al. *Nature* 328:267-270 (1987), as part of a quest for molecules that are preferentially expressed on cytotoxic T lymphocytes. Human CTLA-4 was identified and cloned shortly thereafter by Dariavach et al. *Eur. J Immunol.* 18:1901-1905 (1988). The murine and human CTLA-4 molecules possess approximately 76% overall sequence homology and approach complete sequence identity in their cytoplasmic domains (Dariavach et al. *Eur. J Immunol.* 18:1901-1905 (1988)). CTLA-4 is a member of the immunoglobulin (Ig) superfamily of proteins. The Ig superfamily is a group of proteins that share key structural features of either a variable (V) or constant (C) domain of Ig molecules. Members of the Ig superfamily include, but are not limited to, the immunoglobulins themselves, major histocompatibility complex (MHC) class molecules (i.e., MHC class I and II), and TCR molecules.

In 1991, Linsley et al. *J. Exp. Med.* 174:561-569 (1991), proposed that CTLA-4 was a second receptor for B7. Similarly, Harper et al. *J. Immunol* 147:1037-44 (1991) demonstrated that the CTLA-4 and CD28 molecules are closely related in both mouse and human as to sequence, message expression, gene structure, and chromosomal location. See also Balzano et al. *Int J Cancer Suppl* 7:28-32 (1992). Further evidence of this role arose through functional studies. For example, Lenschow et al. *Science* 257:789-792 (1992) demonstrated that CTLA-4-Ig induced long term survival of pancreatic islet grafts. Freeman et al. *Science* 262:907-909 (1993) examined the role of CTLA-4 in B7 deficient mice. Examination of the ligands for CTLA-4 are described in Lenschow et al. *P.N.A.S.* 90:11054-11058 (1993). Linsley et al. *Science* 257:792-795 (1992) describes immunosuppression in vivo by a soluble form of CTLA-4. Linsley et al. *J Exp Med* 176:1595-604 (1992) prepared antibodies that bound CTLA-4 and that were not cross-reactive with CD28 and concluded that CTLA-4 is coexpressed with CD28 on activated T lymphocytes and cooperatively regulates T cell-adhesion and activation by B7. Kuchroo et al. *Cell* 80:707-18 (1995) demonstrated that the B7-1 and B7-2 costimulatory molecules differentially activated the Th1/Th2 developmental pathways. Yi-qun et al. *Int Immunol* 8:37-44 (1996) demonstrated that there are differential requirements for co-stimulatory signals from B7 family members by resting versus recently activated memory T cells towards soluble recall antigens. See also de Boer et al. *Eur J Immunol* 23:3120-5 (1993).

Several groups proposed alternative or distinct receptor/ligand interactions for CTLA-4 as compared to CD28 and even proposed a third B-7 complex that was recognized by a BB1 antibody. See, for example, Hathcock et al. *Science* 262:905-7 (1993), Freeman et al. *Science* 262:907-9 (1993), Freeman et al. *J Exp Med* 178:2185-92 (1993), Lenschow et al. *Proc Natl Acad Sci USA* 90:11054-8 (1993), Razi-Wolf et al. *Proc Natl Acad Sci USA* 90:11182-6 (1993), and Boussiotis et al. *Proc Natl Acad Sci USA* 90:11059-63 (1993). But, see, Freeman et al. *J Immunol* 161:2708-15 (1998) who discuss finding that BB1 antibody binds a molecule that is identical to the cell surface form of CD74 and, therefore, the BB1 mAb binds to a protein distinct from B7-1, and this epitope is also present on the B7-1 protein. Thus, this observation required the field to reconsider studies using BB1 mAb in the analysis of CD80 expression and function.

Beginning in 1993 and culminating in 1995, investigators began to further delineate the role of CTLA-4 in T-cell stimulation. First, through the use of monoclonal antibodies against CTLA-4, Walunas et al. *Immunity* 1:405-13 (1994) provided evidence that CTLA-4 can function as a negative regulator of T cell activation. Thereafter, Waterhouse et al. *Science* 270:985-988 (1995) demonstrated that mice deficient for CTLA-4 accumulated T cell blasts with up-regulated activation markers in their lymph nodes and spleens. The blast cells also infiltrated liver, heart, lung, and pancreas tissue, and amounts of serum immunoglobulin were elevated and their T cells proliferated spontaneously and strongly when stimulated through the T cell receptor, however, they were sensitive to cell death induced by cross-linking of the Fas receptor and by gamma irradiation. Waterhouse et al. concluded that CTLA-4 acts as a negative regulator of T cell activation and is vital for the control of lymphocyte homeostasis. In a comment in the same issue, Allison and Krummel *Science* 270:932-933 (1995), discussed the work of Waterhouse et al. as demonstrative that CTLA-4 acts to down regulate T-cell responsiveness or has an inhibitory signaling role in T-cell activation and development. Tivol et al. *Immunity* 3:541-7 (1995) also generated CTLA-4-deficient mice and demonstrated that such mice rapidly develop lymphoproliferative disease with multiorgan lymphocytic infiltration and tissue destruction, with particularly severe myocarditis and pancreatitis. They concluded that CTLA-4 plays a key role in down-regulating T cell activation and maintaining immunologic homeostasis. Also, Krummel and Allison *J Exp Med* 182:459-65 (1995) further clarified that CD28 and CTLA-4 have opposing effects on the response of T cells to stimulation. They generated an antibody to CTLA-4 and investigated the effects of its binding to CTLA-4 in a system using highly purified T cells. In their report, they showed that the presence of low levels of B7-2 on freshly explanted T cells can partially inhibit T cell proliferation, and this inhibition was mediated by interactions with CTLA-4. Cross-linking of CTLA-4 together with the TCR and CD28 strongly inhibits proliferation and IL-2 secretion by T cells. Finally, the results showed that CD28 and CTLA-4 deliver opposing signals that appear to be integrated by the T cell in determining the response to antigen. Thus, they concluded that the outcome of T cell antigen receptor stimulation is regulated by CD28 costimulatory signals, as well as inhibitory signals derived from CTLA-4. See also Krummel et al. *Int Immunol* 8:519-23 (1996) and U.S. Pat. No. 5,811,097 and International Patent Application No. WO 97/20574.

A variety of additional experiments have been conducted further elucidating the above function of CTLA-4. For example, Walunas et al. *J Exp Med* 183:2541-50 (1996), through the use of anti-CTLA-4 antibodies, suggested that CTLA-4 signaling does not regulate cell survival or responsiveness to IL-2, but does inhibit CD28-dependent IL-2 production. Also, Perrin et al. *J Immunol* 157:1333-6 (1996), demonstrated that anti-CTLA-4 antibodies in experimental allergic encephalomyelitis (EAE), exacerbated the disease and enhanced mortality. Disease exacerbation was associated with enhanced production of the encephalitogenic cytokines TNF-alpha, IFN-gamma and IL-2. Thus, they concluded that CTLA-4 regulates the intensity of the autoimmune response in EAE, attenuating inflammatory cytokine production and clinical disease manifestations. See also Hurwitz et al. *J Neuroimmunol* 73:57-62 (1997) and Cepero et al. *J Exp Med* 188:199-204 (1998) (an anti-CTLA-4 hairpin ribozyme that specifically abrogates CTLA-4 expression after gene transfer into a murine T-cell model).

In addition, Blair et al. *J Immunol* 160:12-5 (1998) assessed the functional effects of a panel of CTLA-4 monoclonal antibodies (mAbs) on resting human CD4+ T cells. Their results demonstrated that some CTLA-4 mAbs could inhibit proliferative responses of resting CD4+ cells and cell cycle transition from G0 to G1. The inhibitory effects of CTLA-4 were evident within 4 h, at a time when cell surface CTLA-4 expression remained undetectable. Other CTLA-4 mAbs, however, had no detectable inhibitory effects, indicating that binding of mAbs to CTLA-4 alone was not sufficient to mediate down-regulation of T cell responses. Interestingly, while IL-2 production was shut off, inhibitory anti-CTLA-4 mAbs permitted induction and expression of the cell survival gene bcl-X(L). Consistent with this observation, cells remained viable and apoptosis was not detected after CTLA-4 ligation.

In connection with anergy, Perez et al. *Immunity* 6:411-7 (1997) demonstrated that the induction of T cell anergy was prevented by blocking CTLA-4 and concluded that the outcome of antigen recognition by T cells is determined by the interaction of CD28 or CTLA-4 on the T cells with B7 molecules. Also, Van Parijs et al. *J Exp Med* 186:1119-28 (1997) examined the role of interleukin 12 and costimulators in T cell anergy in vivo and found that through inhibiting CTLA-4 engagement during anergy induction, T cell proliferation was blocked, and full Th1 differentiation was not promoted. However, T cells exposed to tolerogenic antigen in the presence of both IL-12 and anti-CTLA-4 antibody were not anergized, and behaved identically to T cells which have encountered immunogenic antigen. These results suggested that two processes contribute to the induction of anergy in vivo: CTLA-4 engagement, which leads to a block in the ability of T cells to proliferate, and the absence of a prototypic inflammatory cytokine, IL-12, which prevents the differentiation of T cells into Th1 effector cells. The combination of IL-12 and anti-CTLA-4 antibody was sufficient to convert a normally tolerogenic stimulus to an immunogenic one.

In connection with infections, McCoy et al. *J Exp Med* 186:183-7 (1997) demonstrated that anti-CTLA-4 antibodies greatly enhanced and accelerated the T cell immune response to *Nippostrongylus brasiliensis*, resulting in a profound reduction in adult worm numbers and early termination of parasite egg production. See also Murphy et al. *J Immunol.* 161:4153-4160 (1998) (*Leishmania donovani*).

In connection with cancer, Kwon et al. *PNAS USA* 94:8099-103 (1997) established a syngeneic murine prostate cancer model and examined two distinct manipulations intended to elicit an antiprostate cancer response through enhanced T cell costimulation: (i) provision of direct costimulation by prostate cancer cells transduced to express the B7.1 ligand and (ii) in vivo antibody-mediated blockade of T cell CTLA-4, which prevents T cell down-regulation. It was demonstrated that in vivo antibody-mediated blockade of CTLA-4 enhanced antiprostate cancer immune responses. Also, Yang et al. *Cancer Res* 57:4036-41 (1997) investigated whether the blockade of the CTLA-4 function leads to enhancement of antitumor T cell responses at various stages of tumor growth. Based on in vitro and in vivo results they found that CTLA-4 blockade in tumor-bearing individuals enhanced the capacity to generate antitumor T-cell responses, but the expression of such an enhancing effect was restricted to early stages of tumor growth in their model. Further, Hurwitz et al. *Proc Natl Acad Sci USA* 95:10067-71 (1998) investigated the generation of a T cell-mediated antitumor response depends on T cell receptor engagement by major histocompatibility complex/antigen as well as CD28 ligation by B7. Certain tumors, such as the SM1 mammary carcinoma, were refractory to anti-CTLA-4 immunotherapy. Thus, through use of a combination of CTLA-4 blockade and a vaccine consisting of granulocyte-macrophage colony-stimulating factor-expressing SM1 cells, regression of parental SM1 tumors was observed, despite the ineffectiveness of either treatment alone. This combination therapy resulted in long-lasting immunity to SM1 and depended on both CD4(+) and CD8(+) T cells. The findings suggested that CTLA-4 blockade acts at the level of a host-derived antigen-presenting cell.

In connection with diabetes, Luhder et al. *J Exp Med* 187: 427-32 (1998) injected an anti-CTLA-4 mAb into a TCR transgenic mouse model of diabetes at different stages of disease. They found that engagement of CTLA-4 at the time when potentially diabetogenic T cells are first activated is a pivotal event; if engagement is permitted, invasion of the islets occurs, but remains quite innocuous for months. If not, insulitis is much more aggressive, and diabetes quickly ensues.

In connection with vaccine immunization, Horspool et al. *J Immunol* 160:2706-14 (1998) found that intact anti-CTLA-4 mAb but not Fab fragments suppressed the primary humoral response to pCIA/beta gal without affecting recall responses, indicating CTLA-4 activation inhibited Ab production but not T cell priming. Blockade of the ligands for CD28 and CTLA-4, CD80 (B7-1) and CD86 (B7-2), revealed distinct and non-overlapping function. Blockade of CD80 at initial immunization completely abrogated primary and secondary Ab responses, whereas blockade of CD86 suppressed primary but not secondary responses. Simultaneous blockade of CD80+CD86 was less effective at suppressing Ab responses than either alone. Enhancement of costimulation via coinjection of B7-expressing plasmids augmented CTL responses but not Ab responses, and without evidence of Th1 to Th2 skewing. These findings suggest complex and distinct roles for CD28, CTLA-4, CD80, and CD86 in T cell costimulation following nucleic acid vaccination.

In connection with allograft rejection, Markees et al. *J Clin Invest* 101:2446-55 (1998) found in a mouse model of skin allograft rejection that acceptance initially depended on the presence of IFN-gamma, CTLA-4, and CD4(+) T cells. Addition of anti-CTLA-4 or anti-IFN-gamma mAb to the protocol was associated with prompt graft rejection, whereas anti-IL-4 mAb had no effect.

In connection with the role of CTLA-4 in relation to CD28, Fallarino et al. *J Exp Med* 188:205-10 (1998) generated TCR transgenic/recombinase activating gene 2-deficient/CD28-wild-type or CD28-deficient mice which were immunized with an antigen-expressing tumor. Primed T cells from both types of mice produced cytokines and proliferated in response to stimulator cells lacking B7 expression. However, whereas the response of CD28+/+ T cells was augmented by costimulation with B7-1, the response of the CD28-/- T cells was strongly inhibited. This inhibition was reversed by monoclonal antibody against B7-1 or CTLA-4. Thus, CTLA-4 can potently inhibit T cell activation in the absence of CD28, indicating that antagonism of a TCR-mediated signal is sufficient to explain the inhibitory effect of CTLA-4. Also, Lin et al. *J Exp Med* 188:199-204 (1998) studied rejection of heart allografts in CD28-deficient mice. H-2(q) hearts were transplanted into allogeneic wild-type or CD28-deficient mice (H-2(b)). Graft rejection was delayed in CD28-deficient compared with wild-type mice. Treatment of wild-type recipients with CTLA-4-immunoglobulin (Ig), or with anti-B7-1 plus anti-B7-2 mAbs significantly prolonged allograft survival. In contrast, treatment of CD28-deficient mice with CTLA-4-Ig, anti-B7-1 plus anti-B7-2 mAbs, or a blocking anti-CTLA-4 mAb induced acceleration of allograft rejection. This increased rate of graft rejection was associated with more severe mononuclear cell infiltration and enhanced levels of IFN-gamma and IL-6 transcripts in donor hearts of untreated wild-type and CTLA-4-Ig- or anti-CTLA-4 mAb-treated CD28-deficient mice. Thus, the negative regulatory role of CTLA-4 extends beyond its potential ability to prevent CD28 activation through ligand competition. Even in the absence of CD28, CTLA-4 plays an inhibitory role in the regulation of allograft rejection.

Also, further characterization of the expression of CTLA-4 has been investigated. For example, Alegre et al. *J Immunol* 157:4762-70 (1996) proposed that surface CTLA-4 is rapidly internalized, which may explain the low levels of expression generally detected on the cell surface. They concluded that both CD28 and IL-2 play important roles in the up-regulation of CTLA-4 expression. In addition, the cell surface accumulation of CTLA-4 appeared to be primarily regulated by its rapid endocytosis. Also, Castan et al. *Immunology* 90:265-71 (1997) based on in situ immunohistological analyses of the expression of CTLA-4, suggested that germinal center T cells, which were CTLA-4 positive, could be important to immune regulation.

Accordingly, in view of the broad and pivotal role that CTLA-4 appears to possess in immune responsiveness, it would be desirable to generate antibodies to CTLA-4 that can be utilized effectively in immunotherapy. Moreover, it would be desirable to generate antibodies against CTLA-4 that can be utilized in chronic diseases in which repeat administrations of the antibodies are required.

BRIEF DESCRIPTION OF THE DRAWING FIGURES

FIG. 1 provides a series of nucleotide and an amino acid sequences of heavy chain and kappa light chain immunoglobulin molecules in accordance with the invention: 4.1.1 (FIG. 1A), 4.8.1 (FIG. 1B), 4.14.3 (FIG. 1C), 6.1.1 (FIG. 1D), 3.1.1 (FIG. 1E), 4.10.2 (FIG. 1F), 2.1.3 (FIG. 1G), 4.13.1 (FIG. 1H), 11.2.1 (FIG. 1I), 11.6.1 (FIG. 1J), 11.7.1 (FIG. 1K), 12.3.1.1 (FIG. 1L), and 12.9.1.1 (FIG. 1M).

FIG. 2 provides a sequence alignment between the predicted heavy chain amino acid sequences from the clones 4.1.1 (SEQ ID NO: 74), 4.8.1 (SEQ ID NO: 75), 4.14.3 (SEQ ID NO: 78), 6.1.1 (SEQ ID NO: 79), 3.1.1 (SEQ ID NO: 73), 4.10.2 (SEQ ID NO: 76), 4.13.1 (SEQ ID NO: 77), 11.2.1 (SEQ ID NO: 80), 11.6.1 (SEQ ID NO: 81), 11.7.1 (SEQ ID NO: 82), 12.3.1.1 (SEQ ID NO: 83), and 12.9.1.1 (SEQ ID NO: 84) and the germline DP-50 (3-33) amino acid sequence (SEQ ID NO: 72). Differences between the DP-50 germline sequence and that of the sequence in the clones are indicated in bold. The FIG. also shows the positions of the CDR1, CDR2, and CDR3 sequences of the antibodies as shaded.

FIG. 3 provides a sequence alignment between the predicted heavy chain amino acid sequence of the clone 2.1.3 (SEQ ID NO: 86) and the germline DP-65 (4-31) amino acid sequence (SEQ ID NO: 85). Differences between the DP-65 germline sequence and that of the sequence in the clone are indicated in bold. The FIG. also shows the positions of the CDR1, CDR2, and CDR3 sequences of the antibody as underlined.

FIG. 4 provides a sequence alignment between the predicted kappa light chain amino acid sequence of the clones 4.1.1 (SEQ ID NO: 88), 4:8.1 (SEQ ID NO: 89), 4.14.3 (SEQ ID NO: 90), 6.1.1 (SEQ ID NO: 91), 4.10.2 (SEQ ID NO: 92), and 4.13.1 (SEQ ID NO: 93) and the germline A27 amino acid sequence (SEQ ID NO: 87). Differences between the A27 germline sequence and that of the sequence in the clone are indicated in bold. The FIG. also shows the positions of the CDR 1, CDR2, and CDR3 sequences of the antibody as underlined. Apparent deletions in the CDR1s of clones 4.8.1, 4.14.3, and 6.1.1 are indicated with "0s".

FIG. 5 provides a sequence alignment between the predicted kappa light chain amino acid sequence of the clones 3.1.1 (SEQ ID NO: 95), 11.2.1 (SEQ ID NO: 96), 11.6.1 (SEQ ID NO: 97), and 11.7.1 (SEQ ID NO: 98) and the germline 012 amino acid sequence (SEQ ID NO: 94). Differences between the 012 germline sequence and that of the sequence in the clone are indicated in bold. The FIG. also shows the positions of the CDR1, CDR2, and CDR3 sequences of the antibody as underlined.

FIG. 6 provides a sequence alignment between the predicted kappa light chain amino acid sequence of the clone 2.1.3 (SEQ ID NO: 112) and the germline A10/A26 amino acid sequence (SEQ ID NO: 99). Differences between the A10/A26 germline sequence and that of the sequence in the clone are indicated in bold. The FIG. also shows the positions of the CDR1, CDR2, and CDR3 sequences of the antibody as underlined.

FIG. 7 provides a sequence alignment between the predicted kappa light chain amino acid sequence of the clone 12.3.1 (SEQ ID NO: 114) and the germline A17 amino acid sequence (SEQ ID NO: 113). Differences between the A17 germline sequence and that of the sequence in the clone are indicated in bold. The FIG. also shows the positions of the CDR1, CDR2, and CDR3 sequences of the antibody as underlined.

FIG. 8 provides a sequence alignment between the predicted kappa light chain amino acid sequence of the clone 12.9.1 (SEQ ID NO: 116) and the gennline A3/A19 amino acid sequence (SEQ ID NO: 115). Differences between the A3/A19 germline sequence and that of the sequence in the clone are indicated in bold. The FIG. also shows the positions of the CDR1, CDR2, and CDR3 sequences of the antibody as underlined.

FIG. 9 provides a summary of N-terminal amino acid sequences generated through direct protein sequencing of the heavy and light chains of the antibodies.

FIG. 10 provides certain additional characterizing information about certain of the antibodies in accordance with the invention. In FIG. 10A, data related to clones 3.1.1, 4.1.1, 4.8.1, 4.10.2, 4.14.3, and 6.1.1 is summarized. Data related to concentration, isoelectric focusing (IEF), SDS-PAGE, size exclusion chromatography, liquid chromatography/mass spectroscopy (LCMS), mass spectroscopy (MALDI), light chain N-terminal sequences is provided. Additional detailed information related to IEF is provided in FIG. 10B; related to SDS-PAGE is provided in 10C; and SEC of the 4.1.1 antibody in 10D.

Figure 10D:
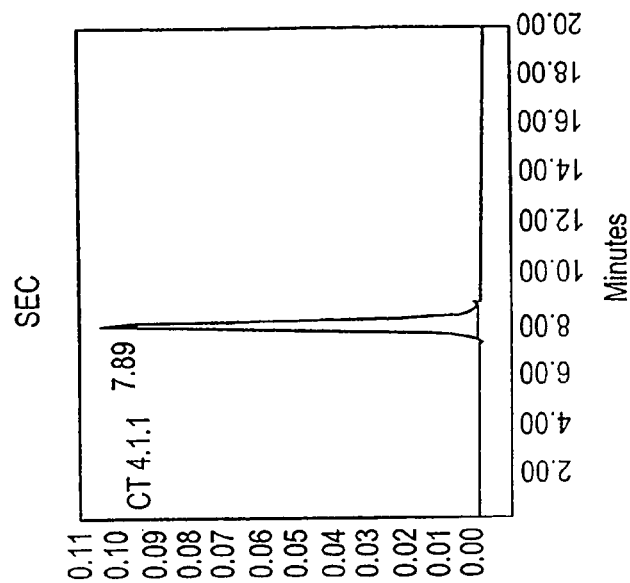

FIG. 22 provides a series of additional nucleotide and amino acid sequences of the following anti-CTLA-4 antibody chains: full length 4.1.1 heavy chain (cDNA 22(a), genomic 22(b), and amino acid 22(c)), full length aglycosylated 4.1.1 heavy chain (cDNA 22(d) and amino acid 22(e)), 4.1.1 light chain (cDNA 22(f) and amino acid 22(g)), full length 4.8.1 heavy chain (cDNA 22(h) and amino acid 22(i)), 4.8.1 light chain (cDNA 22(j) and amino acid 22(k)), full length 6.1.1 heavy chain (cDNA 22(l) and amino acid 22(m)), 6.1.1 light chain (cDNA 22(n) and amino acid 22(o)), full length 11.2.1 heavy chain (cDNA 22(p) and amino acid 22(q)), and 11.2.1 light chain (cDNA 22(r) and amino acid 22(s)).

SUMMARY OF THE INVENTION

In accordance with a first aspect of the present invention, there is provided an antibody that is capable of binding CTLA-4, comprising a heavy chain variable region amino acid sequence that comprises a contiguous amino acid sequence from within an FR1 sequence through an FR3 sequence that is encoded by a human $V_H3$-33 family gene and that comprises at least one of the amino acid substitutions in the CDR1 sequences, CDR2sequences, or framework sequences shown in FIG. 2. In a preferred embodiment, the amino acid sequence comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:63, SEQ ID NO:64, SEQ ID NO:66, SEQ ID NO:68, and SEQ ID NO:70. In another preferred embodiment, the antibody further comprises a light chain variable region amino acid sequence comprising a sequence selected from the group consisting of a sequence comprising SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:65, SEQ ID NO:67, SEQ ID NO:69, and SEQ ID NO:71.

In accordance with a second aspect of the present invention, there is provided an antibody comprising a heavy chain amino acid sequence comprising SEQ ID NO: 1 and a light chain variable amino acid sequence comprising SEQ ID NO: 14.

In accordance with a third aspect of the present invention, there is provided an antibody comprising a heavy chain amino acid sequence comprising SEQ ID NO:2 and a light chain variable amino acid sequence comprising SEQ ID NO:15.

In accordance with a fourth aspect of the present invention, there is provided an antibody comprising a heavy chain amino acid sequence comprising SEQ ID NO:4 and a light chain variable amino acid sequence comprising SEQ ID NO: 17.

In accordance with a fifth aspect of the present invention, there is provided an isolated human monoclonal antibody that is capable of binding to CTLA-4. In a preferred embodiment, antibody is capable of competing for binding with CTLA-4 with an antibody selected from the group consisting of 3.1.1, 4.1.1, 4.8.1, 4.10.2, 4.13.1, 4.14.3, 6.1.1, 11.2.1, 11.6.1, 11.7.1, 12.3.1.1, and 12.9.1.1. In another preferred embodiment, the antibody possesses a substantially similar binding specificity to CTLA-4 as an antibody selected from the group consisting of 3.1.1, 4.1.1, 4.8.1, 4.10.2, 4.13.1, 4.14.3, 6.1.1, 11.2.1, 111.6.1, 11.7.1, 12.3.1.1, and 12.9.1.1. In another preferred embodiment, the antibody is selected from the group consisting of 3.1.1, 4.1.1, 4.8.1, 4.10.2, 4.13.1, 4.14.3, 6.1.1, 11.2.1, 11.6.1, 11.7.1, 12.3.1.1, and 12.9.1.1. In another preferred embodiment, the antibody is not cross reactive with CTLA-4 from lower mammalian species, preferably the lower mammalian species comprises mouse, rat, and rabbit and more preferably mouse and rat. In another preferred embodiment, the antibody is cross reactive with CTLA-4 from primates, preferably the primates comprise cynomolgous and rhesus monkeys. In another preferred embodiment, the antibody possesses a selectivity for CTLA-4 over CD28, B7-2, CD44, and hIgG1 of greater than about 100:1 and preferably about 500:1 or greater. In another preferred embodiment, the binding affinity of the antibody is about $10^{-9}$ M or greater and preferably about $10^{-10}$ M or greater. In another preferred embodiment, the antibody inhibits binding between CTLA-4 and B7-2 with an $IC_{50}$ of lower than about 100 nM and preferably lower than about 0.38 nM. In another preferred embodiment, the antibody inhibits binding between CTLA-4 and B7-1 with an $IC_{50}$ of lower than about 100 nM or greater and preferably lower than about 0.50 nM. In another preferred embodiment, the antibody enhances IL-2 production in a T cell blast/Raji assay by about 500 pg/ml or greater and preferably by about 3846 pg/ml or greater. In another preferred embodiment, the antibody enhances IFN-γ production in a T cell blast/Raji assay by about 500 pg/ml or greater and preferably by about 1233 pg/ml or greater. In another preferred embodiment, the antibody enhances IL-2 production in a hPBMC or whole blood superantigen assay by about 500 pg/ml or greater. In another preferred embodiment, the antibody enhances IL-2 production in a hPBMC or whole blood superantigen assay by about 500 pg/ml or preferably 1500 pg/ml or greater or by greater than about 30% or preferably 50% relative to control.

In accordance with a sixth aspect of the present invention, there is provided a humanized antibody that possesses a substantially similar binding specificity to CTLA-4 as an antibody selected from the group consisting of 3.1.1, 4.1.1, 4.8.1, 4.10.2, 4.13.1, 4.14.3, 6.1.1, 11.2.1, 11.6.1, 11.7.1, 12.3.1.1, and 12.9.1.1. In a preferred embodiment, the antibody is not cross reactive with CTLA-4 from lower mammalian species, preferably the lower mammalian species comprises mouse, rat, and rabbit and preferably mouse and rat. In another preferred embodiment, the antibody is cross reactive with CTLA-4 from primates, preferably the primates comprise cynomolgous and rhesus monkeys. In another preferred embodiment, the antibody possesses a selectivity for CTLA-4 over CD28, B7-2, CD44, and hIgG1 of greater than about 100:1 and preferably about 500:1 or greater. In another preferred embodiment, the binding affinity of the antibody is about $10^{-9}$ M or greater and preferably about $10^{-10}$ M or greater. In another preferred embodiment, the antibody inhibits binding between CTLA-4 and B7-2 with an $IC_{50}$ of lower than about 100 nM and preferably lower than about 0.38 nM. In another preferred embodiment, the antibody inhibits binding between CTLA-4 and B7-1 with an $IC_{50}$ of lower than about 100 nM or greater and preferably lower than about 0.50 nM. In another preferred embodiment, the antibody enhances IL-2 production in a T cell blast/Raji assay by about 500 pg/ml or greater and preferably by about 3846 pg/ml or greater. In another preferred embodiment, the antibody enhances IFN-γ production in a T cell blast/Raji assay by about 500 pg/ml or greater and preferably by about 1233 pg/ml or greater. In another preferred embodiment, the antibody induces IL-2 production in a hPBMC or whole blood superantigen assay by about 500 pg/ml or greater. In another preferred embodiment, the antibody enhances IL-2 production in a hPBMC or whole blood superantigen assay by about 500 pg/ml or preferably 1500 pg/ml or greater or by greater than about 30% or preferably 50% relative to control.

In accordance with a seventh aspect of the present invention, there is provided an antibody that binds to CTLA-4, comprising a heavy chain amino acid sequence comprising human FR1, FR2, and FR3 sequences encoded by a human $V_H3$-33 gene family operably linked in frame with a CDR1, a CDR2, and a CDR3 sequence, the CDR1, CDR2, and CDR3 sequences being independently selected from the CDR1, CDR2, and CDR3 sequences illustrated in FIG. 2. In a preferred embodiment, the antibody of claim 32, further comprising any of the somatic mutations to the FR1, FR2, and FR3 sequences as illustrated in FIG. 2.

In accordance with an eighth aspect of the present invention, there is provided an antibody that binds to CTLA-4, comprising a heavy chain amino acid sequence comprising human FR1, FR2, and FR3 sequences encoded by a human $V_H3$-33 gene family operably linked in frame with a CDR1, a CDR2, and a CDR3 sequence, which antibody has the following properties: a binding affinity for CTLA-4 of about $10^{-9}$ or greater; inhibits binding between CTLA-4 and B7-1 with an $IC_{50}$ of about 100 nM or lower; inhibits binding between CTLA-4 and B7-2 with an $IC_{50}$ of about 100 nM or lower; and enhances cytokine production in an assay of human T cells by 500 pg/ml or greater.

In accordance with a ninth aspect of the present invention, there is provided an antibody that binds to CTLA-4, comprising a heavy chain amino acid sequence comprising FR1, FR2, and FR3 sequences operably linked in frame with a CDR1, a CDR2, and a CDR3 sequence independently selected from the CDR1, CDR2, and CDR3 sequences illustrated in FIGS. 2 and 3, which antibody has the following properties: a binding affinity for CTLA-4 of about $10^{-9}$ or greater; inhibits binding between CTLA-4 and B7-1 with an $IC_{50}$ of about 100 nM or lower; inhibits binding between CTLA-4 and B7-2 with an $IC_{50}$ of about 100 nM or lower; and enhances cytokine production in an assay of human T cells by 500 pg/ml or greater.

In accordance with a tenth aspect of the present invention, there is provided a cell culture system for assaying T cell stimulation, comprising a culture of human T cell blasts co-cultured with a Raji cell line. In a preferred embodiment, the T cell blasts are washed prior to culture with the Raji cell line.

In accordance with an eleventh aspect of the present invention, there is provided an assay for measuring T cell stimulation, comprising: providing a culture of human T cell blasts and a Raji cell line; contacting the culture with an agent; and measuring cytokine production by the culture.

In accordance with an twelfth aspect of the present invention, there is provided a functional assay for screening a moiety for T cell stimulatory function, comprising: providing a culture of human T cell blasts and a Raji cell line; contacting the culture with the moiety; and assessing cytokine production by the culture.

In accordance with a thirteenth aspect of the present invention, there is provided a T cell stimulatory assay for CTLA-4 inhibitory function, comprising contacting a culture comprising human T cell blasts and a Raji cell line with an agent and assessing cytokine production by the culture.

In accordance with a fourteenth aspect of the present invention, there is provided a method for screening an agent for T cell stimulatory activity, comprising: contacting the agent with a cell culture comprising human T cell blasts and a Raji cell line; and assessing cytokine production by the culture.

In each of the tenth through the fourteenth aspects of the present invention, in a preferred embodiment, the T cell blasts are washed prior to culture with the Raji cell line. In another preferred embodiment, the cytokine is IL-2 or IFN-γ. In a preferred embodiment, cytokine production is measured in supernatant isolated from the culture. In a preferred embodiment, the agent is an antibody and preferably binds to CTLA-4.

In accordance with a fifteenth aspect of the present invention, there is provided an assay for measuring T cell stimulation, comprising: providing a population of human peripheral blood mononuclear cells or human whole blood stimulated with *staphylococcus* enterotoxin A; contacting the culture with an agent; and measuring cytokine production by the cell population.

In accordance with a sixteenth aspect of the present invention, there is provided a functional assay for screening a moiety for T cell stimulatory function, comprising: providing a population of human peripheral blood mononuclear cells or human whole blood stimulated with *staphylococcus* enterotoxin A; contacting the culture with the moiety; and assessing cytokine production by the cell population.

In accordance with a seventeenth aspect of the present invention, there is provided a T cell stimulatory assay for CTLA-4 inhibitory function, comprising contacting a population of human peripheral blood mononuclear cells or human whole blood stimulated with *staphylococcus* enterotoxin A with an agent and assessing cytokine production by the cell population.

In accordance with an eighteenth aspect of the present invention, there is provided a method for screening an agent for T cell stimulatory activity, comprising: contacting the agent with a population of human peripheral blood mononuclear cells or human whole blood stimulated with *staphylococcus* enterotoxin A; and assessing cytokine production by the cell population.

In each of the fifteenth through the eighteenth aspects of the present invention, in a preferred embodiment, the cytokine is IL-2. In another preferred embodiment, cytokine production is measured in supernatant isolated from the culture. In a preferred embodiment, the agent is an antibody and preferably binds to CTLA-4.

DETAILED DESCRIPTION OF THE PREFERRED EMBODIMENTS

In accordance with the present invention, there are provided fully human monoclonal antibodies against human CTLA-4. Nucleotide sequences encoding and amino acid sequences comprising heavy and light chain immunoglobulin molecules, particularly sequences corresponding to a contiguous heavy and light chain sequences from FR1 and CDR1 through CDR3 and FR4, are provided. Further provided are antibodies having similar binding properties and antibodies (or other antagonists) having similar functionality as antibodies disclosed herein; Hybridomas expressing such immunoglobulin molecules and monoclonal antibodies are also provided.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" as used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules represented in FIG. 1, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoranilladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology-A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino-acid-substitutions. Conservative amino-acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to CTLA-4, under suitable binding conditions, (2) ability to block CTLA-4 binding with its receptors, or (3) ability to inhibit CTLA-4 expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drus with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). In addition, bispecific antibodies may be formed as "diabodies" (Holliger et al. "'Diabodies': small bivalent and bispecific antibody fragments" *PNAS USA* 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce antibodies having fully human sequences.

Human Antibodies

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs) an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. *Nature Genetics* 7:13-21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J. Exp. Med.* 188:483-495 (1998), and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15,1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International U.S. patent application Ser. Nos. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against CTLA-4 in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris *Immunol Today* 14:43-46 (1993) and Wright et al. *Crit. Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG2, IgG3 and IgG4. Particularly preferred isotypes for antibodies of the invention are IgG2 and IgG4. Either of the human light chain constant regions, kappa or lambda, may be used. The chimeric, humanized antibody is then expressed by conventional methods.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. *Mol. Cell. Bio.* 3:280 (1983)), Rous sarcoma virus LTR (Gorman et al. *P.N.A.S.* 79:6777 (1982)), and moloney murine leukemia virus LTR (Grosschedl et al. *Cell* 41:885 (1985)); native Ig promoters, etc.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau *PNAS USA* 94:4937-4942 (1997) (ribosomal display), Parmley and Smith *Gene* 73:305-318 (1988) (phage display), Scott *TIBS* 17:241-245 (1992), Cwirla et al. *PNAS USA* 87:6378-6382 (1990), Russel et al. *Nucl. Acids Research* 21:1081-1085 (1993), Hoganboom et al. *Immunol. Reviews* 130:43-68 (1992), Chiswell and McCafferty *TIBTECH* 10:80-84 (1992), and U.S. Pat. No. 5,733,743. If display technologies are utilized to produce antibodies that are not human, such antibodies can be humanized as described above.

Using these techniques, antibodies can be generated to CTLA-4 expressing cells, CTLA-4 itself, forms of CTLA-4, epitopes or peptides thereof, and expression libraries thereto (see e.g. U.S. Pat. No. 5,703,057) which can thereafter be screened as described above for the activities described above.

Additional Criteria for Antibody Therapeutics

As will be appreciated, it is generally not desirable to kill CTLA-4 expressing cells. Rather, one generally desires to simply inhibit CTLA-4 binding with its ligands to mitigate T cell down regulation. One of the major mechanisms through which antibodies kill cells is through fixation of complement and participation in CDC. The constant region of an antibody plays an important role in connection with an antibody's ability to fix complement and participate in CDC. Thus, generally one selects the isotype of an antibody to either provide the ability of complement fixation, or not. In the case of the present invention, generally, as mentioned above, it is generally not preferred to utilize an antibody that kills the cells. There are a number of isotypes of antibodies that are capable of complement fixation and CDC, including, without limitation, the following: murine IgM, murine IgG2a, murine IgG2b, murine IgG3, human IgM, human IgG1, and human IgG3. Those isotypes that do not include, without limitation, human IgG2 and human IgG4.

It will be appreciated that antibodies that are generated need not initially possess a particular desired isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. patent application Ser. No. 08/730,639, filed Oct. 11, 1996), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the majority of the CTLA-4 antibodies discussed herein are human anti-CTLA-4 IgG2 antibody. Since such antibodies possess desired binding to the CTLA-4 molecule, any one of such antibodies can be readily isotype switched to generate a human IgG4 isotype, for example, while still possessing the same variable region (which defines the antibody's specificity and some of its affinity).

Accordingly, as antibody candidates are generated that meet desired "structural" attributes as discussed above, they can generally be provided with at least certain additional "functional" attributes that are desired through isotype switching.

Design and Generation of Other Therapeutics

In accordance with the present invention and based on the activity of the antibodies that are produced and characterized herein with respect to CTLA-4, the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunotoxins, and radiolabeled therapeutics, generation of peptide therapeutics, gene therapies, particularly intrabodies, antisense therapeutics, and small molecules. Furthermore, as discussed above, the effector function of the antibodies of the invention may be changed by isotype switching to an IgG1, IgG2, IgG3, IgG4, IgD, IgA, IgE, or IgM for various therapeutic uses.

In connection with the generation of advanced antibody therapeutics, where complement fixation is a desirable attribute, it may be possible to sidestep the dependence on complement for cell killing through the use of bispecifics, immunotoxins, or radiolabels, for example.

In connection with bispecific antibodies, bispecific antibodies can be generated that comprise (i) two antibodies one with a specificity to CTLA-4 and another to a second molecule that are conjugated together, (ii) a single antibody that has one chain specific to CTLA-4 and a second chain specific to a second molecule, or (iii) a single chain antibody that has specificity to CTLA-4 and the other molecule. Such bispecific antibodies can be generated using techniques that are well known for example, in connection with (i) and (ii) see e.g., Fanger et al. *Immunol Methods* 4:72-81 (1994) and Wright and Harris, supra. and in connection with (iii) see e.g., Traunecker et al. *Int. J Cancer (Suppl.)* 7:51-52 (1992).

In addition, "Kappabodies" (III et al. "Design and construction of a hybrid immunoglobulin domain with properties of both heavy and light chain variable regions" *Protein Eng* 10:949-57 (1997)), "Minibodies" (Martin et al. "The affinity-selection of a minibody polypeptide inhibitor of human interleukin-6" *EMBO J* 13:5303-9 (1994)), "Diabodies" (Holliger et al. "'Diabodies': small bivalent and bispecific antibody fragments" *PNAS USA* 90:6444-6448 (1993)), or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52 (1992)) may also be prepared.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing CTLA-4, and particularly those cells in which the antibodies of the invention are effective.

In connection with the generation of therapeutic peptides, through the utilization of structural information related to CTLA-4 and antibodies thereto, such as the antibodies of the invention (as discussed below in connection with small molecules) or screening of peptide libraries, therapeutic peptides can be generated that are directed against CTLA-4. Design and screening of peptide therapeutics is discussed in connection with Houghten et al. *Biotechniques* 13:412-421 (1992), Houghten *PNAS USA* 82:5131-5135 (1985), Pinalla et al. *Biotechniques* 13:901-905 (1992), Blake and Litzi-Davis *BioConjugate Chem.* 3:510-513 (1992). Immunotoxins and radiolabeled molecules can also be prepared, and in a similar manner, in connection with peptidic moieties as discussed above in connection with antibodies.

Important information related to the binding of an antibody to an antigen can be gleaned through phage display experimentation. Such experiments are generally accomplished through panning a phage library expressing random peptides for binding with the antibodies of the invention to determine if peptides can be isolated that bind. If successful, certain epitope information can be gleaned from the peptides that bind.

In general, phage libraries expressing random peptides can be purchased from New England Biolabs (7-mer and 12-mer libraries, Ph.D.-7 Peptide 7-mer Library Kit and Ph.D.-12 Peptide 12-mer Library Kit, respectively) based on a bacteriophage M13 system. The 7-mer library represents a diversity of approximately $2.0 \times 10^9$ independent clones, which represents most, if not all, of the $20^7 = 1.28 \times 10^9$ possible 7-mer sequences. The 12-mer library contains approximately $1.9 \times 10^9$ independent clones and represents only a very small sampling of the potential sequence space of $20^{12} = 4.1 \times 10^{15}$ 12-mer sequences. Each of 7-mer and 12-mer libraries are panned or screened in accordance with the manufacturer's recommendations in which plates were coated with an antibody to capture the appropriate antibody (a goat anti-human IgG Fc for an IgG antibody for example) followed by washing. Bound phage are eluted with 0.2 M glycine-HCl, pH 2.2. After 3 rounds of selection/amplification at constant stringency (0.5% Tween), through use of DNA sequencing, one can characterize clones from the libraries that are reactive with one or more of the antibodies. Reactivity of the peptides can be determined by ELISA. For an additional discussion of epitope analysis of peptides see also Scott, J. K. and Smith, G. P. *Science* 249:386-390 (1990); Cwirla et al. *PNAS USA* 87:6378-6382 (1990); Felici et al. *J. Mol. Biol.* 222:301-310 (1991), and Kuwabara et al. *Nature Biotechnology* 15:74-78 (1997).

The design of gene and/or antisense therapeutics through conventional techniques is also facilitated through the present invention. Such modalities can be utilized for modulating the function of CTLA-4. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. *Human Gene Therapy* 5:595-601 (1994) and Marasco *Gene Therapy* 4:11-15 (1997). General design of and considerations related to gene therapeutics is also discussed in International Patent Application No. WO 97/38137. Genetic materials encoding an antibody of the invention (such as the 4.1.1, 4.8.1, or 6.1.1, or others) may be included in a suitable expression system (whether viral, attenuated viral, non-viral, naked, or otherwise) and administered to a host for in vivo generation of the antibody in the host.

Small molecule therapeutics can also be envisioned in accordance with the present invention. Drugs can be designed to modulate the activity of CTLA-4 based upon the present invention. Knowledge gleaned from the structure of the CTLA-4 molecule and its interactions with other molecules in accordance with the present invention, such as the antibodies of the invention, CD28, B7, B7-1, B7-2, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of CTLA-4. Such structures can be synthesized chemically or expressed in biological systems. This approach has been reviewed in Capsey et al. *Genetically Engineered Human Therapeutic Drugs* (Stockton Press, NY (1988)). Indeed, the rational design of molecules (either peptides, peptidomimetics, small molecules, or the like) based upon known, or delineated, structure-activity relationships with other molecules (such as antibodies in accordance with the invention) has become generally routine. See, e.g., Fry et al. "Specific, irreversible inactivation of the epidermal growth factor receptor and erbB2, by a new class of tyrosine kinase inhibitor" *Proc Natl Acad Sci USA* 95:12022-7 (1998); Hoffman et al. "A model of Cdc25 phosphatase catalytic domain and Cdk-interaction surface based on the presence of a rhodanese homology domain" *J Mol Biol* 282:195-208 (1998); Ginalski et al. "Modelling of active forms of protein kinases: p38—a case study" *Acta Biochim Pol* 44:557-64 (1997); Jouko et al. "Identification of csk tyrosine phosphorylation sites and a tyrosine residue important for kinase domain structure" *Biochem J* 322:927-35 (1997); Singh et al. "Structure-based design of a potent, selective, and irreversible inhibitor of the catalytic domain of the erbB receptor subfamily of protein tyrosine kinases" *J Med Chem* 40:1130-5 (1997); Mandel et al. "ABGEN: a knowledge-based automated approach for antibody structure modeling" *Nat Biotechnol* 14:323-8 (1996); Monfardini et al. "Rational design, analysis, and potential utility of GM-CSF antagonists" *Proc Assoc Am Physicians* 108:420-31 (1996); Furet et al. "Modelling study of protein kinase inhibitors: binding mode of staurosporine and origin of the selectivity of CGP 52411" *J Comput Aided Mol Des* 9:465-72 (1995).

Further, combinatorial libraries can be designed and sythesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15$^{th}$ ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Powell et al. "Compendium of excipients for parenteral formulations" *PDA J Pharm Sci Technol.* 52:238-311 (1998) and the citations therein for additional information related to excipients and carriers well known to pharmaceutical chemists.

Preparation of Antibodies

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08/759,620, filed Dec. 3, 1996, the disclosure of which is hereby incorporated by reference. See also Mendez et al. *Nature Genetics* 15:146-156 (1997), the disclosure of which is hereby incorporated by reference.

Through use of such technology, we have produced fully human monoclonal antibodies to a variety of antigens. Essentially, we immunize XenoMouse™ lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to CTLA-4. Herein, we describe the production of multiple hybridoma cell lines that produce antibodies specific to CTLA-4. Further, we provide a characterization of the antibodies produced by such cell lines, including nucleotide and amino acid sequence analyses of the heavy and light chains of such antibodies.

The antibodies derived from hybridoma cell lines discussed herein are designated 3.1.1, 4.1.1, 4.8.1, 4.10.2, 4.13.1, 4.14.3, 6.1.1, 11.2.1, 11.6.1, 11.7.1, 12.3.1.1, and 12.9.1.1. Each of the antibodies produced by the aforementioned cell lines are either fully human IgG2 or IgG4 heavy chains with human kappa light chains. In general, antibodies in accordance with the invention possess very high affinities, typically possessing Kd's of from about $10^{-9}$ through about $10^{-11}$ M, when measured by either solid phase or solution phase.

As will be appreciated, antibodies in accordance with the present invention can be expressed in cell lines other than hybridoma cell lines. Sequences encoding the cDNAs or genomic clones for the particular antibodies can be used for transformation of a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, $NSO_0$, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive CTLA-4 binding properties.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750, 172, and 5,741,957.

Antibodies in accordance with the present invention have been analyzed structurally and functionally. In connection with the structures of the antibodies, amino acid sequences of the heavy and kappa light chains have been predicted based on cDNA sequences obtained through RT-PCR of the hybridomas. See Examples 3 and 4 and FIGS. 1-8. N-terminal sequencing of the antibodies was also conducted in confirmation of the results discussed in Examples 3 and 4. See Example 5 and FIG. 9. Kinetic analyses of the antibodies were conducted to determine affinities. See Example 2. Antibodies in accordance with the invention (and particularly the 4.1.1, 4.8.1, and 6.1.1 antibodies of the invention) have high affinities (4.1.1:$1.63 \times 10^{10}$ 1/M; 4.8.1:$3.54 \times 10^{10}$ 1/M; and 6.1.1:$7.2 \times 10^9$ 1/M). Further, antibodies were analyzed by isoelectric focusing (IEF), reducing gel electrophoresis (SDS-PAGE), size exclusion chromatography, liquid chromatography/mass spectroscopy, and mass spectroscopy and antibody production by the hybridomas was assessed. See Example 6 and FIG. 10.

In connection with functional analysis of antibodies in accordance with the present invention, such antibodies proved to be potent inhibitors of CTLA-4 and its binding to its ligands of the B7 family of molecules. For example, antibodies in accordance with the present invention were demonstrated to block CTLA-4 binding to either B7-1 or B7-2. See Example 7. Indeed, many of the antibodies in accordance with the invention possess nanomolar and subnanomolar $IC_{50}$s with respect to inhibiting CTLA-4 binding to B7-1 and B7-2. Further, antibodies of the invention possess excellent selectivity for CTLA-4 as compared to CD28, CD44, B7-2, or hIgG1. See Example 8. Selectivity is a ratio that reflects the degree of preferential binding of a molecule with a first agent as compared to the molecules binding with a second, and optionally other molecules. Herein, selectivity refers to the degree of preferential binding of an antibody of the invention to CTLA-4 as compared to the antibody's binding to other molecules such as CD28, CD44, B7-2, or hIgG1. Selectivity values of antibodies of the invention greater than 500:1 are common. Antibodies of the invention have also been demonstrated to induce or enhance expression of certain cytokines (such as IL-2 and IFN-γ) by cultured T cells in a T cell blast model. See Examples 9 and 10 and FIGS. 12-17. Further, it is expected that antibodies of the invention will inhibit the growth of tumors in appropriate in vivo tumor models. The design of which models are discussed in Example 11 and 12.

The results demonstrated in accordance with the present invention indicate that antibodies of the present invention possess certain qualities that may make the present antibodies more efficacious than current therapeutic antibodies against CTLA-4.

In particular, the 4.1.1, 4.8.1, and 6.1.1 antibodies of the invention possess highly desirable properties. Their structural characteristics, functions, or activities provide criteria that facilitate the design or selection of additional antibodies or other molecules as discussed above. Such criteria include one or more of the following:

Ability to compete for binding to CTLA-4 with one or more of the antibodies of the invention;

Similar binding specificity to CTLA-4 as one or more of the antibodies of the invention;

A binding affinity for CTLA-4 of about $10^{-9}$ M or greater and preferably of about $10^{-10}$ M or greater;

Does not cross react with lower mammalian CTLA-4, including, preferably, mouse, rat, or rabbit and preferably mouse or rat CTLA-4;

Cross reacts with primate CTLA-4, including, preferably, cynomolgous and rhesus CTLA-4;

A selectivity for CTLA-4 over CD28, B7-2, CD44, or hIgG1 of at least about 100:1 or greater and preferably of about 300, 400, or 500:1 or greater;

An $IC_{50}$ in blocking CTLA-4 binding to B7-2 of about 100 nM or lower and preferably 5, 4, 3, 2, 1, 0.5, or 0.38 nM or lower;

An $IC_{50}$ in blocking CTLA-4 binding to B7-1 of about of about 100 nM or lower and preferably 5, 4, 3, 2, 1, 0.5, or 0.50 nM or lower;

An enhancement of cytokine production in one or more in vitro assays, for example:

An enhancement of IL-2 production in a T cell blast/Raji assay of about 500 pg/ml or greater and preferably 750, 1000, 1500, 2000, 3000, or 3846 pg/ml or greater;

An enhancement of IFN-γ production in a T cell blast/Raji assay of about 500 pg/ml or greater and preferably 750, 1000, or 1233 pg/ml or greater; or An enhancement of IL-2 production in a hPBMC or whole blood superantigen assay of about 500 pg/ml or greater and preferably 750, 1000, 1200, or 1511 pg/ml or greater. Expressed another way, it is desirable that IL-2 production is enhanced by about 30, 35, 40, 45, 50 percent or more relative to control in the assay.

It is expected that antibodies (or molecules designed or synthesized therefrom) having one or more of these properties will possess similar efficacy to the antibodies described in the present invention.

The desirable functional properties discussed above can often result from binding to and inhibition of CTLA4 by a molecule (i.e., antibody, antibody fragment, peptide, or small molecule) in a similar manner as an antibody of the invention (i.e., binding to the same or similar epitope of the CTLA4 molecule). The molecule may either be administered directly (i.e., direct administration to a patient of such molecules). Or, alternatively, the molecule may be "administered" indirectly (i.e., a peptide or the like that produces an immune response in a patient (similar to a vaccine) wherein the immune response includes the generation of antibodies that bind to the same or similar epitope or an antibody or fragment that is produced in situ after administration of genetic materials that encode such antibodies or fragments thereof which bind to the same or similar epitope). Thus, it will be appreciated that the epitope on CTLA4 to which antibodies of the invention bind to can be useful in connection with the preparation and/or design of therapeutics in accordance with the invention. In drug design, negative information is often useful as well (i.e., the fact that an antibody which binds to CTLA4 does not appear to bind to an epitope that acts as an inhibitor of CTLA4 is useful). Thus, the epitope to which antibodies of the invention bind that do not lead to the desired functionality can also be very useful. Accordingly, also contemplated in accordance with the present invention are molecules (and particularly antibodies) that bind to the same or similar epitopes as antibodies of the invention.

In addition to the fact that antibodies of the invention and the epitopes to which they bind are contemplated in accordance with the invention, we have conducted some preliminary epitope mapping studies of certain antibodies in accordance with the invention and particularly the 4.1.1 and the 11.2.1 antibodies of the invention.

As a first step, we conducted BIAcore competition studies to generate a rough map of binding as between certain antibodies of the invention in connection with their ability to compete for binding to CTLA4. To this end, CTLA4 was bound to a BIAcore chip and a first antibody, under saturating conditions, was bound thereto and competition of subsequent secondary antibodies binding to CTLA4 was measured. This technique enabled generation of a rough map in to which families of antibodies can be classified.

Through this process, we determined that the certain antibodies in accordance with the invention could be categorized as falling into the following epitopic categories:

| Category | Antibodies | Competition for CTLA4 Binding |
|---|---|---|
| A | BO1M* BO2M** | Freely cross-compete with one another; cross-compete with category B; some cross-competition with category D |
| B | 4.1.1 4.13.1 | Freely cross-compete with one another; cross-compete with category A, C and D. |
| C | 6.1.1 3.1.1 4.8.1 11.2.1 11.6.1 11.7.1 | Freely cross-compete with one another; cross-compete with category B and category D |
| D | 4.14.3 | Cross-compete with category C and B; some cross-competition with category A |
| E | 4.9.1 BNI3*** | BNI3 blocks 4.9.1 binding to CTLA4 but not the reverse |

(*)(**)Available from Biostride.
***Available from Pharmingen.

As a next step, we endeavored to determine if the antibodies of the invention recognized a linear epitope on CTLA4 under reducing and non-reducing conditions on Western blots. We observed that none of the 4.1.1, 3.1.1, 11.7.1, 11.6.1, or 11.2.1 antibodies of the invention appeared to recognize a reduced form of CTLA4 on Western blot. Accordingly, it appeared likely that the epitope to which each of these antibodies bound was not a linear epitope but more likely was a conformational epitope the structure of which may have been abrogated under reducing conditions.

Therefore, we sought to determine whether we could learn about residues within the CTLA4 molecule that are important for binding of antibodies of the invention. One manner that we utilized was to conduct kinetic assessments of off-rates as between human CTLA4 and two highly conserved primate CTLA4 molecules (cynomologous and marmoset CTLA4). BIAcore studies demonstrated that the 4.1.1 antibody of the invention bound to human, cynomologous, and marmoset CTLA4 at the same rate. However, with respect to off-rates (affinity), the 4.1.1 antibody had the highest affinity (slowest off-rate) for human, a faster off-rate with cynomologous, and a much faster off-rate for marmoset. The 11.2.1 antibody of the invention, on the other hand, binds to human, cynomologous, and marmoset CTLA4 at the about the same rate and has about the same relative off-rate for each of the three. This information further indicates that the 4.1.1 and 11.2.1 antibodies of the invention bind to different epitopes on CTLA4.

To further study the epitope to which the category B and C antibodies of the invention bind, we conducted certain site directed mutagenesis studies. Marmoset CTLA4 possesses two important changes at residues 105 and 106 relative to human CTLA4. Such differences are a leucine to methionine change at residue 105 and a glycine to serine change at residue 106. Accordingly, we mutated cDNA encoding human CTLA4 to encode a mutated CTLA4 having the L105M and G106S changes. The homologue replacement mutant CTLA4 did not effect binding of a B7.2-IgG1 fusion protein. Further, binding with the 11.2.1 antibody of the invention was not effected. However, such molecule was significantly inhibited in its ability to bind with the 4.1.1 antibody of the invention (similar to marmoset). Next, we mutated a cDNA encoding marmoset CTLA4 to create a mutant marmoset CTLA4 having a S106G change. Such change resulted in restoration of stable binding between the 4.1.1 antibody and the marmoset CTLA4 mutant. In addition, we mutated a cDNA encoding marmoset CTLA4 to create a mutant marmoset CTLA4 having a M105L change. Such change partially restored binding between the 4.1.1 antibody and the mutant CTLA4.

Each of the category B through D antibodies of the invention appear to possess similar functional properties and appear to have the potential to act as strong anti-CTLA4 therapeutic agents. Further, each of the molecules certain cross-competition in their binding for CTLA4. However, as will be observed from the above discussion, each of the molecules in the different categories appear to bind to separate conformational epitopes on CTLA4.

From the foregoing, it will be appreciated that the epitope information discussed above indicates that antibodies (or other molecules, as discussed above) that cross-compete with antibodies of the invention will likely have certain therapeutic potential in accordance with the present invention. Further, it is expected that antibodies (or other molecules, as discussed above) that cross-compete with antibodies of the invention (i.e., cross-compete with category B, C and/or D antibodies) will likely have certain additional therapeutic potential in accordance with the present invention. Additionally, it is expected that antibodies (or other molecules, as discussed above) that cross-compete with antibodies of the invention (i.e., cross-compete with category B, C and/or D antibodies) and that (i) are not reduced in their binding to marmoset CTLA4 (similar to the 11.2.1 antibody) or (ii) are reduced in their binding to marmoset CTLA4 (similar to the 4.1.1 antibody) will likely have certain additional therapeutic potential in accordance with the present invention. Antibodies (or other molecules, as discussed above) that compete with categories A and E may also have certain therapeutic potential.

EXAMPLES

The following examples, including the experiments conducted and results achieved are provided for illustrative purposes only and are not to be construed as limiting upon the present invention.

Example 1

Generation of Anti-CTLA-4-Antibody Producing Hybridomas

Antibodies of the invention were prepared, selected, and assayed in accordance with the present Example.

Antigen Preparation: Three distinct immunogens were prepared for immunization of the XenoMouse™ mice: (i) a CTLA-4-IgG fusion protein, (ii) a CTLA-4 Peptide, and (iii) 300.19 murine lymphoma cells transfected with a mutant of CTLA-4 (Y201V) that is constitutively expressed on the cell surface.

(i) CTLA-4-IgG1 Fusion Protein:

Expression Vector Construction:

The cDNA encoding the mature extracellular domain of CTLA-4 was PCR amplified from human thymus cDNA library (Clontech) using primers designed to published sequence (*Eur. J. Immunol* 18:1901-1905 (1988)). The fragment was directionally subcloned into pSR5, a Sindbis virus expression plasmid (InVitrogen), between the human oncostatin M signal peptide and human IgG gamma 1 (IgG1) CH1/CH2/CH3 domains. The fusion protein does not contain a hinge domain but contains cysteine 120 in the extracellular domain of CTLA-4 to form a covalent dimer. The resulting vector was called CTLA-4-IgG1/pSR5. The complete CTLA-4-IgG1 cDNA in the vector was sequence confirmed in both strands. The amino acid sequence the CTLA4-Ig protein is shown below. The mature extracellular domain for CD44 was PCR amplified from human lymphocyte library (Clontech) and subcloned into pSinRep5 to generate a control protein with the identical IgG1 tail.

OM-CTLA4-IgG1 Fusion Protein (SEQ ID NO: 100).

<u>MGVLLTQRTLLSLVLALLFPSMASMA</u>MHVAQPAVVLASSRGIASFVC

EYASPGKATEVRVTVLRQADSQVTEVCAATYMMGNELTFLDDSICT

GTSSGNQVNLTIQGLRAMDTGLYICKVELMYPPPYYLGIGNGTQIY

VIDPEPCPDSDLEGAPSVFLFPPKPKDTLMISRTPEVTCVVVDVSHEDPE

VKFNWYVDGVEVHNAKTKPREEQYNSTYRVVSVLTVLHQDWLNGKE

YKCKVSNKALPTPIEKTISKAKGQPREPQVYTLPPSRDELTKNQVSLTCL

VKGFYPSDIAVEWESNGQPENNYKTTPPVLDSDGSFFLYSKLTVDKSR

WQQGNVFSCSVMHEALHNHYTQKSLSLSPGK

Underlined: signal peptide

Bold: CTLA4 extracellular domain

The cDNAs for mature extracellular domain of CD28 were PCR amplified from human lymphocyte library (Clontech) and then subcloned into pCDM8 (*J. Immunol.* 151: 5261-71 (1993)) to produce a human IgG1 fusion protein containing both thrombin cleavage and hinge regions. Marmoset, Cynomologous, and Rhesus CTLA4 were cloned from mRNA isolated from PHA stimulated PBMCs using standard techniques of degenerate PCR. Sequencing demonstrated that rhesus and cynomologous amino acid sequence were identical with three differences from mature human CTLA4 extracellular domain (S13N, I17T and L105M). Marmoset demonstrated ten amino acid differences from the mature human CTLA4 extracellular domain (V21A, V33I, A41T, A51G, 54I, S71F, Q75K, T88M, L105M and G106S). Site directed mutagenesis was used to make single point mutations of all amino acids different in marmoset CTLA4 to map amino acids important for integration of the antibodies with human CTLA4-IgG. Mutations of human and marmoset CTLA-IgG for epitope mapping were generated by matchmaker site-directed mutagenesis (Promega). The IgG fusion proteins were produced by transient transfection of Cos7 cells and purified using standard Protein A techniques. Mutant CTLA4-IgG proteins were evaluated for binding to antibodies by immunoblotting and using BIAcore analyses.

Recombinant Protein Expression/Purification:

Recombinant sindbis virus was generated by electroporating (Gibco) Baby Hamster Kidney cells with SP6 in vitro transcribed CTLA-4-IgG1/pSR5 mRNA and DH-26S helper mRNA as described by InVitrogen. Forty eight hours later recombinant virus was harvested and titered for optimal protein expression in Chinese hamster ovary cells (CHO-K1). CHO-K1 cells were cultured in suspension in DMEM/F12 (Gibco) containing 10% heat-inactivated fetal bovine serum (Gibco), non-essential amino acids (Gibco), 4 mM glutamine (Gibco), penicillin/streptomycin (Gibco), 10 mM Hepes pH 7.5 (Gibco). To produce CTLA-4-IgG, the CHO-K1 cells were resuspended at $1 \times 10^7$ cells/ml in DMEM/F12 and incubated with sindbis virus for one hour at room temperature. Cells were then diluted to $1 \times 10^6$/ml in DMEM/F12 containing 1% fetal bovine serum depleted of bovine IgG using protein A sepharose (Pharmacia), non-essential amino acids, 4 mM glutamine, 12.5 mM Hepes pH 7.5, and penicillin/streptomycin. Forty eight hours post-infection cells were pelleted and conditioned media was harvested and supplemented with complete protease inhibitor tablets (Boehringer Mannheim), pH adjusted to 7.5, and filtered 0.2 µ (Nalgene). FPLC (Pharmacia) was used to affinity purify the fusion protein using a 5 ml protein A HiTrap column (Pharmacia) at a 10 ml/min flow rate. The column was washed with 30 bed volumes of PBS and eluted with 0.1M glycine/HCl pH 2.8 at 1 ml/min. Fractions (1 ml) were immediately neutralized to pH 7.5 with Tris pH 9. The fractions containing CTLA-4-IgG1 were identified by SDS-PAGE and then concentrated using centriplus 50 (Amicon) before applying to sepharose 200 column (Pharmacia) at 1 ml/min using PBS as the solvent. Fractions containing CTLA-4-IgG1 were pooled, sterile filtered 0.2 µ (Millipore), aliquoted and frozen at $-80°$ C. CD44-IgG1 was expressed and purified using the same methods. CD28-IgG was purified from conditioned media from transiently transfected Cos7 cells.

Characterization CTLA-4-IgG1:

The purified CTLA-4-IgG1 migrated as a single band on SDS-PAGE using colloidal coomassie staining (Novex). Under non-reducing conditions CTLA-4-IgG1 was a dimer (100 kDa), that reduced to a 50 kDa monomer when treated with 50 mM DTT. Amino acid sequencing of the purified CTLA-4-IgG1 in solution confirmed the N-terminus of CTLA-4 (MHVAQPAVVLAS) (SEQ ID NO: 101), and that the oncostatin-M signal peptide was cleaved from the mature fusion protein. The CTLA-4-IgG1 bound to immobilized B7.1-IgG in a concentration dependent manner and the binding was blocked by a hamster-anti-human anti-CTLA-4 antibody (BNI3: PharMingen). The sterile CTLA-4-IgG was endotoxin free and quantitated by OD280 using 1.4 as the extinction coefficient. The yield of purified CTLA-4-IgG ranged between 0.5-3 mgs/liter of CHO-K1 cells.

(ii) CTLA-4 Peptide:

The following CTLA-4 peptide (SEQ ID NO: 102) was prepared as described below:

NH$_2$: MHVAQPAVVLASSRGIASFVCEYASPGKATEVRVTVLRQADSQVT

EVCAATYMMGNELTFLDDSICTGTSSGNQVNLTIQGLRAMDTGLYICK

VELMYPPPYYLGIGNGTQIYVIDPEPC-CONH$_2$

Abbreviations/Materials:

NMP, N-Methylpyrrolidinone; TFE, 2,2,2-Trifluoroethanol; DCM, Dichloromethane; FMOC, Fluorenyl Methoxycarbonyl. All reagents were supplied by Perkin Elmer, with the following exceptions: TFE, Aldrich Chemical, FMOC-PAL-PEG resin, Perceptive Biosystems. Fmoc-Arg(PMC)-OH, FMOC-Asn(Trt)-OH, FMOC-Asp(tBu)-OH, FMOC-Cys(irt)-OH, FMOC-Glu(tBu)-OH, FMOC-Gln(Trt)-OH, FMOC-His(Boc)-OH, FMOC-Lys(BOC)-OH, FMOC-Ser(tBu)-OH, FMOC-Thr(tBu)-OH and FMOC-Tyr(tBu)-OH were used for those amino acids requiring side chain protecting groups Peptide Synthesis:

Peptide synthesis was performed on a Perkin-Elmer 431A, retrofitted with feedback monitoring via UV absorbance at 301 nm (Perkin-Elmer Model 759A detector). The peptide sequence was assembled on a FMOC-PAL-PEG resin using conditional double coupling cycles. Forced double couplings were performed at cycles 10, 11, 18, 19, 20 and 28 through 33. The resin was washed with a 50% mixture of DCM and TFE at the completion of each acylation cycle, followed by capping of unreacted amino groups with acetic anhydride in NMP. Resin was removed from the reactor after completing cycle 49 and the remainder continued to completion. Peptide cleavage from the resin was performed using Reagent K (King et al. *International Journal of Protein and Peptide Research* 36:255-266 (1990)) for 6 hours on 415 mg of resin affording 186 mg crude CTLA-4 peptide.

Peptide Characterization:

25 mg aliquots of the crude CTLA-4 peptide were dissolved in 5 ml 6M Guanidine HCl/100 mM K$_2$PO$_3$ at pH6.4 and eluted over a Pharmacia Hi Load Superdex 75 16/60 column (16 mm×600 mm, 120 ml bed volume) with 2M Guanidine.HCl/100 mM K$_2$PO$_3$ at pH6.4 at 2 ml/min for 180 minutes collecting 5 ml fractions. The fractions were analyzed by loading 1.7 µl of fractions onto a NuPAGE Laemeli gel running with MES running buffer and visualizing via Daichii silver stain protocol. Those fractions exhibiting a molecular weight of 12 KDa, as judged versus molecular weight standards, were pooled together and stored at 4° C. The combined fractions were analyzed by UV and gel electrophoresis. Amino acid sequencing was performed by absorbing a 100 microliter sample in a ProSorb cartridge (absorbed onto a PVDF membrane) and washing to remove the buffer salts. Sequencing was performed on an Applied Biosystems 420. The expected N-terminal sequence (M H V A Q P A V V L A) was observed. Immunoblotting demonstrated that the peptide was recognized by the BNI3 anti-human CTLA-4 (PharMingen). To desalt, an aliquot containing 648 µg of material was placed in 3500 Da MWCO dialysis tubing and dialyzed against 0.1% TFA/H2O at 4° C. for 9 days with stirring. The entire contents of the dialysis bag was lyophilyzed to a powder.

(iii) 300.19 Cells Transfected with CTLA-4 (Y201V)

The full length CTLA-4 cDNA was PCR amplified from human thymus cDNA library (Stratagene) and subcloned into pIRESneo (Clontech). A mutation of CTLA-4 that results in constitutive cell surface expression was introduced using MatchMaker Mutagenesis System (Promega). Mutation of tyrosine, Y201 to valine inhibits binding of the adaptin protein AP50 that is responsible for the rapid internalization of CTLA-4 (Chuang et al. *J. Immunol.* 159:144-151 (1997)). Mycoplasma-free 300.19 murine lymphoma cells were cultured in RPMI-1640 containing 10% fetal calf serum, non-essential amino acids, penicillin/streptomycin, 2 mM glutamine, 12.5 mM Hepes pH 7.5, and 25 uM beta-mercaptoethanol. Cells were electroporated ($3 \times 10^6$/0.4 ml serum free RPMI) in a 1 ml chamber with 20 ug CTLA-4-Y201V/pIRESneo using 200V/1180 uF (Gibco CellPorator). Cells were rested for 10 minutes and then 8 mls of prewarmed complete RPMI media. At 48 hours cells were diluted to $0.5 \times 10^6$/ml in complete RPMI media containing 1 mg/ml G418 (Gibco). Resistant cells were expanded and shown to express CTLA-4 on the cell surface using the BNI3 antibody conjugated with phycoerythrin (PharMingen). High level expressing cells were isolated by sterile sorting.

Immunization and hybridoma generation: XenoMouse mice (8 to 10 weeks old) were immunized (i) subcutaneously at the base of tails with $1 \times 10^7$ 300.19 cells that were transfected to express CTLA-4 as described above, resuspended in phosphate buffered saline (PBS) with complete Freund's adjuvant, or (ii) subcutaneously at the base of tail with (a) 10 µg the CTLA-4 fusion protein or (b) 10 µg CTLA-4 peptide, emulsified with complete Freund's adjuvant. In each case, the dose was repeated three or four times in incomplete Freund's adjuvant. Four days before fusion, the mice received a final injection of the immunogen or cells in PBS. Spleen and/or lymph node lymphocytes from immunized mice were fused with the [murine non-secretory myeloma P3 cell line] and were subjected to HAT selection as previously described (Galfre, G. and Milstein, C., "Preparation of monoclonal antibodies: strategies and procedures." *Methods Enzymol.* 73:3-46 (1981)). A large panel of hybridomas all secreting CTLA-4 specific human $IgG_2\kappa$ or $IgG_4\kappa$ (as detected below) antibodies were recovered.

Clones 4.1.1 and 11.2.1 were deposited under terms in accordance with the Budapest Treaty with the American Type Culture Collection (ATCC), 10801 University Boulevard. Manassas, Va. 20110-2209 on Jul. 14, 2005. Subclones 4.1.1.1, 4.13.1.1, 6.1.1.3, and 11.2.1.4 were deposited under terms in accordance with the Budapest Treaty with the ATCC on Apr. 29, 2003. The clones and subclones have been assigned the following ATCC accession numbers:

| Clone | | Subclone | |
|---|---|---|---|
| 4.1.1 | PTA-6862 | 4.1.1.1 | PTA-5166 |
| | | 4.13.1.1 | PTA-5167 |
| | | 6.1.1.3 | PTA-5168 |
| 11.2.1 | PTA 6863 | 11.2.1.4 | PTA-5169 |

All restrictions imposed by the depositor on the availability to the public of the deposited materials will be irrevocably removed upon the granting of a patent in this application.

ELISA assay: ELISA for determination of antigen-specific antibodies in mouse serum and in hybridoma supernatants was carried out as described (Coligan et al., Unit 2.1, "Enzyme-linked immunosorbent assays," in *Current protocols in immunology* (1994)) using CTLA-4-Ig fusion protein to capture the antibodies. For animals that are immunized with the CTLA-4-Ig fusion protein, we additionally screen for non-specific reactivity against the human Ig portion of the fusion protein. This is accomplished using ELISA plates coated with human IgG1 as a negative control for specificity.

In a preferred ELISA assay, the following techniques are used:

ELISA plates are coated with 100 µl/well of the antigen in plate coating buffer (0.1 M Carbonate Buffer, pH 9.6 and $NaHCO_3$ (MW 84) 8.4 g/L). Plates are then incubated at 4° C. overnight. After incubation, coating buffer is removed and the plate is blocked with 200 µl/well blocking buffer (0.5% BSA, 0.1% Tween 20, 0.01% Thimerosal in 1×PBS) and incubated at room temperature for 1 hour. Alternatively, the plates are stored in refrigerator with blocking buffer and plate sealers. Blocking buffer is removed and 50 µl/well of hybridoma supernatant, serum or other hybridoma supernatant (positive control) and HAT media or blocking buffer (negative control) is added. The plates are incubated at room temperature for 2 hours. After incubation, the plate is washed with washing buffer (1×PBS). The detecting antibody (i.e., mouse anti-human IgG2-HRP (SB, #9070-05) for IgG2 antibodies or mouse anti-human IgG4-HRP (SB #9200-05) for IgG4 antibodies) is added at 100 µl/well (mouse anti-human IgG2-HRP @1:2000 or mouse anti-human IgG4-HRP @1:1000 (each diluted in blocking buffer)). The plates are incubated at room temperature for 1 hour and then washed with washing buffer. Thereafter, 100 µl/well of freshly prepared developing solution (10 ml Substrate buffer, 5 mg OPD (o-phenylenediamine, Sigma Cat No. P-7288), and 10 µl 30% $H_2O_2$ (Sigma)) is added to the wells. The plates are allowed to develop 10-20 minutes, until negative control wells barely start to show color. Thereafter, 100 µl/well of stop solution (2 M $H_2SO_4$) is added and the plates are read on an ELISA plate reader at wavelength 490 nm.

Determination of Affinity Constants of Fully Human Mabs by BIAcore:

Affinity measurement of purified human monoclonal antibodies, Fab fragments, or hybridoma supernatants by plasmon resonance was carried out using the BIAcore 2000 instrument, using general procedures outlined by the manufacturers.

Kinetic analysis of the antibodies was carried out using antigens immobilized onto the sensor surface at a low density. Three surfaces of the BIAcore sensorchip were immobililized with the CTLA-4-Ig fusion protein at a density ranging from approximately 390-900 using CTLA-4-Ig fusion protein at 20 or 50 µg/ml in 10 mM sodium acetate at pH 5.0 using the amine coupling kit supplied by the manufacturer (BIAcore, Inc.). The fourth surface of the BIAcore sensorchip was immobilized with IgG1 (900 RU) and was used as a negative control surface for non-specific binding. Kinetic analysis was performed at a flow rate of 25 or 50 microliters per minute and dissociation (kd or $k_{off}$) and association (ka or $k_{on}$) rates were determined using the software provided by the manufacturer (BIA evaluation 3.0) that allows for global fitting calculations.

Example 2

Affinity Measurement of Anti-CTLA-4-Antibodies

In the following Table, affinity measurements for certain of the antibodies selected in this manner are provided:

In order to analyze structures of antibodies produced in accordance with the invention, we cloned genes encoding the heavy and light chain fragments out of the particular hybridoma. Gene cloning and sequencing was accomplished as follows:

Poly(A)$^+$ mRNA was isolated from approximately $2\times10^5$ hybridoma cells derived from immunized XenoMouse mice using a Fast-Track kit (Invitrogen). The generation of random primed cDNA was followed by PCR. Human $V_H$ or human $V_\kappa$ family specific variable region primers (Marks et al., "Oligonucleotide primers for polymerase chain reaction amplification of human immunoglobulin variable genes and design of

TABLE I

| | | | Solid Phase (by BIAcore) | | |
|---|---|---|---|---|---|
| Hybridoma | On-rates $K_a$ ($M^{-1}S^{-1} \times 10^6$) | Off-rates $K_d$ ($S^{-1} \times 10^{-4}$) | Association Constant KA (1/M) = $k_a/k_d \times 10^{10}$ | Dissociation Constant KD (M) = $K_d/k_a \times 10^{-10}$ | Surface Density [RU] |
| Moab01 | 0.68 | 1.01 | 0.67 | 1.48 | 878.7 |
| | 0.70 | 4.66 | 0.15 | 6.68 | 504.5 |
| | 0.77 | 6.49 | 0.19 | 8.41 | 457.2 |
| | 0.60 | 3.08 | 0.20 | 5.11 | 397.8 |
| 4.1.1 | 1.85 | 0.72 | 2.58 | 0.39 | 878.7 |
| | 1.88 | 1.21 | 1.55 | 0.64 | 504.5 |
| | 1.73 | 1.54 | 1.13 | 0.88 | 457.2 |
| | 1.86 | 1.47 | 1.26 | 0.79 | 397.8 |
| 4.8.1 | 0.32 | 0.07 | 4.46 | 0.22 | 878.7 |
| | 0.31 | 0.23 | 1.33 | 0.75 | 504.5 |
| | 0.28 | 0.06 | 4.82 | 0.21 | 397.8 |
| 4.14.3 | 2.81 | 3.04 | 0.92 | 1.08 | 878.7 |
| | 2.88 | 3.97 | 0.73 | 1.38 | 504.5 |
| | 2.84 | 6.66 | 0.43 | 2.35 | 457.2 |
| | 3.17 | 5.03 | 0.63 | 1.58 | 397.8 |
| 6.1.1 | 0.43 | 0.35 | 1.21 | 0.83 | 878.7 |
| | 0.46 | 0.90 | 0.51 | 1.98 | 504.5 |
| | 0.31 | 0.51 | 0.61 | 1.63 | 457.2 |
| | 0.45 | 0.79 | 0.57 | 1.76 | 397.8 |
| 3.1.1 | 1.04 | 0.96 | 1.07 | 0.93 | 878.7 |
| | 0.95 | 1.72 | 0.55 | 1.82 | 504.5 |
| | 0.73 | 1.65 | 0.44 | 2.27 | 457.2 |
| | 0.91 | 2.07 | 0.44 | 2.28 | 397.8 |
| 4.9.1 | 1.55 | 13.80 | 0.11 | 8.94 | 878.7 |
| | 1.43 | 19.00 | 0.08 | 13.20 | 504.5 |
| | 1.35 | 20.50 | 0.07 | 15.20 | 397.8 |
| 4.10.2 | 1.00 | 2.53 | 0.39 | 2.54 | 878.7 |
| | 0.94 | 4.30 | 0.22 | 4.55 | 504.5 |
| | 0.70 | 5.05 | 0.14 | 7.21 | 457.2 |
| | 1.00 | 5.24 | 0.19 | 5.25 | 397.8 |
| 2.1.3 | 1.24 | 9.59 | 0.13 | 7.72 | 878.7 |
| | 1.17 | 13.10 | 0.09 | 11.20 | 504.5 |
| | 1.11 | 13.00 | 0.09 | 11.70 | 397.8 |
| 4.13.1 | 1.22 | 5.83 | 0.21 | 4.78 | 878.7 |
| | 1.29 | 6.65 | 0.19 | 5.17 | 504.5 |
| | 1.23 | 7.25 | 0.17 | 5.88 | 397.8 |

As will be observed, antibodies prepared in accordance with the invention possess high affinities and binding constants.

Example 3

Structures of Anti-CTLA-4-Antibodies Prepared in Accordance with the Invention

In the following discussion, structural information related to antibodies prepared in accordance with the invention is provided.

family-specific oligonucleotide probes." *Eur. J Immunol.* 21:985-991 (1991)) or a universal human $V_H$ primer, MG-30 (CAGGTGCAGCTGGAGCAGTCIGG) was used in conjunction with primers specific for the human Cγ2 constant region (MG-40d; 5'-GCTGAGGGAGTAGAGTCCT-GAGGA-3') or $C_\kappa$ constant region (hκP2; as previously described in Green et al., 1994). Sequences of human Mabs-derived heavy and kappa chain transcripts from hybridomas were obtained by direct sequencing of PCR products generated from poly(A$^+$) RNA using the primers described above. PCR products were also cloned into pCRII using a TA cloning kit (Invitrogen) and both strands were sequenced using Prism dye-terminator sequencing kits and an ABI 377 sequencing machine. All sequences were analyzed by alignments to the "V BASE sequence directory" (Tomlinson et al., MRC Centre for Protein Engineering, Cambridge, UK) using MacVector and Geneworks software programs.

Further, each of the antibodies 4.1.1, 4.8.1, 11.2.1, and 6.1.1 were subjected to full length DNA sequences. For such sequencing, Poly(A)$^+$ mRNA was isolated from approximately $4 \times 10^6$ hybridoma cells using mRNA Direct kit (Dynal). The mRNA was reverse transcribed using oligo-dT(18) and the Advantage RT/PCR kit (Clonetech). The Variable region database (V Base) was used to design amplification primers beginning at the ATG start site of the heavy chain DP50 gene (5'-TATCTAAGCTTCTAGACTCGACCGC-CACCATGGAGTTTGGGCTGAGC TG-3') and to the stop codon of the IgG2 constant region (5'-TTCTCTGATCA-GAATTCCTATCATTTACCCGGAGACAGGGAGAGCT-3'). An optimal Kozak sequence (ACCGCCACC) was added 5' to the ATG start site. The same method was used to design a primer to the ATG start site of the kappa chain A27 gene (5'-TCTTCAAGCTTGCCCGGGCCCGCCACC ATGGAAACCCCAGCGCAG-3') and the stop codon of the kappa constant region (5'-TTCTTTGATCAGAATTCTCAC-TAACACTCTCCCCTGTTGAAGC-3'). The 012 cDNA was cloned by using a primer to the ATG start site (5'-TCT-TCAAGCTTGCCCGGGCCCGCCACCATG-GACATGAGGGTCCCCGCT-3) and the kappa constant region stop codon primer above. The heavy chain cDNAs were also cloned as genomic constructs by site directed mutagenesis to add an NheI site at the end of the variable J domain and subcloning an NheI-fragment containing the genomic IgG2 CH1/Hinge/CH2/CH3 regions. The point mutation to generate NheI site does not alter the amino acid sequence from germline. The primer pairs were used to amplify the cDNAs using Advantage High Fidelity PCR Kit (Clonetech). Sequence of the PCR was obtained by direct sequencing using dye-terminator sequencing kits and an ABI sequencing machine. The PCR product was cloned into pEE glutamine synthetase mammalian expression vectors (Lonza) and three clones were sequenced to confirm somatic mutations. For each clone, the sequence was verified on both strands in at least three reactions. An aglycosylated 4.1.1 antibody was generated by site directed mutagenesis of N294Q in the CH2 domain. Recombinant antibodies were produced by transient transfection of Cos7 cells in IgG depleted FCS and purified using standard Protein A sepharose techniques. Stable transfectants were generated by electroporation of murine NSO cells and selection in glutamine free media. Recombinant 4.1.1 with or without glycosylation exhibited identical specificity and affinity for CTLA4 in the in vitro ELISA and BIAcore assays.

Gene Utilization Analysis

The following Table sets forth the gene utilization evidenced by selected hybridoma clones of antibodies in accordance with the invention:

TABLE II

| | Heavy and Light Chain Gene Utilization | | | | |
|---|---|---|---|---|---|
| | Heavy Chain | | | Kappa Light Chain | |
| Clone | VH | D | JH | VK | JK |
| 4.1.1 | DP-50 | DIR4 or DIR3 | JH4 | A27 | JK1 |
| 4.8.1 | DP-50 | 7-27 | JH4 | A27 | JK4 |
| 4.14.3 | DP-50 | 7-27 | JH4 | A27 | JK3 |

TABLE II-continued

| | Heavy and Light Chain Gene Utilization | | | | |
|---|---|---|---|---|---|
| | Heavy Chain | | | Kappa Light Chain | |
| Clone | VH | D | JH | VK | JK |
| 6.1.1 | DP-50 | DIR5 or DIR5rc | JH4 | A27 | JK3 |
| 3.1.1 | DP-50 | 3-3 | JH6 | 012 | JK3 |
| 4.10.2 | DP-50 | 7-27 | JH4 | A27 | JK3 |
| 2.1.3 | DP-65 | 1-26 | JH6 | A10/A26 | JK4 |
| 4.13.1 | DP-50 | 7-27 | JH4 | A27 | JK3 |
| 11.2.1 | DP-50 | D1-26 | JH6 | 012 | JK3 |
| 11.6.1 | DP-50 | D2-2 or D4 | JH6 | 012 | JK3 |
| 11.7.1 | DP-50 | D3-22 or D21-9 | JH4 | 012 | JK3 |
| 12.3.1.1 | DP-50 | D3-3 or DXP4 | JH6 | A17 | JK1 |
| 12.9.1.1 | DP-50 | D6-19 | JH4 | A3/A19 | JK4 |
| 4.9.1 | DP-47 | 5-24 and/or 6-19 | JH4 | L5 | JK1 |

As will be observed, antibodies in accordance with the present invention were generated with a strong bias towards the utilization of the DP-50 heavy chain variable region. The DP-50 gene is also referred to as a $V_H$ 3-33 family gene. Only one antibody that was selected on the basis of CTLA-4 binding and preliminary in vitro functional assays showed a heavy chain gene utilization other than DP-50. That clone, 2.1.3, utilizes a DP-65 heavy chain variable region and is an IgG4 isotype. The DP-65 gene is also referred to as a $V_H$ 4-31 family gene. On the other hand, the clone, 4.9.1, which possesses a DP-47 heavy chain variable region binds to CTLA-4 but does not inhibit binding to B7-1 or B7-2. In XenoMouse mice, there are more than 30 distinct functional heavy chain variable genes with which to generate antibodies. Bias, therefore, is indicative of a preferred binding motif of the antibody-antigen interaction with respect to the combined properties of binding to the antigen and functional activity.

Mutation Analysis

As will be appreciated, gene utilization analysis provides only a limited overview of antibody structure. As the B-cells in XenoMouse animals stocastically generate V-D-J heavy or V-J kappa light chain transcripts, there are a number of secondary processes that occur, including, without limitation, somatic hypermutation, n-additions, and CDR3 extensions. See, for example, Mendez et al. *Nature Genetics* 15:146-156 (1997) and U.S. patent application Ser. No. 08/759,620, filed Dec. 3, 1996. Accordingly, to further examine antibody structure predicted amino acid sequences of the antibodies were generated from the cDNAs obtained from the clones. In addition, N-terminal amino acid sequences were obtained through protein sequencing.

FIG. 1 provides nucleotide and predicted amino acid sequences of the heavy and kappa light chains of the clones 4.1.1 (FIG. 1A), 4.8.1 (FIG. 1B), 4.14.3 (FIG. 1C), 6.1.1 (FIG. 1D), 3.1.1 (FIG. 1E), 4.10.2 (FIG. 1F), 2.1.3 (FIG. 1G), 4.13.1 (FIG. 1H), 11.2.1 (FIG. 1I), 11.6.1 (FIG. 1J), 11.7.1 (FIG. 1K), 12.3.1.1 (FIG. 1L), and 12.9.1.1 (FIG. 1M). In FIGS. 1A, 1B, and 1D, extended sequences of the antibodies 4.1.1, 4.8.1, and 6.1.1 were obtained by full length cloning of the cDNAs as described above. In such Figures, the signal peptide sequence (or the bases encoding the same) are indicated in bold and sequences utilized for the 5' PCR reaction are underlined.

FIG. 2 provides a sequence alignment between the predicted heavy chain amino acid sequences from the clones 4.1.1, 4.8.1, 4.14.3, 6.1.1, 3.1.1, 4.10.2, 4.13.1, 11.2.1, 11.6.1, 11.7.1, 12.3.1.1, and 12.9.1.1 and the germline DP-50 (3-33) amino acid sequence. Differences between the DP-50 germline sequence and that of the sequence in the clones are indicated in bold. The Figure also shows the positions of the CDR1, CDR2, and CDR3 sequences of the antibodies as shaded.

FIG. 3 provides a sequence alignment between the predicted heavy chain amino acid sequence of the clone 2.1.3 and the germline DP-65 (4-31) amino acid sequence. Differences between the DP-65 germline sequence and that of the sequence in the clone are indicated in bold. The Figure also shows the positions of the CDR1, CDR2, and CDR3 sequences of the antibody as underlined.

FIG. 4 provides a sequence alignment between the predicted kappa light chain amino acid sequence of the clones 4.1.1, 4.8.1, 4.14.3, 6.1.1, 4.10.2, and 4.13.1 and the germline A27 amino acid sequence. Differences between the A27 germline sequence and that of the sequence in the clone are indicated in bold. The Figure also shows the positions of the CDR1, CDR2, and CDR3 sequences of the antibody as underlined. Apparent deletions in the CDR1s of clones 4.8.1, 4.14.3, and 6.1.1 are indicated with "0s".

FIG. 5 provides a sequence alignment between the predicted kappa light chain amino acid sequence of the clones 3.1.1, 11.2.1, 11.6.1, and 11.7.1 and the germline O12 amino acid sequence. Differences between the O12 germline sequence and that of the sequence in the clone are indicated in bold. The Figure also shows the positions of the CDR1, CDR2, and CDR3 sequences of the antibody as underlined.

FIG. 6 provides a sequence alignment between the predicted kappa light chain amino acid sequence of the clone 2.1.3 and the germline A10/A26 amino acid sequence. Differences between the A10/A26 germline sequence and that of the sequence in the clone are indicated in bold. The Figure also shows the positions of the CDR1, CDR2, and CDR3 sequences of the antibody as underlined.

FIG. 7 provides a sequence alignment between the predicted kappa light chain amino acid sequence of the clone 12.3.1 and the germline A17 amino acid sequence. Differences between the A17 germline sequence and that of the sequence in the clone are indicated in bold. The Figure also shows the positions of the CDR1, CDR2, and CDR3 sequences of the antibody as underlined.

FIG. 8 provides a sequence alignment between the predicted kappa light chain amino acid sequence of the clone 12.9.1 and the germline A3/A19 amino acid sequence. Differences between the A3/A19 germline sequence and that of the sequence in the clone are indicated in bold. The Figure also shows the positions of the CDR1, CDR2, and CDR3 sequences of the antibody as underlined.

FIG. 22 provides a series of additional nucleotide and amino acid sequences of the following anti-CTLA-4 antibody chains:

4.1.1:
full length 4.1.1 heavy chain (cDNA 22(a), genomic 22(b), and amino acid 22(c));
full length aglycosylated 4.1.1 heavy chain (cDNA 22(d) and amino acid 22(e));
4.1.1 light chain (cDNA 22(f) and amino acid 22(g));
4.8.1:
full length 4.8.1 heavy chain (cDNA 22(h) and amino acid 22(i));
4.8.1 light chain (cDNA 22(j) and amino acid 22(k));
6.1.1:
full length 6.1.1 heavy chain (cDNA 22(l) and amino acid 22(m));
6.1.1 light chain (cDNA 22(n) and amino acid 22(o));
11.2.1:
full length 11.2.1 heavy chain (cDNA 22(p) and amino acid 22(q)); and
11.2.1 light chain (cDNA 22(r) and amino acid 22(s)).

Signal peptide sequences are shown in bold and large text. The open reading frames in the full length 4.1.1 genomic DNA sequence (FIG. 22(*b*)) are underlined. And, the mutations introduced to make the aglycosylated 4.1.1 heavy chain and the resulting change (N294Q) are shown in double underline and bold text (cDNA (FIG. 22(*b*) and amino acid (FIG. 22(*c*)).

Example 4

Analysis of Heavy and Light Chain Amino Acid Substitutions

In FIG. 2, which provides a sequence alignment between the predicted heavy chain amino acid sequences from the clones 4.1.1, 4.8.1, 4.14.3, 6.1.1, 3.1.1, 4.10.2, 4.13.1, 11.2.1, 11.6.1, 11.7.1, 12.3.1.1, and 12.9.1.1 and the germline DP-50 (3-33) amino acid sequence, an interesting pattern emerges. In addition to the fact of the bias for heavy chain DP-50 in the majority of the clones, there is relatively limited hypermutation in the antibodies relative to the germline DP-50 gene. For example, clones 3.1.1 and 11.2.1 have no mutations. Moreover, the mutations in the other clones are generally conservative changes, involving substitutions of amino acids with similar properties to the amino acids in the germline. Mutations within many of the CDR1 and CRD2 sequences are particularly conservative in nature. Three of the heavy chains represented in FIG. 2, 4.10.2, 4.13.1, and 4.14.3, are clearly derived from a single recombination event (i.e., derive from an identical germinal center) and are nearly identical in sequence. If these three are considered as a single sequence, then, among the 10 different antibodies containing the DP50 heavy chain, in CDR1 and CDR2there are 3 positions in which a nonpolar residue is replaced by another nonpolar residue, 12 in which a polar uncharged residue is replaced by another polar uncharged residue, and 1 in which a polar charged residue is replaced by another polar charged residue. Further, there are two positions in which two residues which are very similar structurally, glycine and alanine, are substituted for one another. The only mutations not strictly conservative involve 3 substitutions of a polar charged residue for a polar uncharged residue and one substitution of a nonpolar residue for a polar residue.

The light chains of these antibodies are derived from 5 different Vk genes. The A27 gene is the most heavily represented and is the source of 6 different light chains. Comparison of these 6 sequences reveals two noteworthy features. First, in three of them, 4.8.1, 4.14.3, and 6.1.1, contain deletions of one or two residues in CDR1, a rare event. Second, there is a strong prejudice against the germline serine at position six in CDR3 in that the serine has been replaced in every sequence. This suggests that a serine at this position is incompatible with CTLA4 binding.

It will be appreciated that many of the above-identified amino acid substitutions exist in close proximity to or within a CDR. Such substitutions would appear to bear some effect upon the binding of the antibody to the CTLA-4 molecule. Further, such substitutions could have significant effect upon the affinity of the antibodies.

Example 5

N-Terminal Amino Acid Sequence Analysis of Antibodies in Accordance with the Invention In order to further verify the composition and structure of the antibodies in accordance with the invention identified above, we sequenced certain of the antibodies using a Perkin-Elmer sequencer. Both heavy and kappa light chains of the antibodies were isolated and purified through use of preparative gel electrophoresis and electroblotting techniques and thereafter directly sequenced as described in Example 6. A majority of the heavy the heavy chain sequences were blocked on their amino terminus. Therefore, such antibodies were first treated with pyroglutamate aminopeptidase and thereafter sequenced.

The results from this experiment are shown in FIG. 9. FIG. 9 also provides the molecular weight of the heavy and light chains as determined by mass spectroscopy (MALDI).

Example 6

Additional Characterization of Antibodies in Accordance with the Invention

Figure 10C:
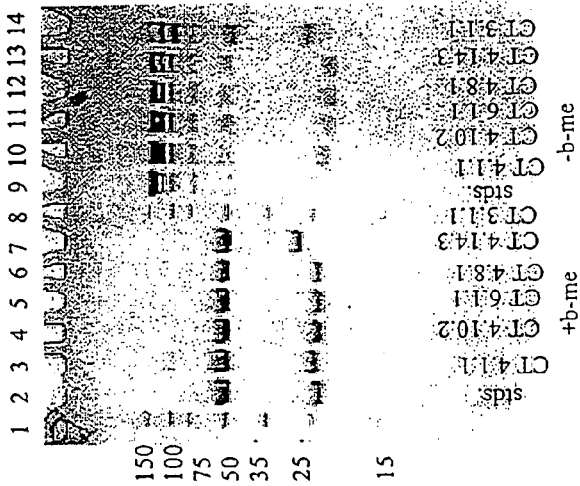
Figure 10B:
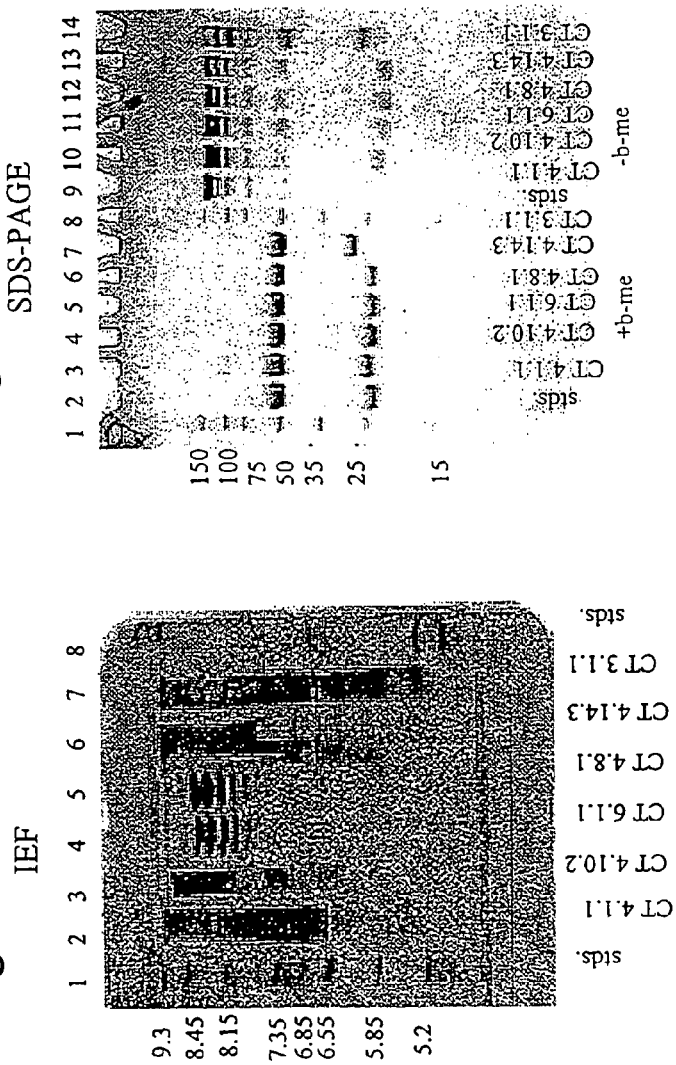

FIG. 10 provides certain additional characterizing information about certain of the antibodies in accordance with the invention. In the Figure, data related to clones 3.1.1, 4.1.1, 4.8.1, 4.10.2, 4.14.3, and 6.1.1 is summarized. The following data is provided: Concentration, isoelectric focusing (IEF), SDS-PAGE, size exclusion chromatography, FACS, mass spectroscopy (MALDI), and light chain N-terminal sequences.

Generally, the data was generated as follows:

Materials and Methods

Protein concentration was determined at 280 nm from a UV scan (200-350 nm), where 1.58 absorbance units at 280 nm equaled 1 mg/ml.

SDS-PAGE was performed using the Novex NuPAGE electrophoresis system with a 10% NuPAGE gel and MES running buffer. Samples were prepared by diluting 3:1 with 4× NuPAGE sample buffer (+/−) beta-mercaptoethanol, heated and ~5 ug of protein was loaded onto the gel. The gel was then stained with Brilliant Blue R staining solution (Sigma cat.#B-6529) and molecular size estimates were made by comparing stained bands to "Perfect Protein Markers" (Novagen cat#69149-3).

For N-terminal sequencing, samples were run as above on NuPAGE gels, transferred to Pro Blot immobilization membrane (Applied Biosystems) then stained with Coomassie Blue R-250. The stained protein bands were excised and subjected to sequence analysis by automated Edman degradation on an Applied Biosystems 494 Procise HT Sequencer.

Isoelectric focusing (IEF) was performed using Pharmacia IEF 3-9 pHast gels (cat#17-0543-01). Samples were diluted in 10% glycerol to ~0.8 mg/ml and 1 ul was loaded onto gel and then silver stained. The pI estimates were made by comparing stained bands to broad range (pH3-10) IEF standards (Pharmacia cat #17-0471-01)

Size exclusion chromatography (SEC) was carried in phosphate buffered saline (PBS) on the Pharmacia SMART system using the Superdex 75 PC 3.2/30 column. Molecular size estimates were made by comparing peak retention time to the retention times of gel For FACS studies, human peripheral T cells were prepared and stimulated for 48 hours. T cells were washed once, resuspended in FACS buffer at $1 \times 10^6$ cells/100 ul and stained for CD3 surface expression with 10 ul of anti-CD3-FITC (Immunotech, Marseille, France) for 30 minutes at room temperature. Cells were washed twice, then fixed, permeabilized (Fix and Perm, Caltag), and stained for intracellular CTLA-4 expression with 10 ul anti-CD152-PE (Pharmingen). Flow cytometry was performed using a Becton Dickinson FACSort. Quadrants were set by analysis of relevant isotype control antibodies (Caltag).

As was discussed above, anti-CTLA-4 antibodies have been demonstrated to possess certain powerful immune modulation activities. The following experiments were carried out in order to determine if antibodies in accordance with the present invention possessed such activities. In general, the experiments were designed to assess ability of the antibodies to inhibit the interaction between CTLA-4 and B7 molecules, be selective as between CTLA-4 and B7 molecules and CD28, and promote T cell cytokine production, including, but not limited to IL-2 and/or IFN-γ expression. Further, examination of cross-reactivity of antibodies of the invention with certain human tissues and CTLA-4 molecules in other species (e.g., mouse and primate) was undertaken.

Example 7

Competition ELISA: Inhibition of CTLA-4/B7-1 or B7-2 Interaction by Antibodies in Accordance with the Invention An in vitro assay was conducted to determine if antibodies in accordance with the present invention were capable of inhibiting the binding of CTLA-4 with either B7-1 or B7-2. As will be appreciated, antibodies of the invention that are capable of inhibiting the binding of CTLA-4 with B7 molecules would be expected to be candidates for immune regulation through the CTLA-4 pathway. In the assay, the following materials and methods were utilized:

Materials and Methods 3 nM B7.1-Ig(G1) or B7.2-Ig(G1) (Repligen, Inc. Needham, Mass.) in Dulbecco's PBS was coated on 96-well MaxiSorp plates (Nunc, Denmark, #439454) and incubated at 4° C. overnight. On day 2, B7-Ig was removed and plates were blocked with 1% BSA plus 0.05% Tween-20 in D-PBS for two hours. Plates were washed 3× with wash buffer (0.05% Tween-20 in D-PBS). Antibody at appropriate test concentrations and CTLA-4-Ig(G4) (0.3 nM final conc.) (Repligen, Inc. Needham, Mass.) were pre-mixed for 15 minutes and then added to the B7-Ig coated plate (60 ul total volume) and incubated at RT for 1.5 hours. Plates were washed 3× and 50 µl of a 1 to 1000 dilution of HRP-labeled mouse anti-human IgG4 antibody (Zymed, San Francisco, Calif., #05-3820) was added and incubated at RT for 1 hour. Plates were washed 3× and 50 µl TMB Microwell peroxidase substrate (Kirkegaard & Perry, Gaithersburg, Md., #50-76-04) was added and incubated at RT for 20 minutes, and then 50 µl 1N $H_2SO_4$ was added to the plate. Plates were read at 450 nm using a Molecular Devices plate reader (Sunnyvale, Calif.). All samples were tested in duplicate. Maximal signal was defined as CTLA-4-Ig binding in the absence of test antibody. Non-specific binding was defined as absorbance in the absence of CTLA-4-Ig and test antibody.

The results from the assay are provided in Table IIIA and IIIB. In Table IIIA, results are shown for a variety of antibodies in accordance with the invention. In Table IIIB, results are shown comparing the 4.1.1 antibody of the invention with the 11.2.1 antibody of the invention from a separate experiment.

TABLE IIIA

| Clone CTLA-4-Ig | Isotype | CTLA4/B7.2 Comp. ELISA IC50 (nM) | CTLA4/B7.1 Comp. ELISA IC50 (nM) |
|---|---|---|---|
| CT3.1.1 | IgG2 | 0.45 ± 0.07 (n = 3) | 0.63 ± 0.10 (n = 2) |
| CT4.1.1 | IgG2 | 0.38 ± 0.06 (n = 5) | 0.50 ± 0.05 (n = 2) |
| CT4.8.1 | IgG2 | 0.57 ± 0.03 (n = 3) | 0.17 ± 0.28 (n = 2) |
| CT4.9.1 | IgG2 | Non-competitive (n = 3) | non-competitive (n = 2) |
| CT4.10.2 | IgG2 | 1.50 ± 0.37 (n = 3) | 3.39 ± 0.31 (n = 2) |
| CT4.13.1 | IgG2 | 0.49 ± 0.05 (n = 3) | 0.98 ± 0.11 (n = 2) |
| CT4.14.3 | IgG2 | 0.69 ± 0.11 (n = 3) | 1.04 ± 0.15 (n = 2) |
| CT6.1.1 | IgG2 | 0.39 ± 0.06 (n = 3) | 0.67 ± 0.07 (n = 2) |

TABLE IIIB

| Clone CTLA-4-Ig | Isotype | CTLA4/B7.2 Comp. ELISA IC50 (nM) | CTLA4/B7.1 Comp. ELISA IC50 (nM) |
|---|---|---|---|
| CT4.1.1 | IgG2 | 0.55 ± 0.08 (n = 4) | 0.87 ± 0.14 (n = 2) |
| CT11.2.1 | IgG2 | 0.56 ± 0.05 (n = 4) | 0.81 ± 0.24 (n = 2) |

Example 8

Selectivity Ratios of Antibodies of the Invention with Respect to CTLA-4 Versus Either CD28 or B7-2

Another in vitro assay was conducted to determine the selectivity of antibodies of the invention with respect to CTLA-4 versus either CD28 or B7-2. The following materials and methods were utilized in connection with the experiments:

CTLA-4 Selectivity ELISA: Materials and Methods

A 96-well FluroNUNC plate (Nunc Cat No. 475515) was platecoated with four antigens: CTLA-4/Ig, CD44/Ig, CD28/Ig, and B7.2/Ig (antigens generated in-house). The antigens were platecoated overnight at +4° C. at 1 ug/ml 100 ul/well in 0.1M sodium bicarbonate buffer, pH 9.6. The plate was then washed with PBST (PBS+0.1% Tween-20) three times using a NUNC plate washer. The plate was blocked with PBST+ 0.5% BSA at 150 ul/well. The plate was incubated at RT for 1 hour then washed with PBST three times. Next the anti-CTLA-4 antibodies of the invention were diluted in block at 1 μg/ml and were added to the plate. The plate was incubated at RT for 1 hour then washed with PBST three times. The wells that contained the antibodies of the invention were then treated with 100 μl/well anti-human IgG2-HRP (Southern Biotech Cat No. 9070-05) at a 1:4000 dilution in block. Also, one row was treated with anti-human IgG (Jackson Cat No. 209-035-088) to normalize for platecoating. This antibody was diluted to 1:5000 in block and added at 100 ul/well. Also, one row was treated with anti-human CTLA-4-HRP (Pharmingen Cat No. 345815/Custom HRP conjugated) as a positive control. This antibody was used at 0.05 ug/ml diluted in block. The plate was incubated at RT for 1 hour then washed with PBST three times. LBA chemiluminescent substrate (Pierce) was added at 100 μl/well and the plate was incubated on a plateshaker for 5 min. The plate was then read using a lumi-imager for a 2 min. exposure.

IGEN CTLA-4-Ig Selectivity Binding Assay: Materials and Methods

M-450 Dynabeads (Dynal A. S, Oslo, Norway #140.02) were washed 3× with Na phosphate buffer, pH 7.4 and resuspended in Na phosphate buffer. 1.0 μg CTLA-4-Ig(G1), 1.0 μg CD28-Ig(G1) or 1.0 to 3.0 μg B7.2-Ig(G1) (Repligen, Inc. Needham, Mass.) were added to 100 μl of beads and incubated overnight on a rotator at 4° C. On day 2 the beads were washed 3× in 1% BSA plus 0.05% Tween-20 in Dulbecco's PBS and blocked for 30 minutes. Beads were diluted 1 to 10 with blocking buffer and 25 μl of the coated beads were added to 12×75 mm polypropylene tubes. All samples were tested in duplicate. 50 μl test antibody (1 μg/ml final concentration) or blocking buffer was added to the tubes and incubated for 30 minutes on the Origen 1.5 Analyzer carousel (IGEN International, Inc., Gaithersburg, Md.) at RT, vortexing at 100 rpm. 25 μl of ruthenylated murine anti-human IgG1, IgG2 or IgG4 (Zymed, Inc. San Francisco, Calif. #05-3300, 05-3500 and 05-3800) (final concentration of 3 μg/ml in 100 μl total volume) was added to the tubes. Tubes were incubated for 30 minutes at RT on the carousel vortexing at 100 rpm. 200 μl of Origen assay buffer (IGEN International, Inc., Gaithersburg, Md. #402-050-03) per tube was added and briefly vortexed and then the tubes were counted in the Origen Analyzer and ECL (electrochemiluminescence) units were determined for each tube. Normalization factors were determined to correct for differences in binding of fusion proteins to Dynabeads, and ECL units were corrected for non-specific binding before calculating selectivity ratios.

The results from the assays are provided in Tables IVA and IVB.

TABLE IVA

| Clone | Isotype | CTLA4/CD28 ELISA | CTLA4/B7.2 ELISA | CTLA4/CD44 ELISA | CTLA4/CD28 IGEN | CTLA4/B7.2 IGEN |
|---|---|---|---|---|---|---|
| 3.1.1 | IgG2 | >500:1 (n = 3) | >500:1 (n = 3) | >500:1 (n = 3) | >500:1 (n = 2) | >500:1 (n = 1) |
|  |  |  |  |  |  | 195:1 (n = 1) |
| 4.1.1 | IgG2 | >500:1 (n = 3) | >500:1 (n = 2) | >500:1 (n = 3) | >500:1 (n = 1) | >500:1 (n = 1) |
|  |  |  | 485:1 (n = 1) |  | 261:1 (n = 1) | 107:1 (n = 1) |
| 4.8.1 | IgG2 | >500:1 (n = 3) | >500:1 (n = 2) | >500:1 (n = 3) | >500:1 (n = 2) | >500:1 (n = 2) |
|  |  |  | 190:1 (n = 1) |  |  |  |
| 4.9.1 | IgG2 | >500:1 (n = 2) | >500:1 (n = 2) | >500:1 (n = 3) | >500:1 (n = 1) | >500:1 (n = 1) |
|  |  | 244:1 (n = 1) | 33:1 (n = 1) |  |  |  |
| 4.10.2 | IgG2 | >500:1 (n = 3) | >500:1 (n = 3) | >500:1 (n = 3) | >500:1 (n = 1) | >500:1 (n = 1) |
| 4.13.1 | IgG2 | >500:1 (n = 2) | >500:1 (n = 3) | >500:1 (n = 3) | >500:1 (n = 1) | >500:1 (n = 2) |
|  |  | 46:1 (n = 1) |  |  | 329:1 (n = 1) |  |
| 4.14.3 | IgG2 | >500:1 (n = 2) | >500:1 (n = 2) | >500:1 (n = 2) | >413:1 (n = 1) | >234:1 (n = 1) |
|  |  | 80:1 (n = 1) | 10:1 (n = 1) | 126:1 (n = 1) |  |  |

TABLE IVA-continued

| Clone | Isotype | CTLA4/CD28 ELISA | CTLA4/B7.2 ELISA | CTLA4/CD44 ELISA | CTLA4/CD28 IGEN | CTLA4/B7.2 IGEN |
|---|---|---|---|---|---|---|
| 6.1.1 | IgG2 | >500:1 (n = 2) 52:1 (n = 1) | >500:1 (n = 3) | >500:1 (n = 3) | >500:1 (n = 2) | >500:1 (n = 2) |

TABLE IVB

| Clone | Isotype | CTLA4/CD28 ELISA | CTLA4/B7.2 ELISA | CTLA4/hIgG ELISA |
|---|---|---|---|---|
| 4.1.1 | IgG2 | >500:1 (n = 3) | >500:1 (n = 2) | >500:1 (n = 3) |
| 11.2.1 | IgG2 | >500:1 (n = 3) | >500:1 (n = 3) | >500:1 (n = 3) |

Example 9

Human T-Cell Signal Model

In order to further define the activity of antibodies in accordance with the invention to act as immune regulators, we developed certain T-cell assays in order to quantify the enhancement of T-cell IL-2 production upon blockade of CTLA-4 signal with the antibodies. The following materials and methods were utilized in connection with the experiments:

Materials and Methods

Freshly isolated human T cells were prepared by using Histopaque (Sigma, St. Louis, Mo. #A-70543) and T-kwik (Lympho-Kwik, One Lambda, Canoga Park, Calif., #LK-50-T), and stimulated with PHA (1 µg/ml) (Purified Phytohemagglutinin, Murex Diagnostics Ltd. Dartford, England, #HA 16) in medium (RPMI 1640 containing L-glutamine, MEM non-essential amino acids, penicillin, streptomycin, 25 mM Hepes and 10% FBS) at a concentration of $1 \times 10^6$ cells/ml and incubated at 37° C. for 2 days. The cells were washed and diluted in medium to $2 \times 10^6$ cells/ml. Raji cells (Burkitt lymphoma, Human ATCC No.: CCL 86 Class II American Type Culture Collection Rockville, Md.) were treated with mitomycin C (Sigma St. Louis, Mo., #M-4287) (25 µg/ml) for one hour at 37° C. The Raji cells were washed 4× in PBS and resuspended at $2 \times 10^6$ cells/ml. Human T cell blasts ($5 \times 10^5$/ml), Raji cells ($5 \times 10^5$/ml) and anti-CTLA-4 antibodies or an isotyped-matched control antibody at various concentrations were added to 96-well microtiter plates and the plates were incubated at 37° C. for 72 hours. Total volume per well was 200 µl. Seventy-two hours post stimulation, the plates were spun down and supernatant removed and frozen for later determination of IL-2 (Quantikine IL-2 ELISA kit, R&D Systems, Minneapolis, Minn., #D2050) and IFN-γ (Quantikine IFN-g ELISA kit, R&D Systems). Cytokine enhancement was defined as the difference between cytokine levels in cultures containing an anti-CTLA-4 blocking mAb versus an isotype-matched control antibody. For flow cytometry experiments, Raji cells were washed 1× with FACS buffer (PBS containing 2% heat inactivated FCS, 0.025% sodium azide). Cell pellets were resuspended in FACS buffer at $1 \times 10^6$ cells/100 µl and incubated with 10 µl of anti-CD80-PE (Becton Dickinson, San Jose, Calif.) or anti-CD86-PE (Pharmingen, San Diego, Calif.) for 30 minutes at room temperature. Cells were washed twice and resuspended in 1 ml FACS buffer. Flow cytometry was performed using a Becton Dickinson FACSort. Histogram markers were set by analysis of relevant isotype control antibodies (Caltag, Burlingame, Calif.).

In general, we have developed an assay that can be used for rapid determination of T-cell IL-2 upregulation. As will be appreciated, stimulation of T cells is B7 and CD28 dependent. Further, washed T blasts do not make detectable IL-2 and Raji cells do not make detectable IL-2 even when stimulated with LPS or PWM. However, in combination, the T blasts co-cultured with Raji cells can model B7, CTLA-4, and CD28 signaling events and the effects of antibodies thereon can be assessed.

Figure 11B:
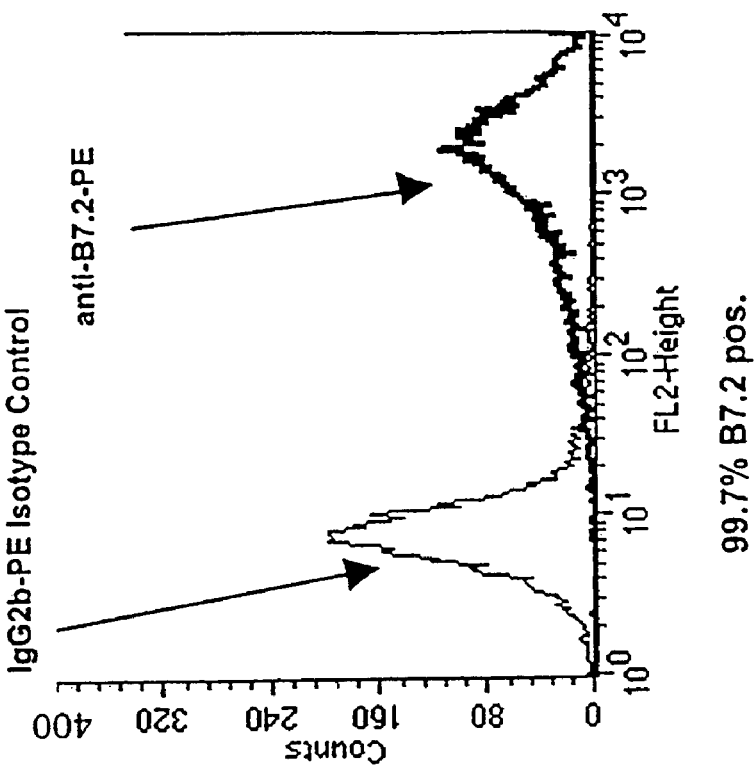
FIG. 11 shows the expression of B7-1 and B7-2 on Raji cells using anti-CD80-PE and anti-CD86-PE mAbs.
Figure 11A:
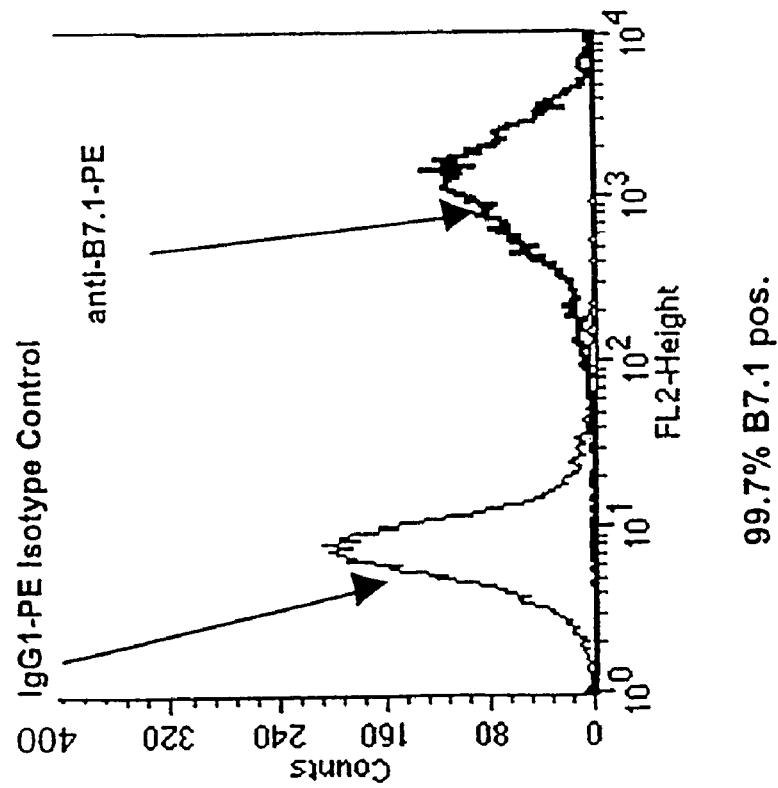

FIG. 11 shows the expression of B7-1 and B7-2 on Raji cells using anti-CD80-PE and anti-CD86-PE mAbs using flow cytometry (FACs) as described in Example 6.

Figure 12:
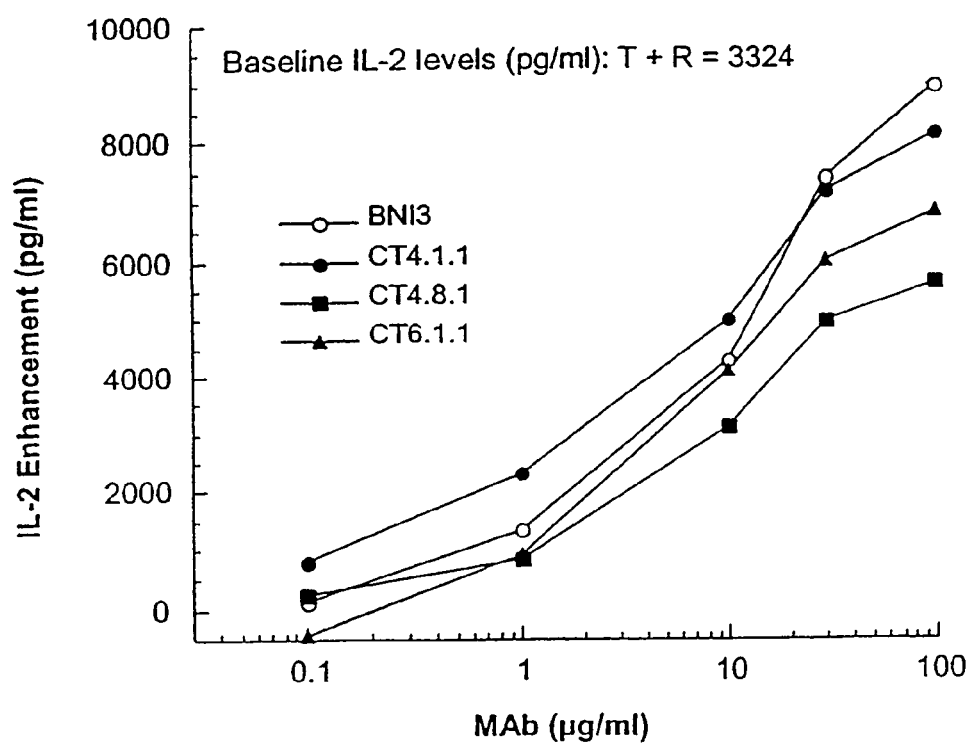
FIG. 12 shows the concentration dependent enhancement of IL-2 production in the T cell blast/Raji assay induced by anti-CTLA-4 blocking antibodies (BNI3, 4.1.1, 4.8.1, and 6.1.1).

FIG. 12 shows the concentration dependent enhancement of IL-2 production in the T cell blast/Raji assay induced by CTLA-4 blocking antibodies (BNI3 (PharMingen) and the 4.1.1, 4.8.1, and 6.1.1 antibodies of the invention).

Figure 13:
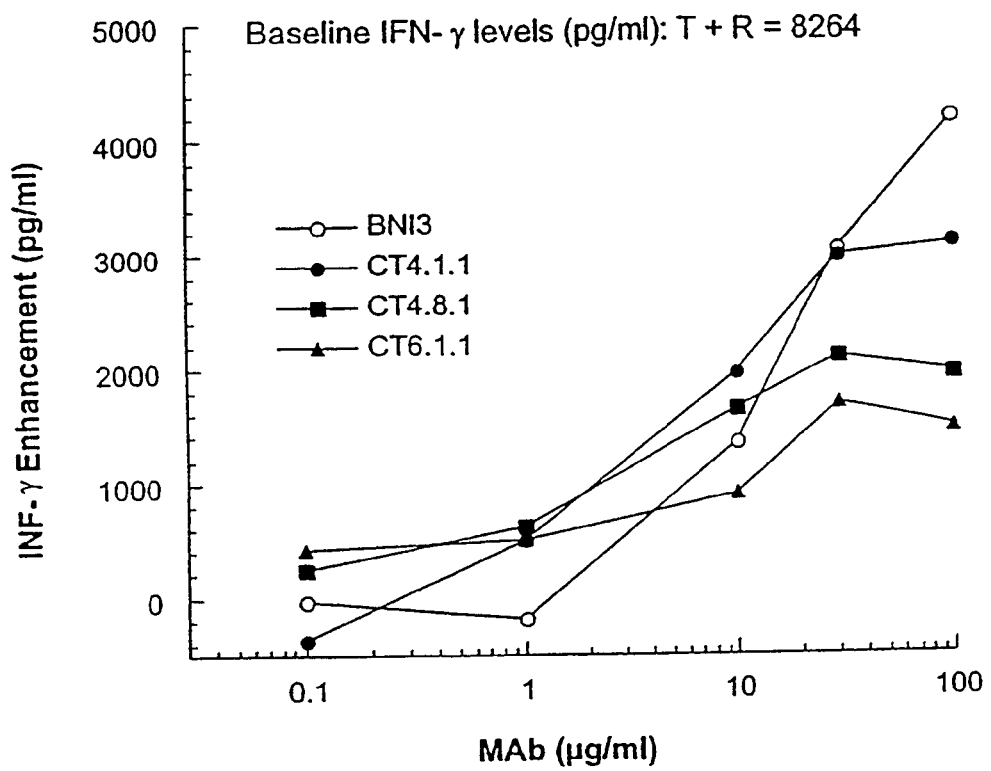
FIG. 13 shows the concentration dependent enhancement of IFN-γ production in the T cell blast/Raji assay induced by anti-CTLA-4 blocking antibodies (BNI3, 4.1.1, 4.8.1, and 6.1.1)(same donor T cells).

FIG. 13 shows the concentration dependent enhancement of IFN-γ production in the T cell blast/Raji assay induced by CTLA-4 blocking antibodies (BNI3 (PharMingen) and the 4.1.1, 4.8.1, and 6.1.1 antibodies of the invention) (same donor T cells).

Figure 14:
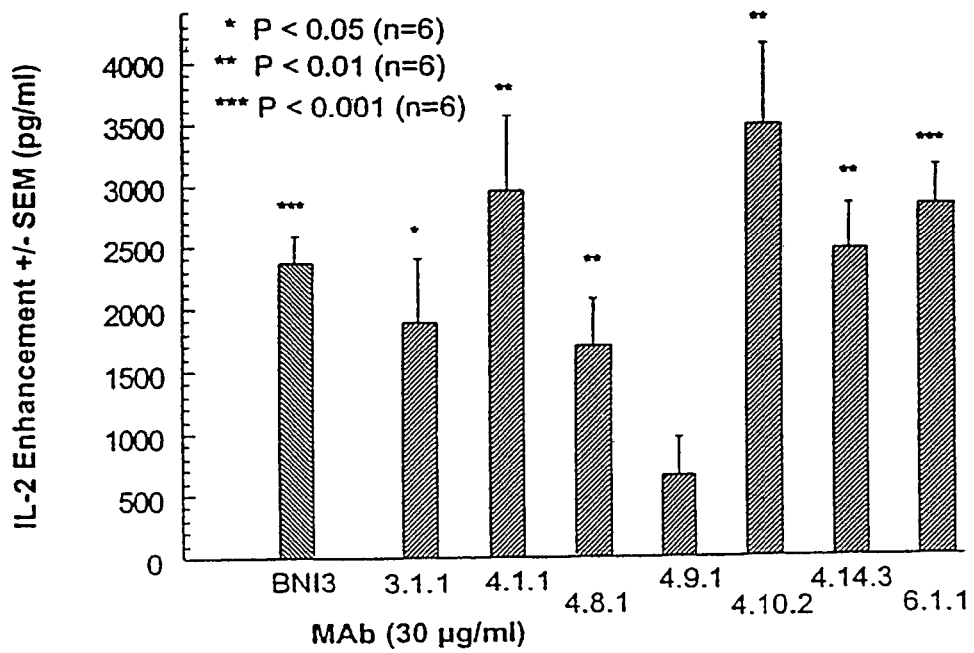
FIG. 14 shows the mean enhancement of IL-2 production in T cells from 6 donors induced by anti-CTLA-4 blocking antibodies in the T cell blast/Raji assay.

FIG. 14 shows the mean enhancement of IL-2 production in T cells from 6 donors induced by CTLA-4 blocking antibodies in the T cell blast/Raji assay. It is interesting to consider that the mAb, CT4.9.1, binds to CTLA4 but does not block B7 binding. Thus, simply binding to CTLA-4 is insufficient by itself to provide a functional antibody of the invention.

Figure 15:
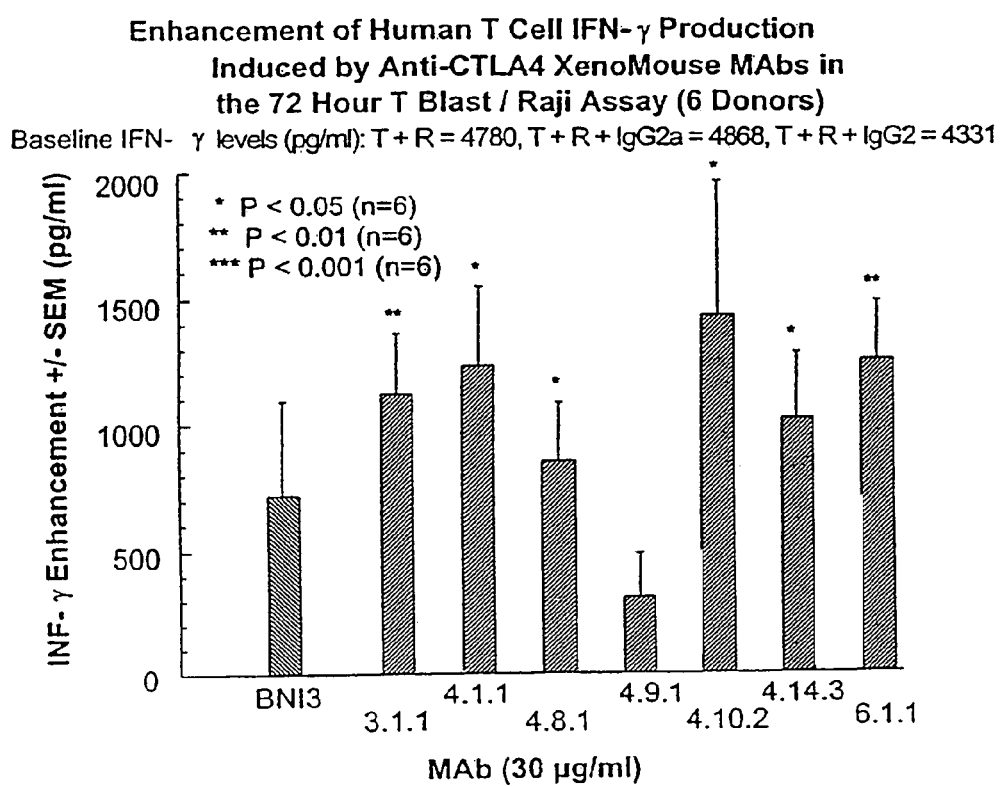
FIG. 15 shows the mean enhancement of IFN-γ production in T cells from 6 donors induced by anti-CTLA-4 blocking antibodies in the T cell blast/Raji assay.

FIG. 15 shows the mean enhancement of IFN-γ production in T cells from 6 donors induced by CTLA-4 blocking antibodies in the T cell blast/Raji assay.

Figure 19:
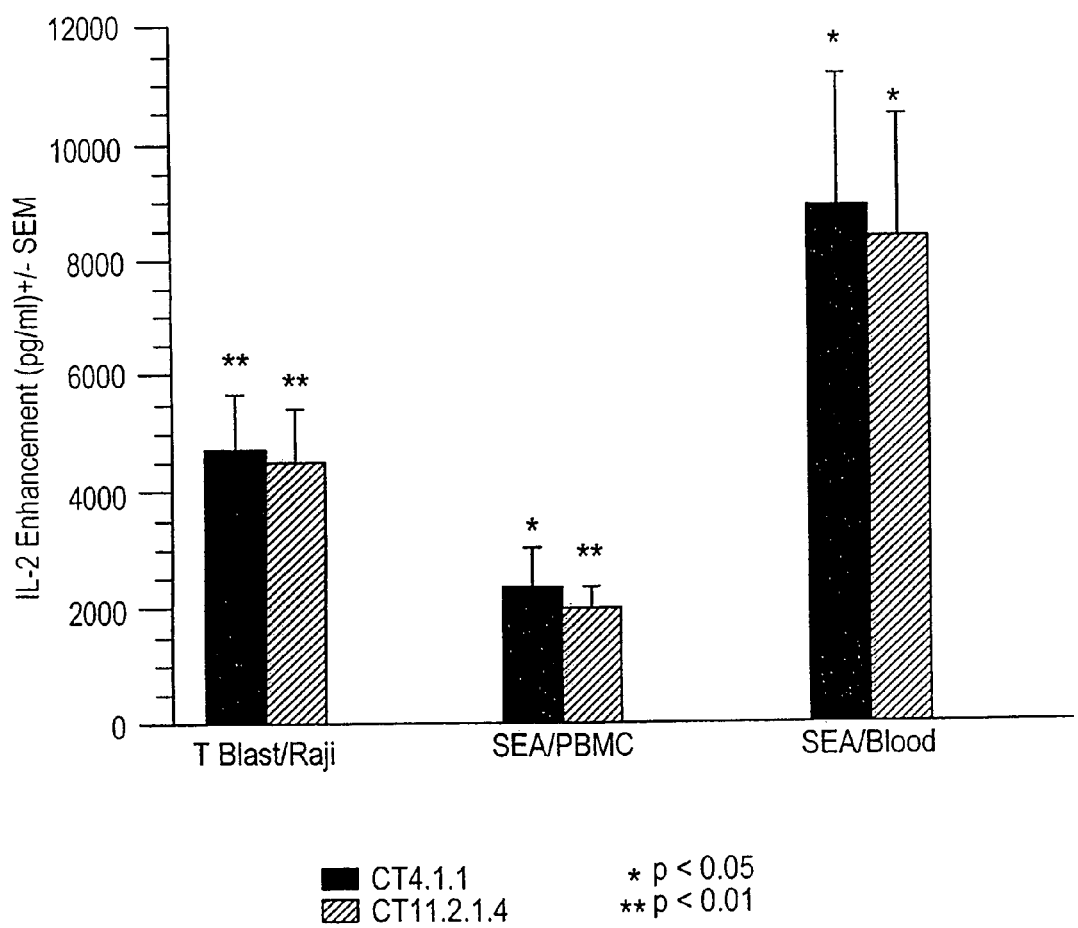
FIG. 19 shows enhancement of IL-2 production induced by anti-CTLA4 antibodies (4.1.1 and 11.2.1) of the invention in a 72 hour T blast/Raji and Superantigen (whole blood and peripheral blood mononuclear cells from 6 donors) assays.

FIG. 19 shows a comparison between the 4.1.1 and 11.2.1 antibodies of the invention at a concentration of 30 µg/ml in the 72 hour T cell blast/Raji assay as described in this Example 9 and the Superantigen assay described in Example 10.

Figure 20:
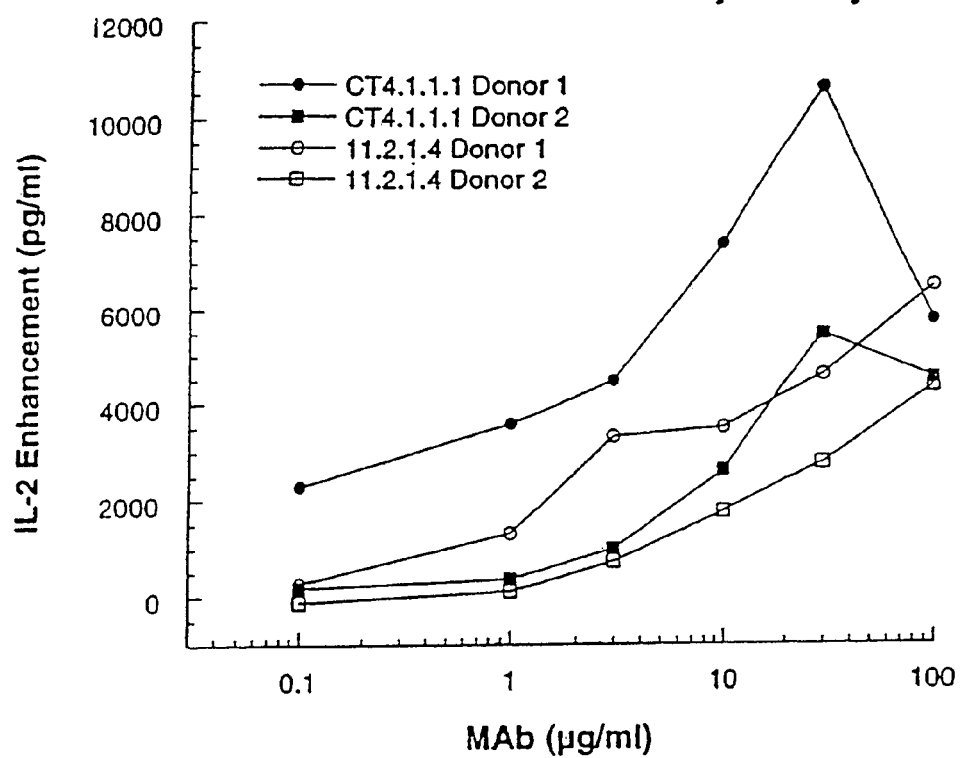
FIG. 20 shows dose dependent enhancement of IL-2 production induced by anti-CTLA4 antibodies (4.1.1 and 11.2.1) of the invention in a 72 hour T blast/Raji assay.

FIG. 20 shows the concentration dependent enhancement of IL-2 production in the T cell blast/Raji assay induced by the 4.1.1 and 11.2.1 CTLA4 antibodies of the invention.

The following Table IVc provides information related to mean enhancement and range of enhancement of cytokine response in the Raji and SEA assays of the invention. Each of the experiments included in the results are based on antibody at a dose of 30 µg/ml and measured at 72 hours. Numbers of donors used in the experiments as well as responses are shown.

TABLE IVC

| Assay | mAb | Cytokine | Mean Enhancement pg/ml | SEM | Range Enhancement pg/ml | n | Donor Response |
|---|---|---|---|---|---|---|---|
| T cell blast/Raji | 4.1.1 | IL-2 | 3329 | 408 | 0 to 8861 | 42 | 19 of 21 |
| T cell blast/Raji | 4.1.1 | IFN-γ | 3630 | 980 | 600 to 13939 | 17 | 13 of 13 |
| T cell blast/Raji | 11.2.1 | IL-2 | 3509 | 488 | 369 to 6424 | 18 | 14 of 14 |
| SEA (PBMC) | 4.1.1 | IL-2 | 2800 | 312 | 330 to 6699 | 42 | 17 of 17 |
| SEA (PBMC) | 11.2.1 | IL-2 | 2438 | 366 | 147 to 8360 | 25 | 15 of 15 |
| SEA (Whole Blood) | 4.1.1 | IL-2 | 6089 | 665 | −168 to 18417 | 46 | 15 of 17 |
| SEA (Whole Blood) | 11.2.1 | IL-2 | 6935 | 700 | −111 to 11803 | 25 | 12 of 14 |

Example 10

Human T-Cell Signal Model

We developed a second cellular assay in order to quantify the enhancement of T-cell IL-2 upregulation upon blockade of CTLA-4 signal with the antibodies. The following materials and methods were utilized in connection with the experiments:

Materials and Methods

Human PBMC were prepared using Accuspin. Microtiter plates were precoated with an anti-CD3 antibody (leu4, Becton Dickinson) (60 ng/ml) and incubated for 2 hours at 37° C. hPBMC were added to the wells at 200,000 cells per well. *Staphylcoccus enterotoxin* A (SEA) (Sigma) was added to the wells at 100 ng/ml. Antibodies were added to the wells, usually at 30 µg/ml. Cells were then stimulated for 48, 72 or 96 hours. Plates were centrifuged at the desired time-point and supernatants were removed from the wells. Thereafter, supernatants were checked for IL-2 production using ELISA (R&D Systems).

Figure 16:
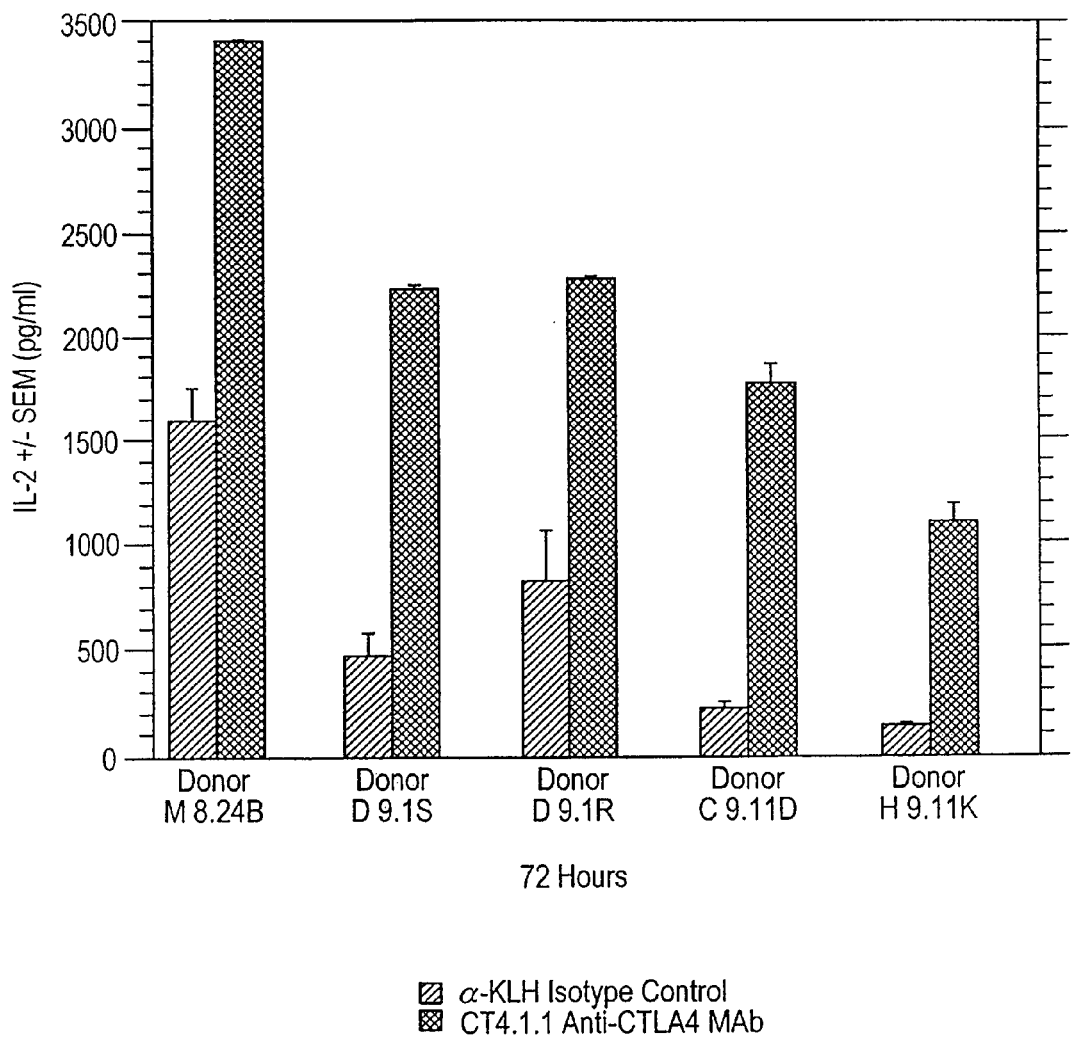
FIG. 16 shows the enhancement of IL-2 production in hPBMC from 5 donors induced by anti-CTLA-4 blocking mAbs as measured at 72 hours after stimulation with SEA.
Figure 17:
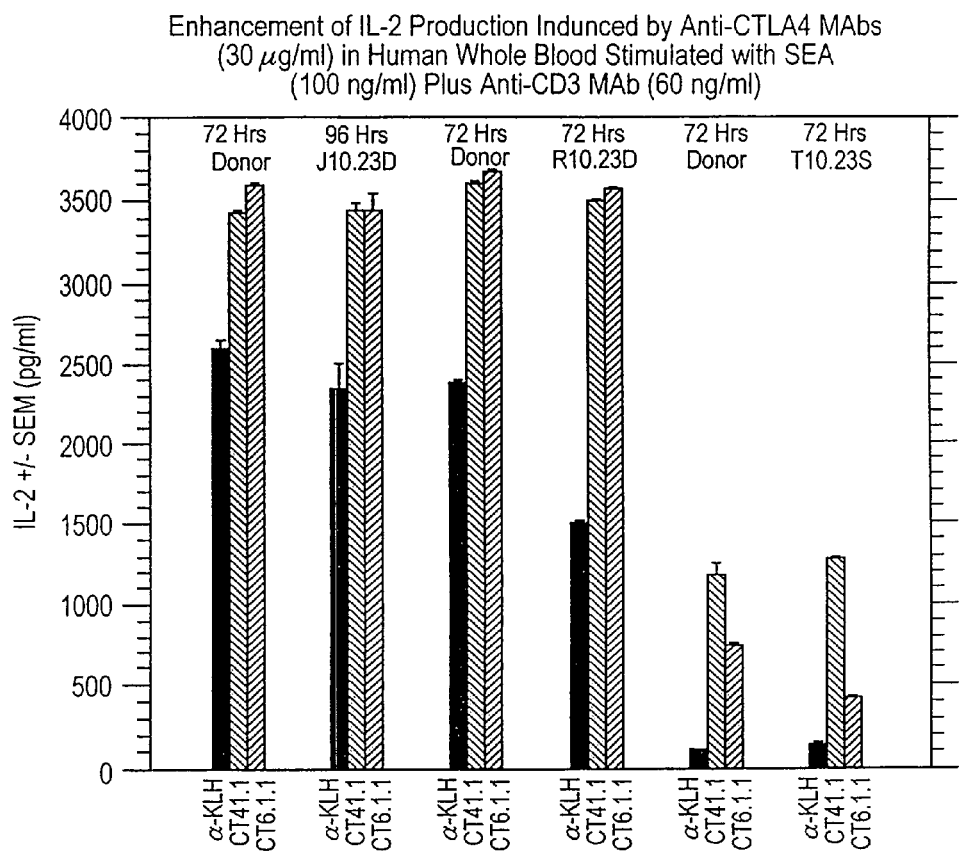
FIG. 17 shows the enhancement of IL-2 production in whole blood from 3 donors induced by anti-CTLA-4 blocking mAbs as measured at 72 and 96 hours after stimulation with SEA.
Figure 21:
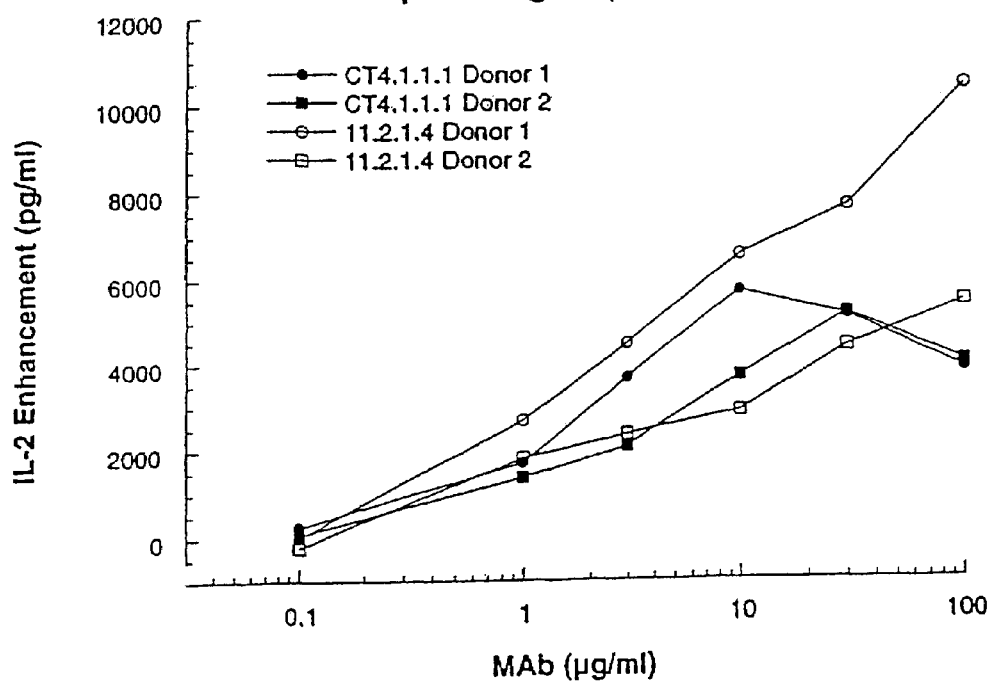
FIG. 21 shows dose dependent enhancement of IL-2 production induced by anti-CTLA4 antibodies (4.1.1 and 11.2.1) of the invention in a 72 hour Superantigen whole blood assay stimulated with 100 ng/ml superantigen.

Results from these experiments are shown in FIGS. 16, 17, and 21. In FIG. 16, induction of IL-2 production in hPBMC from 5 donors was measured 72 hours after stimulation. In FIG. 17, results are shown from measurement of whole blood, analyzing the difference in induction of IL-2 production in the blood of 3 donors as measured at 72 and 96 hours after stimulation.

In FIG. 21, the enhancement of IL-2 production in whole blood of 2 donors as measured at 72 hours after stimulation.

Example 11

Tumor Animal Model

We have established an animal tumor model for the in vivo analysis of anti-murine-CTLA-4 antibodies in inhibiting tumor growth. In the model, a murine fibrosarcoma tumor is grown and the animals are treated with anti-murine-CTLA-4 antibodies. The materials and methods for establishment of the model are provided below:

Materials and Methods

Female A/J mice (6-8 weeks old) were injected subcutaneously on the dorsal side of the neck with 0.2 ml of Sa1N tumor cells (1×10$^6$) (Baskar 1995). Anti-murine CTLA-4 or an isotype matched control antibody (PharMingen, San Diego, Calif., 200 ug/animal) were injected intraperitioneally on days 0, 4, 7 and 14 following the injection of tumor cells. Tumor measurements were taken during the course of the 3-4 week experiments using a Starrett SPC Plus electronic caliper (Athol, Mass.) and tumor size was expressed as the surface area covered by tumor growth (mm$^2$).

Figure 18:
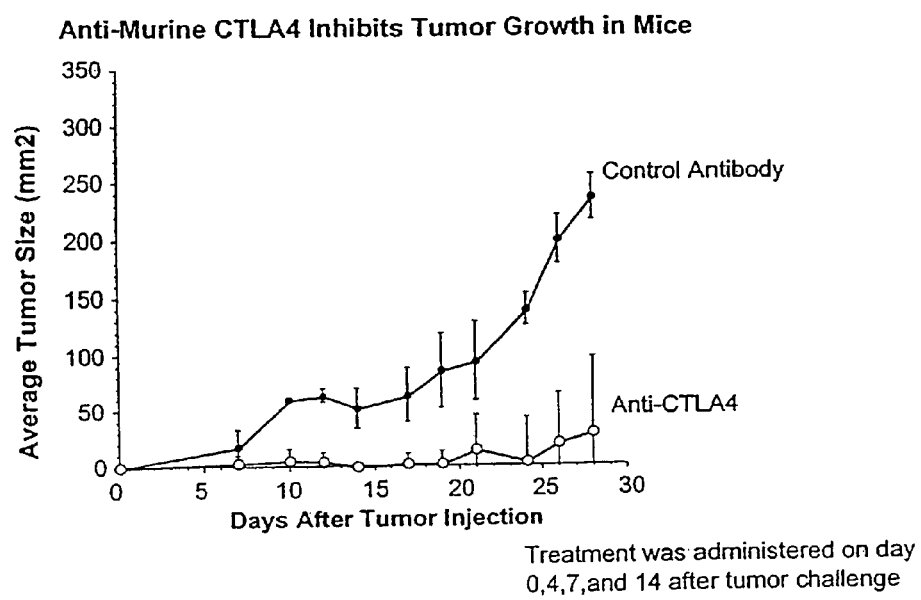
FIG. 18 shows the inhibition of tumor growth with an anti-murine CTLA-4 antibody in a murine fibrosarcoma tumor model.

FIG. 18 shows the inhibition of tumor growth with an anti-murine CTLA-4 antibody in a murine fibrosarcoma tumor model. As shown in FIG. 18, animals treated with anti-CTLA-4 had a reduction in tumor growth as compared to animals treated with an isotype control antibody. Accordingly, anti-murine CTLA4 mAbs are capable of inhibiting growth of a fibrosarcoma in a mouse tumor model.

It is expected that antibodies that are cross-reactive with murine CTLA-4 would perform similarly in the model. However, of the antibodies of the invention that have been checked for cross-reactivity, none are cross-reactive with murine CTLA-4.

Example 12

Tumor Animal Model

In order to further investigate the activity of antibodies in accordance with the invention, a xenograft SCID mouse model was designed to test the eradication of established tumors and their derived metastases. In the model, SCID mice are provided with grafted human T cells and are implanted with patient-derived non-small cell lung cell (NSCL) or colorectal carcinoma (CC) cells. Implantation is made into the gonadal fat pads of SCID mice. The tumors are allowed to grow, and thereafter removed. The mice develop human-like tumor and liver metastases. Such a model is described in Bumpers et al *J. Surgical Res.* 61:282-288 (1996).

It is expected that antibodies of the invention will inhibit growth of tumors formed in such mice.

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

Alegre et al. *J Immunol* 157:4762-70 (1996)
Allison and Krummel *Science* 270:932-933 (1995)
Balzano et al. *Int J Cancer Suppl* 7:28-32 (1992)
Blair et al. *J Immunol* 160:12-5 (1998)
Blake and Litzi-Davis *BioConjugate Chem.* 3:510-513 (1992)
Boussiotis et al. *Proc Natl Acad Sci USA* 90:11059-63 (1993)
Bowie et al. *Science* 253:164 (1991)
Bruggeman et al. *PNAS USA* 86:6709-6713 (1989)

Bruggeman, M. and Neuberger, M. S. in *Methods: A companion to Methods in Enzymology* 2:159-165 (Lerner et al. eds. Academic Press (1991))

Bruggemann et al., "Human antibody production in transgenic mice: expression from 100 kb of the human IgH locus." *Eur. J Immunol.* 21:1323-1326 (1991)

Bruggemann, M. and Neuberger, M. S. "Strategies for expressing human antibody repertoires in transgenic mice." *Immunology Today* 17:391-397 (1996)

Brunet et al. *Nature* 328:267-270 (1987)

Bumpers et al *J. Surgical Res.* 61:282-288 (1996)

Capsey et al. *Genetically Engineered Human Therapeutic Drugs* (Stockton Press, NY (1988))

Castan et al. *Immunology* 90:265-71 (1997)

Cepero et al. *J Exp Med* 188:199-204 (1998)

Chen et al. "Immunoglobulin gene rearrangement in B-cell deficient mice generated by targeted deletion of the $J_H$ locus" *International Immunology* 5:647-656 (1993)

Chen et al. *Cell* 71:1093-1102 (1992)

Chen et al. *Human Gene Therapy* 5:595-601 (1994)

Chiswell and McCafferty *TIBTECH* 10:80-84 (1992)

Choi et al. "Transgenic mice containing a human heavy chain immunoglobulin gene fragment cloned in a yeast artificial chromosome" *Nature Genetics* 4:117-123 (1993)

Chothia & Lesk *J. Mol. Biol.* 196:901-917 (1987)

Chothia et al. *Nature* 342:878-883 (1989)

Chuang et al. *J. Immunol.* 159:144-151(1997)

Coligan et al., Unit 2.1, "Enzyme-linked immunosorbent assays," in *Current protocols in irnmunology* (1994)

Cwirla et al. *PNAS USA* 87:6378-6382 (1990)

Dariavach et al. *Eur. J Immunol.* 18:1901-1905 (1988)

Dayhoff, M. O., in *Atlas of Protein Sequence and Structure*, pp. 101-110 (Volume 5, National Biomedical Research Foundation (1972)) and Supplement 2 to this volume, pp. 1-10 de Boer et al. *Eur J Immunol* 23:3120-5 (1993)

Eckstein, Ed., Oxford University Press, Oxford England (1991))

Evans et al. *J. Med. Chem.* 30:1229 (1987)

Fallarino et al. *J Exp Med* 188:205-10 (1998)

Fanger et al. *Immunol Methods* 4:72-81 (1994)

Fauchere, *J. Adv. Drug Res.* 15:29 (1986)

Fishwild et al., "High-avidity human IgGγ monoclonal antibodies from a novel strain of minilocus transgenic mice." *Nature Biotech.* 14:845-851 (1996).

Freeman et al. *J Exp Med* 178:2185-92 (1993)

Freeman et al. *J Immunol* 161:2708-15 (1998)

Freeman et al. *Science* 262:907-9 (1993)

*Fundamental Immunology* Ch. 7 (Paul, W., ed., 2nd ed. Raven Press, N.Y. (1989))

Galfre, G. and Milstein, C., "Preparation of monoclonal antibodies: strategies and procedures." *Methods Enzymol.* 73:3-46 (1981)

Gorman et al. *P.N.A.S.* 79:6777 (1982)

Green and Jakobovits *J. Exp. Med.* 188:483-495 (1998)

Green et al. *Nature Genetics* 7:13-21 (1994)

Grosschedl et al. *Cell* 41:885 (1985)

Hanes and Plucthau *PNAS USA* 94:4937-4942 (1997)

Harding et al. *Nature* 356:607-609 (1994)

Harper et al. *J Immunol* 147:1037-44 (1991)

Hathcock et al. *Science* 262:905-7 (1993)

Hoganboom et al. *Immunol. Reviews* 130:43-68 (1992)

Horspool et al. *J Immunol* 160:2706-14 (1998)

Houghten et al. *Biotechniques* 13:412-421 (1992)

Houghten *PNAS USA* 82:5131-5135 (1985)

Hurwitz et al. *J Neuroimmunol* 73:57-62 (1997)

Hurwitz et al. *Proc Natl Acad Sci USA* 95:10067-71 (1998)

*Immunology-A Synthesis* (2nd Edition, E. S. Golub and D. R. Gren, Eds., Sinauer Associates, Sunderland, Mass. (1991))

*Introduction to Protein Structure* (C. Branden and J. Tooze, eds., Garland Publishing, New York, N.Y. (1991))

Jakobovits et al., "Germ-line transmission and expression of a human-derived yeast artificial-chromosome." *Nature* 362:255-258 (1993)

Jakobovits, A. et al., "Analysis of homozygous mutant chimeric mice: Deletion of the immunoglobulin heavy-chain joining region blocks B-cell development and antibody production." *Proc. Natl. Acad. Sci. USA* 90:2551-2555 (1993)

Jakobovits, A., "Humanizing the mouse genome." *Current Biology* 4:761-763 (1994)

Jakobovits, A., "Production of fully human antibodies by transgenic mice." *Current Opinion in Biotechnology* 6:561-566 (1995)

Junghans et al. in *Cancer Chemotherapy and Biotherapy* 655-686 (2d edition, Chafner and Longo, eds., Lippincott Raven (1996))

Kabat et al. (1991) Sequences of Proteins of Immunological Interest, N.I.H. publication no. 91-3242

Kabat *Sequences of Proteins of Immunological Interest* (National Institutes of Health, Bethesda, Md. (1987 and 1991))

Kostelny et al. *J. Immunol.* 148:1547-1553 (1992)

Krummel and Allison *J Exp Med* 182:459-65 (1995)

Krummel et al. *Int Immunol* 8:519-23 (1996)

Kuchroo et al. *Cell* 80:707-18 (1995)

Kwon et al. *PNAS USA* 94:8099-103 (1997)

LaPlanche et al. *Nucl. Acids Res.* 14:9081 (1986)

Lenschow et al. *Proc Natl Acad Sci USA* 90:11054-8 (1993)

Lenschow et al. *Science* 257:789-792 (1992)

Lin et al. *J Exp Med* 188:199-204 (1998)

Linsley et al. *J Exp Med* 176:1595-604 (1992)

Linsley et al. *J. Exp. Med.* 174:561-569 (1991)

Linsley et al. *Science* 257:792-795 (1992)

Liu et al. *J. Immunol.* 139:3521 (1987)

Liu et al. *P.N.A.S.* 84:3439 (1987)

Lonberg et al., "Antigen-specific human antibodies from mice comprising four distinct genetic modifications." *Nature* 368:856-859 (1994).

Luhder et al. *J Exp Med* 187:427-32 (1998)

Marasco *Gene Therapy* 4:11-15 (1997)

Markees et al. *J Clin Invest* 101:2446-55 (1998)

Marks et al., "Oligonucleotide primers for polymerase chain reaction amplification of human immunoglobulin variable genes and design of family-specific oligonucleotide probes." *Eur. J Immunol.* 21:985-991 (1991)

McCoy et al. *J Exp Med* 186:183-7 (1997)

Mendez et al. *Nature Genetics* 15:146-156 (1997)

Needleman and Wunsch *J. Mol. Biol.* 48:443 (1970)

Okayama et al. *Mol. Cell. Bio.* 3:280 (1983)

Parmley and Smith *Gene* 73:305-318 (1988)

Pearson and Lipman *Proc. Natl. Acad. Sci. (U.S.A.)* 85:2444 (1988)

Perez et al. *Immunity* 6:411-7 (1997)

Perrin et al. *Immunol Res* 14:189-99 (1995)

Perrin et al. *J Immunol* 157:1333-6 (1996)

Pinalla et al. *Biotechniques* 13:901-905 (1992)

*Proteins, Structures and Molecular Principles* (Creighton, Ed., W. H. Freeman and Company, New York (1984))

Razi-Wolf et al. *Proc Natl Acad Sci USA* 90:11182-6 (1993)

Remington's Pharmaceutical Sciences (15th ed, Mack Publishing Company, Easton, Pa. (1975)), particularly Chapter 87 by Blaug, Seymour Rizo and Gierasch *Ann. Rev. Biochem.* 61:387 (1992)

Russel et al. *Nucl. Acids Research* 21:1081-1085 (1993)

Schwartz *Cell* 71:1065 (1992)
Scott *TIBS* 17:241-245 (1992)
Smith and Waterman *Adv. Appl. Math.* 2:482 (1981)
Songsivilai & Lachmann *Clin. Exp. Immunol.* 79: 315-321 (1990)
Stec et al. *J. Am. Chem. Soc.* 106:6077 (1984)
Stein et al. *Nucl. Acids Res.* 16:3209 (1988)
Taylor et al., "A transgenic mouse that expresses a diversity of human sequence heavy and light chain immunoglobulins." *Nucleic Acids Research* 20:6287-6295 (1992)
Taylor et al., "Human immunoglobulin transgenes undergo rearrangement, somatic mutation and class switching in mice that lack endogenous IgM." *International Irnmunology* 6:579-591 (1994)
*The McGraw-Hill Dictionary of Chemical Terms* (Parker, S., Ed., McGraw-Hill, San Francisco (1985))
Thornton et at. *Nature* 354:105 (1991)
Tivol et al. *Immunity* 3:541-7 (1995)
Townsend and Allison *Science* 259:368 (1993)
Traunecker et al. *Int. J Cancer (Suppl.)* 7:51-52 (1992)
Tuaillon et al. "Analysis of direct and inverted $DJ_H$ rearrangements in a human Ig heavy chain transgenic minilocus" *J. Immunol.* 154:6453-6465 (1995)
Tuaillon et al., "Human immunoglobulin heavy-chain minilocus recombination in transgenic mice: gene-segment use in μ and γ transcripts." *Proc. Natl. Acad. Sci. USA* 90:3720-3724 (1993)
Uhlmann and Peyman *Chemical Reviews* 90:543 (1990)
Van Parijs et al. *J Exp Med* 186:1119-28 (1997)
Veber and Freidinger *TINS* p. 392 (1985)
Vitetta *Immunol Today* 14:252 (1993)
Walunas et al. *Immunity* 1:405-13 (1994)
Walunas et al. *J Exp Med* 183:2541-50 (1996)
Waterhouse et al. *Science* 270:985-988 (1995)
Winter and Harris *Immunol Today* 14:43-46 (1993)
Wright et al. *Crit. Reviews in Immunol.* 12125-168 (1992)
Yang et al. *Cancer Res* 57:4036-41 (1997)
Yi-qun et al. *Int Immunol* 8:37-44 (1996)
Zon et al. *Anti-Cancer Drug Design* 6:539 (1991)
Zon et al. *Oligonucleotides and Analogues: A Practical Approach*, pp. 87-108 (F. Eckstein, Ed., Oxford University Press, Oxford England (1991))
Fry et al. "Specific, irreversible inactivation of the epidermal growth factor receptor and erbB2, by a new class of tyrosine kinase inhibitor" *Proc Natl Acad Sci USA* 95:12022-7 (1998)
Hoffman et al. "A model of Cdc25 phosphatase catalytic domain and Cdk-interaction surface based on the presence of a rhodanese homology domain" *J Mol Biol* 282:195-208 (1998)
Ginalski et al. "Modelling of active forms of protein kinases: p38—a case study" *Acta Biochim Pol* 44:557-64 (1997)
Jouko et al. "Identification of csk tyrosine phosphorylation sites and a tyrosine residue important for kinase domain structure" *Biochem J* 322:927-35 (1997)
Singh et al. "Structure-based design of a potent, selective, and irreversible inhibitor of the catalytic domain of the erbB receptor subfamily of protein tyrosine kinases" *J Med Chem* 40:1130-5 (1997)
Mandel et al. "ABGEN: a knowledge-based automated approach for antibody structure modeling" *Nat Biotechnol* 14:323-8 (1996)
Monfardini et al. "Rational design, analysis, and potential utility of GM-CSF antagonists" *Proc Assoc Am Physicians* 108:420-31 (1996)
Furet et al. "Modelling study of protein kinase inhibitors: binding mode of staurosporine and origin of the selectivity of CGP 52411" *J Comput Aided Mol Des* 9:465-72 (1995)
Ill et al. "Design and construction of a hybrid immunoglobulin domain with properties of both heavy and light chain variable regions" *Protein Eng* 10:949-57 (1997)
Martin et al. "The affinity-selection of a minibody polypeptide inhibitor of human interleukin-6" *EMBO J* 13:5303-9 (1994)
U.S. patent application Ser. No. 07/466,008, filed Jan. 12, 1990
U.S. patent application Ser. No. 07/574,748, filed Aug. 29, 1990
U.S. patent application Ser. No. 07/575,962, filed Aug. 31, 1990
U.S. patent application Ser. No. 07/610,515, filed Nov. 8, 1990
U.S. patent application Ser. No. 07/810,279, filed Dec. 17, 1991
U.S. patent application Ser. No. 07/853,408, filed Mar. 18, 1992
U.S. patent application Ser. No. 07/904,068, filed Jun. 23, 1992
U.S. patent application Ser. No. 07/919,297, filed Jul. 24, 1992
U.S. patent application Ser. No. 07/922,649, filed Jul. 30, 1992
U.S. patent application Ser. No. 07/990,860, filed Dec. 16, 1992
U.S. patent application Ser. No. 08/031,801, filed Mar. 15, 1993
U.S. patent application Ser. No. 08/053,131, filed Apr. 26, 1993
U.S. patent application Ser. No. 08/096,762, filed Jul. 22, 1993
U.S. patent application Ser. No. 08/112,848, filed Aug. 27, 1993
U.S. patent application Ser. No. 08/155,301, filed Nov. 18, 1993
U.S. patent application Ser. No. 08/161,739, filed Dec. 3, 1993
U.S. patent application Ser. No. 08/165,699, filed Dec. 10, 1993
U.S. patent application Ser. No. 08/209,741, filed Mar. 9, 1994
U.S. patent application Ser. No. 08/234,145, filed Apr. 28, 1994
U.S. patent application Ser. No. 08/724,752, filed Oct. 2, 1996
U.S. patent application Ser. No. 08/730,639, filed Oct. 11, 1996
U.S. patent application Ser. No. 08/759,620, filed Dec. 3, 1996
U.S. patent application Ser. No. 08/759,620, filed Dec. 3, 1996
U.S. Pat. No. 4,399,216
U.S. Pat. No. 4,681,581
U.S. Pat. No. 4,683,195
U.S. Pat. No. 4,683,202
U.S. Pat. No. 4,735,210
U.S. Pat. No. 4,740,461
U.S. Pat. No. 4,816,397
U.S. Pat. No. 4,912,040
U.S. Pat. No. 4,959,455
U.S. Pat. No. 5,101,827
U.S. Pat. No. 5,102,990 (RE 35,500)
U.S. Pat. No. 5,151,510

U.S. Pat. No. 5,194,594
U.S. Pat. No. 5,434,131
U.S. Pat. No. 5,530,101
U.S. Pat. No. 5,545,806
U.S. Pat. No. 5,545,807
U.S. Pat. No. 5,585,089
U.S. Pat. No. 5,591,669
U.S. Pat. No. 5,612,205
U.S. Pat. No. 5,625,126
U.S. Pat. No. 5,625,825
U.S. Pat. No. 5,633,425
U.S. Pat. No. 5,643,763
U.S. Pat. No. 5,648,471
U.S. Pat. No. 5,661,016
U.S. Pat. No. 5,693,761
U.S. Pat. No. 5,693,792
U.S. Pat. No. 5,697,902
U.S. Pat. No. 5,703,057
U.S. Pat. No. 5,714,350
U.S. Pat. No. 5,721,367
U.S. Pat. No. 5,733,743
U.S. Pat. No. 5,770,197
U.S. Pat. No. 5,770,429
U.S. Pat. No. 5,773,253
U.S. Pat. No. 5,777,085
U.S. Pat. No. 5,789,215
U.S. Pat. No. 5,789,650
U.S. Pat. No. 5,811,097
European Patent No. EP 0 546 073 B1
European Patent No. EP 0 463 151 B1, grant published Jun. 12, 1996
International Patent Application No. WO 92/02190
International Patent Application No. WO 92/03918
International Patent Application No. WO 92/22645
International Patent Application No. WO 92/22647
International Patent Application No. WO 92/22670
International Patent Application No. WO 93/00431
International Patent Application No. WO 93/12227
International Patent Application No. WO 94/00569
International Patent Application No. WO 94/02602, published Feb. 3, 1994
International Patent Application No. WO 94/25585
International Patent Application No. WO 94/29444
International Patent Application No. WO 95/01994
International Patent Application No. WO 95/03408
International Patent Application No. WO 95/24217
International Patent Application No. WO 95/33770
International Patent Application No. WO 96/14436
International Patent Application No. WO 96/34096, published Oct. 31, 1996
International Patent Application No. WO 97/13852
International Patent Application No. WO 97/20574
International Patent Application No. WO 97/38137
International Patent Application No. WO 98/24884
International Patent Application No. WO 98/24893, published Jun. 11, 1998

Equivalents

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

What we claim is:

1. A human monoclonal antibody or an antigen-binding portion thereof that specifically binds to CTLA-4, wherein said antibody comprises heavy chain CDR1, CDR2, and CDR3 amino acid sequences from a heavy chain variable domain; and wherein said antibody comprises light chain CDR1, CDR2, and CDR3 amino acid sequences from a light chain variable domain; wherein said heavy chain variable domain and said light chain variable domain comprise:
   (a) the amino acid sequence of SEQ ID NO: 73 and the amino acid sequence of SEQ ID NO: 95, respectively;
   (b) the amino acid sequence of SEQ ID NO: 75 and the amino acid sequence of SEQ ID NO: 89, respectively;
   (c) the amino acid sequence of SEQ ID NO: 76 and the amino acid sequence of SEQ ID NO: 92, respectively;
   (d) the amino acid sequence of SEQ ID NO: 78 and the amino acid sequence of SEQ ID NO: 90, respectively;
   (e) the amino acid sequence of SEQ ID NO: 79 and the amino acid sequence of SEQ ID NO: 91, respectively;
   (f) the amino acid sequence of SEQ ID NO: 81 and the amino acid sequence of SEQ ID NO: 97, respectively;
   (g) the amino acid sequence of SEQ ID NO: 82 and the amino acid sequence of SEQ ID NO: 98, respectively;
   (h) the amino acid sequence of SEQ ID NO: 83 and the amino acid sequence of SEQ ID NO: 114, respectively; or
   (i) the amino acid sequence of SEQ ID NO: 84 and the amino acid sequence of SEQ ID NO: 116, respectively.

2. The antibody or antigen-binding portion according to claim 1 that is an Fab fragment, an F(ab')$_2$ fragment, an F$_v$ fragment, a single chain antibody, or a bispecific antibody.

3. The antibody according to claim 1 that is an immunoglobulin G (IgG), an IgM, an IgE, an IgA or an IgD molecule.

4. A pharmaceutical composition comprising the antibody or antigen-binding portion according to claim 1 and a pharmaceutically acceptable carrier.

5. A method for treating a tumor in a subject, comprising the step of administering to the subject the antibody or antigen-binding portion according to claim 1.

6. A monoclonal antibody or an antigen-binding portion thereof, wherein said antibody comprises a heavy chain and a light chain comprising:
   (a) the amino acid sequence of SEQ ID NO: 73 and the amino acid sequence of SEQ ID NO: 95, respectively;
   (b) the amino acid sequence of SEQ ID NO: 75 and the amino acid sequence of SEQ ID NO: 89, respectively;
   (c) the amino acid sequence of SEQ ID NO: 76 and the amino acid sequence of SEQ ID NO: 92, respectively;
   (d) the amino acid sequence of SEQ ID NO: 78 and the amino acid sequence of SEQ ID NO: 90, respectively;
   (e) the amino acid sequence of SEQ ID NO: 79 and the amino acid sequence of SEQ ID NO: 91, respectively;
   (f) the amino acid sequence of SEQ ID NO: 81 and the amino acid sequence of SEQ ID NO: 97, respectively;
   (g) the amino acid sequence of SEQ ID NO: 82 and the amino acid sequence of SEQ ID NO: 98, respectively;
   (h) the amino acid sequence of SEQ ID NO: 83 and the amino acid sequence of SEQ ID NO: 114, respectively; or
   (i) the amino acid sequence of SEQ ID NO: 84 and the amino acid sequence of SEQ ID NO: 116, respectively.

7. The antibody according to claim 6, wherein the heavy chain and light chain comprise:
   (a) a heavy chain comprising the amino acid sequence of SEQ ID NO: 66 and a light chain comprising the amino acid sequence of SEQ ID NO: 67, respectively; or
   (b) a heavy chain comprising the amino acid sequence of SEQ ID NO: 68 and a light chain comprising the amino acid sequence of SEQ ID NO: 69, respectively.

8. A human monoclonal antibody or an antigen-binding portion thereof that specifically binds to CTLA-4, wherein the heavy chain of said antibody comprises an amino acid sequence selected from the group consisting of SEQ ID NOS: 73, 75, 76, 78, 79, and 81-84.

9. The antibody according to claim 8, wherein said heavy chain comprises the amino acid sequence of SEQ ID NO: 66 or 68.

10. The antibody according to claim 8 that is a bispecific antibody.

11. The antibody according to claim 8 that is an immunoglobulin G (IgG), an IgM, an IgE, an IgA or an IgD molecule.

12. A pharmaceutical composition comprising the antibody or portion according to claim 8 and a pharmaceutically acceptable carrier.

13. A method for treating a tumor in a subject, comprising the step of administering to the subject the antibody or portion according to claim 8.

14. A human monoclonal antibody or an antigen-binding portion thereof that specifically binds to CTLA-4, wherein the light chain of said antibody comprises an amino acid sequence selected from the group consisting of SEQ ID NOS: 89-92, 95, 97, 98, 114, and 116.

15. The antibody according to claim 14, wherein the light chain comprises the amino acid sequence of SEQ ID NO: 67 or 69.

16. The antibody according to claim 14 that is a bispecific antibody.

17. The antibody according to claim 14 that is an immunoglobulin G (IgG), an IgM, an IgE, an IgA or an IgD molecule.

18. A pharmaceutical composition comprising the antibody or portion according to claim 14 and a pharmaceutically acceptable carrier.

19. A method for treating a tumor in a subject, comprising the step of administering to the subject the antibody or portion according to claim 14.

* * * * *

UNITED STATES PATENT AND TRADEMARK OFFICE
CERTIFICATE OF CORRECTION

| | | |
|---|---|---|
| PATENT NO. | : 7,824,679 B2 | Page 1 of 1 |
| APPLICATION NO. | : 11/981810 | |
| DATED | : November 2, 2010 | |
| INVENTOR(S) | : Douglas Charles Hanson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 189 days.

Signed and Sealed this
Twenty-sixth Day of July, 2011

David J. Kappos
*Director of the United States Patent and Trademark Office*

SEQUENCE LISTING

<160> NUMBER OF SEQ ID NOS: 147

<210> SEQ ID NO 1
<211> LENGTH: 463
<212> TYPE: PRT
<213> ORGANISM: Homo sapiens

<400> SEQUENCE: 1

Met Glu Phe Gly Leu Ser Trp Val Phe Leu Val Ala Leu Leu Arg Gly
 1               5                   10                  15

Val Gln Cys Gln Val Gln Leu Val Glu Ser Gly Gly Gly Val Val Gln
             20                  25                  30

Pro Gly Arg Ser Leu Arg Leu Ser Cys Val Ala Ser Gly Phe Thr Phe
         35                  40                  45

Ser Ser His Gly Met His Trp Val Arg Gln Ala Pro Gly Lys Gly Leu
     50                  55                  60

Glu Trp Val Ala Val Ile Trp Tyr Asp Gly Arg Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asn Ser Leu Arg Ala Glu Asp Thr Ala Val
            100                 105                 110

Tyr Tyr Cys Ala Arg Gly Gly His Phe Gly Pro Phe Asp Tyr Trp Gly
        115                 120                 125

Gln Gly Thr Leu Val Thr Val Ser Ser Ala Ser Thr Lys Gly Pro Ser

```
            130                 135                 140
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Gln Phe Asn Trp Tyr Val Asp Gly Val Glu Val His Asn Ala Lys
        290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 2
<211> LENGTH: 464
<212> TYPE: PRT
<213> ORGANISM: Homo sapiens

<400> SEQUENCE: 2

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Thr Ala Ser Gly Phe Thr Phe
        35                  40                  45
```

-continued

```
Ser Asn Tyr Gly Met His Trp Val Arg Gln Ala Pro Gly Lys Gly Leu
         50                  55                  60
Glu Trp Val Ala Val Ile Trp Tyr Asp Gly Ser Asn Lys His Tyr Gly
 65                  70                  75                  80
Asp Ser Val Lys Gly Arg Phe Thr Ile Ser Ser Asp Asn Ser Lys Asn
                 85                  90                  95
Thr Leu Tyr Leu Gln Met Asn Ser Leu Arg Ala Glu Asp Thr Ala Val
                100                 105                 110
Tyr Tyr Cys Ala Arg Gly Glu Arg Leu Gly Ser Tyr Phe Asp Tyr Trp
            115                 120                 125
Gly Gln Gly Thr Leu Val Thr Val Ser Ser Ala Ser Thr Lys Gly Pro
        130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Asn Phe Gly Thr Gln Thr Tyr Thr Cys Asn Val Asp
    210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Pro Val Ala Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
        275                 280                 285
Glu Val Gln Phe Asn Trp Tyr Val Asp Gly Val Glu Val His Asn Ala
    290                 295                 300
Lys Thr Lys Pro Arg Glu Glu Gln Phe Asn Ser Thr Phe Arg Val Val
305                 310                 315                 320
Ser Val Leu Thr Val Val His Gln Asp Trp Leu Asn Gly Lys Glu Tyr
                325                 330                 335
Lys Cys Lys Val Ser Asn Lys Gly Leu Pro Ala Pro Ile Glu Lys Thr
            340                 345                 350
Ile Ser Lys Thr Lys Gly Gln Pro Arg Glu Pro Gln Val Tyr Thr Leu
        355                 360                 365
Pro Pro Ser Arg Glu Glu Met Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Met Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
        435                 440                 445
Leu His Asn His Tyr Thr Gln Lys Ser Leu Ser Leu Ser Pro Gly Lys
    450                 455                 460
```

<210> SEQ ID NO 3
<211> LENGTH: 163
<212> TYPE: PRT
<213> ORGANISM: Homo sapiens

<400> SEQUENCE: 3

```
Pro Gly Arg Ser Leu Arg Leu Ser Cys Ala Ala Ser Gly Phe Thr Phe
  1               5                  10                  15

Ser Ser His Gly Ile His Trp Val Arg Gln Ala Pro Gly Lys Gly Leu
             20                  25                  30

Glu Trp Val Ala Val Ile Trp Tyr Asp Gly Arg Asn Lys Asp Tyr Ala
         35                  40                  45

Asp Ser Val Lys Gly Arg Phe Thr Ile Ser Arg Asp Asn Ser Lys Lys
 50                  55                  60

Thr Leu Tyr Leu Gln Met Asn Ser Leu Arg Ala Glu Asp Thr Ala Val
 65                  70                  75                  80

Tyr Tyr Cys Ala Arg Val Ala Pro Leu Gly Pro Leu Asp Tyr Trp Gly
                 85                  90                  95

Gln Gly Thr Leu Val Thr Val Ser Ser Ala Ser Thr Lys Gly Pro Ser
            100                 105                 110

Val Phe Pro Leu Ala Pro Cys Ser Arg Ser Thr Ser Glu Ser Thr Ala
        115                 120                 125

Ala Leu Gly Cys Leu Val Lys Asp Tyr Phe Pro Glu Pro Val Thr Val
    130                 135                 140

Ser Trp Asn Ser Gly Ala Leu Thr Ser Gly Val His Thr Phe Pro Ala
145                 150                 155                 160

Val Leu Gln
```

<210> SEQ ID NO 4
<211> LENGTH: 463
<212> TYPE: PRT
<213> ORGANISM: Homo sapiens

<400> SEQUENCE: 4

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Glu
             20                  25                  30

Pro Gly Arg Ser Leu Arg Leu Ser Cys Thr Ala Ser Gly Phe Thr Phe
         35                  40                  45

Ser Ser Tyr Gly Met His Trp Val Arg Gln Ala Pro Gly Lys Gly Leu
 50                  55                  60

Glu Trp Val Ala Val Ile Trp Tyr Asp Gly Ser Asn Lys His Tyr Ala
 65                  70                  75                  80

Asp Ser Ala Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Ala Gly Leu Leu Gly Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Asp Val Ser His Glu Asp Pro Glu
                275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 5
<211> LENGTH: 169
<212> TYPE: PRT
<213> ORGANISM: Homo sapiens

<400> SEQUENCE: 5

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
                20                  25                  30

Gly Lys Gly Leu Glu Trp Val Ala Val Ile Trp Tyr Asp Gly Ser Asn
            35                  40                  45

Lys Tyr Tyr Ala Asp Ser Val Lys Gly Arg Phe Thr Ile Ser Arg Asp
        50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Gly Ala Arg Ile Ile Thr Pro
```

```
                     85                  90                  95
Cys Met Asp Val Trp Gly Gln Gly Thr Thr Val Thr Val Ser Ser Ala
                100                 105                 110
Ser Thr Lys Gly Pro Ser Val Phe Pro Leu Ala Pro Cys Ser Arg Ser
            115                 120                 125
Thr Ser Glu Ser Thr Ala Ala Leu Gly Cys Leu Val Lys Asp Tyr Phe
        130                 135                 140
Pro Glu Pro Val Thr Val Ser Trp Asn Ser Gly Ala Leu Thr Ser Gly
145                 150                 155                 160
Val His Thr Phe Pro Ala Val Leu Gln
                165
```

<210> SEQ ID NO 6
<211> LENGTH: 167
<212> TYPE: PRT
<213> ORGANISM: Homo sapiens

<400> SEQUENCE: 6

```
Gly Val Val Gln Pro Gly Arg Ser Leu Arg Leu Ser Cys Val Ala Ser
1               5                  10                  15
Gly Phe Ile Phe Ser Ser His Gly Ile His Trp Val Arg Gln Ala Pro
                20                  25                  30
Gly Lys Gly Leu Glu Trp Val Ala Val Ile Trp Tyr Asp Gly Arg Asn
            35                  40                  45
Lys Asp Tyr Ala Asp Ser Val Lys Gly Arg Phe Thr Ile Ser Arg Asp
        50                  55                  60
Asn Ser Lys Asn Thr Leu Tyr Leu Gln Met Asn Ser Leu Arg Ala Glu
65                  70                  75                  80
Asp Thr Ala Val Tyr Tyr Cys Ala Arg Val Ala Pro Leu Gly Pro Leu
                85                  90                  95
Asp Tyr Trp Gly Gln Gly Thr Leu Val Thr Val Ser Ser Ala Ser Thr
                100                 105                 110
Lys Gly Pro Ser Val Phe Pro Leu Ala Pro Cys Ser Arg Ser Thr Ser
            115                 120                 125
Glu Ser Thr Ala Ala Leu Gly Cys Leu Val Lys Asp Tyr Phe Pro Glu
        130                 135                 140
Pro Val Thr Val Ser Trp Asn Ser Gly Ala Leu Thr Ser Gly Val His
145                 150                 155                 160
Thr Phe Pro Ala Val Leu Gln
                165
```

<210> SEQ ID NO 7
<211> LENGTH: 172
<212> TYPE: PRT
<213> ORGANISM: Homo sapiens

<400> SEQUENCE: 7

```
Ser Gly Pro Gly Leu Val Lys Pro Ser Gln Ile Leu Ser Leu Thr Cys
1               5                  10                  15
Thr Val Ser Gly Gly Ser Ile Ser Ser Gly Gly His Tyr Trp Ser Trp
                20                  25                  30
Ile Arg Gln His Pro Gly Lys Gly Leu Glu Trp Ile Gly Tyr Ile Tyr
            35                  40                  45
Tyr Ile Gly Asn Thr Tyr Tyr Asn Pro Ser Leu Lys Ser Arg Val Thr
        50                  55                  60
Ile Ser Val Asp Thr Ser Lys Asn Gln Phe Ser Leu Lys Leu Ser Ser
```

```
                65                  70                  75                  80
        Val Thr Ala Ala Asp Thr Ala Val Tyr Tyr Cys Ala Arg Asp Ser Gly
                        85                  90                  95

Asp Tyr Tyr Gly Ile Asp Val Trp Gly Gln Gly Thr Thr Val Thr Val
                       100                 105                 110

Ser Ser Ala Ser Thr Lys Gly Pro Ser Val Phe Pro Leu Ala Pro Cys
                       115                 120                 125

Ser Arg Ser Thr Ser Glu Ser Thr Ala Ala Leu Gly Cys Leu Val Lys
                   130                 135                 140

Asp Tyr Phe Pro Glu Pro Val Thr Val Ser Trp Asn Ser Gly Ala Leu
        145                 150                 155                 160

Thr Ser Gly Val His Thr Phe Pro Ala Val Leu Gln
                       165                 170
```

<210> SEQ ID NO 8
<211> LENGTH: 153
<212> TYPE: PRT
<213> ORGANISM: Homo sapiens

<400> SEQUENCE: 8

```
        Pro Gly Arg Ser Leu Arg Leu Ser Cys Ala Ala Ser Gly Phe Thr Phe
          1               5                  10                  15

Ser Ser His Gly Ile His Trp Val Arg Gln Ala Pro Gly Lys Gly Leu
                        20                  25                  30

Glu Trp Val Ala Val Ile Trp Tyr Asp Gly Arg Asn Lys Asp Tyr Ala
                    35                  40                  45

Asp Ser Val Lys Gly Arg Phe Thr Ile Ser Arg Asp Asn Ser Lys Asn
         50                  55                  60

Thr Leu Tyr Leu Gln Met Asn Ser Leu Arg Ala Glu Asp Thr Ala Val
         65                  70                  75                  80

Tyr Tyr Cys Ala Arg Val Ala Pro Leu Gly Pro Leu Asp Tyr Trp Gly
                         85                  90                  95

Gln Gly Thr Leu Val Thr Val Ser Ser Ala Ser Thr Lys Gly Pro Ser
                       100                 105                 110

Val Phe Pro Leu Ala Pro Cys Ser Arg Ser Thr Ser Glu Ser Thr Ala
                       115                 120                 125

Ala Leu Gly Cys Leu Val Lys Asp Tyr Phe Pro Glu Pro Val Thr Val
                   130                 135                 140

Ser Trp Asn Ser Gly Ala Leu Thr Ser
        145                 150
```

<210> SEQ ID NO 9
<211> LENGTH: 167
<212> TYPE: PRT
<213> ORGANISM: Homo sapiens
<220> FEATURE:
<221> NAME/KEY: MOD_RES
<222> LOCATION: (103)
<223> OTHER INFORMATION: Any amino acid

<400> SEQUENCE: 9

```
        Gly Val Val Gln Pro Gly Arg Ser Leu Arg Leu Ser Cys Ala Ala Ser
          1               5                  10                  15

Gly Phe Thr Phe Ser Ser Tyr Gly Met His Trp Val Arg Gln Ala Pro
                        20                  25                  30

Gly Lys Gly Leu Glu Trp Val Ala Val Ile Trp Tyr Asp Gly Ser Asn
                    35                  40                  45
```

```
Lys Tyr Tyr Ala Asp Ser Val Lys Gly Arg Phe Thr Ile Ser Arg Asp
 50                  55                  60

Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Asp Pro Arg Gly Ala Thr Leu
                 85                  90                  95

Tyr Tyr Tyr Tyr Tyr Arg Xaa Asp Val Trp Gly Gln Gly Thr Thr Val
                100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 10
<211> LENGTH: 151
<212> TYPE: PRT
<213> ORGANISM: Homo sapiens

<400> SEQUENCE: 10

Gly Val Val Gln Pro Gly Arg Ser Leu Arg Leu Ser Cys Ala Ala Ser
 1               5                  10                  15

Gly Phe Thr Phe Ser Ser Tyr Gly Met His Trp Val Arg Gln Ala Pro
                 20                  25                  30

Gly Lys Gly Leu Glu Trp Val Ala Val Ile Trp Tyr Asp Gly Ser His
             35                  40                  45

Lys Tyr Tyr Ala Asp Ser Val Lys Gly Arg Phe Thr Ile Ser Arg Asp
 50                  55                  60

Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Gly Ala Val Val Pro Ala
                 85                  90                  95

Ala Met Asp Val Trp Gly Gln Gly Thr Thr Val Thr Val Ser Ser Ala
                100                 105                 110

Ser Thr Lys Gly Pro Ser Val Phe Pro Leu Ala Pro Cys Ser Arg Ser
            115                 120                 125

Thr Ser Glu Ser Thr Ala Ala Leu Gly Cys Leu Val Lys Asp Tyr Phe
        130                 135                 140

Pro Glu Pro Val Thr Val Ser
145                 150

<210> SEQ ID NO 11
<211> LENGTH: 146
<212> TYPE: PRT
<213> ORGANISM: Homo sapiens
<220> FEATURE:
<221> NAME/KEY: MOD_RES
<222> LOCATION: (22)
<223> OTHER INFORMATION: Any amino acid

<400> SEQUENCE: 11

Val Val Gln Pro Gly Arg Ser Leu Arg Leu Ser Cys Ala Ala Ser Gly
 1               5                  10                  15

Phe Thr Phe Ser Ser Xaa Gly Met His Trp Val Arg Gln Ala Pro Gly
                 20                  25                  30
```

Lys Gly Leu Glu Trp Val Ala Val Ile Trp Ser Asp Gly Ser His Lys
            35                  40                  45

Tyr Tyr Ala Asp Ser Val Lys Gly Arg Phe Thr Ile Ser Arg Asp Asn
 50                  55                  60

Ser Lys Asn Thr Leu Tyr Leu Gln Met Asn Ser Leu Arg Ala Glu Asp
 65                  70                  75                  80

Thr Ala Val Tyr Tyr Cys Ala Arg Gly Thr Met Ile Val Val Gly Thr
                 85                  90                  95

Leu Asp Tyr Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
            115                 120                 125

Ser Glu Ser Thr Ala Ala Leu Gly Cys Leu Val Lys Asp Tyr Phe Pro
            130                 135                 140

Glu Pro
145

<210> SEQ ID NO 12
<211> LENGTH: 174
<212> TYPE: PRT
<213> ORGANISM: Homo sapiens

<400> SEQUENCE: 12

Ser Gly Gly Gly Val Val Gln Pro Gly Arg Ser Leu Arg Leu Ser Cys
 1               5                  10                  15

Ala Ala Ser Gly Phe Thr Phe Ser Ser Tyr Gly Val His Trp Val Arg
                20                  25                  30

Gln Ala Pro Gly Lys Gly Leu Glu Trp Val Ala Val Ile Trp Tyr Asp
            35                  40                  45

Gly Ser Asn Lys Tyr Tyr Ala Asp Ser Val Lys Gly Arg Phe Thr Ile
 50                  55                  60

Ser Arg Asp Asn Ser Lys Ser Thr Leu Tyr Leu Gln Met Asn Ser Leu
 65                  70                  75                  80

Arg Ala Glu Asp Thr Ala Val Tyr Tyr Cys Ala Arg Asp Ser Tyr Tyr
                 85                  90                  95

Asp Phe Trp Ser Gly Arg Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val
                165                 170

<210> SEQ ID NO 13
<211> LENGTH: 163
<212> TYPE: PRT
<213> ORGANISM: Homo sapiens

<400> SEQUENCE: 13

Val Gln Pro Gly Arg Ser Leu Arg Leu Ser Cys Ala Ala Ser Gly Phe
 1               5                  10                  15

Thr Phe Ser Asn Tyr Ala Met His Trp Val Arg Gln Ala Pro Gly Lys
                20                  25                  30

```
Gly Leu Glu Trp Val Val Ile Trp His Asp Gly Asn Asn Lys Tyr
             35                  40                  45

Tyr Ala Glu Ser Val Lys Gly Arg Phe Thr Ile Ser Arg Asp Asn Ser
 50                  55                  60

Lys Asn Thr Leu Tyr Leu Gln Met Asn Ser Leu Arg Ala Glu Asp Thr
 65                  70                  75                  80

Ala Val Tyr Tyr Cys Ala Arg Asp Gln Gly Thr Gly Trp Tyr Gly Gly
                 85                  90                  95

Phe Asp Phe Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
            115                 120                 125

Ser Glu Ser Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe

<210> SEQ ID NO 14
<211> LENGTH: 235
<212> TYPE: PRT
<213> ORGANISM: Homo sapiens

<400> SEQUENCE: 14

Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Ile Ser Ser Ser Phe Leu Ala Trp Tyr Gln Gln Arg Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Thr Ser Pro Trp Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235
```

<210> SEQ ID NO 15
<211> LENGTH: 233
<212> TYPE: PRT
<213> ORGANISM: Homo sapiens

<400> SEQUENCE: 15

```
Met Glu Thr Pro Ala Gln Leu Phe Leu Leu Leu Leu Trp Leu Pro
 1               5                  10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Thr Ser Val Ser
        35                  40                  45

Ser Ser Tyr Leu Ala Trp Tyr Gln Gln Lys Pro Gly Gln Ala Pro Arg
    50                  55                  60

Leu Leu Ile Tyr Gly Ala Ser Ser Arg Ala Thr Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Tyr Gly Ile
            100                 105                 110

Ser Pro Phe Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 16
<211> LENGTH: 139
<212> TYPE: PRT
<213> ORGANISM: Homo sapiens

<400> SEQUENCE: 16

```
Gly Thr Leu Ser Leu Ser Pro Gly Glu Arg Ala Thr Leu Ser Cys Arg
 1               5                  10                  15

Ala Ser Gln Ser Val Ser Ser Tyr Leu Ala Trp Tyr Gln Gln Lys Pro
            20                  25                  30

Gly Gln Ala Pro Arg Leu Leu Ile Tyr Gly Ala Ser Ser Arg Ala Thr
        35                  40                  45

Gly Ile Pro Asp Arg Phe Ser Gly Ser Gly Ser Gly Thr Asp Phe Thr
    50                  55                  60

Leu Thr Ile Ser Arg Leu Glu Pro Glu Asp Phe Ala Val Tyr Tyr Cys
65                  70                  75                  80

Gln Gln Tyr Gly Arg Ser Pro Thr Phe Gly Pro Gly Thr Lys Val
                85                  90                  95
```

```
Asp Ile Lys Arg Thr Val Ala Ala Pro Ser Val Phe Ile Phe Pro Pro
                100                 105                 110

Ser Asp Glu Gln Leu Lys Ser Gly Thr Ala Ser Val Val Cys Leu Leu
            115                 120                 125

Asn Asn Phe Tyr Pro Arg Glu Ala Lys Val Gln
        130                 135
```

<210> SEQ ID NO 17
<211> LENGTH: 234
<212> TYPE: PRT
<213> ORGANISM: Homo sapiens

<400> SEQUENCE: 17

```
Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Tyr Leu Ala Trp Tyr Gln Gln Lys Pro Gly Gln Ala Pro
     50                  55                  60

Arg Pro Leu Ile Tyr Gly Val Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Tyr Gly
            100                 105                 110

Ile Ser Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 18
<211> LENGTH: 152
<212> TYPE: PRT
<213> ORGANISM: Homo sapiens

<400> SEQUENCE: 18

```
Gln Ser Pro Ser Ser Leu Ser Ala Ser Val Gly Asp Arg Val Thr Ile
  1               5                  10                  15

Thr Cys Arg Ala Ser Gln Ser Ile Asn Thr Tyr Leu Ile Trp Tyr Gln
             20                  25                  30

Gln Lys Pro Gly Lys Ala Pro Asn Phe Leu Ile Ser Ala Thr Ser Ile
         35                  40                  45
```

```
Leu Gln Ser Gly Val Pro Ser Arg Phe Arg Gly Ser Gly Ser Gly Thr
    50                  55                  60

Asn Phe Thr Leu Thr Ile Asn Ser Leu His Pro Glu Asp Phe Ala Thr
 65                  70                  75                  80

Tyr Tyr Cys Gln Gln Ser Tyr Ser Thr Pro Phe Thr Phe Gly Pro Gly
                 85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
            115                 120                 125

Cys Leu Leu Asn Asn Phe Tyr Pro Arg Glu Ala Lys Val Gln Trp Lys
130                 135                 140

Val Asp Asn Ala Leu Gln Ser Gly
145                 150
```

```
<210> SEQ ID NO 19
<211> LENGTH: 142
<212> TYPE: PRT
<213> ORGANISM: Homo sapiens

<400> SEQUENCE: 19

Ser Pro Gly Thr Leu Ser Leu Ser Pro Gly Glu Arg Ala Thr Leu Ser
 1               5                  10                  15

Cys Arg Ala Ser Gln Ser Ile Ser Ser Asn Phe Leu Ala Trp Tyr Gln
             20                  25                  30

Gln Lys Pro Gly Gln Ala Pro Arg Leu Leu Ile Tyr Arg Pro Ser Ser
         35                  40                  45

Arg Ala Thr Gly Ile Pro Asp Ser Phe Ser Gly Ser Gly Ser Gly Thr
    50                  55                  60

Asp Phe Thr Leu Thr Ile Ser Arg Leu Glu Pro Glu Asp Phe Ala Leu
 65                  70                  75                  80

Tyr Tyr Cys Gln Gln Tyr Gly Thr Ser Pro Phe Thr Phe Gly Pro Gly
                 85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
            115                 120                 125

Cys Leu Leu Asn Asn Phe Tyr Pro Arg Glu Ala Lys Val Gln
130                 135                 140
```

```
<210> SEQ ID NO 20
<211> LENGTH: 155
<212> TYPE: PRT
<213> ORGANISM: Homo sapiens

<400> SEQUENCE: 20

Ser Pro Asp Phe Gln Ser Val Thr Pro Lys Glu Lys Val Thr Ile Thr
 1               5                  10                  15

Cys Arg Ala Ser Gln Ser Ile Gly Ser Ser Leu His Trp Tyr Gln Gln
             20                  25                  30

Lys Pro Asp Gln Ser Pro Lys Leu Leu Ile Lys Tyr Ala Ser Gln Ser
         35                  40                  45

Phe Ser Gly Val Pro Ser Arg Phe Ser Gly Ser Gly Ser Gly Thr Asp
    50                  55                  60

Phe Thr Leu Thr Ile Asn Ser Leu Glu Ala Glu Asp Ala Ala Thr Tyr
 65                  70                  75                  80
```

```
Tyr Cys His Gln Ser Ser Leu Pro Leu Thr Phe Gly Gly Gly Thr
                85                  90                  95

Lys Val Glu Ile Lys Arg Thr Val Ala Ala Pro Ser Val Phe Ile Phe
            100                 105                 110

Pro Pro Ser Asp Glu Gln Leu Lys Ser Gly Thr Ala Ser Val Val Cys
        115                 120                 125

Leu Leu Asn Asn Phe Tyr Pro Arg Glu Ala Lys Val Gln Trp Lys Val
    130                 135                 140

Asp Asn Ala Leu Gln Ser Gly Asn Ser Gln Glu
145                 150                 155

<210> SEQ ID NO 21
<211> LENGTH: 146
<212> TYPE: PRT
<213> ORGANISM: Homo sapiens

<400> SEQUENCE: 21

Gln Ser Pro Gly Thr Leu Ser Leu Ser Pro Gly Glu Arg Ala Thr Leu
  1               5                  10                  15

Ser Cys Arg Ala Ser Gln Ser Val Ser Ser Tyr Leu Ala Trp Tyr Gln
             20                  25                  30

Gln Lys Pro Gly Gln Ala Pro Arg Leu Leu Ile Tyr Gly Ala Ser Ser
         35                  40                  45

Arg Ala Thr Gly Ile Pro Asp Arg Phe Ser Gly Ser Gly Ser Gly Thr
     50                  55                  60

Asp Phe Thr Leu Thr Ile Ser Arg Leu Glu Pro Glu Asp Phe Ala Val
 65                  70                  75                  80

Tyr Tyr Cys Gln Gln Tyr Gly Arg Ser Pro Phe Thr Phe Gly Pro Gly
                 85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln Trp Lys
    130                 135                 140

Gly Gly
145

<210> SEQ ID NO 22
<211> LENGTH: 139
<212> TYPE: PRT
<213> ORGANISM: Homo sapiens

<400> SEQUENCE: 22

Pro Ser Ser Leu Ser Ala Ser Val Gly Asp Arg Val Thr Ile Thr Cys
  1               5                  10                  15

Arg Ala Ser Gln Ser Ile Asn Ser Tyr Leu Asp Trp Tyr Gln Gln Lys
             20                  25                  30

Pro Gly Lys Ala Pro Lys Leu Leu Ile Tyr Ala Ala Ser Ser Leu Gln
         35                  40                  45

Ser Gly Val Pro Ser Arg Phe Ser Gly Ser Gly Ser Gly Thr Asp Phe
     50                  55                  60

Thr Leu Thr Ile Ser Ser Leu Gln Pro Glu Asp Phe Ala Thr Tyr Tyr
 65                  70                  75                  80

Cys Gln Gln Tyr Tyr Ser Thr Pro Phe Thr Phe Gly Pro Gly Thr Lys
                 85                  90                  95
```

```
Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
            115                 120                 125

Leu Asn Asn Phe Tyr Pro Arg Glu Ala Lys Val
            130                 135

<210> SEQ ID NO 23
<211> LENGTH: 134
<212> TYPE: PRT
<213> ORGANISM: Homo sapiens

<400> SEQUENCE: 23

Thr Gln Ser Pro Ser Ser Leu Ser Ala Ser Val Gly Asp Arg Val Thr
  1               5                  10                  15

Ile Thr Cys Arg Ala Ser Gln Asn Ile Ser Arg Tyr Leu Asn Trp Tyr
             20                  25                  30

Gln Gln Lys Pro Gly Lys Ala Pro Lys Phe Leu Ile Tyr Val Ala Ser
         35                  40                  45

Ile Leu Gln Ser Gly Val Pro Ser Gly Phe Ser Ala Ser Gly Ser Gly
     50                  55                  60

Pro Asp Phe Thr Leu Thr Ile Ser Ser Leu Gln Pro Glu Asp Phe Ala
 65                  70                  75                  80

Thr Tyr Tyr Cys Gln Gln Ser Tyr Ser Thr Pro Phe Thr Phe Gly Pro
                 85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
            115                 120                 125

Val Cys Leu Leu Asn Asn
            130

<210> SEQ ID NO 24
<211> LENGTH: 150
<212> TYPE: PRT
<213> ORGANISM: Homo sapiens

<400> SEQUENCE: 24

Thr Gln Ser Pro Ser Ser Leu Ser Ala Ser Val Gly Asp Arg Val Thr
  1               5                  10                  15

Ile Thr Cys Arg Ala Ser Gln Ser Ile Cys Asn Tyr Leu Asn Trp Tyr
             20                  25                  30

Gln Gln Lys Pro Gly Lys Ala Pro Arg Val Leu Ile Tyr Ala Ala Ser
         35                  40                  45

Ser Leu Gln Gly Gly Val Pro Ser Arg Phe Ser Gly Ser Gly Ser Gly
     50                  55                  60

Ile Asp Cys Thr Leu Thr Ile Ser Ser Leu Gln Pro Glu Asp Phe Ala
 65                  70                  75                  80

Thr Tyr Tyr Cys Gln Gln Ser Tyr Ile Thr Pro Phe Thr Phe Gly Pro
                 85                  90                  95

Gly Thr Arg Val Asp Ile Glu Arg Thr Val Ala Ala Pro Ser Val Phe
            100                 105                 110

Ile Phe Pro Pro Ser Asp Glu Gln Leu Lys Ser Gly Thr Ala Ser Val
            115                 120                 125

Val Cys Leu Leu Asn Asn Phe Tyr Pro Arg Glu Ala Lys Val Gln Trp
            130                 135                 140
```

Lys Val Asp Asn Ala Tyr
145                 150

<210> SEQ ID NO 25
<211> LENGTH: 139
<212> TYPE: PRT
<213> ORGANISM: Homo sapiens

<400> SEQUENCE: 25

Pro Leu Ser Leu Pro Val Thr Leu Gly Gln Pro Ala Ser Ile Ser Cys
1               5                   10                  15

Arg Ser Ser Gln Ser Leu Val Tyr Ser Asp Gly Asn Thr Tyr Leu Asn
            20                  25                  30

Trp Phe Gln Gln Arg Pro Gly Gln Ser Pro Arg Arg Leu Ile Tyr Lys
        35                  40                  45

Val Ser Asn Trp Asp Ser Gly Val Pro Asp Arg Phe Ser Gly Ser Gly
    50                  55                  60

Ser Gly Thr Asp Phe Thr Leu Lys Ile Ser Arg Val Glu Ala Glu Asp
65                  70                  75                  80

Val Gly Val Tyr Tyr Cys Met Gln Gly Ser His Trp Pro Pro Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro
    130                 135

<210> SEQ ID NO 26
<211> LENGTH: 133
<212> TYPE: PRT
<213> ORGANISM: Homo sapiens

<400> SEQUENCE: 26

Pro Gly Glu Pro Ala Ser Ile Ser Cys Arg Ser Ser Gln Ser Leu Leu
1               5                   10                  15

His Ser Asn Gly Tyr Asn Tyr Leu Asp Trp Tyr Leu Gln Lys Pro Gly
            20                  25                  30

Gln Ser Pro Gln Leu Leu Ile Tyr Leu Gly Ser Asn Arg Ala Ser Gly
        35                  40                  45

Val Pro Asp Arg Phe Ser Gly Ser Gly Ser Gly Thr Asp Phe Thr Leu
    50                  55                  60

Lys Leu Ser Arg Val Glu Ala Glu Asp Val Gly Val Tyr Tyr Cys Met
65                  70                  75                  80

Gln Ala Leu Gln Thr Pro Leu Thr Phe Gly Gly Gly Thr Lys Val Glu
                85                  90                  95

Ile Lys Arg Thr Val Ala Ala Pro Ser Val Phe Ile Phe Pro Pro Ser
            100                 105                 110

Asp Glu Gln Leu Lys Ser Gly Thr Ala Ser Val Val Cys Leu Leu Asn
        115                 120                 125

Asn Phe Tyr Pro Arg
    130

<210> SEQ ID NO 27
<211> LENGTH: 1392
<212> TYPE: DNA
<213> ORGANISM: Homo sapiens

<400> SEQUENCE: 27

```
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgtagcgt ctggattcac cttcagtagc catggcatgc actgggtccg ccaggctcca     180
ggcaaggggc tggagtgggt ggcagttata tggtatgatg aagaaaataa atactatgca     240
gactccgtga agggccgatt caccatctcc agagacaatt ccaagaacac gctgtttctg     300
caaatgaaca gcctgagagc cgaggacacg gctgtgtatt actgtgcgag aggaggtcac     360
ttcggtcctt ttgactactg gggccaggga accctggtca ccgtctcctc agcctccacc     420
aagggcccat cggtcttccc cctggcgccc tgctccagga gcacctccga gagcacagcg     480
gccctgggct gcctggtcaa ggactacttc cccgaaccgg tgacggtgtc gtggaactca     540
ggcgctctga ccagcggcgt gcacaccttc cagctgtcc tacagtcctc aggactctac      600
tccctcagca gcgtggtgac cgtgccctcc agcaacttcg gcacccagac ctacacctgc     660
aacgtagatc acaagcccag caacaccaag gtggacaaga cagttgagcg caaatgttgt     720
gtcgagtgcc caccgtgccc agcaccacct gtggcaggac cgtcagtctt cctcttcccc     780
ccaaaaccca aggacaccct catgatctcc cggacccctg aggtcacgtg cgtggtggtg     840
gacgtgagcc acgaagaccc gaggtccag ttcaactggt acgtgacgg cgtggaggtg      900
cataatgcca agacaaagcc acgggaggag cagttcaaca gcacgttccg tgtggtcagc     960
gtcctcaccg ttgtgcacca ggactggctg aacggcaagg agtacaagtg caaggtctcc    1020
aacaaaggcc tcccagcccc catcgagaaa accatctcca aaaccaaagg gcagccccga    1080
gaaccacagg tgtacaccct gcccccatcc cgggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaat ga                                                       1392
```

<210> SEQ ID NO 28
<211> LENGTH: 1395
<212> TYPE: DNA
<213> ORGANISM: Homo sapiens

<400> SEQUENCE: 28

```
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtacagcgt ctggattcac cttcagtaac tatggcatgc actgggtccg ccaggctcca     180
ggcaaggggc tggagtgggt ggcagttata tggtatgatg aagtaataa acactatgga      240
gactccgtga agggccgatt caccatctcc agtgacaatt ccaagaacac gctgtatctg     300
caaatgaaca gcctgagagc cgaggacacg gctgtgtatt actgtgcgag aggagagaga    360
ctggggtcct actttgacta ctggggccag ggaaccctgg tcaccgtctc ctcagcctcc    420
accaagggcc catcggtctt ccccctggcg ccctgctcca ggagcacctc cgagagcaca    480
gcggccctgg gctgcctggt caaggactac ttccccgaac cggtgacggt gtcgtggaac    540
tcaggcgctc tgaccagcgg cgtgcacacc ttcccagctg tcctacagtc ctcaggactc    600
```

```
tactccctca gcagcgtggt gaccgtgccc tccagcaact tcggcaccca gacctacacc    660
tgcaacgtag atcacaagcc cagcaacacc aaggtggaca agacagttga gcgcaaatgt    720
tgtgtcgagt gcccaccgtg cccagcacca cctgtggcag gaccgtcagt cttcctcttc    780
cccccaaaac ccaaggacac cctcatgatc tcccggaccc ctgaggtcac gtgcgtggtg    840
gtggacgtga gccacgaaga ccccgaggtc cagttcaact ggtacgtgga cggcgtggag    900
gtgcataatg ccaagacaaa gccacgggag gagcagttca acagcacgtt ccgtgtggtc    960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgccccca tcccgggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acacctccca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aatga                                                   1395

<210> SEQ ID NO 29
<211> LENGTH: 489
<212> TYPE: DNA
<213> ORGANISM: Homo sapiens

<400> SEQUENCE: 29
cctgggaggt ccctgagact ctcctgtgca gcgtctggat tcaccttcag tagtcatggc     60
atccactggg tccgccaggc tccaggcaag gggctggagt gggtggcagt tatatggtat    120
gatggaagaa ataaagacta tgcagactcc gtgaagggcc gattcaccat ctccagagac    180
aattccaaga gacgctgta tttgcaaatg aacagcctga gagccgagga cacggctgtg    240
tattactgtg cgagagtggc cccactgggg ccacttgact actggggcca gggaaccctg    300
gtcaccgtct cctcagcctc caccaagggc ccatcggtct tccccctggc gccctgctcc    360
aggagcacct ccgagagcac agcggccctg ggctgcctgg tcaaggacta cttccccgaa    420
ccggtgacgg tgtcgtggaa ctcaggcgct ctgaccagcg gcgtgcacac cttcccagct    480
gtcctacag                                                            489

<210> SEQ ID NO 30
<211> LENGTH: 1392
<212> TYPE: DNA
<213> ORGANISM: Homo sapiens

<400> SEQUENCE: 30
atggagtttg ggctgagctg ggttttcctc gttgctcttt taagaggtgt ccagtgtcag     60
gtgcagctgg tggagtctgg gggaggcgtg gtcgagcctg gaggtccct gagactctcc    120 tgtacagcgt ctggattcac cttcagtagt tatggcatgc actgggtccg ccaggctcca    180 ggcaagggc tggagtgggt ggcagttata tggtatgatg gaagcaataa acactatgca    240
gactccgcga agggccgatt caccatctcc agagacaatt ccaagaacac gctgtatctg    300
caaatgaaca gcctgagagc cgaggacacg gctgtgtatt actgtgcgag agccggactg    360
ctgggttact ttgactactg gggccaggga accctggtca ccgtctcctc agcctccacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
```

-continued

```
ggcgctctga ccagcggcgt gcacaccttc ccagctgtcc tacagtcctc aggactctac      600
tccctcagca gcgtggtgac cgtgccctcc agcaacttcg gcacccagac ctacacctgc      660
aacgtagatc acaagcccag caacaccaag gtggacaaga cagttgagcg caaatgttgt      720
gtcgagtgcc caccgtgccc agcaccacct gtggcaggac cgtcagtctt cctcttcccc      780
ccaaaaccca aggacaccct catgatctcc cggacccctg aggtcacgtg cgtggtggtg      840
gacgtgagcc acgaagaccc cgaggtccag ttcaactggt acgtggacgg cgtggaggtg      900
cataatgcca agacaaagcc acgggaggag cagttcaaca gcacgttccg tgtggtcagc      960
gtcctcaccg ttgtgcacca ggactggctg aacggcaagg agtacaagtg caaggtctcc     1020
aacaaaggcc tcccagcccc catcgagaaa accatctcca aaaccaaagg cagccccga      1080 gaaccacagg tgtacaccct gcccccatcc cgggaggaga tgaccaagaa ccaggtcagc     1140
ctgacctgcc tggtcaaagg cttctacccc agcgacatcg ccgtggagtg ggagagcaat     1200
gggcagccgg agaacaacta caagaccaca cctcccatgc tggactccga cggctccttc     1260
ttcctctaca gcaagctcac cgtggacaag agcaggtggc agcagggaa cgtcttctca     1320 tgctccgtga tgcatgaggc tctgcacaac cactacacgc agaagagcct ctccctgtct     1380
ccgggtaaat ga                                                         1392
```

<210> SEQ ID NO 31
<211> LENGTH: 507
<212> TYPE: DNA
<213> ORGANISM: Homo sapiens

<400> SEQUENCE: 31

```
ggcgtggtcc agcctgggag gtccctgaga ctctcctgtg cagcgtctgg attcaccttc       60
agtagctatg gcatgcactg ggtccgccag gctccaggca aggggctgga gtgggtggca      120
gttatatggt atgatggaag taataaatac tatgcagact ccgtgaaggg ccgattcacc      180
atctccagag acaattccaa gaacacgctg tatctgcaaa tgaacagcct gagagccgag      240
gacacggctg tgtattactg tgcgagaggg gcccgtataa taccccttg tatggacgtc      300 tggggccaag ggaccacggt caccgtctcc tcagcctcca caagggccc atcggtcttc      360 cccctggcgc cctgctccag gagcacctcc gagagcacag cggccctggg ctgcctggtc      420
aaggactact ccccgaacc ggtgacggtg tcgtggaact caggcgctct gaccagcggc      480
gtgcacacct tcccagctgt cctacag                                         507
```

<210> SEQ ID NO 32
<211> LENGTH: 501
<212> TYPE: DNA
<213> ORGANISM: Homo sapiens

<400> SEQUENCE: 32

```
ggcgtggtcc agcctgggag gtccctgaga ctctcctgtg tagcgtctgg attcatcttc       60
agtagtcatg gcatccactg gtccgccag gctccaggca aggggctgga gtgggtggca      120
gttatatggt atgatggaag aaataaagac tatgcagact ccgtgaaggg ccgattcacc      180
atctccagag acaattccaa gaacacgctg tatttgcaaa tgaacagcct gagagccgag      240
gacacggctg tgtattactg tgcgagagtg gccccactgg ggccacttga ctactgggc     300 cagggaaccc tggtcaccgt ctcctcagcc tccaccaagg gcccatcggt cttcccctg      360 gcgccctgct ccaggagcac ctccgagagc acagcggccc tgggctgcct ggtcaaggac     420
```

-continued

| | |
|---|---|
| tacttccccg aaccggtgac ggtgtcgtgg aactcaggcg ctctgaccag cggcgtgcac | 480 |
| accttcccag ctgtcctaca g | 501 |

<210> SEQ ID NO 33
<211> LENGTH: 516
<212> TYPE: DNA
<213> ORGANISM: Homo sapiens

<400> SEQUENCE: 33

| | |
|---|---|
| tcgggcccag gactggtgaa gccttcacag atcctgtccc tcacctgcac tgtctctggt | 60 |
| ggctccatca gcagtggtgg tcactactgg agctggatcc gccagcaccc agggaagggc | 120 |
| ctggagtgga ttgggtacat ctattacatt gggaacacct actacaaccc gtccctcaag | 180 |
| agtcgagtta ccatatcagt agacacgtct aagaaccagt tctccctgaa gctgagctct | 240 |
| gtgactgccg cggacacggc cgtgtattat tgtgcgagag atagtgggga ctactacggt | 300 |
| atagacgtct ggggccaagg gaccacggtc accgtctcct cagcttccac caagggccca | 360 |
| tccgtcttcc ccctggcgcc ctgctccagg agcacctccg agagcacagc cgccctgggc | 420 |
| tgcctggtca aggactactt ccccgaaccg gtgacggtgt cgtggaactc aggcgccctg | 480 |
| accagcggcg tgcacacctt cccggctgtc ctacaa | 516 |

<210> SEQ ID NO 34
<211> LENGTH: 459
<212> TYPE: DNA
<213> ORGANISM: Homo sapiens

<400> SEQUENCE: 34

| | |
|---|---|
| cctgggaggt ccctgagact ctcctgtgca gcgtctggat tcaccttcag tagtcatggc | 60 |
| atccactggg tccgccaggc tccaggcaag gggctggagt gggtggcagt tatatggtat | 120 |
| gatggaagaa ataaagacta tgcagactcc gtgaagggcc gattcaccat ctccagagac | 180 |
| aattccaaga acacgctgta tttgcaaatg aacagcctga gagccgagga cacggctgtg | 240 |
| tattactgtg cgagagtggc cccactgggg ccacttgact actggggcca ggaaccctg | 300 |
| gtcaccgtct cctcagcctc caccaagggc ccatcggtct tccccctggc gcctgctcc | 360 |
| aggagcacct ccgagagcac agcggccctg ggctgcctgg tcaaggacta cttccccgaa | 420 |
| ccggtgacgg tgtcgtggaa ctcaggcgct ctgaccagc | 459 |

<210> SEQ ID NO 35
<211> LENGTH: 503
<212> TYPE: DNA
<213> ORGANISM: Homo sapiens

<400> SEQUENCE: 35

| | |
|---|---|
| ggcgtggtcc agcctgggag gtccctgaga ctctcctgtg cagcgtctgg attcaccttc | 60 |
| agtagctatg gcatgcactg ggtccgccag gctccaggca aggggctgga gtgggtggca | 120 |
| gttatatggt atgatggaag taataaatac tatgcagact ccgtgaaggg ccgattcacc | 180 |
| atctccagag acaattccaa gaacacgctg tatctgcaaa tgaacagcct gagagccgag | 240 |
| gacacggctg tgtattactg tgcgagagat ccgaggggag ctacccttta ctactactac | 300 |
| taccggtkgg acgtctgggg ccaagggacc acggtcaccg tctcctcagc tccaccaag | 360 |
| ggcccatcgg tcttcccct ggcgccctgc tccaggagca cctccgagag cacagcggcc | 420 |
| ctgggctgcc tggtcaagga ctacttcccc gaaccggtga cggtgtcgtg gaactcaggc | 480 |
| gctctgacca gcggcgtgca cac | 503 |

<210> SEQ ID NO 36
<211> LENGTH: 451
<212> TYPE: DNA
<213> ORGANISM: Homo sapiens

<400> SEQUENCE: 36

```
ggcgtggtcc agcctgggag gtccctgaga ctctcctgtg cagcgtctgg attcaccttc      60
agtagctatg gcatgcactg ggtccgccag gctccaggca aggggctgga gtgggtggca     120
gttatatggt atgatggaag tcataaatac tatgcagact ccgtgaaggg ccgattcacc     180
atctccagag acaattccaa gaacacgctg tatctgcaaa tgaacagcct gagagccgag     240
gacacggctg tgtattactg tgcgagaggc gctgtagtag taccagctgc tatggacgtc     300
tggggccaag ggaccacggt caccgtctcc tcagcctcca ccaagggccc atcggtcttc     360
cccctggcgc cctgctccag gagcacctcc gagagcacag cggccctggg ctgcctggtc     420
aaggactact tccccgaacc ggtgacggtg t                                    451
```

<210> SEQ ID NO 37
<211> LENGTH: 438
<212> TYPE: DNA
<213> ORGANISM: Homo sapiens
<220> FEATURE:
<221> NAME/KEY: modified_base
<222> LOCATION: (64)
<223> OTHER INFORMATION: a, c, t, g, other or unknown

<400> SEQUENCE: 37

```
gtggtccagc ctgggaggtc cctgagactc tcctgtgcag cgtctggatt caccttcagt      60
agcngtggca tgcactgggt ccgccaggct ccaggcaagg ggctggagtg gtggcagtt     120
atatggtctg atggaagtca taaatactat gcagactccg tgaagggccg attcaccatc     180
tccagagaca attccaagaa cacgctgtat ctgcaaatga acagcctgag agccgaggac     240
acggctgtgt attactgtgc gagaggaact atgatagtag tgggtaccct tgactactgg     300
ggccagggaa ccctggtcac cgtctcctca gcctccacca agggcccatc ggtcttcccc     360
ctggcgccct gctccaggag cacctccgag agcacagcgg ccctgggctg cctggtcaag     420
gactacttcc ccgaaccg                                                  438
```

<210> SEQ ID NO 38
<211> LENGTH: 562
<212> TYPE: DNA
<213> ORGANISM: Homo sapiens

<400> SEQUENCE: 38

```
tcctgtgcag cgtctggatt caccttcagt tactatggcg tctgggggag gcgtggtcca      60
gcctgggagg tccctgagac tctcctgtgc agcgtctgga ttcaccttca gtagctatgg     120
cgtgcactgg gtccgccagg ctccaggcaa ggggctggag tgggtggcag ttatatggta     180
tgatggaagt aataaatact atgcagactc cgtgaagggc cgattcacca tctccagaga     240
caattccaag agcacgctgt atctgcaaat gaacagcctg agagccgagg acacggctgt     300
gtattattgt gcgagagact cgtattacga tttttggagt ggtcggggcg gtatggacgt     360
ctggggccaa gggaccacgg tcaccgtctc ctcagcctcc accaagggcc catcggtctt     420
cccctggcg cctgctcca ggagcacctc cgagagcaca gcggccctgg gctgcctggt     480
caaggactac ttccccgaac cggtgacggt gtcgtggaac tcaggcgctc tgaccagcgg     540
```
cgtgcacacc ttcccagctg tc                                           562

<210> SEQ ID NO 39
<211> LENGTH: 490
<212> TYPE: DNA
<213> ORGANISM: Homo sapiens

<400> SEQUENCE: 39
gtccagcctg ggaggtccct gagactctcc tgtgcagcgt ctggattcac cttcagtaac      60
tatgccatgc actgggtccg ccaggctcca ggcaaggggc tggagtgggt ggtagttatt     120
tggcatgatg gaaataataa atactatgca gagtccgtga agggccgatt caccatctcc     180
agagacaatt ccaagaacac gctgtatctg caaatgaaca gcctgagagc cgaggacacg     240
gctgtatatt actgtgcgag agatcagggc actggctggt acgaggcttt gacttctgg     300 ggccagggaa ccctggtcac cgtctcctca gcctccacca agggcccatc ggtcttcccc     360
ctggcgccct gctccaggag cacctccgag agcacagcgg ccctgggctg cctggtcaag     420
gactacttcc ccgaaccggt gacggtgtcg tggaactcag cgctctgac cagcggcgtg     480 cacaccttcc                                                          490

<210> SEQ ID NO 40
<211> LENGTH: 708
<212> TYPE: DNA
<213> ORGANISM: Homo sapiens

<400> SEQUENCE: 40
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtattagc agcagcttct agcctggta ccagcagaga     180 cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta cctcaccctg gacgttcggc     360
caagggacca aggtggaaat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg cctccaatc gggtaactcc     540 caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgttag                 708

<210> SEQ ID NO 41
<211> LENGTH: 702
<212> TYPE: DNA
<213> ORGANISM: Homo sapiens

<400> SEQUENCE: 41
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtgt tagcagcagt tacttagcct ggtaccagca gaaacctggc     180
caggctccca ggctcctcat ctatggtgca tccagcaggg ccactggcat cccagacagg     240
ttcagtggca gtgggtctgg gacagacttc actctcacca tcagcagact ggagcctgaa     300
gattttgcag tctattactg tcagcagtat ggcatctcac ccttcacttt cggcggaggg     360

```
accaaggtgg agatcaagcg aactgtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag       540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt ag                         702

<210> SEQ ID NO 42
<211> LENGTH: 417
<212> TYPE: DNA
<213> ORGANISM: Homo sapiens

<400> SEQUENCE: 42
ggcaccctgt ctttgtctcc aggggaaaga gccaccctct cctgcagggc cagtcagagt       60
gtcagcagct acttagcctg gtaccagcag aaacctggcc aggctcccag actcctcatc      120
tatggtgcat ccagcagggc cactggcatc ccagacaggt tcagtggcag tgggtctggg      180
acagacttca ctctcaccat cagcagactg gagcctgagg attttgcagt gtattactgt      240
cagcagtatg gtaggtcacc attcactttc ggccctggga ccaaagtgga tatcaagcga      300
actgtggctg caccatctgt cttcatcttc cgccatctg atgagcagtt gaaatctgga      360
actgcctctg ttgtgtgcct gctgaataac ttctatccca gagaggccaa agtacag        417

<210> SEQ ID NO 43
<211> LENGTH: 705
<212> TYPE: DNA
<213> ORGANISM: Homo sapiens

<400> SEQUENCE: 43
atggaaaccc cagcgcagct tctcttcctc ctgctactct ggctcccaga taccaccgga       60
gaaattgtgt tgacgcagtc tccaggcacc ctgtctttgt ctccagggga aagagccacc      120
ctctcctgta gggccagtca aagtgttagc agctacttag cctggtacca acagaaacct      180
ggccaggctc ccaggcccct catctatggt gtatccagca gggccactgg catcccagac      240
aggttcagtg gcagtgggtc tgggacagac ttcactctca ccatcagcag actggagcct      300
gaagattttg cagtgtatta ctgtcagcag tatggtatct caccattcac tttcggccct      360
gggaccaaag tggatatcaa acgaactgtg gctgcaccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgagctcgc ccgtcacaaa gagcttcaac aggggagagt gttag                      705

<210> SEQ ID NO 44
<211> LENGTH: 458
<212> TYPE: DNA
<213> ORGANISM: Homo sapiens

<400> SEQUENCE: 44
cagtctccat cctccctgtc tgcatctgta ggagacagag tcaccatcac ttgccgggca       60
agtcagagca ttaacaccta tttaatttgg tatcagcaga aaccagggaa agcccctaac      120
```

```
ttcctgatct ctgctacatc cattttgcaa agtggggtcc catcaaggtt ccgtggcagt    180
ggctctggga caaatttcac tctcaccatc aacagtcttc atcctgaaga ttttgcaact    240
tactactgtc aacagagtta cagtacccca ttcactttcg gccctgggac caaagtggat    300
atcaaacgaa ctgtggctgc accatctgtc ttcatcttcc cgccatctga tgagcagttg    360
aaatctggaa ctgcctctgt tgtgtgcctg ctgaataact tctatcccag agaggccaaa    420
gtacagtgga aggtggataa cgccctccaa tcgggtaa                            458

<210> SEQ ID NO 45
<211> LENGTH: 426
<212> TYPE: DNA
<213> ORGANISM: Homo sapiens

<400> SEQUENCE: 45
tctccaggca ccctgtcttt gtctccaggg gaaagagcca ccctctcctg cagggccagt     60
cagagtatta gcagcaattt cttagcctgg taccagcaga aacctggcca ggctcccagg    120
ctcctcatct atcgtccatc agcagggcc actggcatcc agacagtttt cagtggcagt     180
gggtctggga cagacttcac tctcaccatc agcagactgg agcctgagga ttttgcatta    240
tattactgtc agcagtatgg tacgtcacca ttcactttcg gccctgggac caaagtggat    300
atcaagcgaa ctgtggctgc accatctgtc ttcatcttcc cgccatctga tgagcagttg    360
aaatctggaa ctgcctctgt tgtgtgcctg ctgaataact tctatcccag agaggccaaa    420
gtacag                                                               426

<210> SEQ ID NO 46
<211> LENGTH: 465
<212> TYPE: DNA
<213> ORGANISM: Homo sapiens

<400> SEQUENCE: 46
tctccagact ttcagtctgt gactccaaag gagaaagtca ccatcacctg ccgggccagt     60
cagagcattg gtagtagctt acattggtat cagcagaaac cagatcagtc tccaaagctc    120
ctcatcaagt atgcttccca gtccttctct ggggtcccct cgaggttcag tggcagtgga    180
tctgggacag atttcacccct caccatcaat agcctggaag ctgaagatgc tgcaacgtat    240
tactgtcatc agagtagtag tttaccgctc actttcggcg gagggaccaa ggtggagatc    300
aaacgaactg tggctgcacc atctgtcttc atcttcccgc catctgatga gcagttgaaa    360
tctggaactg cctctgttgt gtgcctgctg aataacttct atcccagaga ggccaaagta    420
cagtggaagg tggataacgc cctccaatcg gtaactccc aggag                     465

<210> SEQ ID NO 47
<211> LENGTH: 440
<212> TYPE: DNA
<213> ORGANISM: Homo sapiens

<400> SEQUENCE: 47
cagtctccag gcaccctgtc tttgtctcca ggggaaagag ccaccctctc ctgcagggcc     60
agtcagagtg tcagcagcta cttagcctgg taccagcaga aacctggcca ggctcccagg    120
ctcctcatct atggtgcatc agcagggcc actggcatcc agacaggtt cagtggcagt     180 gggtctggga cagacttcac tctcaccatc agcagactgg agcctgagga ttttgcagtg    240
tattactgtc aacagtatgg taggtcacca ttcactttcg gccctgggac caaagtagat    300
atcaagcgaa ctgtggctgc accatctgtc ttcatcttcc cgccatctga tgagcagttg    360
```

| | |
|---|---|
| aaatctggaa ctgcctctgt tgtgtgcctg ctgaataact tctatcccag agaggccaaa | 420 |
| gtacagtgga aaggtggata | 440 |

<210> SEQ ID NO 48
<211> LENGTH: 417
<212> TYPE: DNA
<213> ORGANISM: Homo sapiens

<400> SEQUENCE: 48

| | |
|---|---|
| ccatcctccc tgtctgcatc tgtaggagac agagtcacca tcacttgccg ggcaagtcag | 60 |
| agcattaaca gctatttaga ttggtatcag cagaaaccag ggaaagcccc taaactcctg | 120 |
| atctatgctg catccagttt gcaaagtggg gtcccatcaa ggttcagtgg cagtggatct | 180 |
| gggacagatt tcactctcac catcagcagt ctgcaacctg aagattttgc aacttactac | 240 |
| tgtcaacagt attacagtac tccattcact ttcggccctg ggaccaaagt ggaaatcaaa | 300 |
| cgaactgtgg ctgcaccatc tgtcttcatc ttcccgccat ctgatgagca gttgaaatct | 360 |
| ggaactgcct ctgttgtgtg cctgctgaat aacttctatc ccagagaggc caaagta | 417 |

<210> SEQ ID NO 49
<211> LENGTH: 402
<212> TYPE: DNA
<213> ORGANISM: Homo sapiens
<220> FEATURE:
<221> NAME/KEY: modified_base
<222> LOCATION: (207)
<223> OTHER INFORMATION: a, c, t, g, other or unknown

<400> SEQUENCE: 49

| | |
|---|---|
| acccagtctc catcctccct gtctgcatct gtaggagaca gagtcaccat cacttgccgg | 60 |
| gcaagtcaga acattagcag gtatttaaat tggtatcaac agaaaccagg gaaagcccct | 120 |
| aagttcctga tctatgttgc atctattttg caaagtgggg tcccatcagg ttcagtgcc | 180 |
| agtggatctg ggcagattt cactctnacc atcagcagtc tgcaacctga agattttgca | 240 |
| acttactact gtcaacagag ttacagtacc ccattcactt tcggccctgg gaccaaagtg | 300 |
| gatatcaaac gaactgtggc tgcaccatct gtcttcatct tcccgccatc tgatgagcag | 360 |
| ttgaaatctg gaactgcctc tgttgtgtgc ctgctgaata ac | 402 |

<210> SEQ ID NO 50
<211> LENGTH: 451
<212> TYPE: DNA
<213> ORGANISM: Homo sapiens

<400> SEQUENCE: 50

| | |
|---|---|
| acccagtctc catcctccct gtctgcatct gtaggagaca gagtcaccat cacttgccgg | 60 |
| gcaagtcaga gcatttgcaa ctatttaaat tggtatcagc agaaaccagg aaaagcccct | 120 |
| agggtcctga tctatgctgc atccagtttg caaggtgggg tcccgtcaag gttcagtggc | 180 |
| agtggatctg ggacagattg cactctcacc atcagcagtc tgcaacctga agattttgca | 240 |
| acttactact gtcaacagag ttacactacc ccattcactt tcggccctgg gaccagagtg | 300 |
| gatatcgaac gaactgtggc tgcaccatct gtcttcatct tcccgccatc tgatgagcag | 360 |
| ttgaaatctg gaactgcctc tgttgtgtgc ctgctgaata acttctatcc cagagaggcc | 420 |
| aaagtacagt ggaaggtgga taacgcctat t | 451 |

<210> SEQ ID NO 51

<211> LENGTH: 419
<212> TYPE: DNA
<213> ORGANISM: Homo sapiens

<400> SEQUENCE: 51

```
ccactctccc tgcccgtcac ccttggacag ccggcctcca tctcctgcag gtctagtcaa      60
agcctcgtat acagtgatgg aaacacctac ttgaattggt tcagcagag gccaggccaa      120
tctccaaggc gcctaattta aaggtttct aactgggact ctggggtccc agacagattc      180
agcggcagtg ggtcaggcac tgatttcaca ctgaaaatca gcagggtgga ggctgaggat      240
gttgggtttt attactgcat gcaaggttca cactggcctc cgacgttcgg ccaagggacc      300
aaggtggaaa tcaaacgaac tgtggctgca ccatctgtct tcatcttccc gccatctgat      360
gagcagttga atctggaac tgcctctgtt gtgtgcctgc tgaataactt ctatcccac       419
```

<210> SEQ ID NO 52
<211> LENGTH: 419
<212> TYPE: DNA
<213> ORGANISM: Homo sapiens

<400> SEQUENCE: 52

```
cctggagagc cggcttccat ctcttgcagg tctagtcaga gcctcctgca tagtaatgga      60
tacaactatt tggattggta cctgcagaag ccaggacagt ctccacagct cctgatctat      120
ttgggttcta atcgggcctc cggggtccct gacaggttca gtggcagtgg atcaggcaca      180
gattttacac tgaaactcag cagagtggag gctgaggatg ttggggttta ttactgcatg      240
caagctctac aaactcctct cactttcggc ggagggacca aggtggagat caaacgaact      300
gtggctgcac catctgtctt catcttcccg ccatctgatg agcagttgaa atctggaact      360
gcctctgttg tgtgcctgct gaataacttc tatcccagar aggccaaagt acattccat      419
```

<210> SEQ ID NO 53
<211> LENGTH: 1392
<212> TYPE: DNA
<213> ORGANISM: Homo sapiens

<400> SEQUENCE: 53

```
atggagtttg ggctgagctg gttttcctc gttgctcttt taagaggtgt ccagtgtcag      60
gtgcagctgg tggagtctgg gggaggcgtg gtccagcctg gaggtccct gagactctcc      120
tgtgtagcgt ctggattcac cttcagtagc catggcatgc actgggtccg ccaggctcca      180
ggcaagggc tggagtgggt ggcagttata tggtatgatg aagaaataa atactatgca      240
gactccgtga agggccgatt caccatctcc agagacaatt ccaagaacac gctgtttctg      300
caaatgaaca gcctgagagc cgaggacacg gctgtgtatt actgtgcgag aggaggtcac      360
ttcggtcctt ttgactactg gggccaggga accctggtca ccgtctcctc agcctccacc      420
aagggcccat cggtcttccc cctggcgccc tgctccagga gcacctccga gagcacagcg      480
gccctgggct gcctggtcaa ggactacttc cccgaaccgg tgacggtgtc gtggaactca      540
ggcgctctga ccagcggcgt gcacaccttc ccagctgtcc tacagtcctc aggactctac      600
tccctcagca gcgtggtgac cgtgccctcc agcaacttcg gcacccagac ctacacctgc      660
aacgtagatc acaagcccag caacaccaag gtggacaaga cagttgagcg caaatgttgt      720
gtcgagtgcc caccgtgccc agcaccacct gtggcaggac cgtcagtctt cctcttcccc      780
ccaaaaccca aggacaccct catgatctcc cggacccctg aggtcacgtg cgtggtggtg      840
gacgtgagcc acgaagaccc cgaggtccag ttcaactggt acgtggacgg cgtggaggtg      900
```

-continued

```
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg gcagccccga   1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaat ga                                                       1392
```

<210> SEQ ID NO 54
<211> LENGTH: 1999
<212> TYPE: DNA
<213> ORGANISM: Homo sapiens

<400> SEQUENCE: 54

```
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtgtagcgt ctggattcac cttcagtagc atggcatgc actgggtccg ccaggctcca    180
ggcaaggggc tggagtgggt ggcagttata tggtatgatg aagaaataa atactatgca    240 gactccgtga agggccgatt caccatctcc agagacaatt ccaagaacac gctgtttctg    300
caaatgaaca gcctgagagc cgaggacacg gctgtgtatt actgtgcgag aggaggtcac    360
ttcggtcctt ttgactactg gggccaggga accctggtca ccgtctcctc agctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttggtga gaggccagct    720
cagggaggga gggtgtctgc tggaagccag gctcagccct cctgcctgga cgcacccgg    780 ctgtgcagcc ccagcccagg cagcaaggc aggcccatc tgtctcctca cccggaggcc    840
tctgcccgcc ccactcatgc tcaggagag ggtcttctgg cttttccac caggctccag    900 gcaggcacag gctgggtgcc cctaccccag gcccttcaca cagggggca ggtgcttggc    960 tcagacctgc caaaagccat atccggggagg accctgcccc tgacctaagc cgaccccaaa   1020
ggccaaactg tccactccct cagctcggac accttctctc ctcccagatc cgagtaactc   1080
ccaatcttct ctctgcagag cgcaaatgtt gtgtcgagtg cccaccgtgc ccaggtaagc   1140
cagcccaggc ctcgccctcc agctcaaggc gggacaggtg ccctagagta gcctgcatcc   1200
agggacaggc cccagctggg tgctgacacg tccacctcca tctcttcctc agcaccacct   1260
gtggcaggac cgtcagtctt cctcttcccc ccaaaaccca aggacaccct catgatctcc   1320
cggacccctg aggtcacgtg cgtggtggtg gacgtgagcc acgaagaccc cgaggtccag   1380
ttcaactggt acgtggacgg cgtggaggtg cataatgcca agacaaagcc acgggaggag   1440
cagttcaaca gcacgttccg tgtggtcagc gtcctcaccg ttgtgcacca ggactggctg   1500
aacggcaagg agtacaagtg caaggtctcc aacaaaggcc tcccagcccc catcgagaaa   1560
```

-continued

```
accatctcca aaaccaaagg tgggacccgc ggggtatgag ggccacatgg acagaggccg    1620
gctcggccca ccctctgccc tgggagtgac cgctgtgcca acctctgtcc ctacagggca    1680
gccccgagaa ccacaggtgt acaccctgcc cccatcccgg gaggagatga ccaagaacca    1740
ggtcagcctg acctgcctgg tcaaaggctt ctaccccagc gacatcgccg tggagtggga    1800
gagcaatggg cagccggaga caactacaa gaccacacct cccatgctgg actccgacgg    1860
ctccttcttc ctctacagca agctcaccgt ggacaagagc aggtggcagc aggggaacgt    1920
cttctcatgc tccgtgatgc atgaggctct gcacaaccac tacacgcaga gagcctctc    1980 cctgtctccg ggtaaatga                                                  1999
```

<210> SEQ ID NO 55
<211> LENGTH: 1392
<212> TYPE: DNA
<213> ORGANISM: Homo sapiens

<400> SEQUENCE: 55

```
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtgtagcgt ctggattcac cttcagtagc catggcatgc actgggtccg ccaggctcca    180
ggcaaggggc tggagtgggt ggcagttata tggtatgatg aagaaataa atactatgca    240 gactccgtga agggccgatt caccatctcc agagacaatt ccaagaacac gctgtttctg    300
caaatgaaca gcctgagagc cgaggacacg gctgtgtatt actgtgcgag aggaggtcac    360
ttcggtcctt ttgactactg gggccaggga accctggtca ccgtctcctc agcctccacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttccaaa gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg gcagccccga   1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaat ga                                                        1392
```

<210> SEQ ID NO 56
<211> LENGTH: 708
<212> TYPE: DNA
<213> ORGANISM: Homo sapiens

<400> SEQUENCE: 56

```
atggaaaccc cagcgcagct tctcttcctc ctgctactct ggctcccaga taccaccgga      60
gaaattgtgt tgacgcagtc tccaggcacc ctgtctttgt ctccagggga agagccacc     120 ctctcctgca gggccagtca gagtattagc agcagcttct tagcctggta ccagcagaga    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgta ttactgtcag cagtatggta cctcaccctg gacgttcggc    360
caagggacca aggtggaaat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac  aaagtctacg cctgcgaagt cacccatcag    660
ggcctgagct cgcccgtcac aaagagcttc aacaggggag agtgttag               708

<210> SEQ ID NO 57
<211> LENGTH: 1395
<212> TYPE: DNA
<213> ORGANISM: Homo sapiens

<400> SEQUENCE: 57
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtacagcgt ctggattcac cttcagtaac tatggcatgc actgggtccg ccaggctcca    180 ggcaagggc tggagtgggt ggcagttata tggtatgatg gaagtaataa acactatgga    240
gactccgtga agggccgatt caccatctcc agtgacaatt ccaagaacac gctgtatctg    300
caaatgaaca gcctgagagc cgaggacacg gctgtgtatt actgtgcgag aggagagaga    360
ctggggtcct actttgacta ctggggccag ggaaccctgg tcaccgtctc ctcagcctcc    420
accaagggcc catcggtctt ccccctggcg ccctgctcca ggagcacctc cgagagcaca    480
gcggccctgg gctgcctggt caaggactac ttccccgaac cggtgacggt gtcgtggaac    540
tcaggcgctc tgaccagcgg cgtgcacacc ttcccagctg tcctacagtc ctcaggactc    600
tactccctca gcagcgtggt gaccgtgccc tccagcaact tcggcaccca gacctacacc    660
tgcaacgtag atcacaagcc cagcaacacc aaggtggaca agacagttga gcgcaaatgt    720
tgtgtcgagt gcccaccgtg cccagcacca cctgtggcag gaccgtcagt cttcctcttc    780
cccccaaaac ccaaggacac cctcatgatc tcccggaccc ctgaggtcac gtgcgtggtg    840
gtggacgtga gccacgaaga ccccgaggtc cagttcaact ggtacgtgga cggcgtggag    900
gtgcataatg ccaagacaaa gccacgggag gagcagttca acagcacgtt ccgtgtggtc    960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgcccca tcccgggagg agatgaccaa gaaccaggtc    1140
agcctgacct gcctggtcaa aggcttctac cccagcgaca tcgccgtgga gtgggagagc   1200
aatgggcagc cggagaacaa ctacaagacc acacctccca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
```

```
tctccgggta aatga                                                          1395

<210> SEQ ID NO 58
<211> LENGTH: 702
<212> TYPE: DNA
<213> ORGANISM: Homo sapiens

<400> SEQUENCE: 58
atggaaaccc cagcgcagct tctcttcctc ctgctactct ggctcccaga taccaccgga           60
gaaattgtgt tgacgcagtc tccaggcacc ctgtctttgt ctccagggga aagagccacc          120
ctctcctgca ggaccagtgt tagcagcagt tacttagcct ggtaccagca gaaacctggc          180
caggctccca ggctcctcat ctatggtgca tccagcaggg ccactggcat cccagacagg          240
ttcagtggca gtgggtctgg gacagacttc actctcacca tcagcagact ggagcctgaa          300
gattttgcag tctattactg tcagcagtat ggcatctcac ccttcacttt cggcggaggg          360
accaaggtgg agatcaagcg aactgtggct gcaccatctg tcttcatctt cccgccatct          420
gatgagcagt tgaaatctgg aactgcctct gttgtgtgcc tgctgaataa cttctatccc          480
agagaggcca aagtacagtg gaaggtggat aacgccctcc aatcgggtaa ctcccaggag          540
agtgtcacag agcaggacag caaggacagc acctacagcc tcagcagcac cctgacgctg          600
agcaaagcag actacgagaa acacaaagtc tacgcctgcg aagtcaccca tcagggcctg          660
agctcgcccg tcacaaagag cttcaacagg ggagagtgtt ag                            702

<210> SEQ ID NO 59
<211> LENGTH: 1392
<212> TYPE: DNA
<213> ORGANISM: Homo sapiens

<400> SEQUENCE: 59
atggagtttg ggctgagctg gttttcctc gttgctcttt taagaggtgt ccagtgtcag            60
gtgcagctgg tggagtctgg gggaggcgtg gtcgagcctg gaggtccct gagactctcc          120 tgtacagcgt ctggattcac cttcagtagt tatggcatgc actgggtccg ccaggctcca          180
ggcaaggggc tggagtgggt ggcagttata tggtatgatg gaagcaataa acactatgca          240
gactccgcga agggccgatt caccatctcc agagacaatt ccaagaacac gctgtatctg          300
caaatgaaca gcctgagagc cgaggacacg gctgtgtatt actgtgcgag agccggactg          360
ctgggttact ttgactactg gggccaggga accctggtca ccgtctcctc agcctccacc          420
aagggcccat cggtcttccc cctggcgccc tgctccagga gcacctccga gagcacagcg          480
gccctgggct gcctggtcaa ggactacttc cccgaaccgg tgacggtgtc gtggaactca          540
ggcgctctga ccagcggcgt gcacaccttc ccagctgtcc tacagtcctc aggactctac          600
tccctcagca gcgtggtgac cgtgccctcc agcaacttcg gcacccagac ctacacctgc          660
aacgtagatc acaagcccag caacaccaag gtggacaaga cagttgagcg caaatgttgt          720
gtcgagtgcc caccgtgccc agcaccacct gtggcaggac cgtcagtctt cctcttcccc          780
ccaaaaccca aggacaccct catgatctcc cggacccctg aggtcacgtg cgtggtggtg          840
gacgtgagcc acgaagaccc cgaggtccag ttcaactggt acgtggacgg cgtggaggtg          900
cataatgcca agacaaagcc acgggaggag cagttcaaca gcacgttccg tgtggtcagc          960
gtcctcaccg ttgtgcacca ggactggctg aacggcaagg agtacaagtg caaggtctcc         1020
aacaaaggcc tcccagcccc catcgagaaa accatctcca aaaccaaagg cagccccga          1080 gaaccacagg tgtacaccct gcccccatcc cgggaggaga tgaccaagaa ccaggtcagc         1140
```

|     |     |
| --- | --- |
| ctgacctgcc tggtcaaagg cttctacccc agcgacatcg ccgtggagtg ggagagcaat | 1200 |
| gggcagccgg agaacaacta caagaccaca cctcccatgc tggactccga cggctccttc | 1260 |
| ttcctctaca gcaagctcac cgtggacaag agcaggtggc agcagggaa cgtcttctca | 1320 |
| tgctccgtga tgcatgaggc tctgcacaac cactacacgc agaagagcct ctccctgtct | 1380 |
| ccgggtaaat ga | 1392 |

<210> SEQ ID NO 60
<211> LENGTH: 705
<212> TYPE: DNA
<213> ORGANISM: Homo sapiens

<400> SEQUENCE: 60

|     |     |
| --- | --- |
| atggaaaccc cagcgcagct tctcttcctc ctgctactct ggctcccaga taccaccgga | 60 |
| gaaattgtgt tgacgcagtc tccaggcacc ctgtctttgt ctccagggga aagagccacc | 120 |
| ctctcctgta gggccagtca agtgttagc agctactag cctggtacca acagaaacct | 180 |
| ggccaggctc ccaggcccct catctatggt gtatccagca gggccactgg catcccagac | 240 |
| aggttcagtg gcagtgggtc tgggacagac ttcactctca ccatcagcag actggagcct | 300 |
| gaagattttg cagtgtatta ctgtcagcag tatggtatct caccattcac tttcggccct | 360 |
| gggaccaaag tggatatcaa cgaactgtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag cacctgacg | 600 |
| ctgagcaaag cagactacga aaacacaaa gtctacgcct gcgaagtcac ccatcagggc | 660 |
| ctgagctcgc ccgtcacaaa gagcttcaac aggggagagt gttag | 705 |

<210> SEQ ID NO 61
<211> LENGTH: 1413
<212> TYPE: DNA
<213> ORGANISM: Homo sapiens

<400> SEQUENCE: 61

|     |     |
| --- | --- |
| atggagtttg gctgagctg gttttcctc gttgctcttt taagaggtgt ccagtgtcag | 60 |
| gtgcagctgg tggagtctgg gggaggcgtg gtccagcctg ggaggtccct gagactctcc | 120 |
| tgtgcagcgt ctggattcac cttcagtagc tatggcatgc actgggtccg ccaggctcca | 180 |
| ggcaaggggc tggagtgggt ggcagttata tggtatgatg gaagtaataa atactatgca | 240 |
| gactccgtga agggccgatt caccatctcc agagacaatt ccaagaacac gctgtatctg | 300 |
| caaatgaaca gcctgagagc cgaggacacg gctgtgtatt actgtgcgag agatccgagg | 360 |
| ggagctaccc tttactacta ctactacggt atggacgtct ggggccaagg gaccacggtc | 420 |
| accgtctcct cagcctccac caagggccca tcggtcttcc ccctggcgcc ctgctccagg | 480 |
| agcacctccg agagcacagc ggccctgggc tgcctggtca aggactactt ccccgaaccg | 540 |
| gtgacggtgt cgtggaactc aggcgctctg accagcggcg tgcacacctt cccagctgtc | 600 |
| ctacagtcct caggactcta ctccctcagc agcgtggtga ccgtgccctc agcaacttc | 660 |
| ggcacccaga cctacacctg caacgtagat cacaagccca gcaacaccaa ggtggacaag | 720 |
| acagttgagc gcaaatgttg tgtcgagtgc ccaccgtgcc cagcaccacc tgtggcagga | 780 |
| ccgtcagtct tcctcttccc cccaaaaccc aaggacaccc tcatgatctc ccggacccct | 840 |

```
gaggtcacgt gcgtggtggt ggacgtgagc cacgaagacc ccgaggtcca gttcaactgg      900
tacgtggacg gcgtggaggt gcataatgcc aagacaaagc cacgggagga gcagttcaac      960
agcacgttcc gtgtggtcag cgtcctcacc gttgtgcacc aggactggct gaacggcaag     1020
gagtacaagt gcaaggtctc caacaaaggc ctcccagccc ccatcgagaa aaccatctcc     1080
aaaaccaaag ggcagccccg agaaccacag gtgtacaccc tgcccccatc ccgggaggag     1140
atgaccaaga accaggtcag cctgacctgc ctggtcaaag gcttctaccc cagcgacatc     1200
gccgtggagt gggagagcaa tgggcagccg gagaacaact acaagaccac acctcccatg     1260
ctggactccg acggctcctt cttcctctac agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa tga                                  1413

<210> SEQ ID NO 62
<211> LENGTH: 714
<212> TYPE: DNA
<213> ORGANISM: Homo sapiens

<400> SEQUENCE: 62
atggacatga gggtccccgc tcagctcctg gggctcctgc tactctggct ccgaggtgcc       60
agatgtgaca tccagatgac ccagtctcca tcctccctgt ctgcatctgt aggagacaga      120
gtcaccatca cttgccgggc aagtcagagc attaacagct atttagattg gtatcagcag      180
aaaccaggga aagcccctaa actcctgatc tatgctgcat ccagtttgca aagtggggtc      240
ccatcaaggt tcagtggcag tggatctggg acagatttca ctctcaccat cagcagtctg      300
caacctgaag attttgcaac ttactactgt caacagtatt acagtactcc attcactttc      360
ggccctggga ccaaagtgga aatcaaacga actgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgtta gtga            714

<210> SEQ ID NO 63
<211> LENGTH: 463
<212> TYPE: PRT
<213> ORGANISM: Homo sapiens

<400> SEQUENCE: 63

Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Val Ala Ser Gly Phe Thr Phe
         35                  40                  45

Ser Ser His Gly Met His Trp Val Arg Gln Ala Pro Gly Lys Gly Leu
     50                  55                  60

Glu Trp Val Ala Val Ile Trp Tyr Asp Gly Arg Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asn Ser Leu Arg Ala Glu Asp Thr Ala Val
```

-continued

```
                100                 105                 110
Tyr Tyr Cys Ala Arg Gly Gly His Phe Gly Pro Phe Asp Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 64
<211> LENGTH: 463
<212> TYPE: PRT
<213> ORGANISM: Homo sapiens

<400> SEQUENCE: 64

```
Met Glu Phe Gly Leu Ser Trp Val Phe Leu Val Ala Leu Leu Arg Gly
 1               5                  10                  15
```

-continued

```
Val Gln Cys Gln Val Gln Leu Val Glu Ser Gly Gly Val Val Gln
             20                  25                  30

Pro Gly Arg Ser Leu Arg Leu Ser Cys Val Ala Ser Gly Phe Thr Phe
             35                  40                  45

Ser Ser His Gly Met His Trp Val Arg Gln Ala Pro Gly Lys Gly Leu
 50                  55                  60

Glu Trp Val Ala Val Ile Trp Tyr Asp Gly Arg Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asn Ser Leu Arg Ala Glu Asp Thr Ala Val
             100                 105                 110

Tyr Tyr Cys Ala Arg Gly Gly His Phe Gly Pro Phe Asp Tyr Trp Gly
             115                 120                 125

Gln Gly Thr Leu Val Thr Val Ser Ser Ala Ser Thr Lys Gly Pro Ser
 130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                 165                 170                 175

Ser Trp Asn Ser Gly Ala Leu Thr Ser Gly Val His Thr Phe Pro Ala
             180                 185                 190

Val Leu Gln Ser Ser Gly Leu Tyr Ser Leu Ser Ser Val Val Thr Val
             195                 200                 205

Pro Ser Ser Asn Phe Gly Thr Gln Thr Tyr Thr Cys Asn Val Asp His
 210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                 245                 250                 255

Phe Leu Phe Pro Pro Lys Pro Lys Asp Thr Leu Met Ile Ser Arg Thr
             260                 265                 270

Pro Glu Val Thr Cys Val Val Val Asp Val Ser His Glu Asp Pro Glu
             275                 280                 285

Val Gln Phe Asn Trp Tyr Val Asp Gly Val Glu Val His Asn Ala Lys
 290                 295                 300

Thr Lys Pro Arg Glu Glu Gln Phe Gln Ser Thr Phe Arg Val Val Ser
305                 310                 315                 320

Val Leu Thr Val Val His Gln Asp Trp Leu Asn Gly Lys Glu Tyr Lys
                 325                 330                 335

Cys Lys Val Ser Asn Lys Gly Leu Pro Ala Pro Ile Glu Lys Thr Ile
             340                 345                 350

Ser Lys Thr Lys Gly Gln Pro Arg Glu Pro Gln Val Tyr Thr Leu Pro
             355                 360                 365

Pro Ser Arg Glu Glu Met Thr Lys Asn Gln Val Ser Leu Thr Cys Leu
 370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                 405                 410                 415

Asp Gly Ser Phe Phe Leu Tyr Ser Lys Leu Thr Val Asp Lys Ser Arg
             420                 425                 430

Trp Gln Gln Gly Asn Val Phe Ser Cys Ser Val Met His Glu Ala Leu
```

His Asn His Tyr Thr Gln Lys Ser Leu Ser Leu Ser Pro Gly Lys
        450                 455                 460

<210> SEQ ID NO 65
<211> LENGTH: 235
<212> TYPE: PRT
<213> ORGANISM: Homo sapiens

<400> SEQUENCE: 65

Met Glu Thr Pro Ala Gln Leu Leu Phe Leu Leu Leu Trp Leu Pro
  1               5                  10                  15

Asp Thr Thr Gly Glu Ile Val Leu Thr Gln Ser Pro Gly Thr Leu Ser
                 20                  25                  30

Leu Ser Pro Gly Glu Arg Ala Thr Leu Ser Cys Arg Ala Ser Gln Ser
             35                  40                  45

Ile Ser Ser Ser Phe Leu Ala Trp Tyr Gln Gln Arg Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
                100                 105                 110

Gly Thr Ser Pro Trp Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 66
<211> LENGTH: 464
<212> TYPE: PRT
<213> ORGANISM: Homo sapiens

<400> SEQUENCE: 66

Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
                 20                  25                  30

Pro Gly Arg Ser Leu Arg Leu Ser Cys Thr Ala Ser Gly Phe Thr Phe
             35                  40                  45

Ser Asn Tyr Gly Met His Trp Val Arg Gln Ala Pro Gly Lys Gly Leu
 50                  55                  60

Glu Trp Val Ala Val Ile Trp Tyr Asp Gly Ser Asn Lys His Tyr Gly

-continued

```
            65                  70                  75                  80
Asp Ser Val Lys Gly Arg Phe Thr Ile Ser Ser Asp Asn Ser Lys Asn
                    85                  90                  95
Thr Leu Tyr Leu Gln Met Asn Ser Leu Arg Ala Glu Asp Thr Ala Val
                100                 105                 110
Tyr Tyr Cys Ala Arg Gly Glu Arg Leu Gly Ser Tyr Phe Asp Tyr Trp
                115                 120                 125
Gly Gln Gly Thr Leu Val Thr Val Ser Ser Ala Ser Thr Lys Gly Pro
130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
                195                 200                 205
Val Pro Ser Ser Asn Phe Gly Thr Gln Thr Tyr Thr Cys Asn Val Asp
210                 215                 220
His Lys Pro Ser Asn Thr Lys Val Asp Lys Thr Val Glu Arg Lys Cys
225                 230                 235                 240
Cys Val Glu Cys Pro Pro Cys Pro Ala Pro Val Ala Gly Pro Ser
                245                 250                 255
Val Phe Leu Phe Pro Pro Lys Pro Lys Asp Thr Leu Met Ile Ser Arg
                260                 265                 270
Thr Pro Glu Val Thr Cys Val Val Val Asp Val Ser His Glu Asp Pro
                275                 280                 285
Glu Val Gln Phe Asn Trp Tyr Val Asp Gly Val Glu Val His Asn Ala
                290                 295                 300
Lys Thr Lys Pro Arg Glu Glu Gln Phe Asn Ser Thr Phe Arg Val Val
305                 310                 315                 320
Ser Val Leu Thr Val Val His Gln Asp Trp Leu Asn Gly Lys Glu Tyr
                325                 330                 335
Lys Cys Lys Val Ser Asn Lys Gly Leu Pro Ala Pro Ile Glu Lys Thr
                340                 345                 350
Ile Ser Lys Thr Lys Gly Gln Pro Arg Glu Pro Gln Val Tyr Thr Leu
                355                 360                 365
Pro Pro Ser Arg Glu Glu Met Thr Lys Asn Gln Val Ser Leu Thr Cys
                370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Met Leu Asp
                405                 410                 415
Ser Asp Gly Ser Phe Phe Leu Tyr Ser Lys Leu Thr Val Asp Lys Ser
                420                 425                 430
Arg Trp Gln Gln Gly Asn Val Phe Ser Cys Ser Val Met His Glu Ala
                435                 440                 445
Leu His Asn His Tyr Thr Gln Lys Ser Leu Ser Leu Ser Pro Gly Lys
                450                 455                 460

<210> SEQ ID NO 67
<211> LENGTH: 233
<212> TYPE: PRT
<213> ORGANISM: Homo sapiens
```

<400> SEQUENCE: 67

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Thr Ser Val Ser
        35                  40                  45

Ser Ser Tyr Leu Ala Trp Tyr Gln Gln Lys Pro Gly Gln Ala Pro Arg
    50                  55                  60

Leu Leu Ile Tyr Gly Ala Ser Ser Arg Ala Thr Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Tyr Gly Ile
            100                 105                 110

Ser Pro Phe Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 68
<211> LENGTH: 463
<212> TYPE: PRT
<213> ORGANISM: Homo sapiens

<400> SEQUENCE: 68

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Glu
            20                  25                  30

Pro Gly Arg Ser Leu Arg Leu Ser Cys Thr Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys His Tyr Ala
65                  70                  75                  80

Asp Ser Ala Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gly Leu Leu Gly Tyr Phe Asp Tyr Trp Gly
        115                 120                 125

```
Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
                275                 280                 285

Val Gln Phe Asn Trp Tyr Val Asp Gly Val Glu Val His Asn Ala Lys
                290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
    450                 455                 460

<210> SEQ ID NO 69
<211> LENGTH: 234
<212> TYPE: PRT
<213> ORGANISM: Homo sapiens

<400> SEQUENCE: 69

Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
```

-continued

```
                35                  40                  45
Val Ser Ser Tyr Leu Ala Trp Tyr Gln Gln Lys Pro Gly Gln Ala Pro
 50                  55                  60

Arg Pro Leu Ile Tyr Gly Val Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Tyr Gly
                100                 105                 110

Ile Ser Pro Phe Thr Phe Gly Pro Gly Thr Lys Val Asp Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 70
<211> LENGTH: 451
<212> TYPE: PRT
<213> ORGANISM: Homo sapiens

<400> SEQUENCE: 70

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Arg Gly Ala Thr Leu Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
        210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 71
<211> LENGTH: 214
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95
```

-continued

```
Thr Phe Gly Pro Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 89
<212> TYPE: PRT
<213> ORGANISM: Homo sapiens

<400> SEQUENCE: 72

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
                20                  25                  30

Gly Lys Gly Leu Glu Trp Val Ala Val Ile Trp Tyr Asp Gly Ser Asn
            35                  40                  45

Lys Tyr Tyr Ala Asp Ser Val Lys Gly Arg Phe Thr Ile Ser Arg Asp
        50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg
                85

<210> SEQ ID NO 73
<211> LENGTH: 169
<212> TYPE: PRT
<213> ORGANISM: Homo sapiens

<400> SEQUENCE: 73

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
                20                  25                  30

Gly Lys Gly Leu Glu Trp Val Ala Val Ile Trp Tyr Asp Gly Ser Asn
            35                  40                  45

Lys Tyr Tyr Ala Asp Ser Val Lys Gly Arg Phe Thr Ile Ser Arg Asp
        50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Gly Arg Ile Ile Thr Pro
                85                  90                  95

Cys Met Asp Val Trp Gly Gln Gly Thr Thr Val Thr Val Ser Ser Ala
                100                 105                 110
```

Ser Thr Lys Gly Pro Ser Val Phe Pro Leu Ala Pro Cys Ser Arg Ser
            115                 120                 125

Thr Ser Glu Ser Thr Ala Ala Leu Gly Cys Leu Val Lys Asp Tyr Phe
        130                 135                 140

Pro Glu Pro Val Thr Val Ser Trp Asn Ser Gly Ala Leu Thr Ser Gly
145                 150                 155                 160

Val His Thr Phe Pro Ala Val Leu Gln
                165

<210> SEQ ID NO 74
<211> LENGTH: 167
<212> TYPE: PRT
<213> ORGANISM: Homo sapiens

<400> SEQUENCE: 74

Gly Val Val Gln Pro Gly Arg Ser Leu Arg Leu Ser Cys Val Ala Ser
1               5                   10                  15

Gly Phe Thr Phe Ser Ser His Gly Met His Trp Val Arg Gln Ala Pro
            20                  25                  30

Gly Lys Gly Leu Glu Trp Val Ala Val Ile Trp Tyr Asp Gly Arg Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Phe Leu Gln Met Asn Ser Leu Arg Ala Glu
65                  70                  75                  80

Asp Thr Ala Val Tyr Tyr Cys Ala Arg Gly His Phe Gly Pro Phe
                85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln
                165

<210> SEQ ID NO 75
<211> LENGTH: 166
<212> TYPE: PRT
<213> ORGANISM: Homo sapiens

<400> SEQUENCE: 75

Gly Val Val Gln Pro Gly Arg Ser Leu Arg Leu Ser Cys Thr Ala Ser
1               5                   10                  15

Gly Phe Thr Phe Ser Asn Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys His Tyr Gly Asp Ser Val Lys Gly Arg Phe Thr Ile Ser Ser Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Gly Glu Arg Leu Gly Ser Tyr
                85                  90                  95

Phe Asp Tyr Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val
                165

<210> SEQ ID NO 76
<211> LENGTH: 167
<212> TYPE: PRT
<213> ORGANISM: Homo sapiens

<400> SEQUENCE: 76

Gly Val Val Gln Pro Gly Arg Ser Leu Arg Leu Ser Cys Val Ala Ser
1               5                   10                  15

Gly Phe Ile Phe Ser Ser His Gly Ile His Trp Val Arg Gln Ala Pro
            20                  25                  30

Gly Lys Gly Leu Glu Trp Val Ala Val Ile Trp Tyr Asp Gly Arg Asn
        35                  40                  45

Lys Asp Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Val Ala Pro Leu Gly Pro Leu
                85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln
                165

<210> SEQ ID NO 77
<211> LENGTH: 153
<212> TYPE: PRT
<213> ORGANISM: Homo sapiens

<400> SEQUENCE: 77

Pro Gly Arg Ser Leu Arg Leu Ser Cys Ala Ala Ser Gly Phe Thr Phe
1               5                   10                  15

Ser Ser His Gly Ile His Trp Val Arg Gln Ala Pro Gly Lys Gly Leu
            20                  25                  30

Glu Trp Val Ala Val Ile Trp Tyr Asp Gly Arg Asn Lys Asp Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

```
Tyr Tyr Cys Ala Arg Val Ala Pro Leu Gly Pro Leu Asp Tyr Trp Gly
                85                  90                  95

Gln Gly Thr Leu Val Thr Val Ser Ser Ala Ser Thr Lys Gly Pro Ser
            100                 105                 110

Val Phe Pro Leu Ala Pro Cys Ser Arg Ser Thr Ser Glu Ser Thr Ala
        115                 120                 125

Ala Leu Gly Cys Leu Val Lys Asp Tyr Phe Pro Glu Pro Val Thr Val
    130                 135                 140

Ser Trp Asn Ser Gly Ala Leu Thr Ser
145                 150
```

<210> SEQ ID NO 78
<211> LENGTH: 163
<212> TYPE: PRT
<213> ORGANISM: Homo sapiens

<400> SEQUENCE: 78

```
Pro Gly Arg Ser Leu Arg Leu Ser Cys Ala Ala Ser Gly Phe Thr Phe
1               5                   10                  15

Ser Ser His Gly Ile His Trp Val Arg Gln Ala Pro Gly Lys Gly Leu
            20                  25                  30

Glu Trp Val Ala Val Ile Trp Tyr Asp Gly Arg Asn Lys Asp Tyr Ala
        35                  40                  45

Asp Ser Val Lys Gly Arg Phe Thr Ile Ser Arg Asp Asn Ser Lys Lys
    50                  55                  60

Thr Leu Tyr Leu Gln Met Asn Ser Leu Arg Ala Glu Asp Thr Ala Val
65                  70                  75                  80

Tyr Tyr Cys Ala Arg Val Ala Pro Leu Gly Pro Leu Asp Tyr Trp Gly
                85                  90                  95

Gln Gly Thr Leu Val Thr Val Ser Ser Ala Ser Thr Lys Gly Pro Ser
            100                 105                 110

Val Phe Pro Leu Ala Pro Cys Ser Arg Ser Thr Ser Glu Ser Thr Ala
        115                 120                 125

Ala Leu Gly Cys Leu Val Lys Asp Tyr Phe Pro Glu Pro Val Thr Val
    130                 135                 140

Ser Trp Asn Ser Gly Ala Leu Thr Ser Gly Val His Thr Phe Pro Ala
145                 150                 155                 160

Val Leu Gln
```

<210> SEQ ID NO 79
<211> LENGTH: 138
<212> TYPE: PRT
<213> ORGANISM: Homo sapiens

<400> SEQUENCE: 79

```
Gly Gly Val Val Glu Pro Gly Arg Ser Leu Arg Leu Ser Cys Thr Ala
1               5                   10                  15

Ser Gly Phe Thr Phe Ser Ser Tyr Gly Met His Trp Val Arg Gln Ala
            20                  25                  30

Pro Gly Lys Gly Leu Glu Trp Val Ala Val Ile Trp Tyr Asp Gly Ser
        35                  40                  45

Asn Lys His Tyr Ala Asp Ser Ala Lys Gly Arg Phe Thr Ile Ser Arg
    50                  55                  60

Asp Asn Ser Lys Asn Thr Leu Tyr Leu Gln Met Asn Ser Leu Arg Ala
65                  70                  75                  80
```

```
Glu Asp Thr Ala Val Tyr Tyr Cys Ala Arg Ala Gly Leu Leu Gly Tyr
                85                  90                  95

Phe Asp Tyr Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu
    130                 135

<210> SEQ ID NO 80
<211> LENGTH: 167
<212> TYPE: PRT
<213> ORGANISM: Homo sapiens

<400> SEQUENCE: 80

Gly Val Val Gln Pro Gly Arg Ser Leu Arg Leu Ser Cys Ala Ala Ser
  1               5                  10                  15

Gly Phe Thr Phe Ser Ser Tyr Gly Met His Trp Val Arg Gln Ala Pro
             20                  25                  30

Gly Lys Gly Leu Glu Trp Val Ala Val Ile Trp Tyr Asp Gly Ser Asn
         35                  40                  45

Lys Tyr Tyr Ala Asp Ser Val Lys Gly Arg Phe Thr Ile Ser Arg Asp
 50                  55                  60

Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Asp Pro Arg Gly Ala Thr Leu
                 85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 81
<211> LENGTH: 150
<212> TYPE: PRT
<213> ORGANISM: Homo sapiens

<400> SEQUENCE: 81

Gly Val Val Gln Pro Gly Arg Ser Leu Arg Leu Ser Cys Ala Ala Ser
  1               5                  10                  15

Gly Phe Thr Phe Ser Ser Tyr Gly Met His Trp Val Arg Gln Ala Pro
             20                  25                  30

Gly Lys Gly Leu Glu Trp Val Ala Val Ile Trp Tyr Asp Gly Ser His
         35                  40                  45

Lys Tyr Tyr Ala Asp Ser Val Lys Gly Arg Phe Thr Ile Ser Arg Asp
 50                  55                  60

Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Gly Ala Val Val Pro Ala
                 85                  90                  95
```

```
Ala Met Asp Val Trp Gly Gln Gly Thr Thr Val Thr Val Ser Ser Ala
            100                 105                 110

Ser Thr Lys Gly Pro Ser Val Phe Pro Leu Ala Pro Cys Ser Arg Ser
        115                 120                 125

Thr Ser Glu Ser Thr Ala Ala Leu Gly Cys Leu Val Lys Asp Tyr Phe
    130                 135                 140

Pro Glu Pro Val Thr Val
145                 150

<210> SEQ ID NO 82
<211> LENGTH: 146
<212> TYPE: PRT
<213> ORGANISM: Homo sapiens

<400> SEQUENCE: 82

Val Val Gln Pro Gly Arg Ser Leu Arg Leu Ser Cys Ala Ala Ser Gly
1               5                   10                  15

Phe Thr Phe Ser Ser Cys Gly Met His Trp Val Arg Gln Ala Pro Gly
            20                  25                  30

Lys Gly Leu Glu Trp Val Ala Val Ile Trp Ser Asp Gly Ser His Lys
        35                  40                  45

Tyr Tyr Ala Asp Ser Val Lys Gly Arg Phe Thr Ile Ser Arg Asp Asn
    50                  55                  60

Ser Lys Asn Thr Leu Tyr Leu Gln Met Asn Ser Leu Arg Ala Glu Asp
65                  70                  75                  80

Thr Ala Val Tyr Tyr Cys Ala Arg Gly Thr Met Ile Val Val Gly Thr
                85                  90                  95

Leu Asp Tyr Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu Val Lys Asp Tyr Phe Pro
    130                 135                 140

Glu Pro
145

<210> SEQ ID NO 83
<211> LENGTH: 171
<212> TYPE: PRT
<213> ORGANISM: Homo sapiens

<400> SEQUENCE: 83

Gly Val Val Gln Pro Gly Arg Ser Leu Arg Leu Ser Cys Ala Ala Ser
1               5                   10                  15

Gly Phe Thr Phe Ser Ser Tyr Gly Val His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Ser Thr Leu Tyr Leu Gln Met Asn Ser Leu Arg Ala Glu
65                  70                  75                  80

Asp Thr Ala Val Tyr Tyr Cys Ala Arg Asp Ser Tyr Tyr Asp Phe Trp
                85                  90                  95

Ser Gly Arg Gly Gly Met Asp Val Trp Gly Gln Gly Thr Thr Val Thr
            100                 105                 110
```

```
Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val
                165                 170

<210> SEQ ID NO 84
<211> LENGTH: 163
<212> TYPE: PRT
<213> ORGANISM: Homo sapiens

<400> SEQUENCE: 84

Val Gln Pro Gly Arg Ser Leu Arg Leu Ser Cys Ala Ala Ser Gly Phe
  1               5                  10                  15

Thr Phe Ser Asn Tyr Ala Met His Trp Val Arg Gln Ala Pro Gly Lys
             20                  25                  30

Gly Leu Glu Trp Val Val Ile Trp His Asp Gly Asn Asn Lys Tyr
         35                  40                  45

Tyr Ala Glu Ser Val Lys Gly Arg Phe Thr Ile Ser Arg Asp Asn Ser
 50                  55                  60

Lys Asn Thr Leu Tyr Leu Gln Met Asn Ser Leu Arg Ala Glu Asp Thr
 65                  70                  75                  80

Ala Val Tyr Tyr Cys Ala Arg Asp Gln Gly Thr Gly Trp Tyr Gly Gly
                 85                  90                  95

Phe Asp Phe Trp Gly Gln Gly Thr Leu Val Thr Val Ser Ser Ala Ser
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe

<210> SEQ ID NO 85
<211> LENGTH: 76
<212> TYPE: PRT
<213> ORGANISM: Homo sapiens

<400> SEQUENCE: 85

Val Ser Gly Gly Ser Ile Ser Ser Gly Gly Tyr Tyr Trp Ser Trp Ile
  1               5                  10                  15

Arg Gln His Pro Gly Lys Gly Leu Glu Trp Ile Gly Tyr Ile Tyr Tyr
             20                  25                  30

Ser Gly Ser Thr Tyr Tyr Asn Pro Ser Leu Lys Ser Arg Val Thr Ile
         35                  40                  45

Ser Val Asp Thr Ser Lys Asn Gln Phe Ser Leu Lys Leu Ser Ser Val
 50                  55                  60

Thr Ala Ala Asp Thr Ala Val Tyr Tyr Cys Ala Arg
 65                  70                  75

<210> SEQ ID NO 86
<211> LENGTH: 172
<212> TYPE: PRT
```

-continued

<213> ORGANISM: Homo sapiens

<400> SEQUENCE: 86

Ser Gly Pro Gly Leu Val Lys Pro Ser Gln Ile Leu Ser Leu Thr Cys
1               5                   10                  15

Thr Val Ser Gly Gly Ser Ile Ser Ser Gly Gly His Tyr Trp Ser Trp
            20                  25                  30

Ile Arg Gln His Pro Gly Lys Gly Leu Glu Trp Ile Gly Tyr Ile Tyr
        35                  40                  45

Tyr Ile Gly Asn Thr Tyr Tyr Asn Pro Ser Leu Lys Ser Arg Val Thr
    50                  55                  60

Ile Ser Val Asp Thr Ser Lys Asn Gln Phe Ser Leu Lys Leu Ser Ser
65                  70                  75                  80

Val Thr Ala Ala Asp Thr Ala Val Tyr Tyr Cys Ala Arg Asp Ser Gly
                85                  90                  95

Asp Tyr Tyr Gly Ile Asp Val Trp Gly Gln Gly Thr Thr Val Thr Val
                100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln
                165                 170

<210> SEQ ID NO 87
<211> LENGTH: 96
<212> TYPE: PRT
<213> ORGANISM: Homo sapiens

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 88
<211> LENGTH: 141
<212> TYPE: PRT
<213> ORGANISM: Homo sapiens

<400> SEQUENCE: 88

Gln Ser Pro Gly Thr Leu Ser Leu Ser Pro Gly Glu Arg Ala Thr Leu
1               5                   10                  15

Ser Cys Arg Ala Ser Gln Ser Ile Ser Ser Ser Phe Leu Ala Trp Tyr
            20                  25                  30

Gln Gln Arg Pro Gly Gln Ala Pro Arg Leu Leu Ile Tyr Gly Ala Ser
        35                  40                  45

```
Ser Arg Ala Thr Gly Ile Pro Asp Arg Phe Ser Gly Ser Gly Ser Gly
        50                  55                  60

Thr Asp Phe Thr Leu Thr Ile Ser Arg Leu Glu Pro Glu Asp Phe Ala
 65                  70                  75                  80

Val Tyr Tyr Cys Gln Gln Tyr Gly Thr Ser Pro Trp Thr Phe Gly Gln
                 85                  90                  95

Gly Thr Lys Val Glu Ile Lys Arg Thr Val Ala Ala Pro Ser Val Phe
            100                 105                 110

Ile Phe Pro Pro Ser Asp Glu Gln Leu Lys Ser Gly Thr Ala Ser Val
            115                 120                 125

Val Cys Leu Leu Asn Asn Phe Tyr Pro Arg Glu Ala Lys
            130                 135                 140
```

<210> SEQ ID NO 89
<211> LENGTH: 141
<212> TYPE: PRT
<213> ORGANISM: Homo sapiens

<400> SEQUENCE: 89

```
Gln Ser Pro Gly Thr Leu Ser Leu Ser Pro Gly Glu Arg Ala Thr Leu
  1               5                  10                  15

Ser Cys Arg Thr Ser Val Ser Ser Ser Tyr Leu Ala Trp Tyr Gln Gln
             20                  25                  30

Lys Pro Gly Gln Ala Pro Arg Leu Leu Ile Tyr Gly Ala Ser Ser Arg
         35                  40                  45

Ala Thr Gly Ile Pro Asp Arg Phe Ser Gly Ser Gly Ser Gly Thr Asp
     50                  55                  60

Phe Thr Leu Thr Ile Ser Arg Leu Glu Pro Glu Asp Phe Ala Val Tyr
 65                  70                  75                  80

Tyr Cys Gln Gln Tyr Gly Ile Ser Pro Phe Thr Phe Gly Gly Gly Thr
                 85                  90                  95

Lys Val Glu Ile Lys Arg Thr Val Ala Ala Pro Ser Val Phe Ile Phe
            100                 105                 110

Pro Pro Ser Asp Glu Gln Leu Lys Ser Gly Thr Ala Ser Val Val Cys
            115                 120                 125

Leu Leu Asn Asn Phe Tyr Pro Arg Glu Ala Lys Val Gln
            130                 135                 140
```

<210> SEQ ID NO 90
<211> LENGTH: 139
<212> TYPE: PRT
<213> ORGANISM: Homo sapiens

<400> SEQUENCE: 90

```
Gly Thr Leu Ser Leu Ser Pro Gly Glu Arg Ala Thr Leu Ser Cys Arg
  1               5                  10                  15

Ala Ser Gln Ser Val Ser Ser Tyr Leu Ala Trp Tyr Gln Gln Lys Pro
             20                  25                  30

Gly Gln Ala Pro Arg Leu Leu Ile Tyr Gly Ala Ser Ser Arg Ala Thr
         35                  40                  45

Gly Ile Pro Asp Arg Phe Ser Gly Ser Gly Ser Gly Thr Asp Phe Thr
     50                  55                  60

Leu Thr Ile Ser Arg Leu Glu Pro Glu Asp Phe Ala Val Tyr Tyr Cys
 65                  70                  75                  80

Gln Gln Tyr Gly Arg Ser Pro Phe Thr Phe Gly Pro Gly Thr Lys Val
                 85                  90                  95
```

-continued

Asp Ile Lys Arg Thr Val Ala Ala Pro Ser Val Phe Ile Phe Pro Pro
            100                 105                 110

Ser Asp Glu Gln Leu Lys Ser Gly Thr Ala Ser Val Val Cys Leu Leu
        115                 120                 125

Asn Asn Phe Tyr Pro Arg Glu Ala Lys Val Gln
    130                 135

<210> SEQ ID NO 91
<211> LENGTH: 142
<212> TYPE: PRT
<213> ORGANISM: Homo sapiens

<400> SEQUENCE: 91

Gln Ser Pro Gly Thr Leu Ser Leu Ser Pro Gly Glu Arg Ala Thr Leu
 1               5                   10                  15

Ser Cys Arg Ala Ser Gln Ser Val Ser Ser Tyr Leu Ala Trp Tyr Gln
            20                  25                  30

Gln Lys Pro Gly Gln Ala Pro Arg Pro Leu Ile Tyr Gly Val Ser Ser
        35                  40                  45

Arg Ala Thr Gly Ile Pro Asp Arg Phe Ser Gly Ser Gly Ser Gly Thr
 50                  55                  60

Asp Phe Thr Leu Thr Ile Ser Arg Leu Glu Pro Glu Asp Phe Ala Val
 65                  70                  75                  80

Tyr Tyr Cys Gln Gln Tyr Gly Ile Ser Pro Phe Thr Phe Gly Pro Gly
                85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln
    130                 135                 140

<210> SEQ ID NO 92
<211> LENGTH: 142
<212> TYPE: PRT
<213> ORGANISM: Homo sapiens

<400> SEQUENCE: 92

Ser Pro Gly Thr Leu Ser Leu Ser Pro Gly Glu Arg Ala Thr Leu Ser
 1               5                   10                  15

Cys Arg Ala Ser Gln Ser Ile Ser Ser Asn Phe Leu Ala Trp Tyr Gln
            20                  25                  30

Gln Lys Pro Gly Gln Ala Pro Arg Leu Leu Ile Tyr Arg Pro Ser Ser
        35                  40                  45

Arg Ala Thr Gly Ile Pro Asp Ser Phe Ser Gly Ser Gly Ser Gly Thr
 50                  55                  60

Asp Phe Thr Leu Thr Ile Ser Arg Leu Glu Pro Glu Asp Phe Ala Leu
 65                  70                  75                  80

Tyr Tyr Cys Gln Gln Tyr Gly Thr Ser Pro Phe Thr Phe Gly Pro Gly
                85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln
    130                 135                 140

```
<210> SEQ ID NO 93
<211> LENGTH: 146
<212> TYPE: PRT
<213> ORGANISM: Homo sapiens

<400> SEQUENCE: 93

Gln Ser Pro Gly Thr Leu Ser Leu Ser Pro Gly Glu Arg Ala Thr Leu
1               5                   10                  15

Ser Cys Arg Ala Ser Gln Ser Val Ser Ser Tyr Leu Ala Trp Tyr Gln
                20                  25                  30

Gln Lys Pro Gly Gln Ala Pro Arg Leu Leu Ile Tyr Gly Ala Ser Ser
            35                  40                  45

Arg Ala Thr Gly Ile Pro Asp Arg Phe Ser Gly Ser Gly Ser Gly Thr
    50                  55                  60

Asp Phe Thr Leu Thr Ile Ser Arg Leu Glu Pro Glu Asp Phe Ala Val
65                  70                  75                  80

Tyr Tyr Cys Gln Gln Tyr Gly Arg Ser Pro Phe Thr Phe Gly Pro Gly
                85                  90                  95

Thr Lys Val Asp Ile Lys Arg Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln Trp Lys
    130                 135                 140

Gly Gly
145

<210> SEQ ID NO 94
<211> LENGTH: 95
<212> TYPE: PRT
<213> ORGANISM: Homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 95
<211> LENGTH: 152
<212> TYPE: PRT
<213> ORGANISM: Homo sapiens

<400> SEQUENCE: 95

Gln Ser Pro Ser Ser Leu Ser Ala Ser Val Gly Asp Arg Val Thr Ile
1               5                   10                  15

Thr Cys Arg Ala Ser Gln Ser Ile Asn Thr Tyr Leu Ile Trp Tyr Gln
                20                  25                  30
```

```
Gln Lys Pro Gly Lys Ala Pro Asn Phe Leu Ile Ser Ala Thr Ser Ile
             35                  40                  45

Leu Gln Ser Gly Val Pro Ser Arg Phe Arg Gly Ser Gly Ser Gly Thr
         50                  55                  60

Asn Phe Thr Leu Thr Ile Asn Ser Leu His Pro Glu Asp Phe Ala Thr
 65                  70                  75                  80

Tyr Tyr Cys Gln Gln Ser Tyr Ser Thr Pro Phe Thr Phe Gly Pro Gly
                 85                  90                  95

Thr Lys Val Asp Ile Lys Arg Thr Val Ala Ala Pro Ser Val Phe Ile
                100                 105                 110

Phe Pro Pro Ser Asp Glu Gln Leu Lys Ser Gly Thr Ala Ser Val Val
            115                 120                 125

Cys Leu Leu Asn Asn Phe Tyr Pro Arg Glu Ala Lys Val Gln Trp Lys
130                 135                 140

Val Asp Asn Ala Leu Gln Ser Gly
145                 150

<210> SEQ ID NO 96
<211> LENGTH: 139
<212> TYPE: PRT
<213> ORGANISM: Homo sapiens

<400> SEQUENCE: 96

Pro Ser Ser Leu Ser Ala Ser Val Gly Asp Arg Val Thr Ile Thr Cys
  1               5                  10                  15

Arg Ala Ser Gln Ser Ile Asn Ser Tyr Leu Asp Trp Tyr Gln Gln Lys
             20                  25                  30

Pro Gly Lys Ala Pro Lys Leu Leu Ile Tyr Ala Ala Ser Ser Leu Gln
         35                  40                  45

Ser Gly Val Pro Ser Arg Phe Ser Gly Ser Gly Ser Gly Thr Asp Phe
     50                  55                  60

Thr Leu Thr Ile Ser Ser Leu Gln Pro Glu Asp Phe Ala Thr Tyr Tyr
 65                  70                  75                  80

Cys Gln Gln Tyr Tyr Ser Thr Pro Phe Thr Phe Gly Pro Gly Thr Lys
                 85                  90                  95

Val Glu Ile Lys Arg Thr Val Ala Ala Pro Ser Val Phe Ile Phe Pro
                100                 105                 110

Pro Ser Asp Glu Gln Leu Lys Ser Gly Thr Ala Ser Val Val Cys Leu
            115                 120                 125

Leu Asn Asn Phe Tyr Pro Arg Glu Ala Lys Val
130                 135

<210> SEQ ID NO 97
<211> LENGTH: 134
<212> TYPE: PRT
<213> ORGANISM: Homo sapiens

<400> SEQUENCE: 97

Thr Gln Ser Pro Ser Ser Leu Ser Ala Ser Val Gly Asp Arg Val Thr
  1               5                  10                  15

Ile Thr Cys Arg Ala Ser Gln Asn Ile Ser Arg Tyr Leu Asn Trp Tyr
             20                  25                  30

Gln Gln Lys Pro Gly Lys Ala Pro Lys Phe Leu Ile Tyr Val Ala Ser
         35                  40                  45

Ile Leu Gln Ser Gly Val Pro Ser Gly Phe Ser Ala Ser Gly Ser Gly
     50                  55                  60
```

```
Pro Asp Phe Thr Leu Thr Ile Ser Ser Leu Gln Pro Glu Asp Phe Ala
 65                  70                  75                  80

Thr Tyr Tyr Cys Gln Gln Ser Tyr Ser Thr Pro Phe Thr Phe Gly Pro
             85                  90                  95

Gly Thr Lys Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn
        130

<210> SEQ ID NO 98
<211> LENGTH: 150
<212> TYPE: PRT
<213> ORGANISM: Homo sapiens

<400> SEQUENCE: 98

Thr Gln Ser Pro Ser Ser Leu Ser Ala Ser Val Gly Asp Arg Val Thr
 1               5                  10                  15

Ile Thr Cys Arg Ala Ser Gln Ser Ile Cys Asn Tyr Leu Asn Trp Tyr
             20                  25                  30

Gln Gln Lys Pro Gly Lys Ala Pro Arg Val Leu Ile Tyr Ala Ala Ser
         35                  40                  45

Ser Leu Gln Gly Gly Val Pro Ser Arg Phe Ser Gly Ser Gly Ser Gly
     50                  55                  60

Ile Asp Cys Thr Leu Thr Ile Ser Ser Leu Gln Pro Glu Asp Phe Ala
 65                  70                  75                  80

Thr Tyr Tyr Cys Gln Gln Ser Tyr Ile Thr Pro Phe Thr Phe Gly Pro
             85                  90                  95

Gly Thr Arg Val Asp Ile Glu Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
    130                 135                 140

Lys Val Asp Asn Ala Tyr
145                 150

<210> SEQ ID NO 99
<211> LENGTH: 96
<212> TYPE: PRT
<213> ORGANISM: Homo sapiens

<400> SEQUENCE: 99

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Gln
             85                  90                  95
```

<210> SEQ ID NO 100
<211> LENGTH: 364
<212> TYPE: PRT
<213> ORGANISM: Homo sapiens

<400> SEQUENCE: 100

Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Leu Glu Gly Ala Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Thr Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 101

```
<211> LENGTH: 12
<212> TYPE: PRT
<213> ORGANISM: Homo sapiens

<400> SEQUENCE: 101

Met His Val Ala Gln Pro Ala Val Val Leu Ala Ser
1               5                   10

<210> SEQ ID NO 102
<211> LENGTH: 120
<212> TYPE: PRT
<213> ORGANISM: Homo sapiens

<400> SEQUENCE: 102

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys
        115                 120

<210> SEQ ID NO 103
<211> LENGTH: 11
<212> TYPE: PRT
<213> ORGANISM: Homo sapiens

<400> SEQUENCE: 103

Met His Val Ala Gln Pro Ala Val Val Leu Ala
1               5                   10

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)
<223> OTHER INFORMATION: i

<400> SEQUENCE: 104
caggtgcagc tggagcagtc ngg                                          23

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 105
gctgagggag tagagtcctg agga                                         24
```

<210> SEQ ID NO 106
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 106
tatctaagct tctagactcg accgccacca tggagtttgg gctgagctg                49

<210> SEQ ID NO 107
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 107
ttctctgatc agaattccta tcatttaccc ggagacaggg agagct                46

<210> SEQ ID NO 108
<211> LENGTH: 9
<212> TYPE: DNA
<213> ORGANISM: Artificial Sequence
<220> FEATURE:
<223> OTHER INFORMATION: Description of Artificial Sequence: Optimal
      Kozak sequence

<400> SEQUENCE: 108 accgccacc                9

<210> SEQ ID NO 109
<211> LENGTH: 45
<212> TYPE: DNA
<213> ORGANISM: Homo sapiens

<400> SEQUENCE: 109
tcttcaagct tgcccgggcc cgccaccatg gaaacccag cgcag                45

<210> SEQ ID NO 110
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 110
ttctttgatc agaattctca ctaacactct ccctgttga agc                43

<210> SEQ ID NO 111
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 111
tcttcaagct tgcccgggcc cgccaccatg gacatgaggg tccccgct                48

<210> SEQ ID NO 112
<211> LENGTH: 155
<212> TYPE: PRT
<213> ORGANISM: Homo sapiens

<400> SEQUENCE: 112

-continued

Ser Pro Asp Phe Gln Ser Val Thr Pro Lys Glu Lys Val Thr Ile Thr
 1               5                  10                  15

Cys Arg Ala Ser Gln Ser Ile Gly Ser Ser Leu His Trp Tyr Gln Gln
             20                  25                  30

Lys Pro Asp Gln Ser Pro Lys Leu Leu Ile Lys Tyr Ala Ser Gln Ser
         35                  40                  45

Phe Ser Gly Val Pro Ser Arg Phe Ser Gly Ser Gly Ser Gly Thr Asp
     50                  55                  60

Phe Thr Leu Thr Ile Asn Ser Leu Glu Ala Glu Asp Ala Ala Thr Tyr
 65                  70                  75                  80

Tyr Cys His Gln Ser Ser Ser Leu Pro Leu Thr Phe Gly Gly Gly Thr
                 85                  90                  95

Lys Val Glu Ile Lys Arg Thr Val Ala Ala Pro Ser Val Phe Ile Phe
             100                 105                 110

Pro Pro Ser Asp Glu Gln Leu Lys Ser Gly Thr Ala Ser Val Val Cys
             115                 120                 125

Leu Leu Asn Asn Phe Tyr Pro Arg Glu Ala Lys Val Gln Trp Lys Val
        130                 135                 140

Asp Asn Ala Leu Gln Ser Gly Asn Ser Gln Glu
145                 150                 155

<210> SEQ ID NO 113
<211> LENGTH: 100
<212> TYPE: PRT
<213> ORGANISM: Homo sapiens

<400> SEQUENCE: 113

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
            100

<210> SEQ ID NO 114
<211> LENGTH: 139
<212> TYPE: PRT
<213> ORGANISM: Homo sapiens

<400> SEQUENCE: 114

Pro Leu Ser Leu Pro Val Thr Leu Gly Gln Pro Ala Ser Ile Ser Cys
 1               5                  10                  15

Arg Ser Ser Gln Ser Leu Val Tyr Ser Asp Gly Asn Thr Tyr Leu Asn
             20                  25                  30

Trp Phe Gln Gln Arg Pro Gly Gln Ser Pro Arg Arg Leu Ile Tyr Lys
         35                  40                  45

Val Ser Asn Trp Asp Ser Gly Val Pro Asp Arg Phe Ser Gly Ser Gly
     50                  55                  60

```
Ser Gly Thr Asp Phe Thr Leu Lys Ile Ser Arg Val Glu Ala Glu Asp
 65                  70                  75                  80

Val Gly Val Tyr Tyr Cys Met Gln Gly Ser His Trp Pro Thr Phe
                 85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro
    130                 135
```

<210> SEQ ID NO 115
<211> LENGTH: 100
<212> TYPE: PRT
<213> ORGANISM: Homo sapiens

<400> SEQUENCE: 115

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100
```

<210> SEQ ID NO 116
<211> LENGTH: 133
<212> TYPE: PRT
<213> ORGANISM: Homo sapiens

<400> SEQUENCE: 116

```
Pro Gly Glu Pro Ala Ser Ile Ser Cys Arg Ser Ser Gln Ser Leu Leu
  1               5                  10                  15

His Ser Asn Gly Tyr Asn Tyr Leu Asp Trp Tyr Leu Gln Lys Pro Gly
             20                  25                  30

Gln Ser Pro Gln Leu Leu Ile Tyr Leu Gly Ser Asn Arg Ala Ser Gly
         35                  40                  45

Val Pro Asp Arg Phe Ser Gly Ser Gly Ser Gly Thr Asp Phe Thr Leu
     50                  55                  60

Lys Leu Ser Arg Val Glu Ala Glu Asp Val Gly Val Tyr Tyr Cys Met
 65                  70                  75                  80

Gln Ala Leu Gln Thr Pro Leu Thr Phe Gly Gly Gly Thr Lys Val Glu
                 85                  90                  95

Ile Lys Arg Thr Val Ala Ala Pro Ser Val Phe Ile Phe Pro Pro Ser
            100                 105                 110

Asp Glu Gln Leu Lys Ser Gly Thr Ala Ser Val Val Cys Leu Leu Asn
        115                 120                 125

Asn Phe Tyr Pro Arg
    130
```

```
<210> SEQ ID NO 117
<211> LENGTH: 20
<212> TYPE: PRT
<213> ORGANISM: Homo sapiens

<400> SEQUENCE: 117

Asp Ile Gln Met Thr Gln Ser Pro Ser Ser Leu Ser Ala Ser Val Gly
 1               5                  10                  15

Asp Arg Val Thr
            20

<210> SEQ ID NO 118
<211> LENGTH: 20
<212> TYPE: PRT
<213> ORGANISM: Homo sapiens

<400> SEQUENCE: 118

Glu Ile Val Leu Thr Gln Ser Pro Gly Thr Leu Ser Leu Ser Pro Gly
 1               5                  10                  15

Glu Arg Ala Thr
            20

<210> SEQ ID NO 119
<211> LENGTH: 20
<212> TYPE: PRT
<213> ORGANISM: Homo sapiens

<400> SEQUENCE: 119

Glu Ile Val Leu Thr Gln Ser Pro Gly Thr Leu Ser Leu Ser Pro Gly
 1               5                  10                  15

Glu Arg Ala Thr
            20

<210> SEQ ID NO 120
<211> LENGTH: 20
<212> TYPE: PRT
<213> ORGANISM: Homo sapiens

<400> SEQUENCE: 120

Asp Ile Gln Met Thr Gln Ser Pro Ser Ser Val Ser Ala Ser Val Gly
 1               5                  10                  15

Asp Arg Val Thr
            20

<210> SEQ ID NO 121
<211> LENGTH: 20
<212> TYPE: PRT
<213> ORGANISM: Homo sapiens

<400> SEQUENCE: 121

Thr Gly Glu Phe Val Leu Thr Gln Ser Pro Gly Thr Leu Ser Leu Ser
 1               5                  10                  15

Pro Gly Glu Arg
            20

<210> SEQ ID NO 122
<211> LENGTH: 20
<212> TYPE: PRT
<213> ORGANISM: Homo sapiens

<400> SEQUENCE: 122
```

-continued

Glu Phe Val Leu Thr Gln Ser Pro Gly Thr Leu Ser Leu Ser Pro Gly
1               5                   10                  15

Glu Arg Ala Thr
        20

<210> SEQ ID NO 123
<211> LENGTH: 20
<212> TYPE: PRT
<213> ORGANISM: Homo sapiens

<400> SEQUENCE: 123

Glu Ile Val Leu Thr Gln Ser Pro Gly Thr Leu Ser Leu Ser Pro Gly
1               5                   10                  15

Glu Arg Ala Thr
        20

<210> SEQ ID NO 124
<211> LENGTH: 20
<212> TYPE: PRT
<213> ORGANISM: Homo sapiens

<400> SEQUENCE: 124

Glu Ile Val Leu Thr Gln Ser Pro Gly Thr Leu Ser Leu Ser Pro Gly
1               5                   10                  15

Glu Arg Ala Thr
        20

<210> SEQ ID NO 125
<211> LENGTH: 20
<212> TYPE: PRT
<213> ORGANISM: Homo sapiens

<400> SEQUENCE: 125

Glu Ile Val Leu Thr Gln Ser Pro Gly Thr Leu Ser Leu Ser Pro Gly
1               5                   10                  15

Glu Arg Ala Thr
        20

<210> SEQ ID NO 126
<211> LENGTH: 21
<212> TYPE: PRT
<213> ORGANISM: Homo sapiens

<400> SEQUENCE: 126

Gln Val Gln Leu Val Glu Ser Gly Gly Gly Val Val Gln Pro Gly Arg
1               5                   10                  15

Ser Leu Arg Leu Ser
        20

<210> SEQ ID NO 127
<211> LENGTH: 5
<212> TYPE: PRT
<213> ORGANISM: Homo sapiens

<400> SEQUENCE: 127

Pro Glu Val Gln Phe
1               5

<210> SEQ ID NO 128
<211> LENGTH: 21
<212> TYPE: PRT
<213> ORGANISM: Homo sapiens

```
<400> SEQUENCE: 128

Gln Val Gln Leu Val Glu Ser Gly Gly Gly Val Val Gln Pro Gly Arg
  1               5                  10                  15

Ser Leu Arg Leu Ser
            20

<210> SEQ ID NO 129
<211> LENGTH: 10
<212> TYPE: PRT
<213> ORGANISM: Homo sapiens

<400> SEQUENCE: 129

Pro Glu Val Gln Phe Asn Trp Tyr Val Asp
  1               5                  10

<210> SEQ ID NO 130
<211> LENGTH: 18
<212> TYPE: PRT
<213> ORGANISM: Homo sapiens

<400> SEQUENCE: 130

Gln Val Gln Leu Val Glu Ser Gly Gly Gly Val Val Gln Pro Gly Arg
  1               5                  10                  15

Ser Leu

<210> SEQ ID NO 131
<211> LENGTH: 8
<212> TYPE: PRT
<213> ORGANISM: Homo sapiens

<400> SEQUENCE: 131

Pro Glu Val Gln Phe Asn Trp Tyr
  1               5

<210> SEQ ID NO 132
<211> LENGTH: 20
<212> TYPE: PRT
<213> ORGANISM: Homo sapiens

<400> SEQUENCE: 132

Glu Val Gln Leu Leu Glu Ser Gly Gly Gly Leu Val Gln Pro Gly Gly
  1               5                  10                  15

Ser Leu Arg Leu
            20

<210> SEQ ID NO 133
<211> LENGTH: 21
<212> TYPE: PRT
<213> ORGANISM: Homo sapiens

<400> SEQUENCE: 133

Gln Val Gln Leu Val Glu Ser Gly Gly Gly Val Val Gln Pro Gly Arg
  1               5                  10                  15

Ser Leu Arg Leu Ser
            20

<210> SEQ ID NO 134
<211> LENGTH: 10
<212> TYPE: PRT
<213> ORGANISM: Homo sapiens

<400> SEQUENCE: 134
```

```
Pro Glu Val Gln Phe Asn Trp Tyr Val Asp
 1               5                  10

<210> SEQ ID NO 135
<211> LENGTH: 21
<212> TYPE: PRT
<213> ORGANISM: Homo sapiens

<400> SEQUENCE: 135

Gln Val Gln Leu Val Glu Ser Gly Gly Gly Val Val Gln Pro Gly Arg
 1               5                  10                  15

Ser Leu Arg Leu Ser
            20

<210> SEQ ID NO 136
<211> LENGTH: 9
<212> TYPE: PRT
<213> ORGANISM: Homo sapiens

<400> SEQUENCE: 136

Pro Glu Val Gln Phe Asn Trp Tyr Val
 1               5

<210> SEQ ID NO 137
<211> LENGTH: 21
<212> TYPE: PRT
<213> ORGANISM: Homo sapiens

<400> SEQUENCE: 137

Gln Val Gln Leu Val Glu Ser Gly Gly Gly Val Val Gln Pro Gly Arg
 1               5                  10                  15

Ser Leu Arg Leu Ser
            20

<210> SEQ ID NO 138
<211> LENGTH: 6
<212> TYPE: PRT
<213> ORGANISM: Homo sapiens

<400> SEQUENCE: 138

Pro Glu Val Gln Phe Asn
 1               5

<210> SEQ ID NO 139
<211> LENGTH: 21
<212> TYPE: PRT
<213> ORGANISM: Homo sapiens

<400> SEQUENCE: 139

Gln Val Gln Leu Val Glu Ser Gly Gly Gly Val Val Glu Pro Gly Arg
 1               5                  10                  15

Ser Leu Arg Leu Ser
            20

<210> SEQ ID NO 140
<211> LENGTH: 10
<212> TYPE: PRT
<213> ORGANISM: Homo sapiens

<400> SEQUENCE: 140

Pro Glu Val Gln Phe Asn Trp Tyr Val Asp
 1               5                  10
```

```
<210> SEQ ID NO 141
<211> LENGTH: 8
<212> TYPE: PRT
<213> ORGANISM: Homo sapiens

<400> SEQUENCE: 141

Asp Ile Gln Met Thr Gln Ser Pro
 1               5

<210> SEQ ID NO 142
<211> LENGTH: 8
<212> TYPE: PRT
<213> ORGANISM: Homo sapiens

<400> SEQUENCE: 142

Glu Ile Val Leu Thr Gln Ser Pro
 1               5

<210> SEQ ID NO 143
<211> LENGTH: 8
<212> TYPE: PRT
<213> ORGANISM: Homo sapiens

<400> SEQUENCE: 143

Glu Ile Val Leu Thr Gln Ser Pro
 1               5

<210> SEQ ID NO 144
<211> LENGTH: 10
<212> TYPE: PRT
<213> ORGANISM: Homo sapiens

<400> SEQUENCE: 144

Thr Gly Glu Phe Val Leu Thr Gln Ser Pro
 1               5                  10

<210> SEQ ID NO 145
<211> LENGTH: 8
<212> TYPE: PRT
<213> ORGANISM: Homo sapiens

<400> SEQUENCE: 145

Glu Phe Val Leu Thr Gln Ser Pro
 1               5

<210> SEQ ID NO 146
<211> LENGTH: 8
<212> TYPE: PRT
<213> ORGANISM: Homo sapiens

<400> SEQUENCE: 146

Glu Ile Val Leu Thr Gln Ser Pro
 1               5

<210> SEQ ID NO 147
<211> LENGTH: 8
<212> TYPE: PRT
<213> ORGANISM: Homo sapiens

<400> SEQUENCE: 147

Glu Ile Val Leu Thr Gln Ser Pro
 1               5
```